(12) United States Patent
Ghosh et al.

(10) Patent No.: US 8,759,295 B2
(45) Date of Patent: *Jun. 24, 2014

(54) PEPTIDE-PEPTIDASE INHIBITOR CONJUGATES AND METHODS OF USING SAME

(75) Inventors: Soumitra S. Ghosh, San Diego, CA (US); Josue Alfaro-Lopez, San Diego, CA (US); Lawrence J. D'Souza, San Diego, CA (US); Odile Esther Levy, San Diego, CA (US); Qing Lin, Buffalo, NY (US); Christopher J. Soares, San Diego, CA (US)

(73) Assignees: Amylin Pharmaceuticals, LLC, San Diego, CA (US); Astrazeneca Pharmaceuticals LP, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/785,396

(22) Filed: May 21, 2010

(65) Prior Publication Data

US 2010/0292172 A1    Nov. 18, 2010

Related U.S. Application Data

(63) Continuation of application No. 12/293,389, filed as application No. PCT/US2007/007163 on Mar. 21, 2007, now abandoned.

(60) Provisional application No. 60/784,795, filed on Mar. 21, 2006.

(51) Int. Cl.
*A61K 38/26* (2006.01)
*C07K 14/605* (2006.01)
*C07K 19/00* (2006.01)
*A61P 3/10* (2006.01)
*A61P 9/00* (2006.01)
*A61P 9/04* (2006.01)
*A61P 9/08* (2006.01)
*A61P 9/10* (2006.01)
*A61P 9/12* (2006.01)

(52) U.S. Cl.
USPC ........... 514/16.2; 514/7.2; 514/7.3; 514/16.3; 514/16.4; 530/308; 530/324; 530/350; 530/402

(58) Field of Classification Search
None
See application file for complete search history.

(56) References Cited

U.S. PATENT DOCUMENTS 4,046,889 A   9/1977  Ondetti et al.
4,168,267 A   9/1979  Petrillo, Jr.

(Continued)

FOREIGN PATENT DOCUMENTS

EP    1520582      4/2005
JP    9-509151     9/1997

(Continued)

OTHER PUBLICATIONS

Bull, H G et al., "Purification of angiotens-converting enzyme from rabbit lung and human plasma by affinity chromatography," The Journal of Biological Chemistry, Mar. 10, 1985, vol. 260, No. 5, pp. 2963-2972.

(Continued)

*Primary Examiner* — Zachary Howard
(74) *Attorney, Agent, or Firm* — Womble Carlyle Sandridge & Rice LLP; Mark J. Pino; Alireza Behrooz

(57) ABSTRACT

Peptide-peptidase inhibitor conjugate molecules are disclosed. These conjugate molecules are useful as agents for the treatment and prevention of metabolic and cardiovascular diseases, disorders, and conditions. Such diseases, conditions and disorders include, but are not limited to, hypertension, dyslipidemia, cardiovascular disease, eating disorders, insulin-resistance, obesity, and diabetes mellitus of any kind, and other diabetes-related disorders.

6 Claims, 15 Drawing Sheets

(56) References Cited

U.S. PATENT DOCUMENTS

| | | | |
|---|---|---|---|
| 4,316,906 A | 2/1982 | Ondetti et al. | |
| 4,337,201 A | 6/1982 | Petrillo, Jr. | |
| 4,344,949 A | 8/1982 | Hoefle et al. | |
| 4,374,829 A | 2/1983 | Harris et al. | |
| 4,452,790 A | 6/1984 | Karanewsky et al. | |
| 4,722,810 A | 2/1988 | Delaney | |
| 4,749,688 A | 6/1988 | Haslanger | |
| 5,223,516 A | 6/1993 | Delaney et al. | |
| 5,225,401 A | 7/1993 | Seymore | |
| 5,362,727 A | 11/1994 | Robl | |
| 5,366,973 A | 11/1994 | Flynn et al. | |
| 5,504,080 A | 4/1996 | Karanewsky | |
| 5,525,723 A | 6/1996 | Robl | |
| 5,552,397 A | 9/1996 | Karanewsky et al. | |
| 5,612,359 A | 3/1997 | Murugesan | |
| 6,011,155 A | 1/2000 | Villhauer | |
| 6,124,305 A | 9/2000 | Villhauer | |
| 6,166,063 A | 12/2000 | Villhauer | |
| 6,172,081 B1 | 1/2001 | Damon | |
| 6,432,969 B1 | 8/2002 | Villhauer | |
| 6,710,040 B1 | 3/2004 | Hulin et al. | |
| 6,869,947 B2 | 3/2005 | Kanstrup et al. | |
| 6,887,470 B1 | 5/2005 | Bridon et al. | |
| 6,995,180 B2 | 2/2006 | Magnin et al. | |
| 6,995,183 B2 | 2/2006 | Hamann et al. | |
| 2003/0221201 A1 | 11/2003 | Prior et al. | |
| 2009/0186817 A1 | 7/2009 | Ghosh et al. | |
| 2010/0292172 A1 | 11/2010 | Ghosh et al. | |

FOREIGN PATENT DOCUMENTS

| | | |
|---|---|---|
| JP | 2002-501559 | 1/2002 |
| WO | WO 95/20567 | 8/1995 |
| WO | WO 03/060071 | 7/2003 |
| WO | WO 03/101476 | 12/2003 |
| WO | WO 2004/078777 | 9/2004 |
| WO | WO 2007/022123 | 2/2007 |
| WO | WO 2006/017688 | 2/2008 |

OTHER PUBLICATIONS

Alfaro-Lopez, Josue et al., "Peptide-Lisinopril Conjugates: Design, Synthesis and Biological Activities," Advances in Experimental Medicine and Biology: The proceedings of the 20th American Peptide Symposium Springer, 233 Spring Street, New York, NY 10013, United States Series: Advances in Experimental Medicine and Biology, 2009, pp. 535-536.

Green et al., "N-terminal His7-modification of glucagon-like peptide-1(7-36) amide generates dipeptidyl peptidase IV-stable analogues with potent antihyperglycaemic activity," Journal of Endocrinology 180, 379-388 (2004).

Lee et al., "Synthesis, Characterization, and Pharmacokinetic Studies of PEGylated Glucagon-like Peptide-1", Bioconjugate Chem. 16:377-382 (2005).

US 4,385,051, 05/24/1983, Oka et al. (withdrawn).

Adelhorst et al., J. Biol. Chem. 269(9):6275-6278 (1994) "Structure-Activity Slides of Glucagon-Like Peptide-1".

Baggio L. et al., Diabetes 53:2492-2500 (2004) A Recombinant Human Glucagon-Like Peptide (GLP-1-Albumin Protein (Albugon Mimics . . . .

Bernkop-Scnhürch et al., Pharmaceutical Research 15(2):263-269 (1998) Synthesis and In Vitro Evaluation of Chitosan-EDTA Protease-Inhibitor Conjugates . . . .

Bork, Genome Research 10:398 (2008) Powers and Pitfalls in Sequence Analysis: the 70% Hurdel.

Brenner, Trends in Genetics 15(4):132 (1999) Errors in Genome Annotation.

Coutts et al., J. Med. Chem. 39:2087-2094 (1996) Structure-Activity Relationship of Boronic Acid Inhibitors of Dipeptidyl Peptidase . . . .

Deacon, C.F. et al., Diabetes 47(5):764-769 (1998) Dipeptidyl Peptidase IV inhibition Potentiates the Insulinotropic Effect of a Glucagon-Like Peptide . . . .

Doerks et al., Trends in Genetics 14(6):248 (1998) Protein Annotation: Detective Work for Function Prediction.

Huang et al., J. Biol. Chem. 278:15532-15540 (2003) Novel Peptide Inhibitors of Angiotensin-Converting Enzyme 2.

Jeanfavre et al., Biochem. Pharmacol. 52:1757-1765 (1996) Effect of Deoxycoformycin and val-boroPro on the Associated Catalytic Activities of Lymphocyte . . . .

Kelly et al., Tetrahedron 49:1009-1016 (1993) The Efficient Synthesis and Simple Resolution of a Prolineboronate Ester Suitable for Enzyme-Inhibiton Studies.

Kok et al., JU. Pharm. And Experimental Therapeutics, 301(3):1139-1143 Abstract (2002) Targeting of Captopril to the Kidney Reduced Renal Angiotensin-Converting Enzyme . . . .

Kok et al., J. Pharm. And Experimental Therapeutics 288(1):281-285 (1999) Specific Delivery of Captopril to the Kidney with the Prodrug Captopril-Lysozyme.

Lee et al., Advanced Drug Delivery Reviews 4(2):171-207 (1990) Penetration and Enzymatic Barriers to Peptide and Protein Absorption.

Leger et al., Bioorganic & Medicinal Chem. Letters 14(6)4395-4398 (2004) Identification of CJC-1131-Albumin Bioconjugate as a Stable and bioactive GLP . . . .

Narazaki et al., J. Pharm. Sci. 86(2):215-219 (1997) Kinetic Analysis of the Covalent Binding of Captopril to Human Serum Albumin.

Ngo et al., Chapter 14, entitled "Computational Complexity, Protein Structure Prediction and the Levinthal Paradox," in The Protein Folding Problem and Tertiary Structure Prediction, pp. 433-440 and 492-495 only, 1994.

Salhanick et al., Bioorganic & Mdc. Chem. Chem. Ltrs 15:4114-4117 (2005) Contribution of site-specific PEGylation to the dipeptidyl peptidase IV stability of glucose-dependent insulinotropic polypeptide.

Skolnick et al., Trends in Biotech 18(1):34 (2000) From genes to protein structure and function: novel applications of computational approaches in the genome era.

Snow et al., J. Am. Chem. Soc. 116:10860-10869 (1994) Studies on Proline Boronic Acid Dipeptide Inhibitors of Dipeptidyl Peptidase . . . .

Van de Garde et al., J. Hypertension 25:235-239 (2007) Antiotensin-converting enzyme inhibitor use and protection against pneumonia in patients with diabetes.

Wells, Biochemistry 29(37):8509-8517 (1990) Additivity of Mutational Effects in Protein.

Yamamoto et al., Pharmaceutical Research 11(10:1496-1500 (1994) Effects of various protease inhibitors on the intestinal absorption and degradation . . . .

[D-Ala²] GIP(1-30)-ex endin-4(31-39)-βAla-βAla-Ado-Ado-Ado-Ado-Lys-Nε-(2-(S)-cyano pyrrolidyl):

SEQ ID NO:299

[D-Ala²] GIP(1-30)-βAla-βAla-Ado-Ado-Ado-Ado-Lys-Nε-(2-(S)-cyano pyrrolidyl):

SEQ ID NO:300

[D-Ala²]GIP-(1-30)-Ado-Ado-Aun-βAla-βAla-ε-NH-Lys(α-NH-Pyroglutamoyl)-Trp-Ala-Pro:

SEQ ID NO:301

[D-Ala2] GIP(1-30)-Ex endin-4 (31-39)-Cys-((S-maleimido propanoyl)-Lys-N-ε-(2-(S)-Cyano pyrrolidyl))

SEQ ID NO:302

[D-Ala2] GIP(1-30)-Ex endin-4 (31-39)-Cys-((S-maleimido propanoyl)-(2(S)-4(S)Amino)Pro-(2-(S)-Boro pyrrolidyl)))

SEQ ID NO:303

SEQUENCE LISTING

```
<160> NUMBER OF SEQ ID NOS: 350

<210> SEQ ID NO 1
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Tyr Ala Glu Gly Thr Phe Ile Ser Asp Tyr Ser Ile Ala Met Asp Lys
1               5                   10                  15
```

Ile His Gln Gln Asp Phe Val Asn Trp Leu Leu Ala Gln Lys Pro Ser
            20                  25                  30

Ser Gly Ala Pro Pro Ser
        35

<210> SEQ ID NO 2
<211> LENGTH: 36
<212> TYPE: PRT
<213> ORGANISM: Homo sapiens

<400> SEQUENCE: 2

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 3
<211> LENGTH: 34
<212> TYPE: PRT
<213> ORGANISM: Homo sapiens

<400> SEQUENCE: 3

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 4
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Tyr Pro Leu Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 5
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Tyr Pro Val Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

```
<210> SEQ ID NO 6
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Tyr Pro Ile Arg Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 7
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Tyr Pro Ile Gln Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 8
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Tyr Pro Ile Asn Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 9
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Tyr Pro Ile Lys Pro Glu Ala Pro Gly Glu Asp Ala Ser Pro Glu Glu
1               5                   10                  15

Leu Asn Arg Tyr Tyr Ala Ser Leu Lys His Tyr Leu Asn Leu Val Thr
            20                  25                  30

Arg Gln Arg Tyr
        35
```

<210> SEQ ID NO 10
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
                20                  25                  30

Arg Pro Arg Tyr
        35

<210> SEQ ID NO 11
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
                20                  25                  30

Arg His Arg Tyr
        35

<210> SEQ ID NO 12
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
                20                  25                  30

Arg Gln Arg Tyr
        35

<210> SEQ ID NO 13
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Tyr Pro Ile Lys Pro Glu Ala Pro Gly Glu Asp Ala Pro Ala Glu Glu
1               5                   10                  15

Leu Asn Arg Tyr Tyr Ala Ser Leu Arg His Tyr Leu Asn Leu Val Thr
                20                  25                  30

Arg Gln Arg Tyr

<210> SEQ ID NO 14
<211> LENGTH: 36
<212> TYPE: PRT
<213> ORGANISM: Artificial Sequence
<220> FEATURE:
<223> OTHER INFORMATION: Description of Artificial Sequence: Synthetic peptide

<400> SEQUENCE: 14

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Leu Thr
            20                  25                  30

Arg Pro Arg Tyr
        35

<210> SEQ ID NO 15
<211> LENGTH: 35
<212> TYPE: PRT
<213> ORGANISM: Artificial Sequence
<220> FEATURE:
<223> OTHER INFORMATION: Description of Artificial Sequence: Synthetic peptide

<400> SEQUENCE: 15

Tyr Pro Ile Pro Glu Ala Pro Gly Glu Asp Ala Ser Pro Glu Glu Leu
1               5                   10                  15

Asn Arg Tyr Tyr Ala Ser Leu Arg His Tyr Leu Asn Leu Val Thr Arg
            20                  25                  30

Gln Arg Tyr
        35

<210> SEQ ID NO 16
<211> LENGTH: 35
<212> TYPE: PRT
<213> ORGANISM: Homo sapiens

<400> SEQUENCE: 16

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg
        35

<210> SEQ ID NO 17
<211> LENGTH: 30
<212> TYPE: PRT
<213> ORGANISM: Homo sapiens

<400> SEQUENCE: 17

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu
            20                  25                  30

<210> SEQ ID NO 18
<211> LENGTH: 25
<212> TYPE: PRT
<213> ORGANISM: Homo sapiens

```
<400> SEQUENCE: 18

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg
            20                  25

<210> SEQ ID NO 19
<211> LENGTH: 15
<212> TYPE: PRT
<213> ORGANISM: Homo sapiens

<400> SEQUENCE: 19

Tyr Pro Ile Lys Pro Glu Ala Pro Gly Glu Asp Ala Ser Pro Glu
1               5                   10                  15

<210> SEQ ID NO 20
<211> LENGTH: 10
<212> TYPE: PRT
<213> ORGANISM: Homo sapiens

<400> SEQUENCE: 20

Tyr Pro Ile Lys Pro Glu Ala Pro Gly Glu
1               5                   10

<210> SEQ ID NO 21
<211> LENGTH: 35
<212> TYPE: PRT
<213> ORGANISM: Homo sapiens

<400> SEQUENCE: 21

Pro Ile Lys Pro Glu Ala Pro Gly Glu Asp Ala Ser Pro Glu Glu Leu
1               5                   10                  15

Asn Arg Tyr Tyr Ala Ser Leu Arg His Tyr Leu Asn Leu Val Thr Arg
            20                  25                  30

Gln Arg Tyr
        35

<210> SEQ ID NO 22
<211> LENGTH: 33
<212> TYPE: PRT
<213> ORGANISM: Homo sapiens

<400> SEQUENCE: 22

Lys Pro Glu Ala Pro Gly Glu Asp Ala Ser Pro Glu Glu Leu Asn Arg
1               5                   10                  15

Tyr Tyr Ala Ser Leu Arg His Tyr Leu Asn Leu Val Thr Arg Gln Arg
            20                  25                  30

Tyr

<210> SEQ ID NO 23
<211> LENGTH: 32
<212> TYPE: PRT
<213> ORGANISM: Homo sapiens

<400> SEQUENCE: 23

Pro Glu Ala Pro Gly Glu Asp Ala Ser Pro Glu Glu Leu Asn Arg Tyr
1               5                   10                  15

Tyr Ala Ser Leu Arg His Tyr Leu Asn Leu Val Thr Arg Gln Arg Tyr
            20                  25                  30

<210> SEQ ID NO 24
```

```
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: isocap-Pro

<400> SEQUENCE: 24

Pro Lys Pro Glu Ala Pro Gly Glu Asp Ala Ser Pro Glu Glu Leu Ala
1               5                   10                  15

Arg Tyr Tyr Ala Ser Leu Arg Ala Tyr Ile Asn Leu Ile Thr Arg Gln
            20                  25                  30

Arg Tyr

<210> SEQ ID NO 25
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: isocap-Tyr

<400> SEQUENCE: 25

Tyr Pro Ile Lys Pro Glu Ala Pro Gly Glu Asp Ala Ser Pro Glu Glu
1               5                   10                  15

Leu Ala Gln Tyr Ala Ala Asp Leu Arg Arg Tyr Ile Asn Met Leu Thr
            20                  25                  30

Arg Gln Arg Tyr
        35

<210> SEQ ID NO 26
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ile Lys Pro Glu Ala Pro Gly Glu Asp Ala Pro Ala Glu Glu Leu Ala
1               5                   10                  15

Arg Tyr Tyr Ala Ser Leu Arg Ala Tyr Ile Asn Leu Ile Thr Arg Gln
            20                  25                  30

Arg Tyr

<210> SEQ ID NO 27
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Tyr Pro Ile Lys Pro Glu Ala Pro Gly Glu Asp Ala Ser Pro Glu Glu
1               5                   10                  15

Leu Ala Arg Tyr Tyr Ser Ala Leu Arg His Tyr Ile Asn Leu Ile Thr
```

```
                    20                  25                  30

Arg Gln Arg Tyr
        35

<210> SEQ ID NO 28
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ile Lys Pro Glu Ala Pro Gly Glu Asp Ala Ser Pro Glu Glu Leu Ala
1               5                   10                  15

Arg Tyr Tyr Ser Ala Leu Arg His Tyr Ile Asn Leu Ile Thr Arg Gln
            20                  25                  30

Arg Tyr

<210> SEQ ID NO 29
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: isocap-Ile

<400> SEQUENCE: 29

Ile Lys Pro Glu Ala Pro Gly Glu Asp Ala Ser Pro Glu Glu Leu Ala
1               5                   10                  15

Arg Tyr Tyr Ser Ala Leu Arg His Tyr Ile Asn Leu Ile Thr Arg Gln
            20                  25                  30

Arg Tyr

<210> SEQ ID NO 30
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Pro Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 31
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: isocap-Pro
```

```
<400> SEQUENCE: 31

Pro Lys Pro Glu His Pro Gly Glu Asp Ala Ser Ala Glu Glu Leu Ala
1               5                   10                  15

Arg Tyr Tyr Ala Ser Leu Arg Ala Tyr Ile Asn Leu Ile Thr Arg Gln
            20                  25                  30

Arg Tyr

<210> SEQ ID NO 32
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Pro Lys Pro Glu His Pro Gly Glu Asp Ala Ser Pro Glu Glu Leu Ala
1               5                   10                  15

Arg Tyr Tyr Ala Ser Leu Arg Ala Tyr Ile Asn Leu Ile Thr Arg Gln
            20                  25                  30

Arg Tyr

<210> SEQ ID NO 33
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Pro Lys Pro Glu His Pro Gly Glu Asp Ala Ser Ala Glu Glu Leu Ala
1               5                   10                  15

Arg Tyr Tyr Ala Ser Leu Arg Ala Tyr Ile Asn Leu Ile Thr Arg Gln
            20                  25                  30

Arg Tyr

<210> SEQ ID NO 34
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Pro Lys Pro Glu Ala Pro Gly Glu Asp Ala Ser Pro Glu Glu Leu Ala
1               5                   10                  15

Lys Tyr Tyr Ala Ser Leu Arg Ala Tyr Ile Asn Leu Ile Thr Arg Gln
            20                  25                  30

Arg Tyr

<210> SEQ ID NO 35
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: isocap-Pro
```

<400> SEQUENCE: 35

Pro Lys Pro Glu Ala Pro Gly Glu Asp Ala Ser Pro Glu Glu Leu Ala
1               5                   10                  15

Lys Tyr Tyr Ala Ser Leu Arg Ala Tyr Ile Asn Leu Ile Thr Arg Gln
            20                  25                  30

Arg Tyr

<210> SEQ ID NO 36
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Pro Lys Pro Glu His Pro Gly Glu Asp Ala Pro Ala Glu Glu Leu Ala
1               5                   10                  15

Lys Tyr Tyr Ala Ser Leu Arg Ala Tyr Ile Asn Leu Ile Thr Arg Gln
            20                  25                  30

Arg Tyr

<210> SEQ ID NO 37
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Pro Lys Pro Glu His Pro Gly Glu Asp Ala Pro Ala Glu Glu Leu Ala
1               5                   10                  15

Arg Tyr Tyr Ala Ser Leu Arg Ala Tyr Ile Asn Leu Ile Thr Arg Gln
            20                  25                  30

Arg Tyr

<210> SEQ ID NO 38
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: octanoic acid-Ile

<400> SEQUENCE: 38

Ile Ala Pro Glu Ala Pro Gly Glu Asp Ala Ser Pro Glu Glu Leu Ala
1               5                   10                  15

Arg Tyr Tyr Ala Ser Leu Arg His Tyr Leu Asn Leu Val Thr Arg Gln
            20                  25                  30

Arg Tyr

<210> SEQ ID NO 39
<211> LENGTH: 35
<212> TYPE: PRT
<213> ORGANISM: Artificial Sequence
<220> FEATURE:
<223> OTHER INFORMATION: Description of Artificial Sequence: Synthetic

```
          peptide
<220> FEATURE:
<221> NAME/KEY: MOD_RES
<222> LOCATION: (1)..(1)
<223> OTHER INFORMATION: octyl-Gly

<400> SEQUENCE: 39

Gly Ile Lys Pro Glu Ala Pro Gly Glu Asp Ala Ser Pro Glu Glu Leu
1               5                   10                  15

Ala Arg Tyr Tyr Ser Ala Leu Arg His Tyr Ile Asn Leu Ile Thr Arg
            20                  25                  30

Gln Arg Tyr
        35

<210> SEQ ID NO 40
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Tyr Pro Ile Arg Pro Glu Ala Pro Gly Glu Asp Ala Ser Pro Glu Glu
1               5                   10                  15

Leu Ala Arg Tyr Tyr Ala Ser Leu Arg His Tyr Ile Asn Leu Ile Thr
            20                  25                  30

Arg Gln Arg Tyr
        35

<210> SEQ ID NO 41
<211> LENGTH: 37
<212> TYPE: PRT
<213> ORGANISM: Homo sapiens

<400> SEQUENCE: 41

His Asp Glu Phe Glu Arg His Ala Glu Gly Thr Phe Thr Ser Asp Val
1               5                   10                  15

Ser Ser Tyr Leu Glu Gly Gln Ala Ala Lys Glu Phe Ile Ala Trp Leu
            20                  25                  30

Val Lys Gly Arg Gly
        35

<210> SEQ ID NO 42
<211> LENGTH: 31
<212> TYPE: PRT
<213> ORGANISM: Homo sapiens

<400> SEQUENCE: 42

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 43
<211> LENGTH: 30
<212> TYPE: PRT
<213> ORGANISM: Homo sapiens
<220> FEATURE:
<221> NAME/KEY: MOD_RES
<222> LOCATION: (30)..(30)
<223> OTHER INFORMATION: Arg-NH2

<400> SEQUENCE: 43
```

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 44
<211> LENGTH: 37
<212> TYPE: PRT
<213> ORGANISM: Xenopus sp.
<220> FEATURE:
<221> NAME/KEY: MOD_RES
<222> LOCATION: (37)..(37)
<223> OTHER INFORMATION: Ser-OH

<400> SEQUENCE: 44

His Ala Glu Gly Thr Tyr Thr Asn Asp Val Thr Glu Tyr Leu Glu Glu
1               5                   10                  15

Lys Ala Ala Lys Glu Phe Ile Glu Trp Leu Ile Lys Gly Lys Pro Lys
            20                  25                  30

Lys Ile Arg Tyr Ser
        35

<210> SEQ ID NO 45
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (37)..(37)
<223> OTHER INFORMATION: Ser-OH

<400> SEQUENCE: 45

His Ala Glu Gly Thr Phe Thr Ser Asp Val Thr Gln Gln Leu Asp Glu
1               5                   10                  15

Lys Ala Ala Lys Glu Phe Ile Asp Trp Leu Ile Asn Gly Gly Pro Ser
            20                  25                  30

Lys Glu Ile Ile Ser
        35

<210> SEQ ID NO 46
<211> LENGTH: 29
<212> TYPE: PRT
<213> ORGANISM: Homo sapiens

<400> SEQUENCE: 46

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly
            20                  25

<210> SEQ ID NO 47
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

His Ala Glu Gly Thr Phe Thr Ser Asp Val Ser Ser Tyr Leu Glu Gly
1               5                   10                  15

```
Gln Ala Ala Lys Glu Phe Ile Ala Trp Leu Val Lys Gly Arg Gly
            20                  25                  30

<210> SEQ ID NO 48
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-Gln

<400> SEQUENCE: 48

His Ala Gln Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 49
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

His Ala Glu Gly Thr Phe Thr Ser Asp Thr Ser Lys Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 50
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

His Ala Glu Gly Thr Phe Thr Ser Asp Val Ser Lys Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 51
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 52
<211> LENGTH: 31
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: acetyl-His

<400> SEQUENCE: 52

His Ala Lys Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 53
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

His Ala Thr Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 54
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-Thr

<400> SEQUENCE: 54

His Ala Thr Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 55
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

His Ala Asn Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 56
<211> LENGTH: 31
<212> TYPE: PRT
<213> ORGANISM: Artificial Sequence
<220> FEATURE:
```

<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-Asn

<400> SEQUENCE: 56

His Ala Asn Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 57
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

His Ala Glu Gly Thr Phe Thr Ser Asp Val Ser Ser Tyr Leu Glu Ser
1               5                   10                  15

Arg Arg Ala Gln Glu Phe Ile Ala Trp Leu Val Lys Gly Arg Gly
            20                  25                  30

<210> SEQ ID NO 58
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

His Ala Glu Gly Thr Phe Thr Ser Asp Val Ser Ser Tyr Leu Glu Gly
1               5                   10                  15

Arg Ala Ala Lys Glu Phe Ile Ala Trp Leu Val Lys Gly Arg Gly
            20                  25                  30

<210> SEQ ID NO 59
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

His Ala Glu Gly Thr Phe Thr Ser Asp Val Ser Ser Tyr Leu Glu Gly
1               5                   10                  15

Gln Arg Ala Lys Glu Phe Ile Ala Trp Leu Val Lys Gly Arg Gly
            20                  25                  30

<210> SEQ ID NO 60
<211> LENGTH: 33
<212> TYPE: PRT
<213> ORGANISM: Homo sapiens

<400> SEQUENCE: 60

His Ala Asp Gly Ser Phe Ser Asp Glu Met Asn Thr Ile Leu Asp Asn
1               5                   10                  15

Leu Ala Ala Arg Asp Phe Ile Asn Trp Leu Ile Glu Thr Lys Ile Thr
            20                  25                  30

Asp

<210> SEQ ID NO 61
<211> LENGTH: 31
<212> TYPE: PRT
<213> ORGANISM: Xenopus sp.

<400> SEQUENCE: 61

His Ala Glu Gly Thr Phe Thr Asn Asp Met Thr Asn Tyr Leu Glu Glu
1               5                   10                  15

Lys Ala Ala Lys Glu Phe Val Gly Trp Leu Ile Lys Gly Arg Pro
            20                  25                  30

<210> SEQ ID NO 62
<211> LENGTH: 37
<212> TYPE: PRT
<213> ORGANISM: Homo sapiens

<400> SEQUENCE: 62

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 63
<211> LENGTH: 39
<212> TYPE: PRT
<213> ORGANISM: Homo sapiens

<400> SEQUENCE: 63

His Ser Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 64
<211> LENGTH: 39
<212> TYPE: PRT
<213> ORGANISM: Homo sapiens

<400> SEQUENCE: 64

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 65
<211> LENGTH: 30
<212> TYPE: PRT
<213> ORGANISM: Homo sapiens

<400> SEQUENCE: 65

His Gly Glu Gly Thr Phe Thr Ser Asp Leu Ser Lys Gln Met Glu Glu
1               5                   10                  15

-continued

Glu Ala Val Arg Leu Phe Ile Glu Trp Leu Lys Asn Gly Gly
            20                  25                  30

<210> SEQ ID NO 66
<211> LENGTH: 28
<212> TYPE: PRT
<213> ORGANISM: Homo sapiens

<400> SEQUENCE: 66

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn
            20                  25

<210> SEQ ID NO 67
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly Ala Pro Pro Pro Ser
        35

<210> SEQ ID NO 68
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

His Gly Glu Gly Ala Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly Ala Pro Pro Pro Ser
        35

<210> SEQ ID NO 69
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

His Gly Glu Gly Thr Phe Thr Ser Asp Leu Ser Lys Gln Leu Glu Glu
1               5                   10                  15

Glu Ala Val Arg Leu Ala Ile Glu Phe Leu Lys Asn Gly Gly Pro Ser
            20                  25                  30

Ser Gly Ala Pro Pro Pro Ser
        35

<210> SEQ ID NO 70

```
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn
            20                  25

<210> SEQ ID NO 71
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 72
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 73
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

His Gly Glu Gly Thr Phe Thr Ser Asp Leu Ser Lys Gln Leu Glu Glu
1               5                   10                  15

Glu Ala Val Arg Leu Ala Ile Glu Phe Leu Lys Asn
            20                  25

<210> SEQ ID NO 74
<211> LENGTH: 42
<212> TYPE: PRT
<213> ORGANISM: Homo sapiens

<400> SEQUENCE: 74

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30
```

```
Lys Asn Asp Trp Lys His Asn Ile Thr Gln
        35                  40
```

<210> SEQ ID NO 75
<211> LENGTH: 42
<212> TYPE: PRT
<213> ORGANISM: Rattus sp.

<400> SEQUENCE: 75

```
Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Gly Lys
            20                  25                  30

Lys Asn Asp Trp Lys His Asn Leu Thr Gln
        35                  40
```

<210> SEQ ID NO 76
<211> LENGTH: 42
<212> TYPE: PRT
<213> ORGANISM: Mus sp.

<400> SEQUENCE: 76

```
Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Arg Gly Lys
            20                  25                  30

Lys Ser Asp Trp Lys His Asn Ile Thr Gln
        35                  40
```

<210> SEQ ID NO 77
<211> LENGTH: 42
<212> TYPE: PRT
<213> ORGANISM: Sus sp.

<400> SEQUENCE: 77

```
Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Gly Lys
            20                  25                  30

Lys Ser Asp Trp Lys His Asn Ile Thr Gln
        35                  40
```

<210> SEQ ID NO 78
<211> LENGTH: 42
<212> TYPE: PRT
<213> ORGANISM: Bos taurus

<400> SEQUENCE: 78

```
Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Gly Lys
            20                  25                  30

Lys Ser Asp Trp Ile His Asn Ile Thr Gln
        35                  40
```

<210> SEQ ID NO 79
<211> LENGTH: 30
<212> TYPE: PRT
<213> ORGANISM: Homo sapiens

<400> SEQUENCE: 79

-continued

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys
            20                  25                  30

<210> SEQ ID NO 80
<211> LENGTH: 26
<212> TYPE: PRT
<213> ORGANISM: Homo sapiens

<400> SEQUENCE: 80

Tyr Ala Glu Gly Thr Phe Ile Ser Asp Tyr Ser Ile Ala Met Asp Lys
1               5                   10                  15

Ile His Gln Gln Asp Phe Val Asn Trp Leu
            20                  25

<210> SEQ ID NO 81
<211> LENGTH: 14
<212> TYPE: PRT
<213> ORGANISM: Homo sapiens

<400> SEQUENCE: 81

Tyr Ala Glu Gly Thr Phe Ile Ser Asp Tyr Ser Ile Ala Met
1               5                   10

<210> SEQ ID NO 82
<211> LENGTH: 11
<212> TYPE: PRT
<213> ORGANISM: Homo sapiens

<400> SEQUENCE: 82

Tyr Ala Glu Gly Thr Phe Ile Ser Asp Tyr Ser
1               5                   10

<210> SEQ ID NO 83
<211> LENGTH: 12
<212> TYPE: PRT
<213> ORGANISM: Homo sapiens

<400> SEQUENCE: 83

Gln Gln Asp Phe Val Asn Trp Leu Leu Ala Gln Lys
1               5                   10

<210> SEQ ID NO 84
<211> LENGTH: 8
<212> TYPE: PRT
<213> ORGANISM: Homo sapiens

<400> SEQUENCE: 84

Gln Gln Asp Phe Val Asn Trp Leu
1               5

<210> SEQ ID NO 85
<211> LENGTH: 39
<212> TYPE: PRT
<213> ORGANISM: Homo sapiens

<400> SEQUENCE: 85

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

```
Lys Asn Asp Trp Lys His Asn
        35

<210> SEQ ID NO 86
<211> LENGTH: 21
<212> TYPE: PRT
<213> ORGANISM: Homo sapiens

<400> SEQUENCE: 86

Gln Gln Asp Phe Val Asn Trp Leu Leu Ala Gln Lys Gly Lys Asn
1               5                   10                  15

Asp Trp Lys His Asn
            20

<210> SEQ ID NO 87
<211> LENGTH: 42
<212> TYPE: PRT
<213> ORGANISM: Homo sapiens

<400> SEQUENCE: 87

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 88
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Ala

<400> SEQUENCE: 88

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 89
<211> LENGTH: 37
<212> TYPE: PRT
<213> ORGANISM: Homo sapiens

<400> SEQUENCE: 89

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
        35

<210> SEQ ID NO 90
<211> LENGTH: 37
<212> TYPE: PRT
```

<213> ORGANISM: Rattus sp.

<400> SEQUENCE: 90

Lys Cys Asn Thr Ala Thr Cys Ala Thr Gln Arg Leu Ala Asn Phe Leu
1               5                   10                  15

Val Arg Ser Ser Asn Asn Leu Gly Pro Val Leu Pro Pro Thr Asn Val
            20                  25                  30

Gly Ser Asn Thr Tyr
        35

<210> SEQ ID NO 91
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys, Ala, Ser or not present
<220> FEATURE:
<221> NAME/KEY: MOD_RES
<222> LOCATION: (2)..(2)
<223> OTHER INFORMATION: Variable amino acid
<220> FEATURE:
<221> NAME/KEY: MOD_RES
<222> LOCATION: (7)..(7)
<223> OTHER INFORMATION: Variable amino acid
<220> FEATURE:
<221> NAME/KEY: MOD_RES
<222> LOCATION: (13)..(13)
<223> OTHER INFORMATION: Ala, Ser or Thr
<220> FEATURE:
<221> NAME/KEY: MOD_RES
<222> LOCATION: (17)..(17)
<223> OTHER INFORMATION: Val, Leu or Ile
<220> FEATURE:
<221> NAME/KEY: MOD_RES
<222> LOCATION: (18)..(18)
<223> OTHER INFORMATION: His or Arg
<220> FEATURE:
<221> NAME/KEY: MOD_RES
<222> LOCATION: (19)..(19)
<223> OTHER INFORMATION: Ser or Thr
<220> FEATURE:
<221> NAME/KEY: MOD_RES
<222> LOCATION: (20)..(20)
<223> OTHER INFORMATION: Ser, Thr, Gln or Asn
<220> FEATURE:
<221> NAME/KEY: MOD_RES
<222> LOCATION: (21)..(21)
<223> OTHER INFORMATION: Asn, Gln or His
<220> FEATURE:
<221> NAME/KEY: MOD_RES
<222> LOCATION: (23)..(23)
<223> OTHER INFORMATION: Phe, Leu or Tyr
<220> FEATURE:
<221> NAME/KEY: MOD_RES
<222> LOCATION: (25)..(25)
<223> OTHER INFORMATION: Ala or Pro
<220> FEATURE:
<221> NAME/KEY: MOD_RES
<222> LOCATION: (26)..(26)
<223> OTHER INFORMATION: Ile, Val, Ala or Leu
<220> FEATURE:
<221> NAME/KEY: MOD_RES
<222> LOCATION: (28)..(28)
<223> OTHER INFORMATION: Ser, Pro, Leu, Ile or Thr
<220> FEATURE:
<221> NAME/KEY: MOD_RES
<222> LOCATION: (29)..(29)
<223> OTHER INFORMATION: Ser, Pro or Thr
<220> FEATURE:
<221> NAME/KEY: MOD_RES
<222> LOCATION: (31)..(31)
<223> OTHER INFORMATION: Asn, Asp or Gln

<400> SEQUENCE: 91

Xaa Xaa Asn Thr Ala Thr Xaa Ala Thr Gln Arg Leu Xaa Asn Phe Leu
1               5                   10                  15

Xaa Xaa Xaa Xaa Xaa Asn Xaa Gly Xaa Xaa Leu Xaa Xaa Thr Xaa Val
            20                  25                  30

Gly Ser Asn Thr Tyr
        35

<210> SEQ ID NO 92
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Cys Asn Thr Ala Thr Cys Ala Thr Gln Arg Leu Ala Asn Phe Leu Val
1               5                   10                  15

His Ser Ser Asn Asn Phe Gly Ala Ile Leu Ser Ser Thr Asn Val Gly
            20                  25                  30

Ser Asn Thr Tyr
        35

<210> SEQ ID NO 93
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Pro Ser Thr Asn Val
            20                  25                  30

Gly Ser Asn Thr Tyr
        35

<210> SEQ ID NO 94
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Lys Cys Asn Thr Ala Thr Cys Ala Thr Gln Arg Leu Ala Asn Phe Leu
1               5                   10                  15

Val His Ser Ser Asn Asn Phe Gly Pro Ile Leu Pro Pro Thr Asn Val
            20                  25                  30

Gly Ser Asn Thr Tyr
        35

<210> SEQ ID NO 95
<211> LENGTH: 37
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 95

Lys Cys Asn Thr Ala Thr Cys Ala Thr Gln Arg Leu Ala Asn Phe Leu
1               5                   10                  15

Val Arg Ser Ser Asn Asn Phe Gly Pro Ile Leu Pro Ser Thr Asn Val
                20                  25                  30

Gly Ser Asn Thr Tyr
            35

<210> SEQ ID NO 96
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Cys Asn Thr Ala Thr Cys Ala Thr Gln Arg Leu Ala Asn Phe Leu Val
1               5                   10                  15

Arg Ser Ser Asn Asn Phe Gly Pro Ile Leu Pro Ser Thr Asn Val Gly
                20                  25                  30

Ser Asn Thr Tyr
            35

<210> SEQ ID NO 97
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Lys Cys Asn Thr Ala Thr Cys Ala Thr Gln Arg Leu Ala Asn Phe Leu
1               5                   10                  15

Val His Ser Ser Asn Asn Phe Gly Pro Val Leu Pro Pro Thr Asn Val
                20                  25                  30

Gly Ser Asn Thr Tyr
            35

<210> SEQ ID NO 98
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Lys Cys Asn Thr Ala Thr Cys Ala Thr Gln Arg Leu Ala Asn Phe Leu
1               5                   10                  15

Val Arg Ser Ser Asn Asn Phe Gly Pro Ile Leu Pro Pro Thr Asn Val
                20                  25                  30

Gly Ser Asn Thr Tyr
            35

<210> SEQ ID NO 99
<211> LENGTH: 36
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 99

Cys Asn Thr Ala Thr Cys Ala Thr Gln Arg Leu Ala Asn Phe Leu Val
1               5                   10                  15

Arg Ser Ser Asn Asn Phe Gly Pro Ile Leu Pro Pro Thr Asn Val Gly
            20                  25                  30

Ser Asn Thr Tyr
        35

<210> SEQ ID NO 100
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Cys Asn Thr Ala Thr Cys Ala Thr Gln Arg Leu Ala Asn Phe Leu Val
1               5                   10                  15

His Ser Ser Asn Asn Phe Gly Pro Ile Leu Pro Pro Thr Asn Val Gly
            20                  25                  30

Ser Asn Thr Tyr
        35

<210> SEQ ID NO 101
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Lys Cys Asn Thr Ala Thr Cys Ala Thr Gln Arg Leu Ala Asn Phe Leu
1               5                   10                  15

Val His Ser Ser Asn Asn Leu Gly Pro Val Leu Pro Pro Thr Asn Val
            20                  25                  30

Gly Ser Asn Thr Tyr
            35

<210> SEQ ID NO 102
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Lys Cys Asn Thr Ala Thr Cys Ala Thr Gln Arg Leu Ala Asn Phe Leu
1               5                   10                  15

Val His Ser Ser Asn Asn Leu Gly Pro Val Leu Pro Ser Thr Asn Val
            20                  25                  30

Gly Ser Asn Thr Tyr
            35

<210> SEQ ID NO 103
<211> LENGTH: 36
```

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Cys Asn Thr Ala Thr Cys Ala Thr Gln Arg Leu Ala Asn Phe Leu Val
1               5                   10                  15

His Ser Ser Asn Asn Leu Gly Pro Val Leu Pro Ser Thr Asn Val Gly
            20                  25                  30

Ser Asn Thr Tyr
        35

<210> SEQ ID NO 104
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Lys Cys Asn Thr Ala Thr Cys Ala Thr Gln Arg Leu Ala Asn Phe Leu
1               5                   10                  15

Val Arg Ser Ser Asn Asn Leu Gly Pro Val Leu Pro Ser Thr Asn Val
            20                  25                  30

Gly Ser Asn Thr Tyr
        35

<210> SEQ ID NO 105
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Lys Cys Asn Thr Ala Thr Cys Ala Thr Gln Arg Leu Ala Asn Phe Leu
1               5                   10                  15

Val Arg Ser Ser Asn Asn Leu Gly Pro Ile Leu Pro Thr Asn Val
            20                  25                  30

Gly Ser Asn Thr Tyr
        35

<210> SEQ ID NO 106
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Lys Cys Asn Thr Ala Thr Cys Ala Thr Gln Arg Leu Ala Asn Phe Leu
1               5                   10                  15

Val Arg Ser Ser Asn Asn Leu Gly Pro Ile Leu Pro Ser Thr Asn Val
            20                  25                  30

Gly Ser Asn Thr Tyr
        35

<210> SEQ ID NO 107

<211> LENGTH: 37
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Lys Cys Asn Thr Ala Thr Cys Ala Thr Gln Arg Leu Ala Asn Phe Leu
1               5                   10                  15

Ile His Ser Ser Asn Asn Leu Gly Pro Ile Leu Pro Pro Thr Asn Val
            20                  25                  30

Gly Ser Asn Thr Tyr
        35

<210> SEQ ID NO 108
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Lys Cys Asn Thr Ala Thr Cys Ala Thr Gln Arg Leu Ala Asn Phe Leu
1               5                   10                  15

Ile His Ser Ser Asn Asn Phe Gly Pro Ile Leu Pro Pro Thr Asn Val
            20                  25                  30

Gly Ser Asn Thr Tyr
        35

<210> SEQ ID NO 109
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Cys Asn Thr Ala Thr Cys Ala Thr Gln Arg Leu Ala Asn Phe Leu Ile
1               5                   10                  15

His Ser Ser Asn Asn Leu Gly Pro Ile Leu Pro Pro Thr Asn Val Gly
            20                  25                  30

Ser Asn Thr Tyr
        35

<210> SEQ ID NO 110
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Lys Cys Asn Thr Ala Thr Cys Ala Thr Gln Arg Leu Ala Asn Phe Leu
1               5                   10                  15

Ile Arg Ser Ser Asn Asn Leu Gly Ala Ile Leu Ser Ser Thr Asn Val
            20                  25                  30

Gly Ser Asn Thr Tyr
        35

```
<210> SEQ ID NO 111
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Lys Cys Asn Thr Ala Thr Cys Ala Thr Gln Arg Leu Ala Asn Phe Leu
1               5                   10                  15

Ile Arg Ser Ser Asn Asn Leu Gly Ala Val Leu Ser Pro Thr Asn Val
            20                  25                  30

Gly Ser Asn Thr Tyr
            35

<210> SEQ ID NO 112
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Lys Cys Asn Thr Ala Thr Cys Ala Thr Gln Arg Leu Ala Asn Phe Leu
1               5                   10                  15

Ile Arg Ser Ser Asn Asn Leu Gly Pro Val Leu Pro Pro Thr Asn Val
            20                  25                  30

Gly Ser Asn Thr Tyr
            35

<210> SEQ ID NO 113
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Lys Cys Asn Thr Ala Thr Cys Ala Thr Gln Arg Leu Thr Asn Phe Leu
1               5                   10                  15

Val His Ser Ser His Asn Leu Gly Ala Ala Leu Leu Pro Thr Asp Val
            20                  25                  30

Gly Ser Asn Thr Tyr
            35

<210> SEQ ID NO 114
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Lys Cys Asn Thr Ala Thr Cys Ala Thr Gln Arg Leu Thr Asn Phe Leu
1               5                   10                  15

Val His Ser Ser His Asn Leu Gly Ala Ala Leu Ser Pro Thr Asp Val
            20                  25                  30

Gly Ser Asn Thr Tyr
            35
```

<210> SEQ ID NO 115
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Cys Asn Thr Ala Thr Cys Ala Thr Gln Arg Leu Thr Asn Phe Leu Val
1               5                   10                  15

His Ser Ser His Asn Leu Gly Ala Ala Leu Pro Ser Thr Asp Val Gly
            20                  25                  30

Ser Asn Thr Tyr
        35

<210> SEQ ID NO 116
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Lys Cys Asn Thr Ala Thr Cys Ala Thr Gln Arg Leu Thr Asn Phe Leu
1               5                   10                  15

Val Arg Ser Ser His Asn Leu Gly Ala Ala Leu Ser Pro Thr Asp Val
            20                  25                  30

Gly Ser Asn Thr Tyr
        35

<210> SEQ ID NO 117
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Lys Cys Asn Thr Ala Thr Cys Ala Thr Gln Arg Leu Thr Asn Phe Leu
1               5                   10                  15

Val Arg Ser Ser His Asn Leu Gly Ala Ile Leu Pro Pro Thr Asp Val
            20                  25                  30

Gly Ser Asn Thr Tyr
        35

<210> SEQ ID NO 118
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Lys Cys Asn Thr Ala Thr Cys Ala Thr Gln Arg Leu Thr Asn Phe Leu
1               5                   10                  15

Val Arg Ser Ser His Asn Leu Gly Pro Ala Leu Pro Pro Thr Asp Val
            20                  25                  30

Gly Ser Asn Thr Tyr
        35

<210> SEQ ID NO 119
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Lys Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 120
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: isocap-Cys

<400> SEQUENCE: 120

Cys Asn Thr Ala Thr Cys Val Leu Gly Arg Leu Ser Gln Glu Leu His
1               5                   10                  15

Arg Leu Gln Thr Tyr Pro Arg Thr Asn Thr Gly Ser Asn Thr Tyr
            20                  25                  30

<210> SEQ ID NO 121
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Cys Ser Asn Leu Ser Thr Cys Ala Thr Gln Arg Leu Ala Asn Glu Leu
1               5                   10                  15

Val Arg Leu Gln Thr Tyr Pro Arg Thr Asn Val Gly Ser Asn Thr Tyr
            20                  25                  30

<210> SEQ ID NO 122
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Lys Cys Asn Thr Ala Thr Cys Ala Thr Gln Arg Leu Ala Asn Glu Leu
1               5                   10                  15

Val Arg Leu Gln Thr Tyr Pro Arg Thr Asn Val Gly Ser Asn Thr Tyr
            20                  25                  30

<210> SEQ ID NO 123
<211> LENGTH: 32
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 123

Cys Ser Asn Leu Ser Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 124
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Ala Thr Gln Arg Leu Ala Asn Glu Leu Val Arg Leu Gln Thr Tyr Pro
1               5                   10                  15

Arg Thr Asn Val Gly Ser Asn Thr Tyr
            20                  25

<210> SEQ ID NO 125
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Ala Thr Gln Gln Leu Ala Asn Gln Leu Val Arg Leu Gln Thr Tyr Pro
1               5                   10                  15

Arg Thr Asn Val Gly Ser Asn Thr Tyr
            20                  25

<210> SEQ ID NO 126
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Ala Thr Gln Leu Leu Ala Asn Gln Leu Val Arg Leu Gln Thr Tyr Pro
1               5                   10                  15

Arg Thr Asn Val Gly Ser Asn Thr Tyr
            20                  25

<210> SEQ ID NO 127
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Ala Thr Gln Arg Leu Ala Asn Gln Leu Val Arg Leu Gln Thr Tyr Pro
1               5                   10                  15

Arg Thr Asn Val Gly Ser Asn Thr Tyr
            20                  25
```

<210> SEQ ID NO 128
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Ala Thr Gln Leu Leu Ala Asn Glu Leu Val Arg Leu Gln Thr Tyr Pro
1               5                   10                  15

Arg Thr Asn Val Gly Ser Asn Thr Tyr
            20                  25

<210> SEQ ID NO 129
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Ala Thr Gln Gln Leu Ala Asn Glu Leu Val Arg Leu Gln Thr Tyr Pro
1               5                   10                  15

Arg Thr Asn Val Gly Ser Asn Thr Tyr
            20                  25

<210> SEQ ID NO 130
<211> LENGTH: 32
<212> TYPE: PRT
<213> ORGANISM: Homo sapiens

<400> SEQUENCE: 130

Cys Gly Asn Leu Ser Thr Cys Met Leu Gly Thr Tyr Thr Gln Asp Phe
1               5                   10                  15

Asn Lys Phe His Thr Phe Pro Gln Thr Ala Ile Gly Val Gly Ala Pro
            20                  25                  30

<210> SEQ ID NO 131
<211> LENGTH: 32
<212> TYPE: PRT
<213> ORGANISM: Salmo sp.

<400> SEQUENCE: 131

Cys Ser Asn Leu Ser Thr Cys Val Leu Gly Lys Leu Ser Gln Glu Leu
1               5                   10                  15

His Lys Leu Gln Thr Tyr Pro Arg Thr Asn Thr Gly Ser Gly Thr Pro
            20                  25                  30

<210> SEQ ID NO 132
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Cys Gly Asn Leu Ser Thr Cys Gly Leu Gly Thr Tyr Thr Gln Asp Phe
1               5                   10                  15

Asn Lys Phe His Thr Phe Pro Gln Thr Ala Ile Gly Val Gly Ala Pro
            20                  25                  30

<210> SEQ ID NO 133
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Cys Gly Asn Leu Ser Thr Cys Met Leu Gly Thr Tyr Thr Gln Asp Phe
1               5                   10                  15

Asn Lys Phe His Thr Leu Pro Gln Thr Ala Ile Gly Val Gly Ala Pro
            20                  25                  30

<210> SEQ ID NO 134
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Cys Gly Ser Leu Ser Thr Cys Gly Leu Gly Thr Tyr Thr Gln Asp Phe
1               5                   10                  15

Asn Lys Phe His Thr Phe Pro Gln Thr Ala Ile Gly Val Gly Ala Pro
            20                  25                  30

<210> SEQ ID NO 135
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Cys Ser Asn Leu Ser Thr Cys Val Leu Gly Lys Leu Ser Gln Glu Leu
1               5                   10                  15

His Lys Leu Gln Thr Tyr Pro Arg Thr Asn Thr Gly Ser Gly Thr Pro
            20                  25                  30

<210> SEQ ID NO 136
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Cys Ser Asn Leu Ser Thr Cys Val Leu Gly Lys Leu Ser Gln Glu Leu
1               5                   10                  15

His Arg Leu Gln Thr Tyr Pro Arg Thr Asn Thr Gly Ser Gly Thr Pro
            20                  25                  30

<210> SEQ ID NO 137
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

```
Cys Ser Asn Leu Ser Thr Cys Val Leu Gly Arg Leu Ser Gln Glu Leu
1               5                   10                  15

His Arg Leu Gln Thr Tyr Pro Arg Thr Asn Thr Gly Ser Gly Thr Pro
            20                  25                  30
```

<210> SEQ ID NO 138
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

```
Cys Ser Asn Leu Ser Thr Cys Val Leu Gly Lys Leu Ser Gln Glu Leu
1               5                   10                  15

His Arg Leu Gln Thr Tyr Pro Arg Thr Asn Thr Gly Ser Gly Thr Pro
            20                  25                  30
```

<210> SEQ ID NO 139
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

```
Cys Ser Asn Leu Ser Thr Cys Val Leu Gly Arg Leu Ser Gln Glu Leu
1               5                   10                  15

His Arg Leu Gln Thr Tyr Pro Arg Thr Asn Thr Gly Ser Gly Thr Pro
            20                  25                  30
```

<210> SEQ ID NO 140

<400> SEQUENCE: 140

000

<210> SEQ ID NO 141

<400> SEQUENCE: 141

000

<210> SEQ ID NO 142

<400> SEQUENCE: 142

000

<210> SEQ ID NO 143

<400> SEQUENCE: 143

000

<210> SEQ ID NO 144

<400> SEQUENCE: 144

000

<210> SEQ ID NO 145

<400> SEQUENCE: 145

000

<210> SEQ ID NO 146

<400> SEQUENCE: 146

000

<210> SEQ ID NO 147

<400> SEQUENCE: 147

000

<210> SEQ ID NO 148

<400> SEQUENCE: 148

000

<210> SEQ ID NO 149
<211> LENGTH: 47
<212> TYPE: PRT
<213> ORGANISM: Homo sapiens

<400> SEQUENCE: 149

Thr Gln Ala Gln Leu Leu Arg Val Gly Cys Val Leu Gly Thr Cys Gln
1               5                   10                  15

Val Gln Asn Leu Ser His Arg Leu Trp Gln Leu Met Gly Pro Ala Gly
            20                  25                  30

Arg Gln Asp Ser Ala Pro Val Asp Pro Ser Ser Pro His Ser Tyr
        35                  40                  45

<210> SEQ ID NO 150
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Val Gly Cys Val Leu Gly Thr Cys Gln Val Gln Asn Leu Ser His Arg
1               5                   10                  15

Leu Trp Gln Leu Met Gly Pro Ala Gly Arg Gln Asp Ser Ala Pro Val
            20                  25                  30

Asp Pro Ser Ser Pro His Ser Tyr
        35                  40

<210> SEQ ID NO 151
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Arg Val Gly Cys Val Leu Gly Thr Cys Gln Val Gln Asn Leu Ser His
1               5                   10                  15

Arg Leu Trp Gln Leu Met Gly Pro Ala Gly Arg Gln Asp Ser Ala Pro
            20                  25                  30

Val Asp Pro Ser Ser Pro His Ser Tyr

```
              35                  40

<210> SEQ ID NO 152
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Gly Cys Val Leu Gly Thr Cys Gln Val Gln Asn Leu Ser His Arg Leu
1               5                   10                  15

Trp Gln Leu Met Gly Pro Ala Gly Arg Gln Asp Ser Ala Pro Val Asp
            20                  25                  30

Pro Ser Ser Pro His Ser Tyr
        35

<210> SEQ ID NO 153
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Cys Val Leu Gly Thr Cys Gln Val Gln Asn Leu Ser His Arg Leu Trp
1               5                   10                  15

Gln Leu Met Gly Pro Ala Gly Arg Gln Asp Ser Ala Pro Val Asp Pro
            20                  25                  30

Ser Ser Pro His Ser Tyr
        35

<210> SEQ ID NO 154
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Thr Gln Ala Gln Leu Leu Arg Val Gly Cys Val Leu Gly Thr Cys Gln
1               5                   10                  15

Val Gln Asn Leu Ser His Arg Leu Trp Gln Leu Arg Gln Asp Ser Ala
            20                  25                  30

Pro Val Asp Pro Ser Ser Pro His Ser Tyr
        35                  40

<210> SEQ ID NO 155
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Thr Gln Ala Gln Leu Leu Arg Val Gly Cys Val Leu Gly Thr Cys Gln
1               5                   10                  15

Val Gln Asn Leu Ser His Arg Leu Trp Gln Leu Asp Ser Ala Pro Val
            20                  25                  30
```

```
Asp Pro Ser Ser Pro His Ser Tyr
        35                  40

<210> SEQ ID NO 156
<211> LENGTH: 33
<212> TYPE: PRT
<213> ORGANISM: Homo sapiens

<400> SEQUENCE: 156

Lys Ala Pro Ser Gly Arg Met Ser Ile Val Lys Asn Leu Gln Asn Leu
1               5                   10                  15

Asp Pro Ser His Arg Ile Ser Asp Arg Asp Tyr Met Gly Trp Met Asp
            20                  25                  30

Phe

<210> SEQ ID NO 157
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Tyr(SO3)

<400> SEQUENCE: 157

Asp Tyr Met Gly Trp Met Asp Phe
1               5

<210> SEQ ID NO 158
<211> LENGTH: 5
<212> TYPE: PRT
<213> ORGANISM: Homo sapiens

<400> SEQUENCE: 158

Gly Trp Met Asp Phe
1               5

<210> SEQ ID NO 159
<211> LENGTH: 4
<212> TYPE: PRT
<213> ORGANISM: Homo sapiens

<400> SEQUENCE: 159

Trp Met Asp Phe
1

<210> SEQ ID NO 160
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Asp Tyr Met Gly Trp Met Asp Phe
1               5

<210> SEQ ID NO 161
<211> LENGTH: 6
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 161

Met Gly Trp Met Asp Phe
1               5

<210> SEQ ID NO 162
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Tyr(SO3H)

<400> SEQUENCE: 162

Lys Asp Tyr Met Gly Trp Met Asp Phe
1               5

<210> SEQ ID NO 163
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Lys Asp Tyr Met Gly Trp Met Asp Phe
1               5

<210> SEQ ID NO 164
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Lys Met Gly Trp Met Asp Phe
1               5

<210> SEQ ID NO 165
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Lys Gly Trp Met Asp Phe
1               5

<210> SEQ ID NO 166
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166
```

```
Lys Trp Met Asp Phe
1               5
```

<210> SEQ ID NO 167
<211> LENGTH: 167
<212> TYPE: PRT
<213> ORGANISM: Homo sapiens

<400> SEQUENCE: 167

```
Met His Trp Gly Thr Leu Cys Gly Phe Leu Trp Leu Trp Pro Tyr Leu
1               5                   10                  15

Phe Tyr Val Gln Ala Val Pro Ile Gln Lys Val Gln Asp Asp Thr Lys
                20                  25                  30

Thr Leu Ile Lys Thr Ile Val Thr Arg Ile Asn Asp Ile Ser His Thr
            35                  40                  45

Gln Ser Val Ser Ser Lys Gln Lys Val Thr Gly Leu Asp Phe Ile Pro
    50                  55                  60

Gly Leu His Pro Ile Leu Thr Leu Ser Lys Met Asp Gln Thr Leu Ala
65                  70                  75                  80

Val Tyr Gln Gln Ile Leu Thr Ser Met Pro Ser Arg Asn Val Ile Gln
                85                  90                  95

Ile Ser Asn Asp Leu Glu Asn Leu Arg Asp Leu Leu His Val Leu Ala
            100                 105                 110

Phe Ser Lys Ser Cys His Leu Pro Trp Ala Ser Gly Leu Glu Thr Leu
        115                 120                 125

Asp Ser Leu Gly Gly Val Leu Glu Ala Ser Gly Tyr Ser Thr Glu Val
    130                 135                 140

Val Ala Leu Ser Arg Leu Gln Gly Ser Leu Gln Asp Met Leu Trp Gln
145                 150                 155                 160

Leu Asp Leu Ser Pro Gly Cys
                165
```

<210> SEQ ID NO 168
<211> LENGTH: 146
<212> TYPE: PRT
<213> ORGANISM: Homo sapiens

<400> SEQUENCE: 168

```
Val Pro Ile Gln Lys Val Gln Asp Asp Thr Lys Thr Leu Ile Lys Thr
1               5                   10                  15

Ile Val Thr Arg Ile Asn Asp Ile Ser His Thr Gln Ser Val Ser Ser
                20                  25                  30

Lys Gln Lys Val Thr Gly Leu Asp Phe Ile Pro Gly Leu His Pro Ile
            35                  40                  45

Leu Thr Leu Ser Lys Met Asp Gln Thr Leu Ala Val Tyr Gln Gln Ile
    50                  55                  60

Leu Thr Ser Met Pro Ser Arg Asn Val Ile Gln Ile Ser Asn Asp Leu
65                  70                  75                  80

Glu Asn Leu Arg Asp Leu Leu His Val Leu Ala Phe Ser Lys Ser Cys
                85                  90                  95

His Leu Pro Trp Ala Ser Gly Leu Glu Thr Leu Asp Ser Leu Gly Gly
            100                 105                 110

Val Leu Glu Ala Ser Gly Tyr Ser Thr Glu Val Val Ala Leu Ser Arg
        115                 120                 125

Leu Gln Gly Ser Leu Gln Asp Met Leu Trp Gln Leu Asp Leu Ser Pro
    130                 135                 140
```

Gly Cys
145

<210> SEQ ID NO 169
<211> LENGTH: 145
<212> TYPE: PRT
<213> ORGANISM: Homo sapiens

<400> SEQUENCE: 169

Val Pro Ile Gln Lys Val Gln Asp Asp Thr Lys Thr Leu Ile Lys Thr
1               5                   10                  15

Ile Val Thr Arg Ile Asn Asp Ile Ser His Thr Ser Val Ser Ser Lys
                20                  25                  30

Gln Lys Val Thr Gly Leu Asp Phe Ile Pro Gly Leu His Pro Ile Leu
            35                  40                  45

Thr Leu Ser Lys Met Asp Gln Thr Leu Ala Val Tyr Gln Gln Ile Leu
        50                  55                  60

Thr Ser Met Pro Ser Arg Asn Val Ile Gln Ile Ser Asn Asp Leu Glu
65                  70                  75                  80

Asn Leu Arg Asp Leu Leu His Val Leu Ala Phe Ser Lys Ser Cys His
                85                  90                  95

Leu Pro Trp Ala Ser Gly Leu Glu Thr Leu Asp Ser Leu Gly Gly Val
            100                 105                 110

Leu Glu Ala Ser Gly Tyr Ser Thr Glu Val Val Ala Leu Ser Arg Leu
        115                 120                 125

Gln Gly Ser Leu Gln Asp Met Leu Trp Gln Leu Asp Leu Ser Pro Gly
    130                 135                 140

Cys
145

<210> SEQ ID NO 170
<211> LENGTH: 167
<212> TYPE: PRT
<213> ORGANISM: Artificial Sequence
<220> FEATURE:
<223> OTHER INFORMATION: Description of Artificial Sequence: Synthetic
      protein

<400> SEQUENCE: 170

Met His Trp Gly Thr Leu Cys Gly Phe Leu Trp Leu Trp Pro Tyr Leu
1               5                   10                  15

Phe Tyr Val Gln Ala Val Pro Ile Gln Lys Val Gln Asp Asp Thr Lys
                20                  25                  30

Thr Leu Ile Lys Thr Ile Val Thr Arg Ile Asp Asp Ile Ser His Thr
            35                  40                  45

Gln Ser Val Ser Ser Lys Gln Lys Val Thr Gly Leu Asp Phe Ile Pro
        50                  55                  60

Gly Leu His Pro Ile Leu Thr Leu Ser Lys Met Asp Gln Thr Leu Ala
65                  70                  75                  80

Val Tyr Gln Gln Ile Leu Thr Ser Met Pro Ser Arg Asn Val Ile Gln
                85                  90                  95

Ile Ser Asn Asp Leu Glu Asn Leu Arg Asp Leu Leu His Val Leu Ala
            100                 105                 110

Phe Ser Lys Ser Cys His Leu Pro Trp Ala Ser Gly Leu Glu Thr Leu
        115                 120                 125

Asp Ser Leu Gly Gly Val Leu Glu Ala Ser Gly Tyr Ser Thr Glu Val
    130                 135                 140

Val Ala Leu Ser Arg Leu Gln Gly Ser Leu Gln Asp Met Leu Trp Gln
145                 150                 155                 160

Leu Asp Leu Ser Pro Gly Cys
            165

<210> SEQ ID NO 171
<211> LENGTH: 167
<212> TYPE: PRT
<213> ORGANISM: Artificial Sequence
<220> FEATURE:
<223> OTHER INFORMATION: Description of Artificial Sequence: Synthetic
      protein

<400> SEQUENCE: 171

Met His Trp Gly Thr Leu Cys Gly Phe Leu Trp Leu Trp Pro Tyr Leu
1               5                   10                  15

Phe Tyr Val Gln Ala Val Pro Ile Gln Lys Val Gln Asp Asp Thr Lys
            20                  25                  30

Thr Leu Ile Lys Thr Ile Val Thr Arg Ile Glu Asp Ile Ser His Thr
        35                  40                  45

Gln Ser Val Ser Ser Lys Gln Lys Val Thr Gly Leu Asp Phe Ile Pro
    50                  55                  60

Gly Leu His Pro Ile Leu Thr Leu Ser Lys Met Asp Gln Thr Leu Ala
65                  70                  75                  80

Val Tyr Gln Gln Ile Leu Thr Ser Met Pro Ser Arg Asn Val Ile Gln
                85                  90                  95

Ile Ser Asn Asp Leu Glu Asn Leu Arg Asp Leu Leu His Val Leu Ala
            100                 105                 110

Phe Ser Lys Ser Cys His Leu Pro Trp Ala Ser Gly Leu Glu Thr Leu
        115                 120                 125

Asp Ser Leu Gly Gly Val Leu Glu Ala Ser Gly Tyr Ser Thr Glu Val
    130                 135                 140

Val Ala Leu Ser Arg Leu Gln Gly Ser Leu Gln Asp Met Leu Trp Gln
145                 150                 155                 160

Leu Asp Leu Ser Pro Gly Cys
            165

<210> SEQ ID NO 172
<211> LENGTH: 167
<212> TYPE: PRT
<213> ORGANISM: Artificial Sequence
<220> FEATURE:
<223> OTHER INFORMATION: Description of Artificial Sequence: Synthetic
      protein

<400> SEQUENCE: 172

Met His Trp Gly Thr Leu Cys Gly Phe Leu Trp Leu Trp Pro Tyr Leu
1               5                   10                  15

Phe Tyr Val Gln Ala Val Pro Ile Gln Lys Val Gln Asp Asp Thr Lys
            20                  25                  30

Thr Leu Ile Lys Thr Ile Val Thr Arg Ile Asn Asp Ile Ser His Ala
        35                  40                  45

Gln Ser Val Ser Ser Lys Gln Lys Val Thr Gly Leu Asp Phe Ile Pro
    50                  55                  60

Gly Leu His Pro Ile Leu Thr Leu Ser Lys Met Asp Gln Thr Leu Ala
65                  70                  75                  80

Val Tyr Gln Gln Ile Leu Thr Ser Met Pro Ser Arg Asn Val Ile Gln
                85                  90                  95

```
Ile Ser Asn Asp Leu Glu Asn Leu Arg Asp Leu Leu His Val Leu Ala
            100                 105                 110

Phe Ser Lys Ser Cys His Leu Pro Trp Ala Ser Gly Leu Glu Thr Leu
        115                 120                 125

Asp Ser Leu Gly Gly Val Leu Glu Ala Ser Gly Tyr Ser Thr Glu Val
    130                 135                 140

Val Ala Leu Ser Arg Leu Gln Gly Ser Leu Gln Asp Met Leu Trp Gln
145                 150                 155                 160

Leu Asp Leu Ser Pro Gly Cys
                165

<210> SEQ ID NO 173
<211> LENGTH: 167
<212> TYPE: PRT
<213> ORGANISM: Artificial Sequence
<220> FEATURE:
<223> OTHER INFORMATION: Description of Artificial Sequence: Synthetic
      protein

<400> SEQUENCE: 173

Met His Trp Gly Thr Leu Cys Gly Phe Leu Trp Leu Trp Pro Tyr Leu
1               5                   10                  15

Phe Tyr Val Gln Ala Val Pro Ile Gln Lys Val Gln Asp Asp Thr Lys
                20                  25                  30

Thr Leu Ile Lys Thr Ile Val Thr Arg Ile Asn Asp Ile Ser His Thr
            35                  40                  45

Glu Ser Val Ser Ser Lys Gln Lys Val Thr Gly Leu Asp Phe Ile Pro
    50                  55                  60

Gly Leu His Pro Ile Leu Thr Leu Ser Lys Met Asp Gln Thr Leu Ala
65                  70                  75                  80

Val Tyr Gln Gln Ile Leu Thr Ser Met Pro Ser Arg Asn Val Ile Gln
                85                  90                  95

Ile Ser Asn Asp Leu Glu Asn Leu Arg Asp Leu Leu His Val Leu Ala
            100                 105                 110

Phe Ser Lys Ser Cys His Leu Pro Trp Ala Ser Gly Leu Glu Thr Leu
        115                 120                 125

Asp Ser Leu Gly Gly Val Leu Glu Ala Ser Gly Tyr Ser Thr Glu Val
    130                 135                 140

Val Ala Leu Ser Arg Leu Gln Gly Ser Leu Gln Asp Met Leu Trp Gln
145                 150                 155                 160

Leu Asp Leu Ser Pro Gly Cys
                165

<210> SEQ ID NO 174
<211> LENGTH: 166
<212> TYPE: PRT
<213> ORGANISM: Artificial Sequence
<220> FEATURE:
<223> OTHER INFORMATION: Description of Artificial Sequence: Synthetic
      protein

<400> SEQUENCE: 174

Met His Trp Gly Thr Leu Cys Gly Phe Leu Trp Leu Trp Pro Tyr Leu
1               5                   10                  15

Phe Tyr Val Gln Ala Val Pro Ile Gln Lys Val Gln Asp Asp Thr Lys
                20                  25                  30

Thr Leu Ile Lys Thr Ile Val Thr Arg Ile Asn Asp Ile Ser His Thr
            35                  40                  45
```

Ser Val Ser Ser Lys Gln Lys Val Thr Gly Leu Asp Phe Ile Pro Gly
 50                  55                  60

Leu His Pro Ile Leu Thr Leu Ser Lys Met Asp Gln Thr Leu Ala Val
 65                  70                  75                  80

Tyr Gln Gln Ile Leu Thr Ser Met Pro Ser Arg Asn Val Ile Gln Ile
                 85                  90                  95

Ser Asn Asp Leu Glu Asn Leu Arg Asp Leu Leu His Val Leu Ala Phe
                100                 105                 110

Ser Lys Ser Cys His Leu Pro Trp Ala Ser Gly Leu Glu Thr Leu Asp
                115                 120                 125

Ser Leu Gly Gly Val Leu Glu Ala Ser Gly Tyr Ser Thr Glu Val Val
130                 135                 140

Ala Leu Ser Arg Leu Gln Gly Ser Leu Gln Asp Met Leu Trp Gln Leu
145                 150                 155                 160

Asp Leu Ser Pro Gly Cys
                165

<210> SEQ ID NO 175
<211> LENGTH: 167
<212> TYPE: PRT
<213> ORGANISM: Artificial Sequence
<220> FEATURE:
<223> OTHER INFORMATION: Description of Artificial Sequence: Synthetic
      protein

<400> SEQUENCE: 175

Met His Trp Gly Thr Leu Cys Gly Phe Leu Trp Leu Trp Pro Tyr Leu
 1               5                  10                  15

Phe Tyr Val Gln Ala Val Pro Ile Gln Lys Val Gln Asp Asp Thr Lys
                 20                  25                  30

Thr Leu Ile Lys Thr Ile Val Thr Arg Ile Asn Asp Ile Ser His Thr
             35                  40                  45

Gln Ser Val Ser Ser Lys Gln Lys Val Thr Gly Leu Asp Phe Ile Pro
 50                  55                  60

Gly Leu His Pro Ile Leu Thr Leu Ser Lys Ala Asp Gln Thr Leu Ala
 65                  70                  75                  80

Val Tyr Gln Gln Ile Leu Thr Ser Met Pro Ser Arg Asn Val Ile Gln
                 85                  90                  95

Ile Ser Asn Asp Leu Glu Asn Leu Arg Asp Leu Leu His Val Leu Ala
                100                 105                 110

Phe Ser Lys Ser Cys His Leu Pro Trp Ala Ser Gly Leu Glu Thr Leu
                115                 120                 125

Asp Ser Leu Gly Gly Val Leu Glu Ala Ser Gly Tyr Ser Thr Glu Val
130                 135                 140

Val Ala Leu Ser Arg Leu Gln Gly Ser Leu Gln Asp Met Leu Trp Gln
145                 150                 155                 160

Leu Asp Leu Ser Pro Gly Cys
                165

<210> SEQ ID NO 176
<211> LENGTH: 167
<212> TYPE: PRT
<213> ORGANISM: Artificial Sequence
<220> FEATURE:
<223> OTHER INFORMATION: Description of Artificial Sequence: Synthetic
      protein

<400> SEQUENCE: 176

```
Met His Trp Gly Thr Leu Cys Gly Phe Leu Trp Leu Trp Pro Tyr Leu
1               5                   10                  15

Phe Tyr Val Gln Ala Val Pro Ile Gln Lys Val Gln Asp Asp Thr Lys
            20                  25                  30

Thr Leu Ile Lys Thr Ile Val Thr Arg Ile Asn Asp Ile Ser His Thr
        35                  40                  45

Gln Ser Val Ser Ser Lys Gln Lys Val Thr Gly Leu Asp Phe Ile Pro
    50                  55                  60

Gly Leu His Pro Ile Leu Thr Leu Ser Lys Met Asp Gln Thr Leu Ala
65                  70                  75                  80

Val Tyr Gln Gln Ile Leu Thr Ser Leu Pro Ser Arg Asn Val Ile Gln
                85                  90                  95

Ile Ser Asn Asp Leu Glu Asn Leu Arg Asp Leu Leu His Val Leu Ala
            100                 105                 110

Phe Ser Lys Ser Cys His Leu Pro Trp Ala Ser Gly Leu Glu Thr Leu
            115                 120                 125

Asp Ser Leu Gly Gly Val Leu Glu Ala Ser Gly Tyr Ser Thr Glu Val
            130                 135                 140

Val Ala Leu Ser Arg Leu Gln Gly Ser Leu Gln Asp Met Leu Trp Gln
145                 150                 155                 160

Leu Asp Leu Ser Pro Gly Cys
                165

<210> SEQ ID NO 177
<211> LENGTH: 167
<212> TYPE: PRT
<213> ORGANISM: Artificial Sequence
<220> FEATURE:
<223> OTHER INFORMATION: Description of Artificial Sequence: Synthetic
      protein

<400> SEQUENCE: 177

Met His Trp Gly Thr Leu Cys Gly Phe Leu Trp Leu Trp Pro Tyr Leu
1               5                   10                  15

Phe Tyr Val Gln Ala Val Pro Ile Gln Lys Val Gln Asp Asp Thr Lys
            20                  25                  30

Thr Leu Ile Lys Thr Ile Val Thr Arg Ile Asn Asp Ile Ser His Thr
        35                  40                  45

Gln Ser Val Ser Ser Lys Gln Lys Val Thr Gly Leu Asp Phe Ile Pro
    50                  55                  60

Gly Leu His Pro Ile Leu Thr Leu Ser Lys Met Asp Gln Thr Leu Ala
65                  70                  75                  80

Val Tyr Gln Gln Ile Leu Thr Ser Met Pro Ser Arg Asp Val Ile Gln
                85                  90                  95

Ile Ser Asn Asp Leu Glu Asn Leu Arg Asp Leu Leu His Val Leu Ala
            100                 105                 110

Phe Ser Lys Ser Cys His Leu Pro Trp Ala Ser Gly Leu Glu Thr Leu
            115                 120                 125

Asp Ser Leu Gly Gly Val Leu Glu Ala Ser Gly Tyr Ser Thr Glu Val
            130                 135                 140

Val Ala Leu Ser Arg Leu Gln Gly Ser Leu Gln Asp Met Leu Trp Gln
145                 150                 155                 160

Leu Asp Leu Ser Pro Gly Cys
                165

<210> SEQ ID NO 178
```

```
<211> LENGTH: 167
<212> TYPE: PRT
<213> ORGANISM: Artificial Sequence
<220> FEATURE:
<223> OTHER INFORMATION: Description of Artificial Sequence: Synthetic
      protein

<400> SEQUENCE: 178

Met His Trp Gly Thr Leu Cys Gly Phe Leu Trp Leu Trp Pro Tyr Leu
1               5                   10                  15

Phe Tyr Val Gln Ala Val Pro Ile Gln Lys Val Gln Asp Asp Thr Lys
            20                  25                  30

Thr Leu Ile Lys Thr Ile Val Thr Arg Ile Asn Asp Ile Ser His Thr
        35                  40                  45

Gln Ser Val Ser Ser Lys Gln Lys Val Thr Gly Leu Asp Phe Ile Pro
    50                  55                  60

Gly Leu His Pro Ile Leu Thr Leu Ser Lys Met Asp Gln Thr Leu Ala
65                  70                  75                  80

Val Tyr Gln Gln Ile Leu Thr Ser Met Pro Ser Arg Glu Val Ile Gln
                85                  90                  95

Ile Ser Asn Asp Leu Glu Asn Leu Arg Asp Leu Leu His Val Leu Ala
            100                 105                 110

Phe Ser Lys Ser Cys His Leu Pro Trp Ala Ser Gly Leu Glu Thr Leu
        115                 120                 125

Asp Ser Leu Gly Gly Val Leu Glu Ala Ser Gly Tyr Ser Thr Glu Val
    130                 135                 140

Val Ala Leu Ser Arg Leu Gln Gly Ser Leu Gln Asp Met Leu Trp Gln
145                 150                 155                 160

Leu Asp Leu Ser Pro Gly Cys
                165

<210> SEQ ID NO 179
<211> LENGTH: 167
<212> TYPE: PRT
<213> ORGANISM: Artificial Sequence
<220> FEATURE:
<223> OTHER INFORMATION: Description of Artificial Sequence: Synthetic
      protein

<400> SEQUENCE: 179

Met His Trp Gly Thr Leu Cys Gly Phe Leu Trp Leu Trp Pro Tyr Leu
1               5                   10                  15

Phe Tyr Val Gln Ala Val Pro Ile Gln Lys Val Gln Asp Asp Thr Lys
            20                  25                  30

Thr Leu Ile Lys Thr Ile Val Thr Arg Ile Asn Asp Ile Ser His Thr
        35                  40                  45

Gln Ser Val Ser Ser Lys Gln Lys Val Thr Gly Leu Asp Phe Ile Pro
    50                  55                  60

Gly Leu His Pro Ile Leu Thr Leu Ser Lys Met Asp Gln Thr Leu Ala
65                  70                  75                  80

Val Tyr Gln Gln Ile Leu Thr Ser Met Pro Ser Arg Asn Val Ile Gln
                85                  90                  95

Ile Ala Asn Asp Leu Glu Asn Leu Arg Asp Leu Leu His Val Leu Ala
            100                 105                 110

Phe Ser Lys Ser Cys His Leu Pro Trp Ala Ser Gly Leu Glu Thr Leu
        115                 120                 125

Asp Ser Leu Gly Gly Val Leu Glu Ala Ser Gly Tyr Ser Thr Glu Val
    130                 135                 140
```

Val Ala Leu Ser Arg Leu Gln Gly Ser Leu Gln Asp Met Leu Trp Gln
145                 150                 155                 160

Leu Asp Leu Ser Pro Gly Cys
                165

<210> SEQ ID NO 180
<211> LENGTH: 167
<212> TYPE: PRT
<213> ORGANISM: Artificial Sequence
<220> FEATURE:
<223> OTHER INFORMATION: Description of Artificial Sequence: Synthetic
      protein

<400> SEQUENCE: 180

Met His Trp Gly Thr Leu Cys Gly Phe Leu Trp Leu Trp Pro Tyr Leu
1               5                   10                  15

Phe Tyr Val Gln Ala Val Pro Ile Gln Lys Val Gln Asp Asp Thr Lys
                20                  25                  30

Thr Leu Ile Lys Thr Ile Val Thr Arg Ile Asn Asp Ile Ser His Thr
            35                  40                  45

Gln Ser Val Ser Ser Lys Gln Lys Val Thr Gly Leu Asp Phe Ile Pro
    50                  55                  60

Gly Leu His Pro Ile Leu Thr Leu Ser Lys Met Asp Gln Thr Leu Ala
65                  70                  75                  80

Val Tyr Gln Gln Ile Leu Thr Ser Met Pro Ser Arg Asn Val Ile Gln
                85                  90                  95

Ile Ser Asn Asp Leu Glu Asn Leu Arg Asp Leu Leu His Val Leu Ala
            100                 105                 110

Phe Ser Lys Ser Ser His Leu Pro Trp Ala Ser Gly Leu Glu Thr Leu
    115                 120                 125

Asp Ser Leu Gly Gly Val Leu Glu Ala Ser Gly Tyr Ser Thr Glu Val
    130                 135                 140

Val Ala Leu Ser Arg Leu Gln Gly Ser Leu Gln Asp Met Leu Trp Gln
145                 150                 155                 160

Leu Asp Leu Ser Pro Gly Cys
                165

<210> SEQ ID NO 181
<211> LENGTH: 167
<212> TYPE: PRT
<213> ORGANISM: Artificial Sequence
<220> FEATURE:
<223> OTHER INFORMATION: Description of Artificial Sequence: Synthetic
      protein

<400> SEQUENCE: 181

Met His Trp Gly Thr Leu Cys Gly Phe Leu Trp Leu Trp Pro Tyr Leu
1               5                   10                  15

Phe Tyr Val Gln Ala Val Pro Ile Gln Lys Val Gln Asp Asp Thr Lys
                20                  25                  30

Thr Leu Ile Lys Thr Ile Val Thr Arg Ile Asn Asp Ile Ser His Thr
            35                  40                  45

Gln Ser Val Ser Ser Lys Gln Lys Val Thr Gly Leu Asp Phe Ile Pro
    50                  55                  60

Gly Leu His Pro Ile Leu Thr Leu Ser Lys Met Asp Gln Thr Leu Ala
65                  70                  75                  80

Val Tyr Gln Gln Ile Leu Thr Ser Met Pro Ser Arg Asn Val Ile Gln
                85                  90                  95

```
Ile Ser Asn Asp Leu Glu Asn Leu Arg Asp Leu Leu His Val Leu Ala
            100                 105                 110

Phe Ser Lys Ser Cys His Leu Pro Trp Ala Ser Gly Leu Glu Thr Leu
        115                 120                 125

Asp Ser Leu Gly Gly Val Leu Glu Ala Ser Leu Tyr Ser Thr Glu Val
    130                 135                 140

Val Ala Leu Ser Arg Leu Gln Gly Ser Leu Gln Asp Met Leu Trp Gln
145                 150                 155                 160

Leu Asp Leu Ser Pro Gly Cys
                165

<210> SEQ ID NO 182
<211> LENGTH: 167
<212> TYPE: PRT
<213> ORGANISM: Artificial Sequence
<220> FEATURE:
<223> OTHER INFORMATION: Description of Artificial Sequence: Synthetic
      protein

<400> SEQUENCE: 182

Met His Trp Gly Thr Leu Cys Gly Phe Leu Trp Leu Trp Pro Tyr Leu
1               5                   10                  15

Phe Tyr Val Gln Ala Val Pro Ile Gln Lys Val Gln Asp Asp Thr Lys
            20                  25                  30

Thr Leu Ile Lys Thr Ile Val Thr Arg Ile Asn Asp Ile Ser His Thr
        35                  40                  45

Gln Ser Val Ser Ser Lys Gln Lys Val Thr Gly Leu Asp Phe Ile Pro
    50                  55                  60

Gly Leu His Pro Ile Leu Thr Leu Ser Lys Met Asp Gln Thr Leu Ala
65                  70                  75                  80

Val Tyr Gln Gln Ile Leu Thr Ser Met Pro Ser Arg Asn Val Ile Gln
                85                  90                  95

Ile Ser Asn Asp Leu Glu Asn Leu Arg Asp Leu Leu His Val Leu Ala
            100                 105                 110

Phe Ser Lys Ser Cys His Leu Pro Trp Ala Ser Gly Leu Glu Thr Leu
        115                 120                 125

Asp Ser Leu Gly Gly Val Leu Glu Ala Ser Leu Tyr Ser Thr Glu Val
    130                 135                 140

Val Ala Leu Ser Arg Leu Gln Gly Ser Leu Gln Asp Met Leu Trp Gln
145                 150                 155                 160

Leu Asp Leu Ser Pro Gly Ser
                165

<210> SEQ ID NO 183
<211> LENGTH: 167
<212> TYPE: PRT
<213> ORGANISM: Artificial Sequence
<220> FEATURE:
<223> OTHER INFORMATION: Description of Artificial Sequence: Synthetic
      protein

<400> SEQUENCE: 183

Met His Trp Gly Thr Leu Cys Gly Phe Leu Trp Leu Trp Pro Tyr Leu
1               5                   10                  15

Phe Tyr Val Gln Ala Val Pro Ile Gln Lys Val Gln Asp Asp Thr Lys
            20                  25                  30

Thr Leu Ile Lys Thr Ile Val Thr Arg Ile Asp Asp Ile Ser His Thr
        35                  40                  45
```

Glu Ser Val Ser Ser Lys Gln Lys Val Thr Gly Leu Asp Phe Ile Pro
            50                  55                  60

Gly Leu His Pro Ile Leu Thr Leu Ser Lys Met Asp Gln Thr Leu Ala
65                  70                  75                  80

Val Tyr Gln Gln Ile Leu Thr Ser Met Pro Ser Arg Asn Val Ile Gln
                85                  90                  95

Ile Ser Asn Asp Leu Glu Asn Leu Arg Asp Leu Leu His Val Leu Ala
            100                 105                 110

Phe Ser Lys Ser Cys His Leu Pro Trp Ala Ser Gly Leu Glu Thr Leu
            115                 120                 125

Asp Ser Leu Gly Gly Val Leu Glu Ala Ser Gly Tyr Ser Thr Glu Val
            130                 135                 140

Val Ala Leu Ser Arg Leu Gln Gly Ser Leu Gln Asp Met Leu Trp Gln
145                 150                 155                 160

Leu Asp Leu Ser Pro Gly Cys
                165

<210> SEQ ID NO 184
<211> LENGTH: 167
<212> TYPE: PRT
<213> ORGANISM: Artificial Sequence
<220> FEATURE:
<223> OTHER INFORMATION: Description of Artificial Sequence: Synthetic
      protein

<400> SEQUENCE: 184

Met His Trp Gly Thr Leu Cys Gly Phe Leu Trp Leu Trp Pro Tyr Leu
1               5                   10                  15

Phe Tyr Val Gln Ala Val Pro Ile Gln Lys Val Gln Asp Asp Thr Lys
                20                  25                  30

Thr Leu Ile Lys Thr Ile Val Thr Arg Ile Asp Asp Ile Ser His Thr
            35                  40                  45

Gln Ser Val Ser Ser Lys Gln Lys Val Thr Gly Leu Asp Phe Ile Pro
        50                  55                  60

Gly Leu His Pro Ile Leu Thr Leu Ser Lys Ala Asp Gln Thr Leu Ala
65                  70                  75                  80

Val Tyr Gln Gln Ile Leu Thr Ser Met Pro Ser Arg Asn Val Ile Gln
                85                  90                  95

Ile Ser Asn Asp Leu Glu Asn Leu Arg Asp Leu Leu His Val Leu Ala
            100                 105                 110

Phe Ser Lys Ser Cys His Leu Pro Trp Ala Ser Gly Leu Glu Thr Leu
            115                 120                 125

Asp Ser Leu Gly Gly Val Leu Glu Ala Ser Gly Tyr Ser Thr Glu Val
            130                 135                 140

Val Ala Leu Ser Arg Leu Gln Gly Ser Leu Gln Asp Met Leu Trp Gln
145                 150                 155                 160

Leu Asp Leu Ser Pro Gly Cys
                165

<210> SEQ ID NO 185
<211> LENGTH: 167
<212> TYPE: PRT
<213> ORGANISM: Artificial Sequence
<220> FEATURE:
<223> OTHER INFORMATION: Description of Artificial Sequence: Synthetic
      protein

<400> SEQUENCE: 185

```
Met His Trp Gly Thr Leu Cys Gly Phe Leu Trp Leu Trp Pro Tyr Leu
1               5                   10                  15

Phe Tyr Val Gln Ala Val Pro Ile Gln Lys Val Gln Asp Asp Thr Lys
            20                  25                  30

Thr Leu Ile Lys Thr Ile Val Thr Arg Ile Asn Asp Ile Ser His Thr
        35                  40                  45

Gln Ser Val Ser Ser Lys Gln Lys Val Thr Gly Leu Asp Phe Ile Pro
    50                  55                  60

Gly Leu His Pro Ile Leu Thr Leu Ser Lys Met Asp Gln Thr Leu Ala
65                  70                  75                  80

Val Tyr Gln Gln Ile Leu Thr Ser Leu Pro Ser Arg Asn Val Ile Gln
                85                  90                  95

Ile Ser Asn Asp Leu Glu Asn Leu Arg Asp Leu Leu His Val Leu Ala
            100                 105                 110

Phe Ser Lys Ser Ser His Leu Pro Trp Ala Ser Gly Leu Glu Thr Leu
        115                 120                 125

Asp Ser Leu Gly Gly Val Leu Glu Ala Ser Gly Tyr Ser Thr Glu Val
    130                 135                 140

Val Ala Leu Ser Arg Leu Gln Gly Ser Leu Gln Asp Met Leu Trp Gln
145                 150                 155                 160

Leu Asp Leu Ser Pro Gly Cys
                165

<210> SEQ ID NO 186
<211> LENGTH: 167
<212> TYPE: PRT
<213> ORGANISM: Artificial Sequence
<220> FEATURE:
<223> OTHER INFORMATION: Description of Artificial Sequence: Synthetic
      protein

<400> SEQUENCE: 186

Met His Trp Gly Thr Leu Cys Gly Phe Leu Trp Leu Trp Pro Tyr Leu
1               5                   10                  15

Phe Tyr Val Gln Ala Val Pro Ile Gln Lys Val Gln Asp Asp Thr Lys
            20                  25                  30

Thr Leu Ile Lys Thr Ile Val Thr Arg Ile Asn Asp Ile Ser His Thr
        35                  40                  45

Gln Ser Val Ser Ser Lys Gln Lys Val Thr Gly Leu Asp Phe Ile Pro
    50                  55                  60

Gly Leu His Pro Ile Leu Thr Leu Ser Lys Met Asp Gln Thr Leu Ala
65                  70                  75                  80

Val Tyr Gln Gln Ile Leu Thr Ser Met Pro Ser Arg Glu Val Ile Gln
                85                  90                  95

Ile Ser Asn Asp Leu Glu Asn Leu Arg Asp Leu Leu His Val Leu Ala
            100                 105                 110

Phe Ser Lys Ser Cys His Leu Pro Trp Ala Ser Gly Leu Glu Thr Leu
        115                 120                 125

Asp Ser Leu Gly Gly Val Leu Glu Ala Ser Gly Tyr Ser Thr Glu Val
    130                 135                 140

Val Ala Leu Ser Arg Leu Gln Gly Ser Leu Gln Asp Met Leu Trp Gln
145                 150                 155                 160

Leu Asp Leu Ser Pro Gly Ser
                165
```

```
<210> SEQ ID NO 187
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Phe Ile Glu Trp Leu Lys Asn Gly Gly Pro Ser Ser Gly Ala Pro Pro
1               5                   10                  15

Pro Ser

<210> SEQ ID NO 188
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Pro Ser Ser Gly Ala Pro Pro Pro Ser
1               5

<210> SEQ ID NO 189
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Lys Asn Gly Gly Pro Ser Ser Gly Ala Pro Pro Pro Ser
1               5                   10

<210> SEQ ID NO 190
<211> LENGTH: 54
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Ala Ser Leu Arg His Tyr Leu Asn Leu
        35                  40                  45

Val Thr Arg Gln Arg Tyr
    50

<210> SEQ ID NO 191
<211> LENGTH: 51
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

His Gly Glu Gly Thr Phe Thr Ser Asp Leu Ser Lys Gln Met Glu Glu
1               5                   10                  15
```

```
Glu Ala Val Arg Leu Phe Ile Glu Trp Leu Lys Asn Gly Gly Pro Ser
            20                  25                  30

Ser Gly Ala Pro Pro Ser Arg His Tyr Leu Asn Leu Val Thr Arg
        35                  40                  45

Gln Arg Tyr
    50

<210> SEQ ID NO 192
<211> LENGTH: 58
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Asn Arg Tyr Tyr Ala Ser Leu Arg His
        35                  40                  45

Tyr Leu Asn Leu Val Thr Arg Gln Arg Tyr
    50                  55

<210> SEQ ID NO 193
<211> LENGTH: 56
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (40)..(41)
<223> OTHER INFORMATION: beta-Ala

<400> SEQUENCE: 193

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Ala Ala Ala Ser Leu Arg His Tyr Leu
        35                  40                  45

Asn Leu Val Thr Arg Gln Arg Tyr
    50                  55

<210> SEQ ID NO 194
<211> LENGTH: 53
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (40)..(41)
<223> OTHER INFORMATION: beta-Ala

<400> SEQUENCE: 194

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
```

```
                    20                  25                  30

Ser Gly Ala Pro Pro Ser Ala Ala Arg His Tyr Leu Asn Leu Val
        35                  40                  45

Thr Arg Gln Arg Tyr
        50

<210> SEQ ID NO 195
<211> LENGTH: 47
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (40)..(41)
<223> OTHER INFORMATION: beta-Ala

<400> SEQUENCE: 195

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Pro Ser Ala Ala Val Thr Arg Gln Arg Tyr
        35                  40                  45

<210> SEQ ID NO 196
<211> LENGTH: 43
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Ala Ser Leu Arg
                20                  25                  30

His Tyr Leu Asn Leu Val Thr Arg Gln Arg Tyr
        35                  40

<210> SEQ ID NO 197
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Arg His Tyr Leu
                20                  25                  30

Asn Leu Val Thr Arg Gln Arg Tyr
        35                  40

<210> SEQ ID NO 198
<211> LENGTH: 47
<212> TYPE: PRT
<213> ORGANISM: Artificial Sequence
<220> FEATURE:
<223> OTHER INFORMATION: Description of Artificial Sequence: Synthetic
```

```
                            peptide

<400> SEQUENCE: 198

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Asn Arg Tyr Tyr
            20                  25                  30

Ala Ser Leu Arg His Tyr Leu Asn Leu Val Thr Arg Gln Arg Tyr
        35                  40                  45

<210> SEQ ID NO 199
<211> LENGTH: 45
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (29)..(30)
<223> OTHER INFORMATION: beta-Ala

<400> SEQUENCE: 199

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Ala Ala Ala Ser
            20                  25                  30

Leu Arg His Tyr Leu Asn Leu Val Thr Arg Gln Arg Tyr
        35                  40                  45

<210> SEQ ID NO 200
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (29)..(30)
<223> OTHER INFORMATION: beta-Ala

<400> SEQUENCE: 200

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Ala Ala Arg His
            20                  25                  30

Tyr Leu Asn Leu Val Thr Arg Gln Arg Tyr
        35                  40

<210> SEQ ID NO 201
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (29)..(30)
<223> OTHER INFORMATION: beta-Ala

<400> SEQUENCE: 201

His Gly Glu Gly Thr Phe Thr Ser Asp Leu Ser Lys Gln Met Glu Glu
1               5                   10                  15
```

```
Glu Ala Val Arg Leu Phe Ile Glu Trp Leu Lys Asn Ala Ala Val Thr
            20                  25                  30

Arg Gln Arg Tyr
        35
```

<210> SEQ ID NO 202
<211> LENGTH: 47
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

```
His Gly Glu Gly Ala Phe Thr Ser Asp Leu Ser Lys Gln Leu Glu Glu
1               5                   10                  15

Glu Ala Val Arg Leu Phe Ile Glu Phe Leu Lys Asn Asn Arg Tyr Tyr
            20                  25                  30

Ala Ser Leu Arg His Tyr Leu Asn Leu Val Thr Arg Gln Arg Tyr
        35                  40                  45
```

<210> SEQ ID NO 203
<211> LENGTH: 43
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

```
His Gly Glu Gly Ala Phe Thr Ser Asp Leu Ser Lys Gln Leu Glu Glu
1               5                   10                  15

Glu Ala Val Arg Leu Phe Ile Glu Phe Leu Lys Asn Ala Ser Leu Arg
            20                  25                  30

His Tyr Leu Asn Leu Val Thr Arg Gln Arg Tyr
        35                  40
```

<210> SEQ ID NO 204
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

```
His Gly Glu Gly Ala Phe Thr Ser Asp Leu Ser Lys Gln Leu Glu Glu
1               5                   10                  15

Glu Ala Val Arg Leu Phe Ile Glu Phe Leu Lys Asn Arg His Tyr Leu
            20                  25                  30

Asn Leu Val Thr Arg Gln Arg Tyr
        35                  40
```

<210> SEQ ID NO 205
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

```
His Gly Glu Gly Ala Phe Thr Ser Asp Leu Ser Lys Gln Leu Glu Glu
1               5                   10                  15
```

```
Glu Asn Arg Tyr Tyr Ala Ser Leu Arg His Tyr Leu Asn Leu Val Thr
            20                  25                  30

Arg Gln Arg Tyr
        35

<210> SEQ ID NO 206
<211> LENGTH: 45
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (29)..(30)
<223> OTHER INFORMATION: beta-Ala

<400> SEQUENCE: 206

His Gly Glu Gly Ala Phe Thr Ser Asp Leu Ser Lys Gln Leu Glu Glu
1               5                   10                  15

Glu Ala Val Arg Leu Phe Ile Glu Phe Leu Lys Asn Ala Ala Ala Ser
            20                  25                  30

Leu Arg His Tyr Leu Asn Leu Val Thr Arg Gln Arg Tyr
        35                  40                  45

<210> SEQ ID NO 207
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (29)..(30)
<223> OTHER INFORMATION: beta-Ala

<400> SEQUENCE: 207

His Gly Glu Gly Ala Phe Thr Ser Asp Leu Ser Lys Gln Leu Glu Glu
1               5                   10                  15

Glu Ala Val Arg Leu Phe Ile Glu Phe Leu Lys Asn Ala Arg His Tyr
            20                  25                  30

Leu Asn Leu Val Thr Arg Gln Arg Tyr
        35                  40

<210> SEQ ID NO 208
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (29)..(30)
<223> OTHER INFORMATION: beta-Ala

<400> SEQUENCE: 208

His Gly Glu Gly Ala Phe Thr Ser Asp Leu Ser Lys Gln Leu Glu Glu
1               5                   10                  15

Glu Ala Val Arg Leu Phe Ile Glu Phe Leu Lys Asn Ala Ala Val Thr
            20                  25                  30

Arg Gln Arg Tyr
        35
```

<210> SEQ ID NO 209
<211> LENGTH: 47
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Asp Tyr Met Gly Trp Met Asp Phe
        35                  40                  45

<210> SEQ ID NO 210
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Asp Tyr Met Gly
            20                  25                  30

Trp Met Asp Phe
        35

<210> SEQ ID NO 211
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (36)..(36)
<223> OTHER INFORMATION: Phe(CH2SO3)

<400> SEQUENCE: 211

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Asp Tyr Met Gly
            20                  25                  30

Trp Met Asp Phe
        35

<210> SEQ ID NO 212
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (29)..(29)
<223> OTHER INFORMATION: 8-amino-3,6-dioxactoanoyl-Asp

<400> SEQUENCE: 212

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Asp Tyr Met Gly
            20                  25                  30

Trp Met Asp Phe
            35

<210> SEQ ID NO 213
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (29)..(29)
<223> OTHER INFORMATION: 8-amino-3,6-dioxactoanoyl-Asp
<220> FEATURE:
<221> NAME/KEY: MOD_RES
<222> LOCATION: (36)..(36)
<223> OTHER INFORMATION: Phe(CH2SO3)

<400> SEQUENCE: 213

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Asp Tyr Met Gly
            20                  25                  30

Trp Met Asp Phe
            35

<210> SEQ ID NO 214
<211> LENGTH: 59
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Lys Cys Asn Thr Ala
            20                  25                  30

Thr Cys Val Leu Gly Arg Leu Ser Gln Glu Leu His Arg Leu Gln Thr
            35                  40                  45

Tyr Pro Arg Thr Asn Thr Gly Ser Asn Thr Tyr
        50                  55

<210> SEQ ID NO 215
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Lys Ala Asn Thr Ala
            20                  25                  30

Thr Ala Val Leu Gly
            35

```
<210> SEQ ID NO 216
<211> LENGTH: 66
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (29)..(29)
<223> OTHER INFORMATION: 12-Ado

<400> SEQUENCE: 216

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Xaa Lys Cys Asn
            20                  25                  30

Thr Ala Thr Cys Val Leu Gly Arg Leu Ser Gln Glu Leu His Arg Leu
        35                  40                  45

Gln Thr Tyr Pro Arg Thr Asn Thr Gly Ser Gly Thr Pro Gly Ser Asn
    50                  55                  60

Thr Tyr
65

<210> SEQ ID NO 217
<211> LENGTH: 65
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (29)..(29)
<223> OTHER INFORMATION: 12-Ado

<400> SEQUENCE: 217

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Xaa Cys Asn Thr
            20                  25                  30

Ala Thr Cys Val Leu Gly Arg Leu Ser Gln Glu Leu His Arg Leu Gln
        35                  40                  45

Thr Tyr Pro Arg Thr Asn Thr Gly Ser Gly Thr Pro Gly Ser Asn Thr
    50                  55                  60

Tyr
65

<210> SEQ ID NO 218
<211> LENGTH: 65
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (28)..(28)
<223> OTHER INFORMATION: 3,6-dioxaoctanoyl-Asn

<400> SEQUENCE: 218

His Gly Glu Gly Thr Phe Thr Ser Asp Leu Ser Lys Gln Met Glu Glu
1               5                   10                  15
```

```
Glu Ala Val Arg Leu Phe Ile Glu Trp Leu Lys Asn Lys Cys Asn Thr
            20                  25                  30

Ala Thr Cys Val Leu Gly Arg Leu Ser Gln Glu Leu His Arg Leu Gln
        35                  40                  45

Thr Tyr Pro Arg Thr Asn Thr Gly Ser Gly Thr Pro Gly Ser Asn Thr
    50                  55                  60

Tyr
65

<210> SEQ ID NO 219
<211> LENGTH: 64
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (28)..(28)
<223> OTHER INFORMATION: 3,6-dioxaoctanoyl-Asn

<400> SEQUENCE: 219

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Cys Asn Thr Ala
            20                  25                  30

Thr Cys Val Leu Gly Arg Leu Ser Gln Glu Leu His Arg Leu Gln Thr
        35                  40                  45

Tyr Pro Arg Thr Asn Thr Gly Ser Gly Thr Pro Gly Ser Asn Thr Tyr
    50                  55                  60

<210> SEQ ID NO 220
<211> LENGTH: 66
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (29)..(29)
<223> OTHER INFORMATION: 5-Apa

<400> SEQUENCE: 220

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Xaa Lys Cys Asn
            20                  25                  30

Thr Ala Thr Cys Val Leu Gly Arg Leu Ser Gln Glu Leu His Arg Leu
        35                  40                  45

Gln Thr Tyr Pro Arg Thr Asn Thr Gly Ser Gly Thr Pro Gly Ser Asn
    50                  55                  60

Thr Tyr
65

<210> SEQ ID NO 221
<211> LENGTH: 65
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

<222> LOCATION: (29)..(29)
<223> OTHER INFORMATION: 5-Apa

<400> SEQUENCE: 221

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Xaa Cys Asn Thr
            20                  25                  30

Ala Thr Cys Val Leu Gly Arg Leu Ser Gln Glu Leu His Arg Leu Gln
        35                  40                  45

Thr Tyr Pro Arg Thr Asn Thr Gly Ser Gly Thr Pro Gly Ser Asn Thr
    50                  55                  60

Tyr
65

<210> SEQ ID NO 222
<211> LENGTH: 67
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (29)..(30)
<223> OTHER INFORMATION: beta-Ala

<400> SEQUENCE: 222

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Ala Ala Lys Cys
            20                  25                  30

Asn Thr Ala Thr Cys Val Leu Gly Arg Leu Ser Gln Glu Leu His Arg
        35                  40                  45

Leu Gln Thr Tyr Pro Arg Thr Asn Thr Gly Ser Gly Thr Pro Gly Ser
    50                  55                  60

Asn Thr Tyr
65

<210> SEQ ID NO 223
<211> LENGTH: 66
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (29)..(30)
<223> OTHER INFORMATION: beta-Ala

<400> SEQUENCE: 223

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Ala Ala Cys Asn
            20                  25                  30

Thr Ala Thr Cys Val Leu Gly Arg Leu Ser Gln Glu Leu His Arg Leu
        35                  40                  45

Gln Thr Tyr Pro Arg Thr Asn Thr Gly Ser Gly Thr Pro Gly Ser Asn
    50                  55                  60

Thr Tyr
65

<210> SEQ ID NO 224
<211> LENGTH: 65
<212> TYPE: PRT
<213> ORGANISM: Artificial Sequence
<220> FEATURE:
<223> OTHER INFORMATION: Description of Artificial Sequence: Synthetic
    peptide
<220> FEATURE:
<221> NAME/KEY: MOD_RES
<222> LOCATION: (28)..(28)
<223> OTHER INFORMATION: 4,7,10-trioxa-13-tridecanamine succinimidyl-Lys

<400> SEQUENCE: 224

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Lys Cys Asn Thr
            20                  25                  30

Ala Thr Cys Val Leu Gly Arg Leu Ser Gln Glu Leu His Arg Leu Gln
        35                  40                  45

Thr Tyr Pro Arg Thr Asn Thr Gly Ser Gly Thr Pro Gly Ser Asn Thr
    50                  55                  60

Tyr
65

<210> SEQ ID NO 225
<211> LENGTH: 64
<212> TYPE: PRT
<213> ORGANISM: Artificial Sequence
<220> FEATURE:
<223> OTHER INFORMATION: Description of Artificial Sequence: Synthetic
    peptide
<220> FEATURE:
<221> NAME/KEY: MOD_RES
<222> LOCATION: (28)..(28)
<223> OTHER INFORMATION: 4,7,10-trioxa-13-tridecanamine succinimidyl-Cys

<400> SEQUENCE: 225

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Cys Asn Thr Ala
            20                  25                  30

Thr Cys Val Leu Gly Arg Leu Ser Gln Glu Leu His Arg Leu Gln Thr
        35                  40                  45

Tyr Pro Arg Thr Asn Thr Gly Ser Gly Thr Pro Gly Ser Asn Thr Tyr
    50                  55                  60

<210> SEQ ID NO 226
<211> LENGTH: 42
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 226

Asp Tyr Met Gly Trp Met Asp Phe Gly Lys Arg Lys Cys Asn Thr Ala
1               5                   10                  15

Thr Cys Ala Thr Gln Arg Leu Ala Asn Glu Leu Val Arg Leu Gln Thr
            20                  25                  30

Tyr Pro Arg Thr Asn Gly Ser Asn Thr Tyr
        35                  40

```
<210> SEQ ID NO 227
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Lys Cys Asn Thr Ala Thr Cys Ala Thr Gln Arg Leu Ala Asn Phe Leu
1               5                   10                  15

Val His Arg Tyr Tyr Ala Ser Leu Arg His Tyr Leu Asn Leu Val Thr
            20                  25                  30

Arg Gln Arg Tyr
        35

<210> SEQ ID NO 228
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: isocap-Ser
<220> FEATURE:
<221> NAME/KEY: MOD_RES
<222> LOCATION: (6)..(6)
<223> OTHER INFORMATION: Aib
<220> FEATURE:
<221> NAME/KEY: MOD_RES
<222> LOCATION: (7)..(7)
<223> OTHER INFORMATION: Lys(formyl)
<220> FEATURE:
<221> NAME/KEY: MOD_RES
<222> LOCATION: (13)..(13)
<223> OTHER INFORMATION: Aib
<220> FEATURE:
<221> NAME/KEY: MOD_RES
<222> LOCATION: (14)..(14)
<223> OTHER INFORMATION: Lys(formyl)

<400> SEQUENCE: 228

Ser Thr Ala Val Leu Xaa Lys Leu Ser Gln Glu Leu Xaa Lys Leu Gln
1               5                   10                  15

Thr Arg Tyr Tyr Ala Ser Leu Arg His Tyr Leu Asn Leu Val Thr Arg
            20                  25                  30

Gln Arg Tyr
        35

<210> SEQ ID NO 229
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: isocap-Ser
<220> FEATURE:
<221> NAME/KEY: MOD_RES
<222> LOCATION: (6)..(6)
<223> OTHER INFORMATION: Aib
<220> FEATURE:
<221> NAME/KEY: MOD_RES
<222> LOCATION: (7)..(7)
<223> OTHER INFORMATION: Lys(formyl)
```

```
<220> FEATURE:
<221> NAME/KEY: MOD_RES
<222> LOCATION: (13)..(13)
<223> OTHER INFORMATION: Aib
<220> FEATURE:
<221> NAME/KEY: MOD_RES
<222> LOCATION: (14)..(14)
<223> OTHER INFORMATION: Lys(formyl)

<400> SEQUENCE: 229

Ser Thr Ala Val Leu Xaa Lys Leu Ser Gln Glu Leu Xaa Lys Leu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 230
<211> LENGTH: 43
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: succinoyl-Cys

<400> SEQUENCE: 230

Asp Tyr Met Gly Trp Met Asp Phe Cys Ile Lys Pro Glu Ala Pro Gly
1               5                   10                  15

Glu Asp Ala Ser Pro Glu Glu Leu Asn Arg Tyr Tyr Ala Ser Leu Arg
            20                  25                  30

His Tyr Leu Asn Leu Val Thr Arg Gln Arg Tyr
        35                  40

<210> SEQ ID NO 231
<211> LENGTH: 43
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Bis-Cys(N-acetyl)

<400> SEQUENCE: 231

Asp Tyr Met Gly Trp Met Asp Phe Cys Ile Lys Pro Glu Ala Pro Gly
1               5                   10                  15

Glu Asp Ala Ser Pro Glu Glu Leu Asn Arg Tyr Tyr Ala Ser Leu Arg
            20                  25                  30

His Tyr Leu Asn Leu Val Thr Arg Gln Arg Tyr
        35                  40

<210> SEQ ID NO 232
<211> LENGTH: 43
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
```

<223> OTHER INFORMATION: Gly-Aminoxymethylcarbonyl

<400> SEQUENCE: 232

Asp Tyr Met Gly Trp Met Asp Phe Gly Ile Lys Pro Glu Ala Pro Gly
1               5                   10                  15

Glu Asp Ala Ser Pro Glu Glu Leu Asn Arg Tyr Tyr Ala Ser Leu Arg
            20                  25                  30

His Tyr Leu Asn Leu Val Thr Arg Gln Arg Tyr
        35                  40

<210> SEQ ID NO 233
<211> LENGTH: 63
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (31)..(31)
<223> OTHER INFORMATION: 12-Ado

<400> SEQUENCE: 233

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Xaa Lys
            20                  25                  30

Cys Asn Thr Ala Thr Cys Val Leu Gly Arg Leu Ser Gln Glu Leu His
        35                  40                  45

Arg Leu Gln Thr Tyr Pro Arg Thr Asn Thr Gly Ser Asn Thr Tyr
    50                  55                  60

<210> SEQ ID NO 234
<211> LENGTH: 62
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (31)..(31)
<223> OTHER INFORMATION: 12-Ado

<400> SEQUENCE: 234

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Xaa Cys
            20                  25                  30

Asn Thr Ala Thr Cys Val Leu Gly Arg Leu Ser Gln Glu Leu His Arg
        35                  40                  45

Leu Gln Thr Tyr Pro Arg Thr Asn Thr Gly Ser Asn Thr Tyr
    50                  55                  60

<210> SEQ ID NO 235
<211> LENGTH: 62
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (31)..(31)
<223> OTHER INFORMATION: 3,6-dioxaoctanoyl-Lys

<400> SEQUENCE: 235

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Lys Cys
            20                  25                  30

Asn Thr Ala Thr Cys Val Leu Gly Arg Leu Ser Gln Glu Leu His Arg
        35                  40                  45

Leu Gln Thr Tyr Pro Arg Thr Asn Thr Gly Ser Asn Thr Tyr
    50                  55                  60

<210> SEQ ID NO 236
<211> LENGTH: 61
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (31)..(31)
<223> OTHER INFORMATION: 3,6-dioxaoctanoyl-Cys

<400> SEQUENCE: 236

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Cys Asn
            20                  25                  30

Thr Ala Thr Cys Val Leu Gly Arg Leu Ser Gln Glu Leu His Arg Leu
        35                  40                  45

Gln Thr Tyr Pro Arg Thr Asn Thr Gly Ser Asn Thr Tyr
    50                  55                  60

<210> SEQ ID NO 237
<211> LENGTH: 63
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (31)..(31)
<223> OTHER INFORMATION: 5-Apa

<400> SEQUENCE: 237

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Xaa Lys
            20                  25                  30

Cys Asn Thr Ala Thr Cys Val Leu Gly Arg Leu Ser Gln Glu Leu His
        35                  40                  45

Arg Leu Gln Thr Tyr Pro Arg Thr Asn Thr Gly Ser Asn Thr Tyr
    50                  55                  60

<210> SEQ ID NO 238
<211> LENGTH: 62
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (31)..(31)
<223> OTHER INFORMATION: 5-Apa

<400> SEQUENCE: 238

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Xaa Cys
            20                  25                  30

Asn Thr Ala Thr Cys Val Leu Gly Arg Leu Ser Gln Glu Leu His Arg
        35                  40                  45

Leu Gln Thr Tyr Pro Arg Thr Asn Thr Gly Ser Asn Thr Tyr
    50                  55                  60

<210> SEQ ID NO 239
<211> LENGTH: 64
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (31)..(32)
<223> OTHER INFORMATION: beta-Ala

<400> SEQUENCE: 239

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Ala Ala
            20                  25                  30

Lys Cys Asn Thr Ala Thr Cys Val Leu Gly Arg Leu Ser Gln Glu Leu
        35                  40                  45

His Arg Leu Gln Thr Tyr Pro Arg Thr Asn Thr Gly Ser Asn Thr Tyr
    50                  55                  60

<210> SEQ ID NO 240
<211> LENGTH: 63
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (31)..(32)
<223> OTHER INFORMATION: beta-Ala

<400> SEQUENCE: 240

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Ala Ala
            20                  25                  30

Cys Asn Thr Ala Thr Cys Val Leu Gly Arg Leu Ser Gln Glu Leu His
        35                  40                  45

Arg Leu Gln Thr Tyr Pro Arg Thr Asn Thr Gly Ser Asn Thr Tyr
    50                  55                  60

<210> SEQ ID NO 241
<211> LENGTH: 62
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<221> NAME/KEY: MOD_RES
<222> LOCATION: (31)..(31)
<223> OTHER INFORMATION: 4,7,10-trioxa-13-tridecanamine succinimidyl-Lys

<400> SEQUENCE: 241

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Lys Cys
            20                  25                  30

Asn Thr Ala Thr Cys Val Leu Gly Arg Leu Ser Gln Glu Leu His Arg
        35                  40                  45

Leu Gln Thr Tyr Pro Arg Thr Asn Thr Gly Ser Asn Thr Tyr
    50                  55                  60

<210> SEQ ID NO 242
<211> LENGTH: 61
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (30)..(30)
<223> OTHER INFORMATION: 4,7,10-trioxa-13-tridecanamine succinimidyl-Lys

<400> SEQUENCE: 242

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Cys Asn
            20                  25                  30

Thr Ala Thr Cys Val Leu Gly Arg Leu Ser Gln Glu Leu His Arg Leu
        35                  40                  45

Gln Thr Tyr Pro Arg Thr Asn Thr Gly Ser Asn Thr Tyr
    50                  55                  60

<210> SEQ ID NO 243
<211> LENGTH: 65
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Gly
            20                  25                  30

Gly Lys Cys Asn Thr Ala Thr Cys Val Leu Gly Arg Leu Ser Gln Glu
        35                  40                  45

Leu His Arg Leu Gln Thr Tyr Pro Arg Thr Asn Thr Gly Ser Asn Thr
    50                  55                  60

Tyr
65

<210> SEQ ID NO 244
<211> LENGTH: 64
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 244

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Gly
            20                  25                  30

Gly Cys Asn Thr Ala Thr Cys Val Leu Gly Arg Leu Ser Gln Glu Leu
        35                  40                  45

His Arg Leu Gln Thr Tyr Pro Arg Thr Asn Thr Gly Ser Asn Thr Tyr
    50                  55                  60

<210> SEQ ID NO 245
<211> LENGTH: 62
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (31)..(31)
<223> OTHER INFORMATION: 4,7,10-trioxa-13-tridecanamine succinimidyl-Lys

<400> SEQUENCE: 245

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Lys Cys
            20                  25                  30

Asn Thr Ala Thr Cys Val Leu Gly Arg Leu Ser Gln Glu Leu His Arg
        35                  40                  45

Leu Gln Thr Tyr Pro Arg Thr Asn Thr Gly Ser Asn Thr Tyr
    50                  55                  60

<210> SEQ ID NO 246
<211> LENGTH: 61
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (30)..(30)
<223> OTHER INFORMATION: 4,7,10-trioxa-13-tridecanamine succinimidyl-Lys

<400> SEQUENCE: 246

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Cys Asn
            20                  25                  30

Thr Ala Thr Cys Val Leu Gly Arg Leu Ser Gln Glu Leu His Arg Leu
        35                  40                  45

Gln Thr Tyr Pro Arg Thr Asn Thr Gly Ser Asn Thr Tyr
    50                  55                  60

<210> SEQ ID NO 247
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:

```
<221> NAME/KEY: MOD_RES
<222> LOCATION: (1)..(1)
<223> OTHER INFORMATION: Ac-Gly
<220> FEATURE:
<221> NAME/KEY: MOD_RES
<222> LOCATION: (26)..(26)
<223> OTHER INFORMATION: Gly-NH2

<400> SEQUENCE: 247

Gly Asp Tyr Ser His Cys Ser Pro Leu Arg Tyr Tyr Pro Trp Trp Lys
1               5                   10                  15

Cys Thr Tyr Pro Asp Pro Glu Gly Gly Gly
            20                  25

<210> SEQ ID NO 248
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (36)..(36)
<223> OTHER INFORMATION: N-methyl-Tyr

<400> SEQUENCE: 248

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 249
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (34)..(34)
<223> OTHER INFORMATION: N-methyl-Tyr

<400> SEQUENCE: 249

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 250
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (25)..(25)
<223> OTHER INFORMATION: N-methyl-Tyr

<400> SEQUENCE: 250

Ala Ser Pro Glu Glu Leu Asn Arg Tyr Tyr Ala Ser Leu Arg His Tyr
```

```
                 1               5                  10                 15
Leu Asn Leu Val Thr Arg Gln Arg Tyr
                 20                 25

<210> SEQ ID NO 251
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: N-methyl-Tyr

<400> SEQUENCE: 251

Asn Arg Tyr Tyr Ala Ser Leu Arg His Tyr Leu Asn Leu Val Thr Arg
1               5                  10                 15
Gln Arg Tyr

<210> SEQ ID NO 252
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: N-methyl-Tyr

<400> SEQUENCE: 252

Ala Ser Leu Arg His Tyr Leu Asn Leu Val Thr Arg Gln Arg Tyr
1               5                  10                 15

<210> SEQ ID NO 253
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (36)..(36)
<223> OTHER INFORMATION: N-methyl-Tyr

<400> SEQUENCE: 253

Tyr Pro Ile Lys Pro Glu Ala Pro Gly Glu Asp Ala Ser Pro Glu Glu
1               5                  10                 15
Leu Asn Arg Tyr Tyr Ala Ser Leu Arg His Tyr Leu Asn Leu Val Thr
                 20                 25                 30
Arg Gln Arg Tyr
        35

<210> SEQ ID NO 254
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (34)..(34)
<223> OTHER INFORMATION: N-methyl-Tyr
```

<400> SEQUENCE: 254

Ile Lys Pro Glu Ala Pro Gly Glu Asp Ala Ser Pro Glu Glu Leu Asn
1               5                   10                  15
Arg Tyr Tyr Ala Ser Leu Arg His Tyr Leu Asn Leu Val Thr Arg Gln
            20                  25                  30
Arg Tyr

<210> SEQ ID NO 255
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (25)..(25)
<223> OTHER INFORMATION: N-methyl-Tyr

<400> SEQUENCE: 255

Ala Ser Pro Glu Glu Leu Asn Arg Tyr Tyr Ala Ser Leu Arg His Tyr
1               5                   10                  15
Leu Asn Leu Val Thr Arg Gln Arg Tyr
            20                  25

<210> SEQ ID NO 256
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: N-methyl-Tyr

<400> SEQUENCE: 256

Asn Arg Tyr Tyr Ala Ser Leu Arg His Tyr Leu Asn Leu Val Thr Arg
1               5                   10                  15
Gln Arg Tyr

<210> SEQ ID NO 257
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: N-methyl-Tyr

<400> SEQUENCE: 257

Ala Ser Leu Arg His Tyr Leu Asn Leu Val Thr Arg Gln Arg Tyr
1               5                   10                  15

<210> SEQ ID NO 258

<400> SEQUENCE: 258

000

<210> SEQ ID NO 259

<400> SEQUENCE: 259

000

<210> SEQ ID NO 260

<400> SEQUENCE: 260

000

<210> SEQ ID NO 261

<400> SEQUENCE: 261

000

<210> SEQ ID NO 262

<400> SEQUENCE: 262

000

<210> SEQ ID NO 263

<400> SEQUENCE: 263

000

<210> SEQ ID NO 264

<400> SEQUENCE: 264

000

<210> SEQ ID NO 265

<400> SEQUENCE: 265

000

<210> SEQ ID NO 266
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: N-methyl-Tyr

<400> SEQUENCE: 266

Ile Lys Pro Glu Ala Pro Gly Glu Ala Ser Leu Arg His Tyr Leu Asn
1               5                   10                  15

Leu Val Thr Arg Gln Arg Tyr
            20

<210> SEQ ID NO 267
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (33)..(33)

<223> OTHER INFORMATION: N-methyl-Arg

<400> SEQUENCE: 267

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 268
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (33)..(33)
<223> OTHER INFORMATION: D-Arg
<220> FEATURE:
<221> NAME/KEY: MOD_RES
<222> LOCATION: (34)..(34)
<223> OTHER INFORMATION: N-methyl-Tyr

<400> SEQUENCE: 268

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 269
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (33)..(33)
<223> OTHER INFORMATION: N-methyl-D-Arg

<400> SEQUENCE: 269

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 270
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (32)..(32)
<223> OTHER INFORMATION: N-methyl-Gln

<400> SEQUENCE: 270

Ile Lys Pro Glu Ala Pro Gly Glu Asp Ala Ser Pro Glu Glu Leu Asn
1               5                   10                  15

```
Arg Tyr Tyr Ala Ser Leu Arg His Tyr Leu Asn Leu Val Thr Arg Gln
            20                  25                  30

Arg Tyr

<210> SEQ ID NO 271
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (32)..(32)
<223> OTHER INFORMATION: D-Gln
<220> FEATURE:
<221> NAME/KEY: MOD_RES
<222> LOCATION: (34)..(34)
<223> OTHER INFORMATION: N-methyl-Tyr

<400> SEQUENCE: 271

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 272
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (32)..(32)
<223> OTHER INFORMATION: N-methyl-D-Gln

<400> SEQUENCE: 272

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 273
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (31)..(31)
<223> OTHER INFORMATION: N-methyl-Arg

<400> SEQUENCE: 273

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr
```

<210> SEQ ID NO 274
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (31)..(31)
<223> OTHER INFORMATION: D-Arg
<220> FEATURE:
<221> NAME/KEY: MOD_RES
<222> LOCATION: (34)..(34)
<223> OTHER INFORMATION: N-methyl-Tyr

<400> SEQUENCE: 274

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 275
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (31)..(31)
<223> OTHER INFORMATION: N-methyl-D-Arg

<400> SEQUENCE: 275

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 276
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: N-methyl-Ala

<400> SEQUENCE: 276

Ile Lys Pro Glu Ala Pro Gly Glu Asp Ala Ser Pro Glu Glu Leu Asn
1               5                   10                  15

Ala Tyr Tyr Ala Ser Leu Arg His Tyr Leu Asn Leu Val Thr Arg Gln
            20                  25                  30

Arg Tyr

<210> SEQ ID NO 277
<211> LENGTH: 34
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: D-Ala
<220> FEATURE:
<221> NAME/KEY: MOD_RES
<222> LOCATION: (34)..(34)
<223> OTHER INFORMATION: N-methyl-Tyr

<400> SEQUENCE: 277

Ile Lys Pro Glu Ala Pro Gly Glu Asp Ala Ser Pro Glu Glu Leu Asn
1               5                   10                  15

Ala Tyr Tyr Ala Ser Leu Arg His Tyr Leu Asn Leu Val Thr Arg Gln
            20                  25                  30

Arg Tyr

<210> SEQ ID NO 278
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: N-methyl-D-Ala

<400> SEQUENCE: 278

Ile Lys Pro Glu Ala Pro Gly Glu Asp Ala Ser Pro Glu Glu Leu Asn
1               5                   10                  15

Ala Tyr Tyr Ala Ser Leu Arg His Tyr Leu Asn Leu Val Thr Arg Gln
            20                  25                  30

Arg Tyr

<210> SEQ ID NO 279

<400> SEQUENCE: 279

000

<210> SEQ ID NO 280

<400> SEQUENCE: 280

000

<210> SEQ ID NO 281

<400> SEQUENCE: 281

000

<210> SEQ ID NO 282

<400> SEQUENCE: 282

000

<210> SEQ ID NO 283

<400> SEQUENCE: 283

000
```

<210> SEQ ID NO 284

<400> SEQUENCE: 284

000

<210> SEQ ID NO 285

<400> SEQUENCE: 285

000

<210> SEQ ID NO 286

<400> SEQUENCE: 286

000

<210> SEQ ID NO 287

<400> SEQUENCE: 287

000

<210> SEQ ID NO 288

<400> SEQUENCE: 288

000

<210> SEQ ID NO 289

<400> SEQUENCE: 289

000

<210> SEQ ID NO 290

<400> SEQUENCE: 290

000

<210> SEQ ID NO 291
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

Tyr Ala Glu Gly Thr Phe Ile Ser Asp Tyr Ser Ile Ala Leu Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 292
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Ala

<400> SEQUENCE: 292

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 293
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Ala

<400> SEQUENCE: 293

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys
            20                  25                  30

<210> SEQ ID NO 294
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Ala

<400> SEQUENCE: 294

Tyr Ala Glu Gly Thr Phe Ile Ser Asp Tyr Ser Ile Ala Leu Asp Lys
1               5                   10                  15

Ile His Gln Gln Asp Phe Val Asn Trp Leu Leu Ala Gln Lys
            20                  25                  30

<210> SEQ ID NO 295
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

Tyr Ala Glu Gly Thr Phe Ile Ser Asp Tyr Ser Ile Ala Leu Asp Lys
1               5                   10                  15

Ile His Gln Gln Asp Phe Val Asn Trp Leu Leu Ala Gln Lys
            20                  25                  30

<210> SEQ ID NO 296
<211> LENGTH: 8
<212> TYPE: PRT
<213> ORGANISM: Artificial Sequence
<220> FEATURE:

-continued

<223> OTHER INFORMATION: Description of Artificial Sequence: Synthetic
     peptide

<400> SEQUENCE: 296

Ile Lys Pro Glu Ala Pro Gly Glu
1               5

<210> SEQ ID NO 297
<211> LENGTH: 30
<212> TYPE: PRT
<213> ORGANISM: Artificial Sequence
<220> FEATURE:
<223> OTHER INFORMATION: Description of Artificial Sequence: Synthetic
     peptide
<220> FEATURE:
<221> NAME/KEY: MOD_RES
<222> LOCATION: (2)..(2)
<223> OTHER INFORMATION: Aib

<400> SEQUENCE: 297

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 298
<211> LENGTH: 36
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 298

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Gln Gly Gly Pro Lys
            20                  25                  30

Ile Arg Tyr Ser
        35

<210> SEQ ID NO 299
<211> LENGTH: 36
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 299

Glu Gly Thr Phe Ile Ser Asp Tyr Ser Ile Ala Met Asp Lys Ile His
1               5                   10                  15

Gln Gln Asp Phe Val Asn Trp Leu Leu Ala Gln Lys Pro Ser Ser Gly
            20                  25                  30

Ala Pro Pro Pro
        35

<210> SEQ ID NO 300
<211> LENGTH: 27
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 300

Glu Gly Thr Phe Ile Ser Asp Tyr Ser Ile Ala Met Asp Lys Ile His
1               5                   10                  15

Gln Gln Asp Phe Val Asn Trp Leu Leu Ala Gln
            20                  25

<210> SEQ ID NO 301
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301

Glu Gly Thr Phe Ile Ser Asp Tyr Ser Ile Ala Met Asp Lys Ile His
1               5                   10                  15

Gln Gln Asp Phe Val Asn Trp Leu Leu Ala Gln
            20                  25

<210> SEQ ID NO 302
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

Glu Gly Thr Phe Ile Ser Asp Tyr Ser Ile Ala Met Asp Lys Ile His
1               5                   10                  15

Gln Gln Asp Phe Val Asn Trp Leu Leu Ala Gln Lys Pro Ser Ser Gly
            20                  25                  30

Ala Pro Pro Ser
        35

<210> SEQ ID NO 303
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 303

Glu Gly Thr Phe Ile Ser Asp Tyr Ser Ile Ala Met Asp Lys Ile His
1               5                   10                  15

Gln Gln Asp Phe Val Asn Trp Leu Leu Ala Gln Lys Pro Ser Ser Gly
            20                  25                  30

Ala Pro Pro Ser
        35

<210> SEQ ID NO 304
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

Ala Glu Gly Thr Phe Ile Ser Asp Tyr Ser Ile Ala Met Asp Lys Ile
1               5                   10                  15

His Gln Gln Asp Phe Val Asn Trp Leu Leu Ala Gln Lys Pro Ser Ser

```
                  20                  25                  30

Gly Ala Pro Pro Pro
        35

<210> SEQ ID NO 305
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

Ala Glu Gly Thr Phe Ile Ser Asp Tyr Ser Ile Ala Met Asp Lys Ile
1               5                   10                  15

His Gln Gln Asp Phe Val Asn Trp Leu Leu Ala Gln
            20                  25

<210> SEQ ID NO 306
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

Pro Ser Ser Gly Ala Pro Pro Pro Asn
1               5

<210> SEQ ID NO 307
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307

Ala Glu Gly Thr Phe Ile Ser Asp Tyr Ser Ile Ala Met Asp
1               5                   10

<210> SEQ ID NO 308
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

Ile His Gln Gln Asp Phe Val Asn Trp Leu Leu Ala Gln Lys Pro Ser
1               5                   10                  15

Ser Gly Ala Pro Pro Pro
            20

<210> SEQ ID NO 309
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Lys Pro Glu Ala Pro Gly Glu Asp Ala Ser Pro Glu Glu Leu Asn Arg
```

```
                1               5                   10                  15
Tyr Tyr Ala Ser Leu Arg His Tyr Leu Asn Leu Val Thr Arg Gln Arg
                20                  25                  30

<210> SEQ ID NO 310
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

Pro Glu Ala Pro Gly Glu Asp Ala Ser Pro Glu Glu Leu Asn Arg Tyr
1               5                   10                  15
Tyr Ala Ser Leu Arg His Tyr Leu Asn Leu Val Thr Arg Gln Arg
                20                  25                  30

<210> SEQ ID NO 311
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 311

Lys Pro Glu Ala Pro Gly Glu Asp Ala Ser Pro Glu
1               5                   10

<210> SEQ ID NO 312
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 312

Leu Asn Arg Tyr Tyr Ala Ser Leu Arg His Tyr Leu Asn Leu Val Thr
1               5                   10                  15
Arg Gln Arg

<210> SEQ ID NO 313
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 313

Lys Pro Glu Ala Pro Gly Glu Asp Ala Ser Pro Glu Glu Leu Asn Arg
1               5                   10                  15
Tyr

<210> SEQ ID NO 314
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314
```

```
Ala Ser Leu Arg His Tyr Leu Asn Leu Val Thr Arg Gln Arg
1               5                   10
```

```
<210> SEQ ID NO 315
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: pyroglutamic acid

<400> SEQUENCE: 315

Glu Trp Pro Arg Pro Gln Ile Pro Pro
1               5
```

```
<210> SEQ ID NO 316
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: pyroglutamic acid

<400> SEQUENCE: 316

Glu Lys Trp Ala Pro
1               5
```

```
<210> SEQ ID NO 317
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 317

Arg Gln Arg Tyr
1
```

```
<210> SEQ ID NO 318
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 318

Arg Gln Arg Trp
1
```

```
<210> SEQ ID NO 319
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 319

His Ala Glu Gly Thr Phe Thr Ser Asp Val Ser Ser Tyr Leu Glu Gly
```

```
                1               5                  10                  15
Gln Ala Ala Lys Glu Phe Ile Ala Trp Leu Val Lys Gly Arg Gly
            20                  25                  30
```

<210> SEQ ID NO 320
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

```
His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn
            20                  25
```

<210> SEQ ID NO 321
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 321

```
His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30
```

<210> SEQ ID NO 322
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

```
His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30
```

<210> SEQ ID NO 323
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 323

```
His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn
            20                  25
```

<210> SEQ ID NO 324
<211> LENGTH: 28
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 324

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn
            20                  25

<210> SEQ ID NO 325
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: pyroglutamic acid
<220> FEATURE:
<221> NAME/KEY: MOD_RES
<222> LOCATION: (5)..(5)
<223> OTHER INFORMATION: Pro-OH

<400> SEQUENCE: 325

Glu Lys Trp Ala Pro
1               5

<210> SEQ ID NO 326
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 326

Glu Gly Thr Phe Ile Ser Asp Tyr Ser Ile Ala Leu Asp Lys Ile His
1               5                   10                  15

Gln Gln Asp Phe Val Asn Trp Leu Leu Ala Gln Asn
            20                  25

<210> SEQ ID NO 327
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 327

Glu Gly Thr Phe Ile Ser Asp Tyr Ser Ile Ala Met Asp Lys Ile His
1               5                   10                  15

Gln Gln Asp Phe Val Asn Trp Leu Leu Ala Gln Lys Pro Ser Ser Gly
            20                  25                  30

Ala Pro Pro Pro
        35

<210> SEQ ID NO 328
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 328

Glu Gly Thr Phe Ile Ser Asp Tyr Ser Ile Ala Met Asp Lys Ile His
1               5                   10                  15

Gln Gln Asp Phe Val Asn Trp Leu Leu Ala Gln Lys Pro Ser Ser Gly
            20                  25                  30

Ala Pro Pro Pro Ser
            35

<210> SEQ ID NO 329
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 329

Ala Glu Gly Thr Phe Ile Ser Asp Tyr Ser Ile Ala Met Asp Lys Ile
1               5                   10                  15

His Gln Gln Asp Phe Val Asn Trp Leu Leu Ala Gln
            20                  25

<210> SEQ ID NO 330
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 330

Ala Glu Gly Thr Phe Ile Ser Asp Tyr Ser Ile Ala Met Asp Lys Ile
1               5                   10                  15

His Gln Gln Asp Phe Val Asn Trp Leu Leu Ala Gln Lys Pro Ser Ser
            20                  25                  30

Gly Ala Pro Pro Pro
            35

<210> SEQ ID NO 331
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 331

Ala Glu Gly Thr Phe Ile Ser Asp Tyr Ser Ile Ala Met Asp Lys Ile
1               5                   10                  15

His Gln Gln Asp Phe Val Asn Trp Leu Leu Ala Gln
            20                  25

<210> SEQ ID NO 332
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 332

Ala Glu Gly Thr Phe Ile Ser Asp Tyr Ser Ile Ala Met Asp Lys Ile
1               5                   10                  15
```

His Gln Gln Asp Phe Val Asn Trp Leu Leu Ala Gln Lys Pro Ser Ser
            20                  25                  30

Gly Ala Pro Pro Pro
        35

<210> SEQ ID NO 333
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 333

Ala Glu Gly Thr Phe Ile Ser Asp Tyr Ser Ile Ala Met Asp Lys Ile
1               5                   10                  15

His Gln Gln Asp Phe Val Asn Trp Leu Leu Ala Gln
            20                  25

<210> SEQ ID NO 334
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 334

Ala Glu Gly Thr Phe Ile Ser Asp Tyr Ser Ile Ala Leu Asp Lys Ile
1               5                   10                  15

His Gln Gln Asp Phe Val Asn Trp Leu Leu Ala Gln Lys Pro Ser Ser
            20                  25                  30

Gly Ala Pro Pro Pro
        35

<210> SEQ ID NO 335
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 335

Ala Glu Gly Thr Phe Ile Ser Asp Tyr Ser Ile Ala Leu Asp Lys Ile
1               5                   10                  15

His Gln Gln Asp Phe Val Asn Trp Leu Leu Ala Gln
            20                  25

<210> SEQ ID NO 336
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 336

Glu Gly Thr Phe Ile Ser Asp Tyr Ser Ile Ala Met Asp Lys Ile His
1               5                   10                  15

Gln Gln Asp Phe Val Asn Trp Leu Leu Ala Gln Lys Pro Ser Ser Gly
            20                  25                  30

Ala Pro Pro Pro
        35

```
<210> SEQ ID NO 337
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 337

Ala Glu Gly Thr Phe Ile Ser Asp Tyr Ser Ile Ala Met Asp Lys Ile
1               5                   10                  15

His Gln Gln Asp Phe Val Asn Trp Leu Leu Ala Gln
            20                  25

<210> SEQ ID NO 338
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 338

Glu Gly Thr Phe Ile Ser Asp Tyr Ser Ile Ala Met Asp
1               5                   10

<210> SEQ ID NO 339
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 339

Ile His Gln Gln Asp Phe Val Asn Trp Leu Leu Ala Gln Lys Pro Ser
1               5                   10                  15

Ser Gly Ala Pro Pro Pro
            20

<210> SEQ ID NO 340
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 340

Ala Glu Gly Thr Phe Ile Ser Asp Tyr Ser Ile Ala Met Asp Lys Ile
1               5                   10                  15

His Gln Gln Asp Phe Val Asn Trp Leu Leu Ala Gln Lys Pro Ser Ser
            20                  25                  30

Gly Ala Pro Pro Pro
        35

<210> SEQ ID NO 341
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 341
```

```
Glu Gly Thr Phe Ile Ser Asp Tyr Ser Ile Ala Met Asp Lys Ile His
1               5                   10                  15

Gln Gln Asp Phe Val Asn Trp Leu Leu Ala Gln Lys Pro Ser Ser Gly
            20                  25                  30

Ala Pro Pro Pro
        35

<210> SEQ ID NO 342
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 342

Ala Glu Gly Thr Phe Ile Ser Asp Tyr Ser Ile Ala Met Asp Lys Ile
1               5                   10                  15

His Gln Gln Asp Phe Val Asn Trp Leu Leu Ala Gln
            20                  25

<210> SEQ ID NO 343
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 343

Glu Gly Thr Phe Ile Ser Asp Tyr Ser Ile Ala Met Asp Lys Ile His
1               5                   10                  15

Gln Gln Asp Phe Val Asn Trp Leu Leu Ala Gln Lys Pro Ser Ser Gly
            20                  25                  30

Ala Pro Pro Pro Ser
        35

<210> SEQ ID NO 344
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 344

Glu Gly Thr Phe Ile Ser Asp Tyr Ser Ile Ala Met Asp Lys Ile His
1               5                   10                  15

Gln Gln Asp Phe Val Asn Trp Leu Leu
            20                  25

<210> SEQ ID NO 345
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 345

Gln Lys Pro Ser Ser Gly Ala Pro Pro Pro
1               5                   10
```

<210> SEQ ID NO 346
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 346

Glu Gly Thr Phe Ile Ser Asp Tyr Ser Ile Ala
1               5                   10

<210> SEQ ID NO 347
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 347

Asp Lys Ile His Gln Gln Asp Phe Val Asn Trp Leu Leu Ala Gln Lys
1               5                   10                  15

Pro Ser Ser Gly Ala Pro Pro Pro
            20

<210> SEQ ID NO 348
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 348

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 349
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 349

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
            35

<210> SEQ ID NO 350
<211> LENGTH: 8
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 350

Pro Ser Ser Gly Ala Pro Pro Pro
1               5
```

PEPTIDE-PEPTIDASE INHIBITOR CONJUGATES AND METHODS OF USING SAME

CROSS-REFERENCE TO RELATED APPLICATION

This is a continuation of U.S. application Ser. No. 12/293,389 filed Jan. 5, 2009, which is a §371 of PCT/US2007/007163 filed Mar. 21, 2007, which claims priority to U.S. Application No. 60/784,795, filed Mar. 21, 2006, the entire contents of which are incorporated herein for all purposes.

TECHNICAL FIELD

The present disclosure relates to peptide molecules and, more particularly, to peptide-peptidase inhibitor conjugate molecules. The disclosure also relates to the medical field, in particular to the fields of metabolic and cardiovascular diseases.

BACKGROUND

Many peptides and peptide hormones are involved in the body's regulation of a normal, healthy metabolic state. Central to many metabolic diseases and disorders is the regulation of insulin levels and blood glucose levels. A number of hormones that lower blood glucose levels are released from the gastrointestinal mucosa in response to the presence and adsorption of nutrients in the gut.

Insulin secretion is modulated in part by secretagogue hormones, termed incretins, which are produced by enteroendocrine cells. The incretin hormone, glucagon-like peptide-1 (GLP-1) is a peptide hormone secreted by intestinal cells that has been shown to produce an enhancing effect on insulin secretion. GLP-1 is processed from proglucagon in the gut and enhances nutrient-induced insulin release (Krcymann, et al. (1987) *Lancet* 2:1300-1303). GLP-1 and various truncated forms of GLP-1, such as GLP-1 (7-36) amide, and GLP-1 (7-37) acid, are known to stimulate insulin secretion (insulinotropic action) and cAMP formation (see, e.g., Mojsov (1992) *Int. J. Pep. Pro. Res.* 40:333-343, Gutniak et al. (1992) *New Eng. J. of Med.* 326:1316-1322, Nauck et al. (1993) *Diabetologia* 36:741-744; Nauck et al., (1993) *J. Clin. Invest.* 91:301-307, and Thorens et al. (1993) *Diabetes* 42:1219-1225). GLP-1 (7-37) acid is C-terminally truncated and amidated to form GLP-1 (7-36) $NH_2$. The biological effects and metabolic turnover of the free acid GLP-1(7-37) OH, and the amide GLP-1(7-36) $NH_2$, are indistinguishable.

GLP-1(7-36) amide exerts a pronounced antidiabetogenic effect in insulin-dependent diabetics by stimulating insulin sensitivity and by enhancing glucose-induced insulin release at physiological concentrations. When administered to non-insulin dependent diabetics, GLP-1(7-36) amide stimulates insulin release, lowers glucagon secretion, inhibits gastric emptying and enhances glucose utilization. The use of GLP-1 type molecules for prolonged therapy of diabetes has been complicated because the serum half-life of such peptides is quite short.

The plasma half-life of active GLP-1 is <5 minutes, and its metabolic clearance rate is about 12-13 minutes. The major protease involved in the metabolism of GLP-1 is dipeptidyl peptidase (DPP) IV (CD26) which cleaves the N-terminal His-Ala dipeptide, thus producing metabolites, GLP-1 (9-37) OH or GLP-1 (9-36) $NH_2$, which are variously described as inactive, weak agonists or antagonists of GLP-1 receptor. The stimulation of GLP-1 receptor by GLP-1(7-37) OH or GLP-1(7-36)$NH_2$ results in adenylate cyclase activation, cAMP synthesis, membrane depolarization, rise in intracellular calcium and increase in glucose-induced insulin secretion.

Other important effects of GLP-1 on glucose homeostasis are suppression of glucagon secretion and inhibition of gastric motility. GLP-1 inhibitory actions on pancreatic alpha cell secretion of glucagon leads to decreases in hepatic glucose production via reduction in gluconeogenesis and glycogenolysis. This antiglucagon effect of GLP-1 is preserved in diabetic patients. Central effects of GLP-1 include increases in satiety, coupled with decreased food intake.

Native human GIP (gastric inhibitory peptide or glucose-dependent insulinotropic peptide), related to GLP-1, is a single 42 amino acid peptide synthesized in and secreted by specialized enteroendocrine K-cells. These cells are found throughout the intestine, concentrated primarily in the duodenum and proximal jejunum. The main stimulant for GIP secretion is ingestion of carbohydrate and lipid-rich meals. Following meal ingestion, circulating plasma GIP levels increase 10- to 20-fold. The half-life of intact GIP is estimated to be approximately 7.3 minutes in healthy subjects and 5.2 minutes in diabetic subjects. In serum, GIP is degraded by DPP-IV. The resulting short biological half-life limits the therapeutic use of GIP.

GIP stimulates insulin secretion in the presence of elevated glucose concentrations. Thus, the effect of endogenously released GIP appears to be an important mechanism of postprandial insulin secretion and does not appear to play a role in the fasting state. GIP stimulates beta-cell proliferation and cell survival in INS-1 islet cell line studies. Further, unlike GLP-1, GIP appears to act by accelerating emptying of the stomach rather than by inhibiting gastrointestinal motility.

Another family of peptide hormones implicated in metabolic diseases and disorders is the amylin family of peptide hormones, including amylin, calcitonin, calcitonin gene related peptide, adrenomedullin, and intermedin (also referred to as AFP-6). See, for example, Wimalawansa (1997) *Crit Rev Neurobiol.* 11:167-239. Amylin regulates the rate of glucose appearance in circulation through a slowing of gastrointestinal motility and gastric emptying and through suppression of postprandial glucagon secretion and food intake. Amylin has been shown to reduce weight or weight gain. Amylin may also be used to treat pain, bone disorders, gastritis, to modulate lipids, in particular triglycerides, or to affect body composition such as the preferential loss of fat and sparing of lean tissue. Calcitonin (CT) was named for its secretion in response to induced hypercalcemia and its rapid hypocalcemic effect. CT has an effect on plasma calcium levels and inhibits osteoclast function and is widely used for the treatment of osteoporosis. Therapeutically, salmon CT (sCT) appears to increase bone density and decrease fracture rates with minimal adverse effects.

Calcitonin gene related peptide (CGRP) is a neuropeptide whose receptors are widely distributed in the body, including the nervous system and the cardiovascular system. This peptide seems to modulate sensory neurotransmission and is a potent endogenous vasodilatory peptide. Reported biological effects for CGRP include: modulation of substance P in inflammation, nicotinic receptor activity at the neuromuscular junction, stimulation of pancreatic enzyme secretion, a reduction of gastric acid secretion, peripheral vasodilation, cardiac acceleration, neuro-modulation, regulation of calcium metabolism, osteogenic stimulation, insulin secretion, an increase in body temperature, and a decrease in food intake. An important role of CGRP is to control blood flow to various organs by its potent vasodilatory actions. Prolonged infusion of CGRP into patients with congestive cardiac failure has shown a sustained beneficial effect on hemodynamic functions without adverse effects, suggesting a use in heart failure. Other indications of CGRP use include renal failure, acute and chronic coronary artery ischemia, treatment of cardiac arrhythmia, other peripheral vascular disease such as Raynaud's phenomenon, subarachnoid hemorrhage, hypertension, and pulmonary hypertension.

Adrenomedullin (ADM) has effects on the cardiovascular system, cellular growth, the central nervous system and the endocrine system, with a range of biological actions including vasodilation, cell growth, regulation of hormone secretion, and natriuresis. Hinson et al. (2000) *Endocrine Reviews* 21:138-167. ADM affects such endocrine organs as the pituitary, the adrenal gland, reproductive organs and the pancreas. The peptide appears to have a role in inhibiting ACTH release from the pituitary. In the adrenal gland, it appears to affect the secretory activity of the adrenal cortex and it increases adrenal blood flow, acting as a vasodilator in the adrenal vascular bed. ADM has been shown to be present throughout the female reproductive tract and plasma levels are elevated in normal pregnancy. In the pancreas, ADM most likely plays an inhibitory role since it attenuated and delayed insulin response to an oral glucose challenge, resulting in initial elevated glucose levels. ADM can also affect renal function. A bolus administered peripherally can significantly lower mean arterial pressure and raise renal blood flow, glomerular filtration rate and urine flow. In some cases, there is also an increase in Na+ excretion.

Studies have also demonstrated that ADM acts on fetal and adult rodent osteoblasts to increase cell growth comparable to those of known osteoblast growth factors such as transforming growth factor-$\beta$. In the lung, ADM not only causes pulmonary vasodilation, but also inhibits bronchoconstriction induced by histamine or acetylcholine. In healthy volunteers, i.v. infusion of ADM has been shown to reduce arterial pressure and to stimulate heart rate, cardiac output, plasma levels of cAMP, prolactin, norepinephrine and rennin. In these patients, there was little or no increase in urine volume or sodium excretion observed. In patients with heart failure or chronic renal failure, i.v. ADM had similar effects to those seen in normal subjects, and also induced diuresis and natriuresis, depending on the dose administered (Nicholls et al. (2001) *Peptides* 22:1745-1752). Experimental ADM treatment has also been shown to be beneficial in arterial and pulmonary hypertension, septic shock and ischemia/reperfusion injury (Beltowski (2004) *Pol. J. Pharmacol.* 56:5-27). Other indications for ADM treatment include: peripheral vascular disease, subarachnoid hemorrhage, hypertension, preeclamptic toxemia of pregnancy and preterm labor, and osteoporosis.

Expression of AFP-6 (i.e., intermedin) is primarily in the pituitary and gastrointestinal tract. In in vivo studies, AFP-6 administration led to blood pressure reduction in both normal and spontaneously hypertensive rats. In vivo administration in mice led to a suppression of gastric emptying and food intake (Roh et al. (2004) *J. Biol. Chem.* 279:7264-7274.)

Yet another peptide hormone family implicated in metabolic diseases and disorders is the leptin family. Leptin is an afferent signal in a negative feedback loop regulating food intake and body weight and the mature form of circulating leptin is a 146-amino acid protein.

Another peptide hormone implicated in metabolic diseases and disorders is cholecystokinin (CCK). Reported biological actions of CCK include stimulation of pancreatic secretion and pancreatic growth, stimulation of gallbladder contraction, delayed gastric emptying, inhibition of gastric acid secretion, stimulation of intestinal motility, stimulation of insulin secretion, and vasodilation. The actions of CCK also reportedly include effects on cardiovascular function, respiratory function, neurotoxicity and seizures, cancer cell proliferation, analgesia, sleep, sexual and reproductive behaviors, memory, anxiety and dopamine-mediated behaviors. It has also been reported that CCK in physiological plasma concentrations inhibits increases satiety and inhibits food intake in both lean and obese humans. See, for example, Lieverse et al. (1994) *Ann. N.Y. Acad. Sci.* 713:268-272, Crawley et al. (1994) *Peptides* 15:731-755, Walsh, "Gastrointestinal Hormones," In Physiology of the Gastrointestinal Tract (3d ed. 1994; Raven Press, New York).

Another family of peptide hormones implicated in metabolic diseases and disorders is the pancreatic polypeptide family (PPF). The PPF includes pancreatic polypeptide (PP), Peptide YY (PYY), and Neuropeptide Y (NPY). These three related peptides have been reported to exert various biological effects. Effects of PP include inhibition of pancreatic secretion and relaxation of the gallbladder, and centrally administered PP produces modest increases in feeding that may be mediated by receptors localized to the hypothalamus and brainstem (reviewed in Gehlert, *Proc. Soc. Exp. Biol. Med.* 218: 7-22 (1998)). Peripheral administration of PYY reportedly reduces gastric acid secretion, gastric motility, exocrine pancreatic secretion, gallbladder contraction, and intestinal motility (Yoshinaga et al. (1992) *Am. J. Physiol.* 263:G695-701, Guan et al. (1991) *Endocrinology* 128: 911-916, Pappas et al. (1986) *Gastroenterology* 91:1386-1389, Savage et al. (1987) *Gut* 28:166-170). The effects of central administration (injection in or around the hindbrain/brainstem) of PYY on gastric emptying, gastric motility and gastric acid secretion may differ from those effects observed after peripheral injection (Chen et al. (1995) *Am. J. Physiol.* 269: R787-792, Chen et al. (1986) *Regul. Pept.* 61:95-98 (1996) Yang et al. (1995) *Am. J. Physiol.* 268: G943-948, Chen et al. (1997) *Neurogastroenterol. Motil.* 9:109-116). PYY has been shown to stimulate food and water intake after central administration (Morley et al. (1985) *Brain Res.* 341:200-203, Corp et al. (1990) *Am. J. Physiol.* 259: R317-323).

Metabolic diseases and disorders take on many forms, including obesity, diabetes, dyslipidemia, and insulin resistance. Obesity and its associated disorders are common and very serious public health problems in the United States and throughout the world. Upper body obesity is the strongest risk factor known for type 2 diabetes mellitus and is a strong risk factor for cardiovascular disease. Obesity is a recognized risk factor for hypertension, atherosclerosis, congestive heart failure, stroke, gallbladder disease, osteoarthritis, sleep apnea, reproductive disorders such as polycystic ovarian syndrome, cancers of the breast, prostate, and colon, and increased incidence of complications of general anesthesia (see, e.g., Kopelman (2000) *Nature* 404:635-643).

Obesity reduces life-span and carries a serious risk of the co-morbidities listed above, as well disorders such as infections, varicose veins, acanthosis nigricans, eczema, exercise intolerance, insulin resistance, hypertension hypercholesterolemia, cholelithiasis, orthopedic injury, and thromboembolic disease (Rissanen et al. (1990) *Br. Med. J.* 301:835-837). Obesity is also a risk factor for the group of conditions called insulin resistance syndrome, or "Syndrome X" and metabolic syndrome. The worldwide medical cost of obesity and associated disorders is enormous. The pathogenesis of obesity appears to be multifactorial but the basic problem is that in obese subjects nutrient availability and energy expenditure do not come into balance until there is excess adipose tissue. Obesity is currently a poorly treatable, chronic, essentially intractable metabolic disorder. A therapeutic drug useful in weight reduction of obese persons could have a profound beneficial effect on their health.

Diabetes is a disorder of carbohydrate metabolism characterized by hyperglycemia and glucosuria resulting from insufficient production or utilization of insulin. Diabetes severely affects the quality of life of large parts of the populations in developed countries. Insufficient production of insulin is characterized as type 1 diabetes and insufficient utilization of insulin is type 2 diabetes. However, it is now widely recognized that there are many distinct diabetes related diseases which have their onset long before patients are diagnosed as having overt diabetes. Also, the effects from the suboptimal control of glucose metabolism in diabetes give rise to a wide spectrum of related lipid and cardiovascular disorders.

Dyslipidemia, or abnormal levels of lipoproteins in blood plasma, is a frequent occurrence among diabetics. Dyslipidemia is typically characterized by elevated plasma triglycerides, low HDL (high density lipoprotein) cholesterol, normal to elevated levels of LDL (low density lipoprotein) cholesterol and increased levels of small dense, LDL particles in the blood. Dyslipidemia is one of the main contributors to the increased incidence of coronary events and deaths among diabetic subjects. Epidemiological studies have confirmed this by showing a several-fold increase in coronary deaths among diabetic subjects when compared with non-diabetic subjects. Several lipoprotein abnormalities have been described among diabetic subjects.

Insulin resistance is the diminished ability of insulin to exert its biologically action across a broad range of concentrations. In insulin resistance, the body secretes abnormally high amounts of insulin to compensate for this defect and a state of impaired glucose tolerance develops. Failing to compensate for the defective insulin action, the plasma glucose concentration inevitably rises, resulting in the clinical state of diabetes. It is being recognized that insulin resistance and relative hyperinsulinemia have a contributory role in obesity, hypertension, atherosclerosis and type 2 diabetes. The association of insulin resistance with obesity, hypertension and angina has been described as a syndrome, Syndrome X, having insulin resistance as the common pathogenic link.

Hypertension, or high blood pressure, may or may not be associated with a metabolic disease or disorder in a patient. Hypertension is the most common disease affecting the heart and blood vessels and statistics indicate that it occurs in more than 50 million Americans. The prevalence of hypertension increases with age. Hypertension is of considerable concern because of the harm it can do to the heart, brain and kidneys if it remains uncontrolled.

There remains a need for effective methods of producing bioactive peptides in forms that are effective for the treatment for diseases, conditions, and disorders, including metabolic and cardiovascular diseases and related disorders.

All patents, patent applications, and publications cited herein are hereby incorporated by reference in their entirety.

SUMMARY

In one general aspect, provided are peptide-peptidase inhibitor conjugate compounds having a peptide covalently linked to a peptidase inhibitor. In certain embodiments, the peptide-peptidase inhibitor conjugate comprises a peptide analog, a peptide derivative, or a peptide hybrid of a native peptide hormone. In some embodiments, the peptide-peptidase inhibitor conjugate has a plasma half-life greater than the plasma half-life of the peptide when not conjugated to the peptidase inhibitor. In some embodiments, the peptidase inhibitor of the peptide-peptidase inhibitor conjugate reduces the activity of a regulatory peptidase. In some embodiments, the peptidase inhibitor is selected from a group consisting of an angiotensin converting enzyme inhibitor, a vasopeptidase inhibitor, endothelial converting enzyme inhibitor, human neutral endopeptidase inhibitor, dipeptidyl peptidase IV inhibitor, aminopeptidase inhibitor, cysteine protease inhibitor, serine protease inhibitor, and carboxypeptidase inhibitor.

In some embodiments, the peptide is a hybrid peptide hormone. In some embodiments, the peptide is selected from a group consisting of a GLP-1, a GLP-2, a GIP, an exendin, a PYY, an amylin, a calcitonin, a leptin, and analogs thereof. In some embodiments, the peptide is a hormone agonist. In some embodiments, the peptide is a hormone antagonist.

In other embodiments, pharmaceutical compositions are provided comprising the disclosed peptide-peptidase inhibitor conjugates. In some embodiments, the peptide-peptidase inhibitor conjugates are of use in the preparation of pharmaceutical compositions.

In another aspect, methods provided include the use of the peptide-peptidase inhibitor conjugates in effective amounts for decreasing degradation of a peptidase-sensitive peptide in plasma. In addition, methods provided include the use of the peptide-peptidase inhibitor conjugates in effective amounts for increasing the plasma half-life of a peptidase-sensitive peptide.

In another aspect, methods provided include the use of peptide-peptidase inhibitor conjugates in therapeutically effective amounts for the treatment of a metabolic disorder. In certain embodiments, the metabolic disorder is obesity, diabetes (e.g., type 2 or non-insulin dependent diabetes, type 1 diabetes, and gestational diabetes), eating disorders, insulin-resistance syndrome, and/or cardiovascular disease. In certain embodiments, methods are provided for the reduction in nutrient availability through the administration of peptide-peptidase inhibitor conjugates. In some embodiments, methods provided include the use of peptide-peptidase inhibitor conjugates in therapeutically effective amounts for the treatment of conditions, diseases, and disorders that would benefit from a reduction in nutrient availability.

DETAILED DESCRIPTION

Figure 1A:
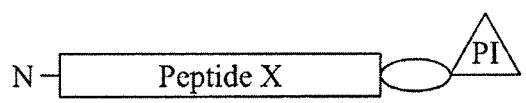
FIG. 1 depicts exemplary designs of peptide-peptidase inhibitor conjugated compounds (Peptide X rectangle, peptide; PI triangle, peptidase inhibitor; PX-1 and PX-2 rectangles, two portions of a single peptide; dark oval, linker).
Figure 1B:
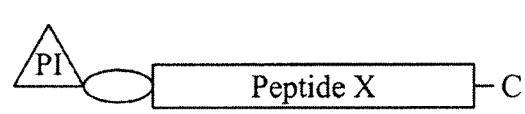
Figure 1C:
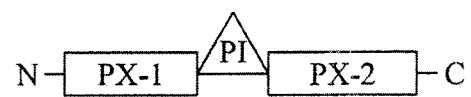
Figure 1D:
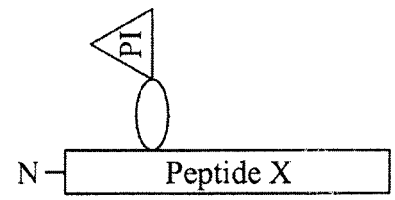

Proteolytic cleavage of peptide bonds by regulatory peptidases, as well non-specific peptidases, is the principal mechanism of inactivation and clearance of bioactive peptides and peptide drugs in vivo. We have discovered a new approach to peptide drug design in which peptidase-inhibiting motifs are strategically and covalently linked to bioactive peptides to render the peptides peptidase resistant. Such peptide-peptidase inhibitor conjugates can thus have a prolonged serum half-life relative to the unconjugated peptide. In some cases, a prolonged half-life can allow administration of less of the peptide without compromising effectiveness of the treatment. Also, the peptide in such conjugates can serve to specifically and effectively deliver the peptidase inhibitor to a site rich in peptide receptor. This will allow the peptidase inhibitor to also inhibit peptidase activity on endogenous peptide molecules at their site of action, e.g., the receptor.

In addition, in cases where the peptidases themselves are therapeutic drug targets in a disease indication or in a comorbidity, the peptide-peptidase inhibitor conjugates as described herein provide a dual mechanism of action in treating the disease or comorbidity. In these cases, the peptide-peptidase inhibitor conjugates target both a peptide receptor and a peptidase and may improve the overall therapeutic outcome with a single chemical entity.

Component peptides for use in the P-PI conjugates disclosed herein include those that are subject to degradation by specific or non-specific peptidases. Exemplary component peptides for use in the P-PI conjugates disclosed herein are subject to degradation by regulatory peptidases. In some embodiments, the peptide components are peptide hormones, peptide fragments with hormonal activity, or structural motifs of peptide hormones that impart chemical, metabolic, and/or other pharmacokinetic stability. The peptide hormones may include native peptide hormones, as well as peptide hormone agonists, analogs, derivatives, and hybrids, as known in the art and described herein. In some embodiments, the peptide components are peptide hormone antagonists, peptide fragments with hormonal antagonist activity, or structural motifs of peptide hormone antagonists that impart chemical, metabolic, and/or other pharmacokinetic stability. The peptide hormone antagonists may include peptide hormone receptor antagonists, as well as other hormone antagonists, analogs, derivatives, and hybrids thereof, as known in the art and described herein.

Component peptidase inhibitors for use in the P-PI conjugates disclosed herein include those that inhibit or reduce the activity of specific peptidases, non-specific peptidases, or both. A component peptidase inhibitor for use in the P-PI conjugates disclosed herein has such inhibitory activity whether or not it is in a P-PI conjugate complex. Exemplary component peptidase inhibitors for use in the P-PI conjugates disclosed herein are inhibitors of regulatory peptidases. The peptidase inhibitors include competitive inhibitors, non-competitive inhibitors, uncompetitive inhibitors, and irreversible active site inhibitors. The peptidase inhibitors include, but are not limited to, small chemical molecules and peptides. As described herein, component peptidase inhibitors include, but are not limited to, angiotensin converting enzyme (ACE) inhibitors, vasopeptidase inhibitors, endothelial converting enzyme inhibitors, human neutral endopeptidase inhibitors, dipeptidyl peptidase IV (DPP-IV) inhibitors, aminopeptidase inhibitors, cysteine protease inhibitors, serine protease inhibitors, and carboxypeptidase inhibitors.

The term "peptide-peptidase inhibitor conjugate" or "P-PI conjugate" refers to a complex in which at least one peptide and at least one peptidase inhibitor are linked. Such conjugate linkages include covalent and/or non-covalent linkages. Non-covalent linkages may be mediated by any non-covalent bonding force, including by hydrophobic interaction, ionic (electrostatic) bonding, metal complexation, hydrogen bonds, van der Waals attractions, or a combination of two or more different interactions. The component peptide and component peptidase inhibitor may be covalently linked together in any manner described herein or known in the art, including but not limited to, direct amide bonds or chemical linker groups.

Peptide-peptidase inhibitor conjugates include those in which the peptidase inhibitor is covalently linked to the backbone of the peptide and those in which the peptidase inhibitor is covalently linked to a side-chain of the peptide. The peptide and the peptidase inhibitor may be directly conjugated or may be conjugated through a linker molecule. Designs of peptide-peptidase inhibitor conjugated compounds include, but are not limited to, those are depicted in FIG. 1. As shown in FIG. 1, the peptide (peptide x) may be conjugated to a peptidase inhibitor motif (PI) at (a) at the carboxy-terminus of the peptide, (b) at the amino-terminus of the peptide, through (c) insertion of the PI into the polypeptide chain of the peptide, or (d) at an amino acid side chain of the peptide. In peptide-peptidase inhibitor conjugates with an Ala$^2$ in the peptide, the Ala$^2$ may be either the L or D isomer. As described herein, any of the linkages between the peptide and the peptidase inhibitor may be through a direct interaction or through a linker molecule. For example, P-PI conjugates including the GIP analog GIP(1-30)-Exendin-4(31-39) (SEQ ID NO:1) include, but are not limited to, the following:

(SEQ ID NO: 304)
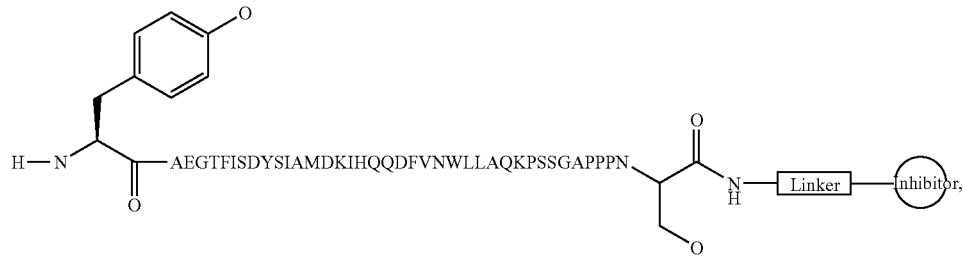
(SEQ ID NO: 304)
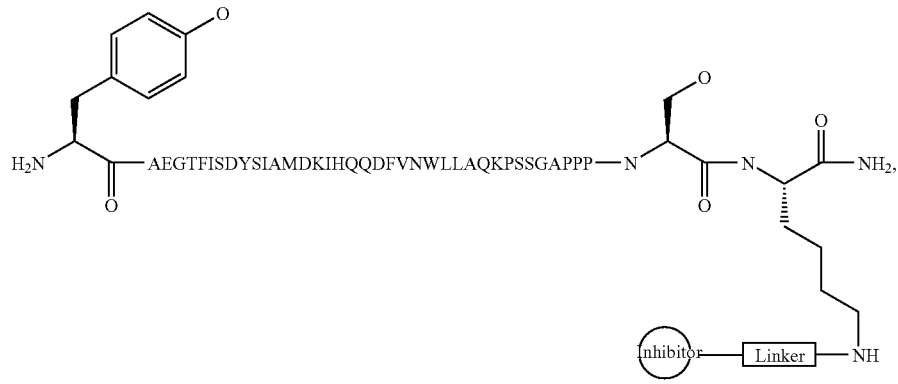
(SEQ ID NO: 304)
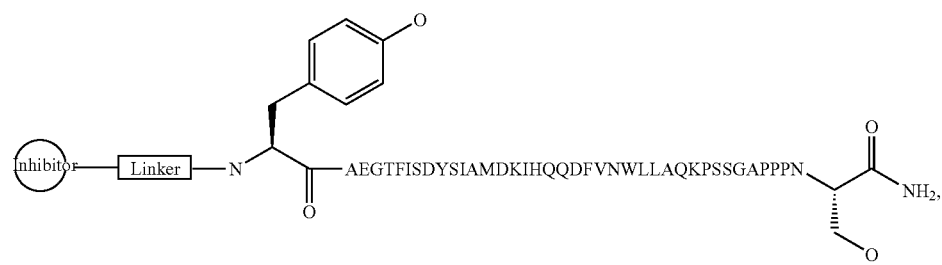
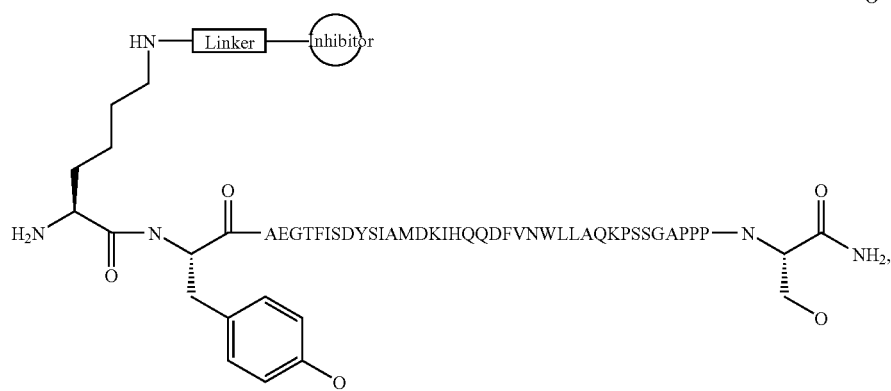
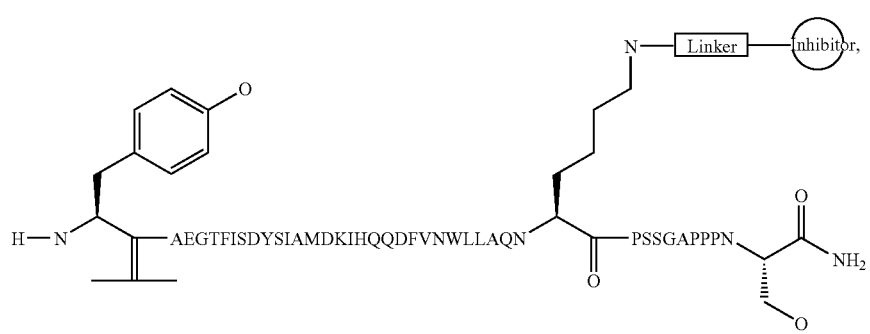

(SEQ ID NO: 307)
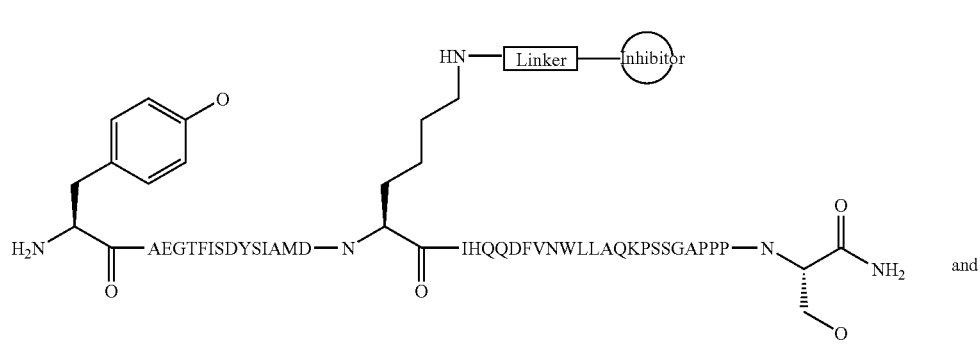
and
(SEQ ID NO: 308)
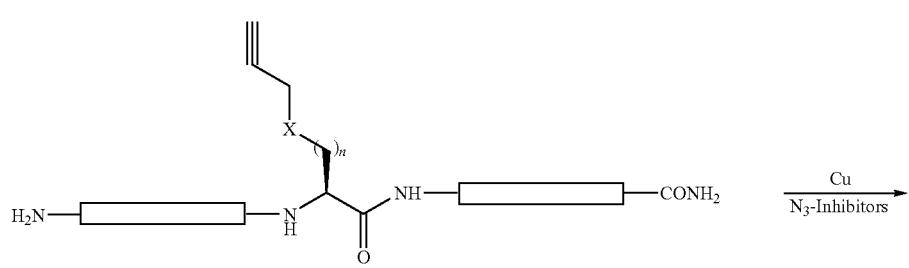
X = CH₂, O, NH, O(CO), NH(CO), (CO)O and 4-phenyloxy
n = 0-8
▯▯▯▯▯ = GIP sequence
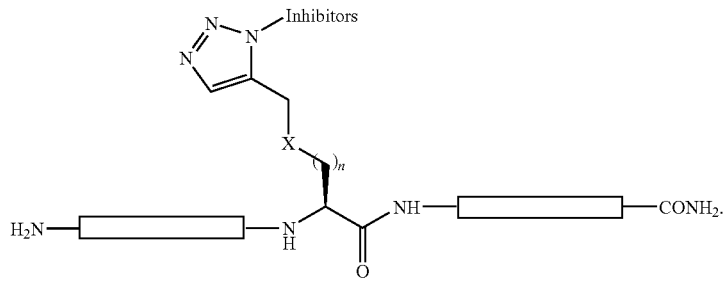
Exemplary, P-PI conjugate also including the PYY analog PYY (3-36) include, but are not limited to, the following:
Inhibitor-Linker-(SEQ ID NO:309);
(SEQ ID NO:309)-Linker-Inhibitor; and
SEQ ID No: 310
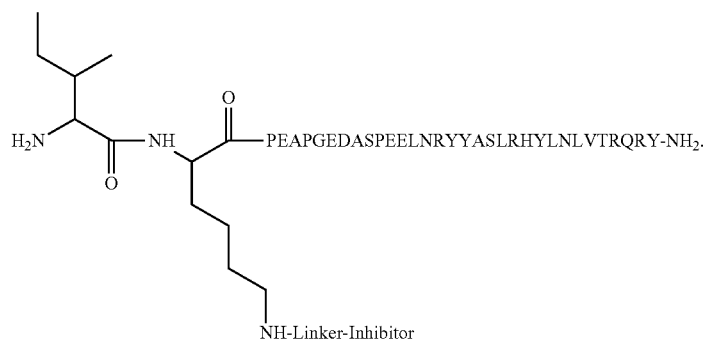

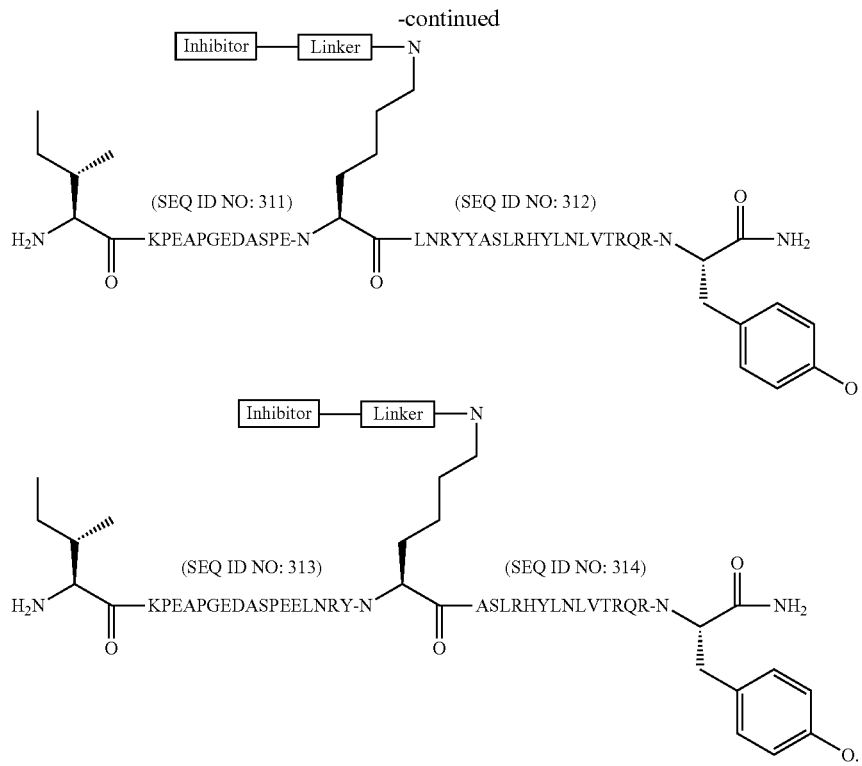

Component peptides useful in the conjugate molecules and methods described herein also include PPF peptide hormones, including PP and PYY. By "PP" is meant human pancreatic peptide polypeptide or species variants thereof, in any physiological form. Thus, the term "PP" includes both the human full length, 36 amino acid peptide, and species variations of PP, including, e.g., murine, hamster, chicken, bovine, rat, and dog PP. In this sense, "PP," "wild-type PP," and "native PP," i.e., unmodified PP, are used interchangeably. By "PYY" is meant human peptide YY polypeptide or species variants thereof, in any physiological form. Thus, the term "PYY" includes both the human full-length 36 amino acid peptide, and species variations of PYY, including e.g., murine, hamster, chicken, bovine, rat, and dog PYY. In this sense, "PYY" and "wild-type PYY" and "native PYY," i.e., unmodified PYY, are used interchangeably. Unless otherwise indicated, modifications discussed herein with reference to the PYY analog peptides are based on the 36 amino acid sequence of native human PYY.

Native PPF peptide hormones are known in art, as are functional PPF peptide agonists, analogs, derivatives, and hybrids. Certain PPF native peptides and peptide agonists, analogs, derivatives, and hybrids are described herein, however, it should be recognized that any PPF peptide or PPF agonist, PPF analog, PPF derivative, or PPF hybrid known in the art may be used in conjunction with the compositions and methods disclosed herein. Exemplary PYY component peptides include human PYY (hPYY) YPIKPEAPGEDASPEELNRYYASLRHYLNLVTRQRY (SEQ ID NO:2) and hPYY (3-36) IKPEAPGEDASPEELNRYYASLRHYLNLVTRQRY (SEQ ID NO:3). In some embodiments, the peptidase inhibitor is not linked to the Lys at position 2 of PYY (3-36) or an analogous Lys of a PYY (3-36) analog.

In one embodiment, the PPF agonists, analogs, derivatives, and hybrids have at least one biological activity of a native PPF peptide. In certain embodiments, the PPF analogs, derivatives, and hybrids are agonists of a receptor which native PPF peptide is capable of specifically binding. In one embodiment, PPF analogs and derivatives generally comprise at least two PYY motifs including a polyproline motif and C-terminal tail motif Such analogs are generally described in U.S. Pat. Application Publication No. 2006-0094653, which is herein incorporated by reference. In one embodiment, a PPF analog, derivative, or hybrid has an amino acid sequence that has about 20 or less, 15 or less, 10 or less, 5 or less, 4 or less, 3 or less, 2 or less, or 1 or less substitutions, additions, or deletions as compared to a naturally occurring PPF, such as PYY.

A "PYY motif" is generally a structural component, primary, secondary, or tertiary, of a native PPF peptide that is critical to biological activity, i.e., biological activity is substantially decreased in the absence or disturbance of the motif. PYY motifs include the N-terminal polyproline type II motif of a native PPF peptide, the type II β-turn motif of native PPF peptide, the α-helical motif at the C-terminal end of native PPF peptide, and the C-terminal tail motif of native PPF peptide. In some embodiments of PPF peptide, in the N-terminal polyproline region, amino acids corresponding to residues 5 and 8 of a native PPF peptide are generally conserved as a proline. The type II β-turn motif will generally include amino acids corresponding to residues 12-14 of a native PPF peptide. The α-helical motif can generally extend from amino acids corresponding to approximately residue 14 of a native PPF peptide to any point up to and including the C-terminal end, so long as the α-helical motif includes a sufficient number of amino acid residues such that an α-helical turn is formed in solution. The α-helical motif can also include amino acid substitutions, insertions and deletions to the native PP family sequence, so long as the α-helical turn is still formed in solution. The C-terminal tail motif generally includes amino acids corresponding to approximately the last 10 residues of a native PPF peptide. In some embodiments, the C-terminal tail motif includes amino acids corresponding to the last 7, 6, or 5 residues of a native PPF peptide, or to amino acid residues 32-35.

Exemplary PYY analogs include those with internal deletions, insertions, and substitutions in areas of the PYY molecule not corresponding to the polyproline motif and/or the C-terminal tail motif. For instance, internal deletions at positions 4, 6, 7, 9, or 10 are contemplated.

Exemplary PPF peptides of use in P-PI conjugates disclosed herein include, but are not limited to, PYY (1-36) (SEQ ID NO:2), PYY (3-36) (SEQ ID NO:3), [3]Leu-PYY (SEQ ID NO:4), [3]Val-PYY (SEQ ID NO:5), [4]Arg-PYY (SEQ ID NO:6), [4]Gln-PYY (SEQ ID NO:7), [4]Asn-PYY (SEQ ID NO:8), [25]Lys-PYY (SEQ ID NO:9), [34]Pro-PYY (SEQ ID NO:10), [34]His-PYY (SEQ ID NO:11), [1,36]Tyr-PYY (SEQ ID NO:12), [13]Pro[14]Ala-PYY (SEQ ID NO:13), [31]Leu[34]Pro-PYY (SEQ ID NO:14), [4]des-PYY (SEQ ID NO:15), PYY (1-35) (SEQ ID NO:16), PYY (1-30) (SEQ ID NO:17), PYY (1-25) (SEQ ID NO:18), PYY (1-15) (SEQ ID NO:19), PYY (1-10) (SEQ ID NO:20), PYY (2-36) (SEQ ID NO:21), PYY (4-36) (SEQ ID NO:22), and PYY (5-36) (SEQ ID NO:23). Other exemplary PPF peptides include, but are not limited to, isocap
(SEQ ID NO: 24)
PKPEAPGEDASPEELARYYASLRAYINLITRQRY, isocap
(SEQ ID NO: 25)
YPIKPEAPGEDASPEELAQYAADLRRYINMLTRQRY, (SEQ ID NO: 26)
IKPEAPGEDAPAEELARYYASLRAYINLITRQRY, (SEQ ID NO: 27)
YPIKPEAPGEDASPEELARYYSALRHYINLITRQRY, (SEQ ID NO: 28)
IKPEAPGEDASPEELARYYSALRHYINLITRQRY, isocap
(SEQ ID NO: 29)
IKPEAPGEDASPEELARYYSALRHYINLITRQRY, (SEQ ID NO: 30)
PKPEAPGEDASPEELNRYYASLRHYLNLVTRQRY, isocap
(SEQ ID NO: 31)
PKPEHPGEDASAEELARYYASLRAYINLITRQRY, (SEQ ID NO: 32)
PKPEHPGEDASPEELARYYASLRAYINLITRQRY, (SEQ ID NO: 33)
PKPEHPGEDASAEELARYYASLRAYINLITRQRY, (SEQ ID NO: 34)
PKPEAPGEDASPEELAKYYASLRAYINLITRQRY, isocap
(SEQ ID NO: 35)
PKPEAPGEDASPEELAKYYASLRAYINLITRQRY, (SEQ ID NO: 36)
PKPEHPGEDAPAEELAKYYASLRAYINLITRQRY, (SEQ ID NO: 37)
PKPEHPGEDAPAEELARYYASLRAYINLITRQRY, octanoic acid
(SEQ ID NO: 38)
IAPEAPGEDASPEELARYYASLRHYLNLVTRQRY, Octyl-Gly
(SEQ ID NO: 39)
IKPEAPGEDASPEELARYYSALRHYINLITRQRY,
and (SEQ ID NO: 40)
YPIRPEAPGEDASPEELARYYASLRHYINLITRQRY.

Exemplary PPF analogs and derivatives useful in the P-PI conjugates are disclosed in U.S. Pat. Application Publication Nos. 2006-0094653, 2006-0135747, and 2002-0141985, the contents of each is hereby incorporated by reference. Other exemplary PPF analogs and derivatives include those described in PCT Publication Nos. WO 03/026591, WO 03/057235, and WO 2005/077094, each are herein incorporated by reference in their entirety.

Component peptide hormones useful in the compositions and methods disclosed herein include the family of incretin hormones and incretin mimetics including, but not limited to GLP-1, GLP-2, oxyntomodulins, and exendins. Component peptide hormones useful in the compositions and methods disclosed herein include GLP-1 peptide hormones. As used herein, "GLP-1" means human glucagon like peptide-1 or species variants thereof, in any physiological form. The term "GLP-1" includes human GLP-1(1-37), GLP-1(7-37), and GLP-1(7-36)amide, with reference to the full length human GLP-1(1-37), and species variations of GLP-1, including, e.g., murine, hamster, chicken, bovine, rat, and dog GLP-1. In this sense, "GLP-1," "wild-type GLP-1," and "native GLP-1," i.e., unmodified GLP-1, are used interchangeably.

Native GLP-1 peptide hormones, including hGLP-1(1-37) HDEFERHAEGTFTSDVSSYLEGQAAKE-FIAWLVKGRG (SEQ ID NO:41), hGLP-1(7-37) HAEGT-FTSDVSSYLEGQAAKEFIAWLVKGRG (SEQ ID NO:42), hGLP-1(7-36)amide HAEGTFTSDVSSYLEGQAAKEFI-AWLVKGR-NH$_2$ (SEQ ID NO:43), and frog GLP-1 (fGLP-1) HAEGTYTNDVTEYLEEKAAKEFIEW-LIKGKPKKIRYS-OH (SEQ ID NO:44) and HAEGTFTSDVTQQLDEKAAKEFIDWLINGGPSKEIIS-OH (SEQ ID NO:45), are known in art, as are functional peptide analogs and derivatives. As used herein, GLP-1 refers to all native forms of GLP-1 peptide hormones. Although certain GLP-1 native peptides, peptide analogs, derivatives, and hybrids are described herein, it should be recognized that any known GLP-1 peptide, GLP-1 analog, GLP-1 derivative, or GLP-1 hybrid that exhibits biological activity known in the art may be used in conjunction with the compositions and methods disclosed herein.

In one embodiment, the GLP-1 peptide analogs, derivatives, and hybrids have at least one hormonal activity of a native GLP-1 peptide. In certain embodiments, the GLP-1 peptide analogs, derivatives, and hybrids are agonists of a receptor to which a native GLP-1 peptide is capable of specifically binding. Such GLP-1 analogs may be amidated as known in the art or may be in the acid form unless otherwise specified.

In one embodiment, a GLP-1 peptide analog, derivative, or hybrid can have one or more amino acid substitutions, deletions, inversion, or additions compared to a native or naturally occurring GLP-1. Thus, GLP-1 peptide analogs, derivatives, and hybrids can have an amino acid sequence that has one or more amino acid substitutions, additions or deletions as compared with a naturally occurring GLP-1. In one embodiment, a GLP-1 peptide analog, derivative, or hybrid has an amino acid sequence that has about 25 or less, 20 or less, 15 or less, 10 or less, 5 or less, 4 or less, 3 or less, 2 or less, or 1 or less substitutions, additions, or deletions as compared to a naturally occurring GLP-1, such as GLP-1(7-37).

Exemplary GLP-1 peptide analogs and derivatives include those described herein and known in the art. Exemplary GLP-1 analogs include, but are not limited to, GLP-1(7-35) (SEQ ID NO:46); $^9$Gln-GLP-1(7-37) (SEQ ID NO:47); D-$^9$Gln-GLP-1(7-37) (SEQ ID NO:48); $^{16}$Thr-$^{18}$Lys-GLP-1(7-37) (SEQ ID NO:49); $^{18}$Lys-GLP-1(7-37) (SEQ ID NO:50); $^8$Gly-GLP-1 (7-36) (SEQ ID NO:51); $^8$Aib-GLP-1 (7-36) (SEQ ID NO:297); acetyl-$^9$Lys-GLP-1(7-37) (SEQ ID NO:52); $^9$Thr-GLP-1(7-37) (SEQ ID NO:53); D-$^9$Thr-GLP-1 (7-37) (SEQ ID NO:54); $^9$Asn-GLP-1 (7-37) (SEQ ID NO:55); D-$^9$Asn-GLP-1(7-37) (SEQ ID NO:56); $^{22}$Ser$^{23}$Arg$^{24}$Arg$^{26}$Gln-GLP-1(7-37) (SEQ ID NO:57); $^{23}$Arg-GLP-1(7-37) (SEQ ID NO:58); and $^{24}$Arg-GLP-1(7-37) (SEQ ID NO:59). Exemplary GLP-1 analogs and derivatives useful in the P-PI conjugates are disclosed in U.S. Pat. Nos. 5,188,666, 5,512,549, 5,545,618, and 6,747,006, and in PCT publication Nos. WO 91/11457 and WO 99/64061, each of which is incorporated herein by reference.

Component peptide hormones useful in the compositions and methods disclosed herein also include GLP-2 peptide hormones. As used herein, "GLP-2" means human glucagon like peptide-2 or species variants thereof, in any physiological form. GLP-2 is a 33 amino acid peptide, co-secreted along with GLP-1 from intestinal endocrine cells in the small and large intestine. Native GLP-2 peptide hormones, e.g., rat GLP-2 and its homologous including ox GLP-2, porcine GLP-2, degu GLP-2, bovine GLP-2, guinea pig GLP-2, hamster GLP-2, human GLP-2, rainbow trout GLP-2, and chicken GLP-2, are known in art, as are functional peptide analogs and derivatives. The amino acid sequence of human GLP-2 is HADGSFSDEMNTILDNLAARDFINWLIETKITD (SEQ ID NO:60) and the amino acid sequence of frog GLP-2 is HAEGTFTNDMTNYLEEKAAKEFVGWLIKGRP (SEQ ID NO:61). Although certain GLP-2 native peptides, peptide analogs, derivatives, and hybrids are described herein, it should be recognized that any known GLP-2 peptides, GLP-2 analogs, GLP-2 derivatives, and GLP-2 hybrids that exhibit biological activity known in the art may be used in conjunction with the compositions and methods disclosed herein.

In one embodiment, the GLP-2 peptide analogs, derivatives, and hybrids have at least one hormonal activity of a native GLP-2 peptide. In certain embodiments, the GLP-2 peptide analogs, derivatives, and hybrids are agonists of a receptor to which a native GLP-2 peptide is capable of specifically binding. In some embodiments, GLP-2 analogs, derivatives, and hybrids include rat or human GLP-2 altered at position 2 to confer DPP-IV resistance by substituting a Gly for an Ala. Exemplary GLP-2 peptide analogs and derivatives useful in the P-PI conjugates include those described in U.S. Pat. Nos. 5,789,379 and 5,990,077, both of which are hereby incorporated by reference.

In one embodiment, a GLP-2 peptide analog, derivative, or hybrid can have one or more amino acid substitutions, deletions, inversion, or additions compared to a native or naturally occurring exendin. Thus, GLP-2 peptide analogs, derivatives, and hybrids can have an amino acid sequence that has one or more amino acid substitutions, additions or deletions as compared with a naturally occurring GLP-2. In one embodiment, a GLP-2 peptide analog, derivative, or hybrid has an amino acid sequence that has about 25 or less, 20 or less, 15 or less, 10 or less, 5 or less, 4 or less, 3 or less, 2 or less, or 1 or less substitutions, additions, or deletions as compared to a naturally occurring GLP-2.

Component peptide hormones useful in the compositions and methods disclosed herein also include oxyntomodulin (OXM) peptide hormones. As used herein, "OXM" means human oxyntomodulin or species variants thereof in any physiological form. OXM is a 37 amino acid peptide that contains the 29 amino acid sequence of glucagon followed by an 8 amino acid carboxyterminal extension. For example, the amino acid sequence of human OXM is HSQGTFTSDYS-KYLDSRRAQDFVQWLMNTKRNRNNIA (SEQ ID NO:62). Native OXM peptide hormones are known in art, as are functional peptide analogs and derivatives. Although certain native OXM peptides, peptide analogs, derivatives, and hybrids are described herein, it should be recognized that any known OXM peptides, OXM analogs, OXM derivatives, and OXM hybrids that exhibit biological activity known in the art may be used in conjunction with the compositions and methods disclosed herein. In one embodiment, the OXM peptide analogs, derivatives, and hybrids have at least one hormonal activity of a native OXM peptide. In certain embodiments, the OXM peptide analogs, derivatives, and hybrids are agonists of a receptor to which a native OXM peptide is capable of specifically binding.

In one embodiment, an OXM peptide analog, derivative, or hybrid can have one or more amino acid substitutions, deletions, inversion, or additions compared to a native or naturally occurring OXM. Thus, OXM peptide analogs, derivatives, and hybrids can have an amino acid sequence that has one or more amino acid substitutions, additions or deletions as compared with a naturally occurring OXM. In one embodiment, an OXM peptide analog, derivative, or hybrid has an amino acid sequence that has about 30 or less, 25 or less, 20 or less, 15 or less, 10 or less, 5 or less, 4 or less, 3 or less, 2 or less, or 1 or less substitutions, additions, or deletions as compared to a naturally occurring OXM.

Component peptide hormones useful in the compositions and methods disclosed herein also include exendin peptide hormones. By "exendin" is meant a peptide hormone found in the saliva of the Gila-monster, a lizard endogenous to Arizona, and the Mexican Beaded Lizard, as well as species variants thereof. Exendin-3 is present in the saliva of *Heloderma horridum*, and exendin-4 is present in the saliva of *Heloderma suspectum* (Eng et al. (1990) *J. Biol. Chem.* 265: 20259-20262; Eng. et al. (1992) *J. Biol. Chem.* 267:7402-7405). The exendins have some sequence similarity to several members of the glucagon-like peptide family, with the highest identity, 53%, being to GLP-1 (Goke et al. (1993) *J. Biol. Chem.* 268:19650-19555). In this sense, "exendin," "wild-type exendin," and "native exendin," i.e., unmodified exendin, are used interchangeably.

Native exendin peptide hormones are known in art, as are functional exendin peptide analogs, derivatives, and hybrids. The amino acid sequence of exendin-3 is HSDGTFTSDL-SKQMEEEAVRLFIEWLKNGGPSSGAPPPS (SEQ ID NO:63) and the amino acid sequence of exendin-4 is HGEGT-FTSDLSKQMEEEAVRLFIEWLKNGGP SSGAPPPS (SEQ ID NO:64). Although certain native exendin peptides, peptide analogs, derivatives and hybrids are described herein, it should be recognized that any known exendin peptides, exendin analogs, exendin derivatives, and exendin hybrids that exhibit biological activity known in the art may be used in conjunction with the compositions and methods disclosed herein.

In one embodiment, the exendin peptide analogs, derivatives, and hybrids have at least one hormonal activity of a native exendin peptide. In certain embodiments, the exendin peptide analogs, derivatives, and hybrids are agonists of a receptor to which a native exendin peptide is capable of specifically binding. Exendin analogs, derivatives, and hybrids may be amidated as known in the art or may be in the acid form unless otherwise specified. In one embodiment, an exendin analog, derivative, or hybrid can have one or more amino acid substitutions, deletions, inversion, or additions compared to a native or naturally occurring exendin. Thus, exendin analogs, derivatives, and hybrids can have an amino acid sequence that has one or more amino acid substitutions, additions or deletions as compared with a naturally occurring exendin, for example, exendin-4. In one embodiment, an exendin analog, derivative, or hybrid has an amino acid sequence that has about 30 or less, 25 or less, 20 or less, 15 or less, 10 or less, 5 or less, 4 or less, 3 or less, 2 or less, or 1 or less substitutions, additions, or deletions as compared to a naturally occurring exendin, such as exendin-4.

Exemplary exendin analogs include, but are not limited to, exendin-4(1-30) (SEQ ID NO:65), exendin-4(1-28) (SEQ ID NO:66), $^{14}$Leu$^{25}$Phe-exendin-4(SEQ ID NO:67), $^{5}$Ala$^{14}$Leu$^{25}$Phe-exendin-4(SEQ ID NO:68), $^{14}$Leu$^{22}$Ala$^{25}$Phe-exendin-4(SEQ ID NO:69), $^{14}$Leu-exendin-4(1-28) (SEQ ID NO:70), $^{14}$Leu$^{25}$Phe exendin-4(1-28) (SEQ ID NO:71), and $^{14}$Leu, $^{22}$Ala, $^{25}$Phe exendin-4 (1-28) (SEQ ID NO:73). Other exemplary exendin analogs and derivatives are disclosed in U.S. Pat. Nos. 6,858,576, 6,956,026 and 6,989,366, each of which is incorporated herein by reference.

Additional exemplary exendin agonists are described in U.S. patent application Ser. No. 10/181,102 and PCT Publication No. WO 99/07404, which are herein incorporated by reference including, for example, compounds of the formula (I), formula (II) and formula (III) of these applications.

Other exendin agonists are described in U.S. patent application Ser. No. 09/554,533 and PCT Publication No. WO 99/25727, which are herein incorporated by reference. Still other exendin agonists are described in U.S. patent application Ser. No. 09/554,531 and PCT Publication No. WO 99/25728, both of which are herein incorporated by reference. Still other exendin agonists are described in U.S. Pat. Application Publication Nos. 2004-0209803, 2004-0266692, 2005-0043238, and 2005-0215469, each of which is hereby incorporated by reference.

Component peptide hormones useful in the compositions and methods disclosed herein also include GIP peptide hormones. By "GIP" is meant a gastric inhibitory peptide or glucose-dependent insulinotropic peptide hormone obtained or derived from any species. The term "GIP", with reference to the full length human GIP(1-42), includes hGIP(1-42) acid, hGIP(1-42) amide, GIP(1-30) acid, GIP(1-30) amide, GIP(1-14), GIP(19-30), GIP(1-11) and species variations of GIP, including, e.g., murine, hamster, chicken, bovine, rat, and dog. The amino acid sequence of human GIP(hGIP) is YAEGTFISDYSIAMDKIHQQDFVNWL-LAQKGKKNDWKHNITQ (SEQ ID NO:74). The amino acid sequence of rat GIP is YAEGTFISDYSIAMDKIRQQD-FVNWLLAQKGKKNDWKHNLTQ (SEQ ID NO:75). The amino acid sequence of mouse GIP is YAEGTFISDYSIAM-DKIRQQDFVNWLLAQ RGKKSDWKHNITQ (SEQ ID NO:76). The amino acid sequence of pig GIP is YAEGTFIS-DYSIAMDKIRQQDFVNWLLAQKGKKSDWKHNITQ (SEQ ID NO:77). The amino acid sequence of bovine GIP is YAEGTFISDYSIAMDKIRQQDFVNWL-LAQKGKKSDWIHNITQ (SEQ ID NO:78). In this sense, "GIP," "wild-type GIP," and "native GIP," i.e., unmodified GIP, are used interchangeably.

Native GIP peptide hormones are known in art, as are functional peptide analogs, derivatives, and hybrids. Although certain native GIP peptides, GIP peptide analogs, derivatives, and hybrids are described herein, it should be recognized that any known GIP peptides, GIP analogs, GIP derivatives, and GIP hybrids that exhibit biological activity known in the art may be used in the compositions and methods disclosed herein. In one embodiment, the GIP peptide analogs, derivatives, and hybrids have at least one hormonal activity of a native GIP peptide. In certain embodiments, the GIP peptide analogs, derivatives, and hybrids are agonists of a receptor to which a native GIP peptide is capable of specifically binding.

In some embodiments, GIP analogs, derivatives, of hybrids of use include those that correspond to at least about 65% of human GIP(1-42) (SEQ ID NO:87) or hGIP(1-30) (SEQ ID NO:79) and have GIP activity. Exemplary GIP analogs having at least 50% sequence identity to native GIP(1-30), GIP (1-26)(SEQ ID NO:80), GIP(1-39)(SEQ ID NO:85), GIP(1-14)(SEQ ID NO:82), GIP(19-30)(SEQ ID NO:84), GIP(19-26), GIP(19-39)(SEQ ID NO:86), or GIP(1-42) (SEQ ID NO:87) over the entire length of each of the above molecules are further embodiments for use in the compositions and methods described herein. In some embodiments, GIP analogs, derivatives, or hybrids of use include those that comprise at least 15 amino acid residues from the N-terminal end of GIP(1-42), have a least one amino acid substitution or modification at position 1-3, and are biologically active. This includes modification by fatty acid addition at an epsilon amino group of at least one lysine residue, either present in or introduced into the molecule. Such modifications include Tyr1-glucitol of a GIP, for example Tyr1-glucitol GIP(1-42) or Tyr1-glucitol GIP(1-30). GIP analogs of interest include those comprising a substitution or modification selected from the group comprising D-amino acid substitutions in 1, 2 and/or 3 positions and/or N-terminal glycation, alkylation, acetylation or acylation, or other N-terminal modifications described herein. Of further interest are analogs wherein the amino acid in the 2 or 3 position is substituted by lysine, serine, 4-amino butyric amino acid, Aib, D-alanine, sarcosine or proline.

In one embodiment, a GIP analog, derivative, or hybrid can have one or more amino acid substitutions, deletions, inversion, or additions compared to a native or naturally occurring GIP. Thus, GIP analogs, derivatives, and hybrids can have an amino acid sequence that has one or more amino acid substitutions, additions or deletions as compared with a naturally occurring GIP. In one embodiment, a GIP analog, derivative, or hybrid has an amino acid sequence that has about 30 or less, 25 or less, 20 or less, 15 or less, 10 or less, 5 or less, 4 or less, 3 or less, 2 or less, or 1 or less substitutions, additions, or deletions as compared to a naturally occurring GIP.

Exemplary GIP analogs include, but are not limited to, hGIP(1-30) YAEGTFISDYSIAMDKIHQQDFVNWL-LAQK (SEQ ID NO:79); GIP(1-26) YAEGTFISDYSIAMD-KIHQQDFVNWL (SEQ ID NO:80); GIP(1-14) YAEGTFIS-DYSIAM (SEQ ID NO:81); GIP(1-11) YAEGTFISDYS (SEQ ID NO:82); GIP(19-30) QQDFVNWLLAQK (SEQ ID NO:83); GIP(19-26) QQDFVNWL (SEQ ID NO:84); GIP(1-39) YAEGTFISDYSIAMDKIHQQDFVNWL-LAQKGKKNDWKHN (SEQ ID NO:85); GIP(19-39) QQD-FVNWLLAQKGKKNDWKHN (SEQ ID NO:86); GIP(1-42) YAEGTFISDYSIAMDKIHQQDFVNWL-LAQKGKKNDWKHNITQ (SEQ ID NO:87); D$^2$-Ala-GIP (1-42) (SEQ ID NO:88); D-Ala$^2$-GIP(1-30) (SEQ ID NO:293); D-Ala$^2$Leu$^{14}$-GIP(1-30) (SEQ ID NO:294); and Leu$^{14}$-GIP(1-30) (SEQ ID NO:295). Other exemplary GIP peptide analogs and derivatives are disclosed in U.S. Pat. Nos. 6,410,508 and 6,921,748, in U.S. Pat. Application Publication Nos. 2003/0232761, 2005/0272652, and 2005/0277590, each of which is incorporated herein by reference.

Component peptide hormones useful in the compositions and methods disclosed herein include amylin family peptide hormones including amylin, adrenomedullin ("ADM"), calcitonin ("CT"), calcitonin gene related peptide ("CGRP"), intermedin (also known as "AFP-6") and related peptides. Native amylin family peptide hormones are known in art, as are functional amylin family peptide analogs, derivatives, and hybrids. Although certain native amylin family peptides, analogs, derivatives, and hybrids are described herein, it should be recognized that any known amylin family peptides, amylin family peptide analogs, amylin family peptide derivatives and amylin family peptide hybrids that exhibit hormonal activity known in the art may be used in the compositions and methods disclosed herein.

Component peptide hormones useful in the compositions and methods disclosed herein also include amylin peptide hormones. By "amylin" is meant the human peptide hormone referred to as amylin and species variations thereof. Amylin is a 37-amino acid polypeptide hormone normally co-secreted with insulin by pancreatic beta cells in response to nutrient intake (Koda et al. (1992) *Lancet* 339:1179-1180). In this sense, "amylin," "wild-type amylin," and "native amylin," i.e., unmodified amylin, are used interchangeably.

Native amylin peptides are known in the art, as are functional amylin peptide analogs, derivatives, and hybrids. The amino acid sequence of human amylin (h-amylin) is KCNTATCATQRLANFLVHSSNNFGAILSSTNVGSNTY (SEQ ID NO:89) and the amino acid sequence of rat amylin (r-amylin) is KCNTATCATQRLANFLVRSSNNLGPVLPPTNVGSNTY (SEQ ID NO:90). Although certain native amylin peptides, peptide analogs, derivatives, and hybrids are described herein, it should be recognized that any known amylin peptides, amylin peptide analogs, amylin peptide derivatives and amylin peptide hybrids that exhibit hormonal activity known in the art may be used in the compositions and methods disclosed herein.

In one embodiment, the amylin peptide analogs, derivatives, and hybrids have at least one hormonal activity of native amylin peptide. In certain embodiments, the amylin peptide analogs, derivatives, and hybrids are agonists of a receptor which native amylin is capable of specifically binding. Amylin peptide analogs, derivatives, and hybrids may be amidated as known in the art or may be in the acid form.

In one embodiment, an amylin analog, derivative, or hybrid can have one or more amino acid substitutions, deletions, inversion, or additions compared to a native or naturally occurring amylin. Thus, amylin analogs, derivatives, and hybrids can have an amino acid sequence that has one or more amino acid substitutions, additions or deletions as compared with a naturally occurring amylin. In one embodiment, an amylin analog, derivative, or hybrid has an amino acid sequence that has about 30 or less, 25 or less, 20 or less, 15 or less, 10 or less, 5 or less, 4 or less, 3 or less, 2 or less, or 1 or less substitutions, additions, or deletions as compared to a naturally occurring amylin.

Amylin analogs contemplated for use in the compositions and methods disclosed herein include those described in U.S. Pat. Nos. 5,686,411, 6,114,304, and 6,410,511, which are herein incorporated by reference in their entirety. Exemplary of such compounds include those having the formula:

(SEQ ID NO: 91)
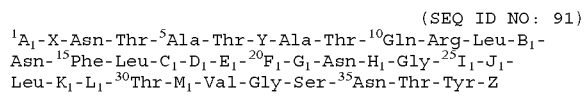

wherein $A_1$ is Lys, Ala, Ser or hydrogen; $B_1$ is Ala, Ser or Thr; $C_1$ is Val, Leu or Ile; $D_1$ is H is or Arg; $E_1$ is Ser or Thr; $F_1$ is Ser, Thr, Gln or Asn; $G_1$ is Asn, Gln or H is; $H_1$ is Phe, Leu or Tyr; $I_1$ is Ala or Pro; $J_1$ is Ile, Val, Ala or Leu; $K_1$ is Ser, Pro, Leu, Ile or Thr; $L_1$ is Ser, Pro or Thr; $M_1$ is Asn, Asp, or Gln; X and Y are independently selected amino acid residues having side chains which are chemically bonded to each other to form an intramolecular linkage; and Z is hydroxy, amino, alkylamino, dialkylamino, cycloalkylamino, arylamino, aralkylamino, alkyloxy, aryloxy or aralkyloxy. Exemplary amylin analogs include but are not limited to, des-$^1$Lys-h-amylin (SEQ ID NO:92), $^{28}$Pro-h-amylin (SEQ ID NO:93), $^{25,28,29}$Pro-h-amylin (SEQ ID NO:94), $^{18}$Arg$^{25,28}$Pro-h-amylin (SEQ ID NO:95), des-$^1$Lys$^{18}$Arg$^{25,28}$pro-h-amylin (SEQ ID NO:96), $^{25}$Pro$^{26}$Val$^{28,29}$ Pro-h-amylin (SEQ ID NO:97), $^{18}$Arg$^{25,28,29}$Pro-h-amylin (SEQ ID NO:98), des-$^1$-Lys$^{18}$Arg$^{25,28,29}$pro-h-amylin (SEQ ID NO:99), des-$^1$ Lys$^{25,}$ $_{28,29}$Pro-h-amylin (SEQ ID NO:100), $^{23}$Leu$^{25}$Pro$^{26}$Val$^{28,}$ $_{29}$Pro-h-amylin (SEQ ID NO:101), $^{23}$Leu$^{25}$Pro$^{26}$Val$^{28}$Pro-h-amylin (SEQ ID NO:102), des-$^1$Lys$^{23}$Leu$^{25}$Pro$^{26}$Val$^{28}$Pro-h-amylin (SEQ ID NO:103), $^{18}$Arg$^{23}$Leu$^{25}$Pro$^{26}$Val$^{28}$Pro-h-amylin (SEQ ID NO:104), $^{18}$Arg$^{23}$Leu$^{25,28,29}$Pro-h-amylin (SEQ ID NO:105), $^{18}$Arg$^{23}$Leu$^{25,28}$Pro-h-amylin (SEQ ID NO:106), $^{17}$Ile$^{23}$Leu$^{25,28,29}$Pro-h-amylin (SEQ ID NO:107), $^{17}$Ile$^{25,28,29}$Pro-h-amylin (SEQ ID NO:108), des-$^1$Lys$^{17}$Ile$^{23}$Leu$^{25,28,29}$Pro-h-amylin (SEQ ID NO:109), $^{17}$Ile$^{18}$Arg$^{23}$Leu-h-amylin (SEQ ID NO:110), $^{17}$Ile$^{18}$Arg$^{23}$Leu$^{26}$Val$^{29}$Pro-h-amylin (SEQ ID NO:111), $^{17}$Ile$^{18}$Arg$^{23}$Leu$^{25}$Pro$^{26}$ Val$^{28,29}$Pro-h-amylin (SEQ ID NO:112), $^{13}$Thr$^{21}$His$^{23}$Leu$^{26}$Ala$^{28}$Leu$^{29}$Pro$^{31}$Asp-h-amylin (SEQ ID NO:113), $^{13}$Thr$^{21}$H is$^{23}$Leu$^{26}$Ala$^{29}$Pro$^{31}$Asp-h-amylin (SEQ ID NO:114), des-$^1$Lys$^{13}$Thr$^{21}$H is$^{23}$Leu$^{26}$Ala$^{28}$Pro$^{31}$Asp-h-amylin (SEQ ID NO:115), $^{13}$Thr$^{18}$Arg$^{21}$His$^{23}$Leu$^{26}$Ala$^{29}$Pro$^{31}$Asp-h-amylin (SEQ ID NO:116), $^{13}$Thr$^{18}$Arg$^{21}$H is$^{23}$Leu$^{28,29}$Pro$^{31}$Asp-h-amylin (SEQ ID NO:117), and $^{13}$Thr$^{18}$Arg$^{21}$H is$^{23}$Leu$^{25}$Pro$^{26}$Ala$^{28,}$ $_{29}$Pro$^{31}$Asp-h-amylin (SEQ ID NO:118).

In some embodiments, amylin analogs and derivatives contemplated for use in the compositions and methods disclosed herein include those described in U.S. Pat. Application No. 60/543,275 and in PCT Publication No. WO 2006/083254, each of which is incorporated herein by reference. Such amylin analogs and derivatives have at least a loop region of amylin or calcitonin and analogs thereof, an α helix region of at least a portion of an α helix region of calcitonin or analogs thereof or an α helix region having a portion of an amylin α helix region and a calcitonin a helix region or their respective analogs, and a C-terminal tail of amylin or calcitonin or analogs thereof, with the proviso that the C-terminal tail of calcitonin or a calcitonin analog is not proline, hydroxyproline (Hyp), homoserine (Hse) or derivatives of Hse. Accordingly, such peptides are referred to herein as LHC (loop helix C-terminus) peptides. Exemplary LHC amylin peptides include, but are not limited to, KCNTATCVLGRLSQELHRLQTYPRTNTGSNTY (SEQ ID NO:119), Isocaproyl-CNTATCVLGRLSQELHRLQTYPRTNTGSNTY (SEQ ID NO:120), CSNLSTCATQRLANELVRLQTYPRTNVGSNTY (SEQ ID NO:121), KCNTATCATQRLANELVRLQTYPRTNVGSNTY (SEQ ID NO:122), and CSNLSTCVLGRLSQELHRLQTYPRTNTGSNTY (SEQ ID NO:123). Other exemplary amylin analogs and derivatives are disclosed in U.S. Pat. Nos. 6,087,334 and 6,936,584, both of which are incorporated herein by reference.

Component peptides useful in the compositions and methods disclosed herein also include amylin antagonist peptides, including for example, those described in U.S. Pat. Nos. 5,625,032 and 5,580,953, which are incorporated herein by reference. Amylin antagonists may be acetylated or non-acetylated at the N-terminus and include acid as well as amide forms of the molecule. Examples of amylin antagonists include, but are not limited to, acetyl-ATQRLANELVRLQ-TYPRTNVGSNTY (SEQ ID NO:124); ATQQLANQLVR-LQTYPRTNVGSNTY (SEQ ID NO:125); ATQLLAN-QLVRLQTYPRTNVGSNTY (SEQ ID NO:126); ATQRLANQLVRLQTYPRTNVGSNTY (SEQ ID NO:127); ATQLLANELVRLQTYPRTNVGSNTY (SEQ ID NO:128); and ATQQLANELVRLQTYPRTNVGSNTY (SEQ ID NO:129).

Component peptide hormones useful in the compositions and methods disclosed herein also include ADM peptides. By "adrenomedullin" or "ADM" is meant the human peptide hormone and species variants thereof. ADM is generated from a 185 amino acid preprohormone through consecutive enzymatic cleavage and amidation. This process culminates in the liberation of a 52 amino acid bioactive peptide. Any known ADM peptide, analog, derivative, or hybrid that exhibits biological activity known in the art may be used in conjunction with the compositions and methods disclosed herein. In one embodiment, the ADM peptides, analogs, derivatives, and hybrids have at least one hormonal activity of native ADM peptide. In certain embodiments, the ADM peptides, analogs, derivatives, and hybrids are agonists of a receptor which native ADM is capable of specifically binding.

Component peptide hormones useful in the compositions and methods disclosed herein also include calcitonin (CT) peptides. By "calcitonin" or "CT" is meant the human peptide hormone and species variants thereof, including salmon calcitonin (sCT). CT is a 32 amino acid peptide cleaved from a larger prohormone. It contains a single disulfide bond, which causes the amino terminus to assume the shape of a ring. Native CT peptides are known in the art, as are functional CT peptide analogs, derivatives, and hybrids. The amino acid sequence of human CT (hCT) is CGNLSTCMLGTYTQD-FNKFHTFPQTAIGVGAP (SEQ ID NO:130) and the amino acid sequence of sCT is CSNLSTCVLGKLSQELHKLQ-TYPRTNTGSGTP (SEQ ID NO:131). Any CT peptide analog, derivative, or hybrid known in the art that exhibits biological activity known in the art may be used in conjunction with the compositions and methods disclosed herein. In one embodiment, the CT peptides, analogs, derivatives, and hybrids have at least one hormonal activity of native CT peptide. In certain embodiments, the CT peptides, analogs, derivatives, and hybrids are agonists of a receptor which native CT is capable of specifically binding. CT peptide analogs, derivatives, and hybrids may be amidated as known in the art or may be in the acid form.

In one embodiment, a CT analog, derivative, or hybrid can have one or more amino acid substitutions, deletions, inversion, or additions compared to a native or naturally occurring CT. Thus, CT analogs, derivatives, and hybrids can have an amino acid sequence that has one or more amino acid substitutions, additions or deletions as compared with a naturally occurring CT, for example, sCT. In one embodiment, an CT analog, derivative, or hybrid has an amino acid sequence that has about 25 or less, 20 or less, 15 or less, 10 or less, 5 or less, 4 or less, 3 or less, 2 or less, or 1 or less substitutions, additions, or deletions as compared to a naturally occurring CT, such as sCT.

Exemplary CT analogs include, but are not limited to, $^{8}$Gly-CT (SEQ ID NO:132), $^{22}$Leu-CT (SEQ ID NO:133), $^{2}$Gly$^{3}$Ser$^{8}$Gly$^{22}$des-Tyr-CT (SEQ ID NO:134), $^{14}$Gln-sCT (SEQ ID NO:135), $^{18}$Arg-sCT (SEQ ID NO:136), $^{11,18}$Arg-sCT (SEQ ID NO:137), $^{14}$Gln$^{18}$Arg-sCT (SEQ ID NO:138), and $^{14}$Gln$^{11,18}$Arg-sCT (SEQ ID NO:139). Other exemplary CT analogs and derivatives are disclosed in U.S. Pat. Nos. 4,652,627, 4,606,856, 4,604,238, 4,597,900, 4,537,716, 4,497,731, 4,495,097, 4,444,981, 4,414,149, 4,401,593, and 4,397,780, which are hereby incorporated by reference.

Component peptide hormones useful in the compositions and methods disclosed herein also include calcitonin gene related peptide (CGRP). By "calcitonin gene related peptide" or "CGRP" is meant the human peptide hormone and species variants thereof, in any physiological form. CGRP is a 37 amino acid peptide and is encoded and expressed from alternative splicing of calcitonin pre-mRNA. Any CGRP, CGRP analog, derivative, or hybrid known in the art that exhibits biological activity known in the art may be used in conjunction with the compositions and methods disclosed herein. In one embodiment, the CGRP peptides, analogs, derivatives, and hybrids have at least one hormonal activity of native CGRP. In certain embodiments, the CGRP peptides, analogs, derivatives, and hybrids are agonists of a receptor which native CGRP is capable of specifically binding. CGRP peptide analogs, derivatives, and hybrids may be amidated as known in the art or may be in the acid form.

In one embodiment, a CGRP analog, derivative, or hybrid can have one or more amino acid substitutions, deletions, inversion, or additions compared to a native or naturally occurring CGRP. Thus, CGRP analogs, derivatives, and hybrids can have an amino acid sequence that has one or more amino acid substitutions, additions or deletions as compared with a naturally occurring CGRP. In one embodiment, a CGRP analog, derivative, or hybrid has an amino acid sequence that has about 30 or less, 25 or less, 20 or less, 15 or less, 10 or less, 5 or less, 4 or less, 3 or less, 2 or less, or 1 or less substitutions, additions, or deletions as compared to a naturally occurring CGRP.

Exemplary CGRP analogs include, but are not limited to, $^{36}$D-Ser-CGRP (SEQ ID NO:140), $^{36}$D-Thr-CGRP (SEQ ID NO:141), $^{36}$D-Asp-CGRP (SEQ ID NO:142), $^{36}$D-Asn-CGRP (SEQ ID NO:143), $^{36}$Ser-CGRP (SEQ ID NO:144), $^{36}$Hse-CGRP (SEQ ID NO:145), $^{36}$Asp-CGRP (SEQ ID NO:146), $^{36}$Thr-CGRP (SEQ ID NO:147), and $^{36}$Asn-CGRP (SEQ ID NO:148). Other exemplary CGRP analogs and derivatives are disclosed in U.S. Pat. Nos. 4,697,002; and 4,687,839, which are hereby incorporated by reference.

Component peptide hormones useful in the compositions and methods disclosed herein also include intermedin or AFP-6 peptides. By "intermedin" or "AFP-6" is meant the human peptide hormone and species variants thereof, in any physiological form. Native AFP-6 peptides are known in the ate, as are functional AFP-6 peptide analogs, derivatives, and hybrids. The amino acid sequence of human AFP-6 (or intermedin) is TQAQLLRVGCVLGTCQVQNLSHRL-WQLMGPAGRQDSAPVDPSSPHSY (SEQ ID NO:149). Any AFP-6 peptide, analog, derivative, or hybrid known in the art that exhibits biological activity known in the art may be used in conjunction with the compositions and methods disclosed herein. In one embodiment, the AFP-6 peptides, analogs, derivatives, and hybrids have at least one hormonal activity of native AFP-6. In certain embodiments, the AFP-6 peptides, analogs, derivatives, and hybrids are agonists of a receptor which native AFP-6 is capable of specifically binding. AFP-6 peptide analogs, derivatives, and hybrids may be amidated as known in the art or may be in the acid form.

Exemplary AFP-6 analogs include, but are not limited to, VGCVLGTCQVQNLSHRLWQLMGPAGRQD-SAPVDPSSPHSY (SEQ ID NO:150), RVGCVLGTC-QVQNLSHRLWQLMGPAGRQDSAPVDPSSPHSY (SEQ ID NO:151), GCVLGTCQVQNLSHRLWQLMG-PAGRQDSAPVDPSSPHSY (SEQ ID NO:152), CVLGTC- QVQNLSHRLWQLMGPAGRQDSAPVDPSSPHSY (SEQ ID NO:153), TQAQLLRVGCVLGTCQVQNLSHRLWQLRQDSAPVDPSSPHSY (SEQ ID NO:154), and TQAQLLRVGCVLGTCQVQNLSHRLWQLDSAPVDPSSPHSY (SEQ ID NO:155). Other exemplary AFP-6 analogs and derivatives are disclosed in U.S. Pat. No. 6,965,013 and PCT Publication Nos. WO 2004/048547 and WO 2006/042242, each of which is herein incorporated by reference.

Component peptide hormones useful in the compositions and methods disclosed herein also include members of the cholecystokinin (CCK) hormones, including CCK agonists. By "CCK" is meant the human peptide hormone and species variants thereof. More particularly, CCK is a 33-amino acid sequence first identified in humans, and includes an 8-amino acid in vivo C-terminal fragment ("CCK-8") that has been reportedly demonstrated in pig, rat, chicken, chinchilla, dog and humans. Other species variants include a 39-amino acid sequence found in pig, dog and guinea pig, and a 58-amino acid found in cat, dog and humans, and a 47-amino acid sequences homologous to both CCK and gastrin. The C-terminal sulfated octapeptide sequence (CCK-8) is relatively conserved across species, and may be the minimum sequence for biological activity in the periphery of rodents. Thus, the term CCK-33 will generally refer to human CCK(1-33) KAPSGRMSIVKNLQNLDPSH RISDRDYMGWMDF (SEQ ID NO:156), while CCK-8 (CCK(26-33), will refer to the C-terminal octapeptide generically in both the sulfated and unsulfated unless otherwise specified. Sulfated CCK-8 has the amino acid sequence DY(SO$_3$)MGWMDF (SEQ ID NO:157). Further, pentagastrin or CCK-5 will refer to the C-terminal peptide CCK(29-33) GWMDF (SEQ ID NO:158), and the CCK-4 will refer to the C-terminal tetrapeptide CCK(30-33) WMDF (SEQ ID NO:159). However, as used herein, CCK will generally refer to all naturally occurring variations of the hormone, including CCK-33, CCK-8, CCK-5, and CCK-4, in the sulfated and unsulfated form unless otherwise specified. CCKs and various analogs thereof are known in the art.

Various in vivo and in vitro screening methods for CCK analogs are known in the art. Examples include in vivo assays involving the contraction of the dog or guinea pig gallbladder after rapid intravenous injection of the compound to be tested for CCK-like activity, and in vitro assays measuring using strips of rabbit gallbladder. See. E.g., Walsh, "Gastrointestinal Hormones", In Physiology of the Gastrointestinal Tract (3d ed. 1994; Raven Press, New York).

Exemplary CCKs and CCK analogs include, but are not limited to, DY(SO$_3$H)MGWMDF (SEQ ID NO:157), DYMGWMDF (SEQ ID NO:160), MGWMDF (SEQ ID NO:161), GWMDF (SEQ ID NO:158), WMDF (SEQ ID NO:159), KDY(SO$_3$H)MGWMDF (SEQ ID NO:162), KDYMGWMDF (SEQ ID NO:163), KMGWMDF (SEQ ID NO:164), KGWMDF (SEQ ID NO:165), and KWMDF (SEQ ID NO:166). As known in the art, such CCK peptides are may be amidated or may optionally be in the acid form.

Component peptide hormones useful in the compositions and methods disclosed herein also include ghrelins. In some embodiments, the peptides are ghrelin antagonists such as those described in PCT Publication Nos. WO 01/87335 and WO 02/08250. Ghrelin antagonists are also known as GHS (growth hormone secretagogue receptor) antagonists. The compositions and methods provided therefore contemplate the use GHS antagonists in place of ghrelin antagonists.

Component peptide hormones useful in the compositions and methods disclosed herein also include leptin family peptide hormones. By "leptin" is meant the naturally occurring leptin from any species, as well as biologically active D-isoforms, or fragments of naturally occurring leptin and variants thereof, and combinations of the preceding. Leptin is the polypeptide product of the ob gene as described in U.S. Pat. No. 6,001,968. Native leptin family peptide hormones are known in art, as are functional peptide analogs, derivatives, and hybrids. Although certain leptin native peptides, analogs, derivatives and hybrids are described herein, it should be recognized that any known leptin peptides, analogs, derivatives, or hybrids that exhibit hormonal activity known in the art may be used in the compositions and methods disclosed herein. In one embodiment, the leptin analogs, derivatives, and hybrids have at least one hormonal activity of native leptin. In certain embodiments, the leptin analogs, derivatives and hybrids are agonists of a receptor which native leptin is capable of specifically binding. Means for testing for leptin agonism or antagonism are described, for example, in U.S. Pat. Nos. 6,007,998 and 5,856,098.

Human leptin is 167 amino acids in length: MHWGTLCGFLWLWPYLFYVQAVPIQKVQDDTKTLIKTIVTRINDISHTQSVSSKQKVTGLDFIPGLHPILTLSKMDQTLAVYQQILTSMPSRNVIQISNDLENLRDLLHVLAFSKSCHLPWASGLETLDSLGGVLEASGYSTEVVALSRLQGSLQDMLWQLDLSPGC (SEQ ID NO:167). This leptin polypeptide contains a signal sequence cleavage site located after amino acid 21 (Ala). Consequently, the mature human leptin protein extends from amino acid 22 (Val) to amino acid 167 (Cys) ans is 146 amino acids in length: VPIQKVQDDTKTLIKTIVTRINDISHTQSVSSKQKVTGLDFIPGLHPILTLSKMDQTLAVYQQILTSMPSRNVIQISNDLENLRDLLHVLAFSKSCHLPWASGLETLDSLGGVLEASGYSTEVVALSRLQGSLQDMLWQLDLSPGC (SEQ ID NO:168).

Another exemplary leptin analog is a natural variant of human leptin which has a Gln absent from position 28 of mature leptin and is 145 amino acids in length: VPIQKVQDDTKTLIKTIVTRINDISHTSVSSKQKVTGLDFIPGLHPILTLSKMDQTLAVYQQILTSMPSRNVIQISNDLENLRDLLHVLAFSKSCHLPWASGLETLDSLGGVLEASGYSTEVVALSRLQGSLQDMLWQLDLSPGC (SEQ ID NO:169). In some embodiments, the leptin component peptide is recombinant and has a methionyl residue at the N-terminus.

Exemplary leptin analogs include those where the amino acid at position 43 of SEQ ID NO:167 is substituted with Asp or Glu; position 48 is substituted Ala; position 49 is substituted with Glu, or absent; position 75 is substituted with Ala; position 89 is substituted with Leu; position 93 is substituted with Asp or Glu; position 98 is substituted with Ala; position 117 is substituted with Ser, position 139 is substituted with Leu, position 167 is substituted with Ser, and any combination thereof. Exemplary leptin analogs include, but are not limited to, $^{43}$Asp-leptin (SEQ ID NO:170), $^{43}$Glu-leptin (SEQ ID NO:171), $^{48}$Ala-leptin (SEQ ID NO:172), $^{49}$Glu-leptin (SEQ ID NO:173), $^{49}$Des-leptin (SEQ ID NO:174), $^{75}$Ala-leptin (SEQ ID NO:175), $^{89}$Leu-leptin (SEQ ID NO:176), $^{93}$Asp-leptin (SEQ ID NO:177), $^{93}$Glu-leptin (SEQ ID NO:178), $^{98}$Ala-leptin (SEQ ID NO:179), $^{117}$Ser-leptin (SEQ ID NO:180), $^{139}$Leu-leptin (SEQ ID NO:181), $^{167}$Ser-leptin (SEQ ID NO:182), $^{43}$Asp$^{49}$Glu-leptin (SEQ ID NO:183), $^{43}$Asp$^{75}$Ala-leptin (SEQ ID NO:184), $^{89}$Leu$^{117}$Ser-leptin (SEQ ID NO:185), and $^{93}$Glu$^{167}$Ser-leptin (SEQ ID NO:186).

Other exemplary leptin peptides, analogs, and derivatives are disclosed in U.S. Pat. Nos. 5,935,810, 6,001,968, 6,429, 290, 6,309,853, 5,521,283, 5,532,336, 6,777,388 and 6,936, 439, each of which is incorporated herein by reference. Other exemplary leptin peptides, analogs, and derivatives are disclosed in PCT Publication Nos. WO 2004/039832, WO 97/02004, WO 97/06816, WO 97/18833, WO 97/38014, and WO 98/28427, and in U.S. Pat. Publication Nos. 2004/0072219, 2003/049693, 2003/0166847, 2003/0092126, all of which are hereby incorporated by reference.

Component peptides useful in the compositions and methods disclosed herein also include hybrid polypeptides. As used herein, a "hybrid peptide" or "hybrid polypeptide" or "hybrid peptide hormone" refer to a polypeptide comprising at least two peptide hormone portions linked together, where the at least two peptide hormones are not the same peptide hormone. In some embodiments, the hybrid polypeptides comprise portions of at least two peptide hormones covalently linked together. In some embodiments, the peptide hormones portions are directly linked together and, in other embodiments, the peptide hormones portions are indirectly linked together, e.g., through a linker group. In some embodiments, the hybrid polypeptide exhibits at least one biological activity of a component peptide. Exemplary hybrid polypeptides include those comprising one or more of the following a component peptides: an amylin, an ADM, a CT, a leptin, a PYY, an NPY, a GLP-1, an AFP-6, a CCK, a CGRP, a GLP-2, an OXM, an exendin, and a GIP.

For example, reference sequences for some hybrid polypeptides include human GIP, truncated GIP, human GLP-1 and exendin-4, an exemplary Trp-cage (FIEWLKNG-GPSSGAPPPS (SEQ ID NO:187)), an exemplary short exendin tail (PSSGAPPPS (SEQ ID NO:188)), and an exemplary long exendin tail (KNGGPSSGAPPPS (SEQ ID NO:189)). The exendin tail and/or Trp cage sequences, and analogs and derivatives disclosed herein and in the incorporated documents, exemplify peptidic enhancers.

Exemplary GIP hybrid molecules include, for example, [Leu$^{14}$]GIP(1-30)-exendin-4(31-39) (SEQ ID NO:291), [D-Ala$^2$]GIP(1-30)-exendin-4(31-39) (SEQ ID NO:292), and GIP(1-30)-exendin-4(31-39) (SEQ ID NO:1). Exemplary exendin hybrid molecules include, for example, [Leu$^{14}$, Gln$^{28}$]exendin-4(1-31)-fGLP-1(33-37) (SEQ ID NO:298).

GIP hybrids can comprise a peptidic enhancer: a C-terminal Trp-cage motif sequence. In one such embodiment are GIP hybrids of the formula D-L-C-S, where the "D" region comprises optionally-modified N-terminal GIP sequences. Region "S" in the formulas can be a C-terminal sequence of a Trp-cage sequence that when adjacent to an N-terminal portion of a Trp-cage sequence is capable of forming a Trp-cage. Such peptidic enhancer sequences are believed to shield the novel GIP analog from protease digestion and enhance stability. The S region typically comprises at least one proline or proline-like residue capable of interacting with a tryptophan or typtophan-like residue in an adjoining sequence to form a Trp-cage. Region C comprises a C-terminal sequence of a GIP. In some embodiments of these molecules, the tryptophan or tryptophan-like residue that is capable of interacting with the at least one proline or proline-like residue in region S is located in region "C". In alternative embodiments, when region C is absent, the Trp or Trp-like residue can be provided in a linker region "L".

In exemplary GIP hybrid embodiments, the GIP portion comprises a GIP N-terminal region modified or substituted to provide DPP-IV resistance superior to that of native GIP. Compounds or fragments thereof suitable to comprise hybrid molecules with GIP include incretins (e.g., GLP-1, exendin), amylin family peptides (e.g., amylin, calcitonin, calcitonin related gene peptide, adrenomedullin, intermedin), cholecystokinins (CCK), gastrin, PPFs (e.g., PP, PYY), secretin, natriuretic peptides, neuromedins, and urocortin.

In certain embodiments, a peptide hormone amidated at the C-terminal end is a component of the P-PI conjugate. In other embodiments, the peptide hormone component may not be amidated. In some embodiments, P-PI conjugates with amidated peptide hormones include, but are not limited to, those with amylin family peptide hormones, CCK, PYY, hGLP-1 (7-36), and hGLP-2. In other embodiments, P-PI conjugates with peptide hormones without amidated C-terminal ends include, but are not limited to, those with exendin-4, exendin-4(1-28), GIP, GLP-1(7-37), frog GLP-1(7-36), and frog GLP-2. However, in other embodiments, these component peptide hormones may be amidated at the C-terminal end.

Exemplary hybrid polypeptides for use in the compositions and methods described herein include, but are not limited to, exendin-4-PYY(22-36) (SEQ ID NO:190), exendin-4-PYY(25-36) (SEQ ID NO:191), exendin-4-PYY(18-36) (SEQ ID NO:192), exendin-4-βAla-βAla-PYY(22-36) (SEQ ID NO:193), exendin-4-βAla-βAla-PYY(25-36) (SEQ ID NO:194), exendin-4-βAla-βAla-PYY(31-36) (SEQ ID NO:195), exendin-4(1-28)-PYY(22-36) (SEQ ID NO:196), exendin-4(1-28)-PYY(25-36) (SEQ ID NO:197), exendin-4(1-28)-PYY(18-36) (SEQ ID NO:198), exendin-4(1-28)-βAla-βAla-PYY(22-36) (SEQ ID NO:199), exendin-4(1-28)-βAla-βAla-PYY(25-36) (SEQ ID NO:200), exendin-4(1-28)-βAla-βAla-PYY(31-36) (SEQ ID NO:201), $^5$Ala$^{14}$Leu$^{25}$Phe-exendin-4(1-28)-PYY(18-36) (SEQ ID NO:202), $^5$Ala$^{14}$Leu$^{25}$Phe-exendin-4(1-28)-PYY(22-36) (SEQ ID NO:203), $^5$Ala$^{14}$Leu$^{25}$Phe-exendin-4(1-28)-PYY(25-36) (SEQ ID NO:204), $^5$Ala$^{14}$Leu$^{25}$Phe-exendin-4(1-17)-PYY(18-36) (SEQ ID NO:205), $^5$Ala$^{14}$Leu$^{25}$Phe-exendin-4(1-28)βAla-βAla-PYY(22-36) (SEQ ID NO:206), $^5$Ala$^{14}$Leu$^{25}$Phe-exendin-4(1-28)-βAla-βAla-PYY(25-36) (SEQ ID NO:207), $^5$Ala$^{14}$Leu$^{25}$Phe-exendin-4(1-28)-βAla-βAla-PYY(31-36) (SEQ ID NO:208), exendin-4-CCK-8 (SEQ ID NO:209), exendin-4(1-28)-CCK-8 (SEQ ID NO:210), exendin-4(1-28)-CCK-8(Phe(CH$_2$SO$_3$)) (SEQ ID NO:211), exendin-4(1-28)-(8-amino-3,6-dioxactoanoyl)-CCK-8 (SEQ ID NO:212), exendin-4(1-28)-(8-amino-3,6-dioxactoanoyl)-CCK-8(Phe(CH$_2$SO$_3$)) (SEQ ID NO:213), exendin-4(1-27)-hAmylin(1-7)-$^{14}$Gln,$^{11,18}$Arg-sCT(8-27)-Amylin(33-37) (SEQ ID NO:214), exendin-4(1-27)-$^{2,7}$Ala-hAmylin(1-7)-sCT(8-10) (SEQ ID NO:215), $^{29}$12 Ado-exendin(1-28)-hAmylin(1-7)-$^{11,18}$Arg-sCT(8-32)-hAmylin(33-37) (SEQ ID NO:216), $^{29}$12 Ado-exendin(1-28)-$^1$des-Lys-hAmylin(1-7)-$^{11,18}$Arg-sCT(8-32)-hAmylin(33-37) (SEQ ID NO:217), $^{29}$3,6-dioxaoctanoyl-exendin(1-28)-hAmylin(1-7)-$^{11,18}$Arg-sCT(8-32)-hAmylin(33-37) (SEQ ID NO:218), $^{29}$3,6-dioxaoctanoyl-exendin(1-28)-$^1$des-Lys-hAmylin(1-7)-$^{11,18}$Arg-sCT(8-32)-hAmylin(33-37) (SEQ ID NO:219), $^{29}$5 Apa-exendin(1-28)-hAmylin(1-7)-$^{11,18}$Arg-sCT(8-32)-hAmylin(33-37) (SEQ ID NO:220), $^{29}$5 Apa-exendin(1-28)-$^1$des-Lys-hAmylin(1-7)-$^{11,18}$Arg-sCT(8-32)-hAmylin(33-37) (SEQ ID NO:221), $^{29}$βAla-βAla-exendin(1-28)-hAmylin(1-7)-$^{11,18}$Arg-sCT(8-32)-hAmylin(33-37) (SEQ ID NO:222), $^{29}$βAla-βAla-exendin(1-28)-$^1$des-Lys-hAmylin(1-7)-$^{11,18}$Arg-sCT(8-32)-hAmylin(33-37) (SEQ ID NO:223), $^{29}$4,7,10-trioxa-13-tridecanamine succinimidyl-exendin(1-28)-hAmylin(1-7)$^{11,18}$Arg-sCT(8-32)-hAmylin(33-37) (SEQ ID NO:224), $^{29}$4,7,10-trioxa-13-tridecanamine succinimidyl-exendin(1-28)-$^1$des-Lys-hAmylin(1-7)-$^{11,18}$Arg-sCT(8-32)-hAmylin(33-37) (SEQ ID NO:225), CCK-8-GKR-$^{15}$Glu-h-amylin(1-17)-$^{18}$Arg-sCT(18-26)-amylin(32-37) (SEQ ID NO:226), amylin(1-18)-PYY(19-36) (SEQ ID NO:227), isocaproyl-STAVL-(Aib)-K(formyl)-LSQEL-(Aib)-K(formyl)-LQT-PYY(18-36) (SEQ ID NO:228), isocaproyl-STAVL-(Aib)-K(formyl)-LSQEL-(Aib)-K(formyl)-L-PYY(16-36) (SEQ ID NO:229), CCK-8-[Succinoyl-Cys]-PYY(3-36) (SEQ ID NO:230), CCK-8-[Bis-Cys(N-Acetyl)]-PYY(3-36) (SEQ ID NO:231), and CCK-8-[Gly-Aminoxymethylcarbonyl]-PYY(3-36) (SEQ ID NO:232).

Other exemplary hybrid polypeptides for use in the compositions and methods described herein include, but are not limited to, GIP(1-30)-(12 Ado)-hAmylin(1-7)-$^{11,18}$Arg-sCT(8-27)-hAmylin(33-37) (SEQ ID NO:233), GIP(1-30)-(12 Ado)-$^{1}$des-Lys-hAmylin(1-7)-$^{11,18}$Arg-sCT(8-27)-hAmylin(33-37) (SEQ ID NO:234), GIP(1-30)-(3,6-dioxaoctanoyl)-hAmylin(1-7)-$^{11,18}$Arg-sCT(8-27)-hAmylin(33-37) (SEQ ID NO:235), GIP(1-30)-(3,6-dioxaoctanoyl)-$^{1}$des-Lys-hAmylin(1-7)-$^{11,18}$Arg-sCT(8-27)-hAmylin(33-37) (SEQ ID NO:236), GIP(1-30)-(5 Apa)-hAmylin(1-7)-$^{11,18}$Arg-sCT(8-27)-hAmylin(33-37) (SEQ ID NO:237), GIP(1-30)-(5 Apa)-$^{1}$des-Lys-hAmylin(1-7)-$^{11,18}$Arg-sCT(8-27)-hAmylin(33-37) (SEQ ID NO:238), GIP(1-30)-(βAla-(βAla)-hAmylin(1-7)-$^{11,18}$Arg-sCT(8-27)-hAmylin(33-37) (SEQ ID NO:239), GIP(1-30)-(βAla-(βAla)-$^{1}$des-Lys-hAmylin(1-7)-$^{11,18}$Arg-sCT(27)-hAmylin(33-37) (SEQ ID NO:240), GIP(1-30)-(4,7,10-trioxa-13-tridecanamine succinimidyl)-hAmylin(1-7)$^{11,18}$Arg-sCT(8-27)-hAmylin(33-37) (SEQ ID NO:241), GIP(1-30)-(4,7,10-trioxa-13-tridecanamine succinimidyl)-$^{1}$des-Lys-hAmylin(1-7)-$^{11,18}$Arg-sCT(8-27)-hAmylin(33-37) (SEQ ID NO:242), GIP(1-30)-(Gly-Gly-Gly)-hAmylin(1-7)-$^{11,18}$Arg-sCT(8-27)-hAmylin(33-37) (SEQ ID NO:243), GIP(1-30)-(Gly-Gly-Gly)-$^{1}$des-Lys-hAmylin(1-7)-$^{11,18}$Arg-sCT(27)-hAmylin(33-37) (SEQ ID NO:244), GIP(1-30)-(4,7,10-trioxa-13-tridecanamine succinimidyl)-hAmylin(1-7)-$^{11,18}$Arg-sCT(8-27)-hAmylin(33-37) (SEQ ID NO:245), and GIP(1-30)-(4,7,10-trioxa-13-tridecanamine succinimidyl)-$^{1}$des-Lys-hAmylin(1-7)-$^{11,18}$Arg-sCT(8-27)-hAmylin(33-37) (SEQ ID NO:246).

Exemplary hybrid polypeptides for use in the compositions and methods described herein include those described in U.S. Provisional Application Nos. 60/653,433, 60/651,647, 60/707,244, 60/707,369, 60/709,316 and 60/709,320, each of which is incorporated by reference herein for those molecules. Exemplary hybrid polypeptides for use in the compositions and methods described herein also include those described in U.S. application Ser. No. 11/201,664, U.S. Application Publication Nos. 2006-0094652 and 2006-0293232, and PCT Publication No. WO 2005/077072, each of which is incorporated by reference herein for those molecules.

Component peptidase inhibitors useful in the conjugate molecules and methods described herein can be in the active drug form or the pro-drug form that is converted to an active form in vivo. As demonstrated herein, P-PI conjugates with lisinopril ester are inactive in in vitro ACE inhibitor assays but P-PI conjugates with de-esterified lisinopril demonstrate ACE inhibitor activity. Exemplary component peptidase inhibitors are listed herein as either the active drug form or as the pro-drug form of the inhibitor, and either form may be of use in the conjugate molecules and methods disclosed herein.

Component peptidase inhibitors useful in the conjugate molecules and methods described herein include, but are not limited to, vasopeptidase inhibitors, such as angiotensin-converting enzyme (ACE) inhibitors, neutral endopeptidase (NEP) inhibitors, endothelin-converting enzyme (ECE) inhibitors, ACE/NEP inhibitors, NEP/ECE inhibitors, and ACE/NEP/ECE inhibitors. Angiotensin I-converting enzyme is a dipeptidyl carboxypeptidase that plays an important role in blood pressure regulation and electrolyte balance by hydrolyzing angiotensin I into angiotensin II, a potent vasopressor, and aldosterone-stimulating peptide. ACE is also able to hydrolyze other biologically active polypeptides, such as kinins, e.g., bradykinin. Bradykinin is a vasodilator, which acts at least in part by inducing release of vasodilator prostaglandins, and which is inactivated upon hydrolysis by ACE. Thus, ACE increases blood pressure at least in part by producing angiotensin II, a vasoconstrictor, and by inactivating bradykinin, a vasodilator. ACE, also referred to as peptidyl dipeptidase A (EC 3.4.15.1) and kininase II, is a metallopeptidase, more particularly a zinc peptidase.

Exemplary ACE inhibitors for use in the conjugate molecules and methods described herein include, but are not limited to, benazepril, captopril (1-[(2S)-3-mercapto-2-methylpropionyl]-L-proline), ceronapril, enalapril (N-(1-ethoxycarbonyl-3-phenylpropyl)-L-alanyl-L-proline), enalaprilat, fentiapril, fosinopril, imidapril, lisinopril (Merck, Astra-Zeneca), moexipril, perindopril (Servier), quinapril (Warner-Lambert), ramipril, and trandolapril. Other nonlimiting examples of ACE inhibitors that may be employed herein include cetapril, cilazapril, delapril, indolapril (Schering), spirapril (Schering), and zofenopril. In some embodiments, the ACE inhibitor is a peptide, for example, pGluW-PRPQIPP (SEQ ID NO: 315) or pGluKWAP (SEQ ID NO: 316), where pGlu refers to pyroglutamic acid. Exemplary ACE inhibitors include those disclosed in, for example, U.S. Pat. Nos. 4,046,889, 4,316,906, 4,374,829, 4,452,790, 4,168,267, 4,337,201, 4,385,051, and 4,344,949.

As discussed herein, component peptidase inhibitors useful in the conjugate molecules and methods described herein also include NEP inhibitors. Similar to ACE, NEP is an endothelial cell surface metalloproteinase, which is involved in the degradation of several regulatory peptides including the natriuretic peptides and thus augments vasodilatation and natriuresis through increased levels of atrial natriuretic peptide. Examples of NEP inhibitors include, but are not limited to, phosphoramidon, thiophan, retrothiorphan, candoxatril, and acetorphan. Also, component peptidase inhibitors useful in the conjugate molecules and methods described herein include ECE inhibitors. ECE is the main enzyme responsible for the formation of the biologically active endothelin peptides, potent vasoconstrictors.

Vasopeptidase inhibitors also include NEP/ACE inhibitors that possess NEP and ACE inhibitory activity. Examples of NEP/ACE inhibitors include, but are not limited to, tricyclic benzazepinone thiols, omapatrilat, gemopatrilat, mixanpril, racecadotril, fasidotril, sampatrilat, MDL 100.240, Z13752A, BMS189921, BMS182657, and CGS 30008. Examples of NEP/ACE inhibitors suitable for use herein include those disclosed in U.S. Pat. Nos. 5,362,727, 5,366,973, 5,225,401, 4,722,810, 5,223,516, 4,749,688, 5,552,397, 5,504,080, 5,612,359, and 5,525,723. Exemplary NEP/ACE inhibitors include the following:

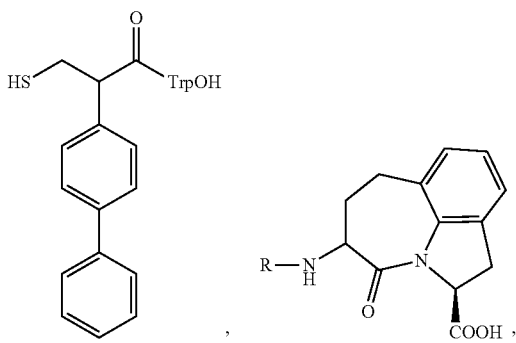

Vasopeptidase inhibitors also include NEP/ECE inhibitors that possess NEP and ECE inhibitory activity. Examples of NEP/ECE inhibitors include, but are not limited to, phosphoramidon, Vasopeptidase inhibitors also include NEP/ACE/ECE inhibitors that possess ACE, NEP and ACE inhibitory activity. Examples of NEP/ACE/ECE inhibitors include, but are not limited to, CGS 26582 and N-[2-(Indan-1-yl)-3-mercapto-propionyl]amino acid analogs (Inguimbert et al. (2002) Bioorg. Med. Chem. Lett. 12:2001-2005). Exemplary NEP/ACE/ECE inhibitors include the following:

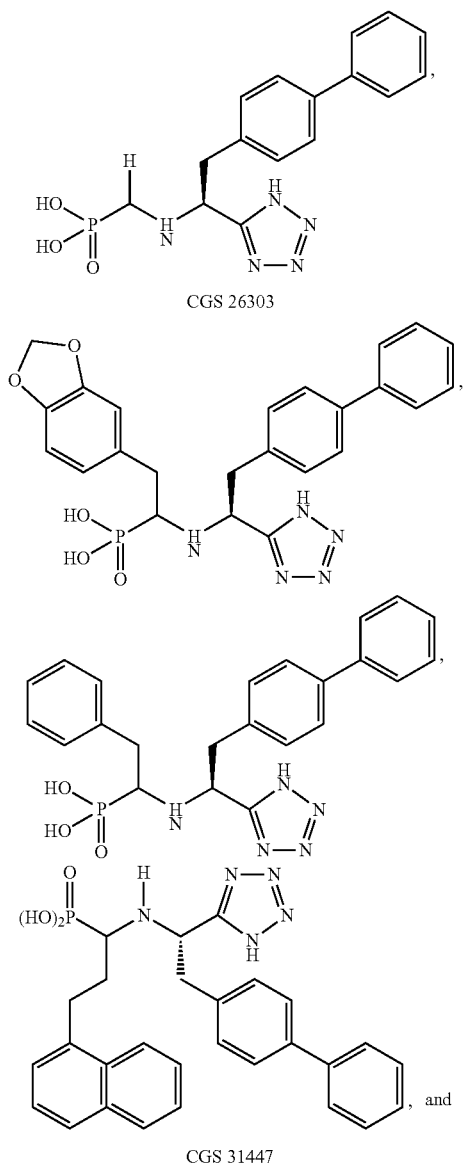

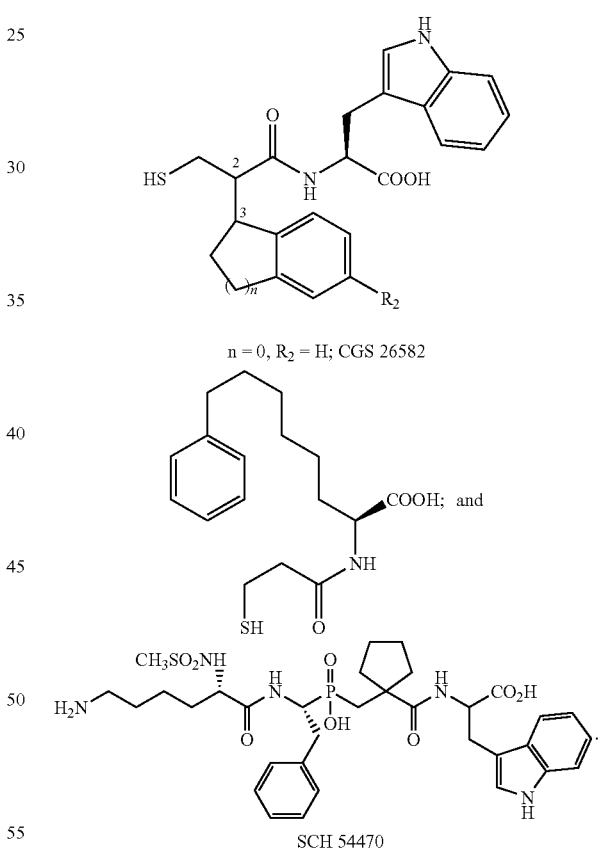

Component peptidase inhibitors useful in the conjugate molecules and methods described herein include, inhibitors of angiotensin-converting enzyme-related carboxypeptidase (ACE2). ACE2 is a zinc metallopeptidase and a homolog of ACE but ACE2 has different substrate specificities than ACE (Vickers et al. (2002) J. Biol. Chem. 277:14838-14843). ACE2 cleaves and inactivates des-Arg bradykinin, a local vasodilator functioning through binding to the bradykinin B1 receptor expressed when inflammation or tissue damage occurs. Exemplary ACE2 inhibitors for use in the conjugate molecules and methods described herein include, but are not limited to, MLN-4760 ((S,S)-2-{-carboxy-2-[3-(3,5-dichlorobenzyl)-3H-imidazol4-yl]-ethylamino}-4-methylpentanoic acid; Towler et al. (2004) *J. Biol. Chem.* 279:17996-18007), N-(2-aminoethyl)-1 aziridine-ethanamine (Huentelman et al. (2004) *Hypertension* 44:903-906, and peptide inhibitors of ACE2 such as Ac-GDYSHCSPLRYYP-WWKCTYPDPEGGG-NH$_2$ (SEQ ID NO:247) and others described in Huang et al. (2003) *J. Biol. Chem.* 278:15532-15540.

Dipeptidyl peptidase-IV (DPP-IV) (EC 3.4.14.5) is a serine protease that preferentially hydrolyzes an N-terminal dipeptide from peptide substrates having proline or alanine in the 2 position. DPP-IV has been implicated in the control of glucose homeostasis because its substrates include GLP-1 and GIP. Members of the PFF members, such as PYY and NPY, are also substrates of DPP-IV. Cleavage of the N-terminal amino acids from these peptides renders them functionally inactive. Accordingly, DPP-IV may have a physiological role in diabetes, glucose tolerance, obesity, appetite regulation, cardiovascular diseases, and other conditions or disorders described herein. Administration of DPP-IV inhibitors in vivo prevents N-terminal degradation of GLP-1 and GIP and resulting in higher circulating concentrations of these peptides. In addition, treatment with DPP-IV inhibitors prevents degradation of PYY and NPY.

Accordingly, component peptidase inhibitors useful in the conjugate molecules and methods described herein also include DPP-IV inhibitors. Examples of DPP-IV inhibitors include, but are not limited to, N-(substituted glycyl)-2-cyanopyrrolidine, tetrahydroisoquinoline 3-carboxamide derivatives, fluorinated cyclic amides, adamantylglycine-based inhibitors, and glycinenitrile-based inhibitors. Cyanopyrrolidine inhibitors include, but are not limited to, reversible inhibitors such as the following slow reversible inhibitors:

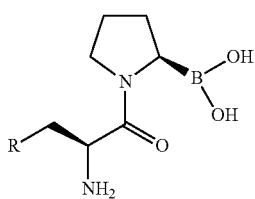

and

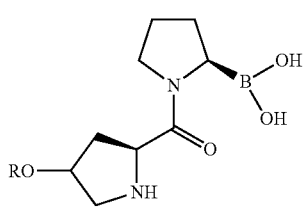

wherein R=covalent or non-covalent linker for peptide modification. Examples of DPP-IV inhibitors suitable for use herein include those disclosed in U.S. Pat. Nos. 6,011,155, 6,124,305, 6,166,063, 6,432,969, 6,172,081, 6,710,040, 6,869,947, 6,995,183 and 6,995,180.

Examples of DPP-IV inhibitors include, but are not limited to, the following (DPP-IV inhibitor compound numbers beneath structure):

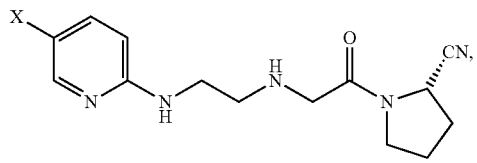

1a, X = CN (DPP728)
1b, X = I

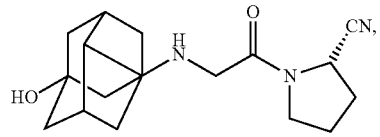

2 (LAF237)

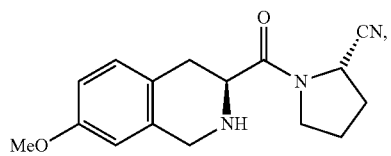

3

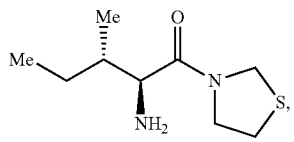

4 (P32/98)

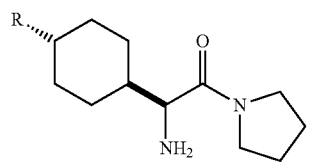

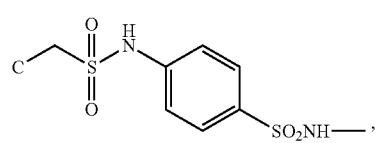

5, R = H
6, R = F$_3$

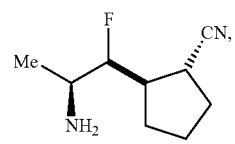

7

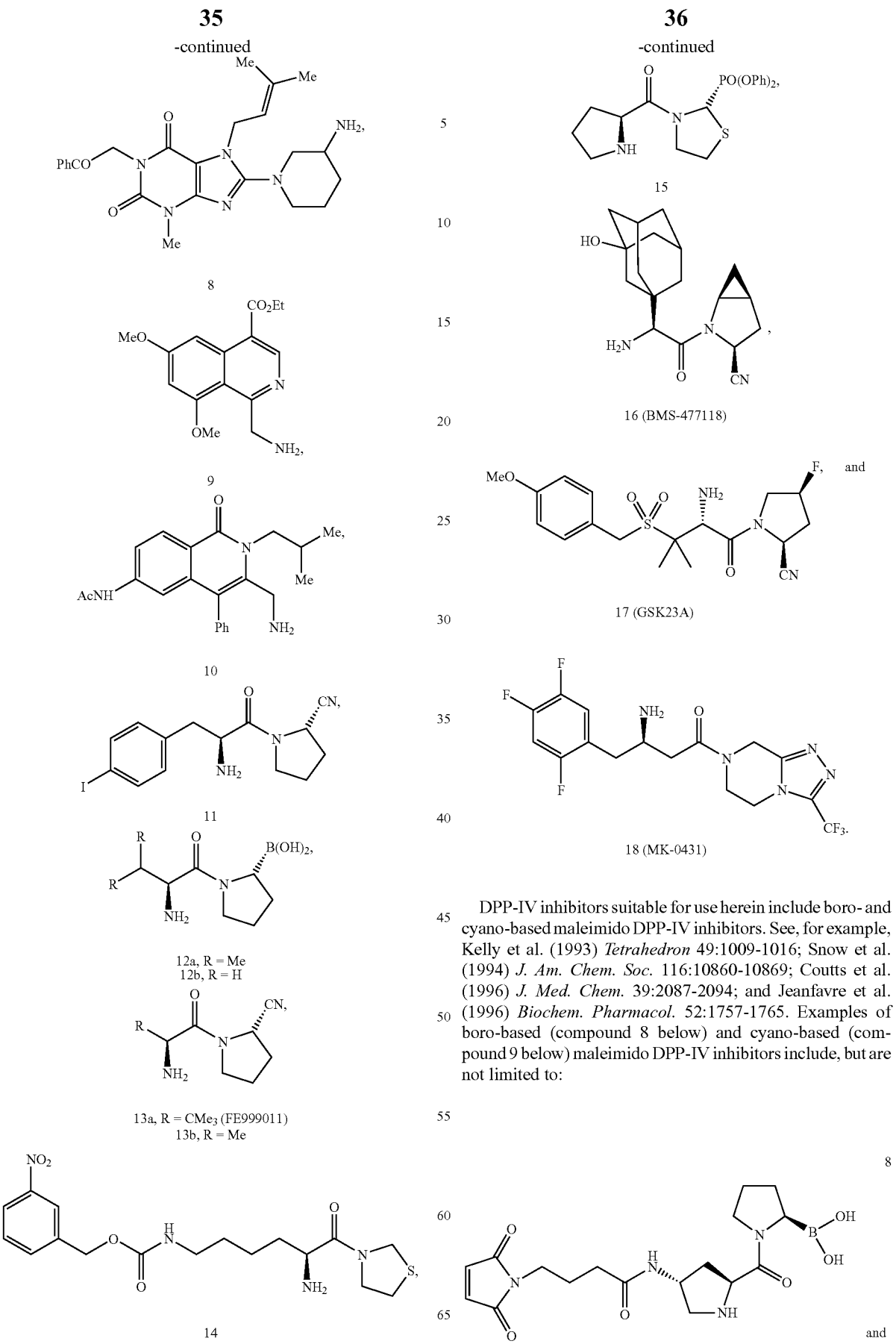
DPP-IV inhibitors suitable for use herein include boro- and cyano-based maleimido DPP-IV inhibitors. See, for example, Kelly et al. (1993) *Tetrahedron* 49:1009-1016; Snow et al. (1994) *J. Am. Chem. Soc.* 116:10860-10869; Coutts et al. (1996) *J. Med. Chem.* 39:2087-2094; and Jeanfavre et al. (1996) *Biochem. Pharmacol.* 52:1757-1765. Examples of boro-based (compound 8 below) and cyano-based (compound 9 below) maleimido DPP-IV inhibitors include, but are not limited to:

Synthesis of the 2-boro-based DPPIV inhibitor (compound 8) can be accomplished as follows:
Synthesis of the 2-cyano-based DPPIV inhibitor (compound 9) can be accomplished as follows:
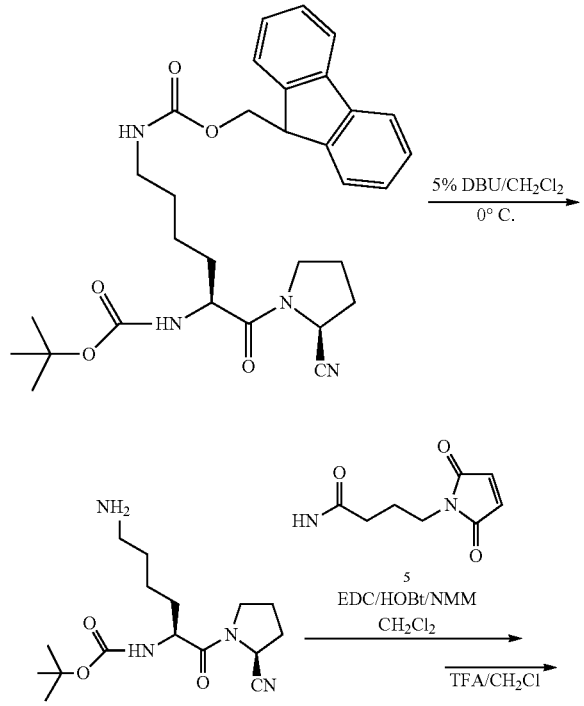
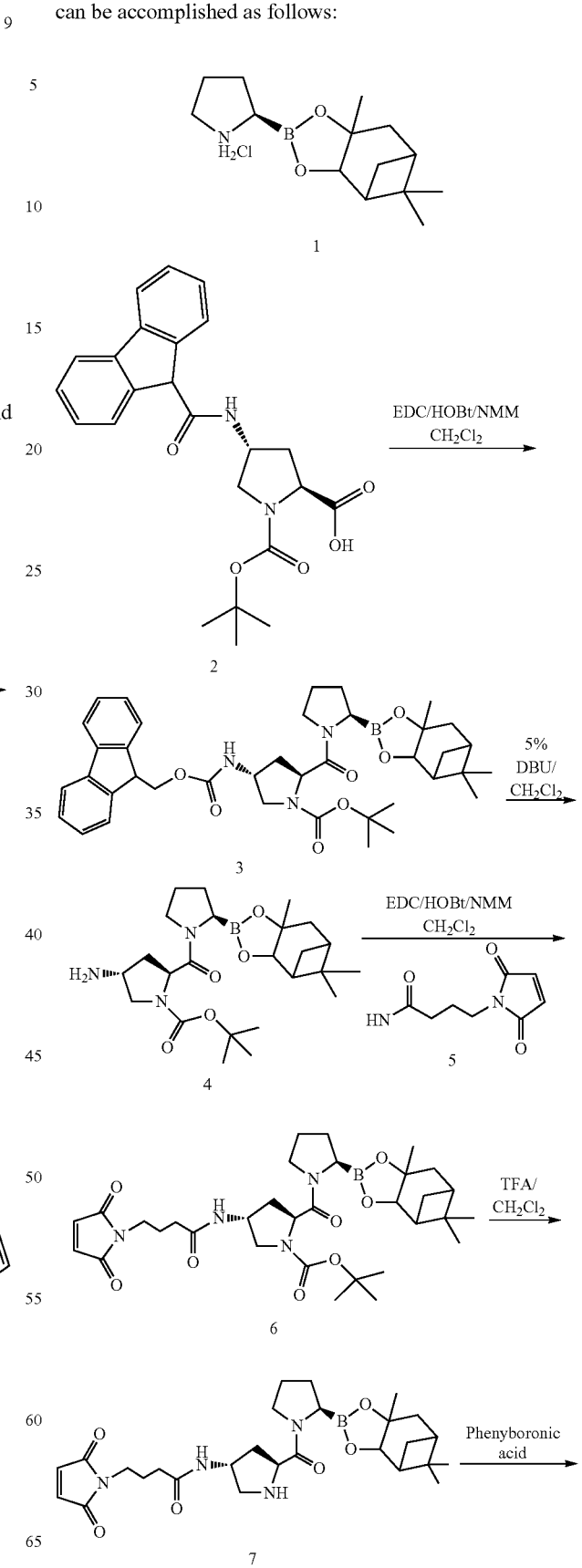

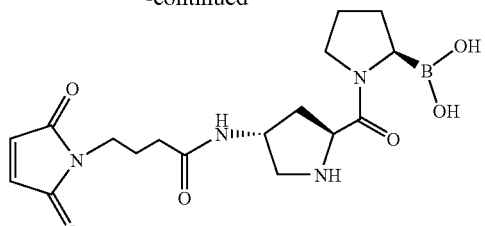

8

Component peptidase inhibitors useful in the conjugate molecules and methods described herein also include serine protease inhibitors. Serine protease inhibitors are well-known in the art. Examples of serine protease inhibitors of use include, but are not limited to, 4-(2-aminoethyl)-benzenesulfonylfluoride (AEBSF), aprotinin, elastinal, Glu-Gly-Arg-chloromethylketone (GGACK), leupeptin, phenylmethylsulphonylfluoride (PMSF), chymostatin, anti-thrombin III, 3,4-dichloroisocomarin, tosyl-L-lysine chloromethyl ketone (TLCK), tosyl-L-phenylalanine chloromethyl ketone (TPCK), diphenyliodonium hexafluorophosphate (DIFP), antipain, and α2-macroglobulin. In some embodiments, the P-PI conjugate includes AEBSF as the component peptidase inhibitor.

Component peptidase inhibitors useful in the conjugate molecules and methods described herein also include carboxypeptidase inhibitors. In one embodiment, the carboxypeptidase inhibitor for use in the P-PI conjugate is a peptide. In some embodiments, the carboxypeptidase inhibitor is a peptide which inhibits the activity of a carboxypeptidase that acts on a substrate peptide having a carboxy-terminal amino acid motif of RQRY (SEQ ID NO: 317) or RQRW (SEQ ID NO: 318) to remove the C-terminal amino acid from the substrate peptide. In some embodiments, the substrate peptide of the carboxypeptidase is PYY(1-36), PYY(3-36), and NPY, for example amidated PYY(1-36), PYY(3-36), and NPY.

In some embodiments, the carboxypeptidase inhibitor is a modified PYY peptide or a modified NPY peptide, for example, a PYY or NPY peptide modified at position 36. Exemplary carboxypeptidase inhibitors include, but are not limited to, PYY or NPY peptides with a methyl group at the α-amino nitrogen of Tyr$^{36}$, for example, $^{36}$N-methyl-Tyr-PYY(1-36) (SEQ ID NO:248), $^{36}$N-methyl-Tyr-PYY(3-36) (SEQ ID NO:249), $^{36}$N-methyl-Tyr-PYY(12-36) (SEQ ID NO:250), $^{36}$N-methyl-Tyr-PYY(18-36) (SEQ ID NO:251), $^{36}$N-methyl-Tyr-PYY(22-36) (SEQ ID NO:252), $^{36}$N-methyl-D-Tyr-PYY(1-36) (SEQ ID NO:253), $^{36}$N-methyl-D-Tyr-PYY(3-36) (SEQ ID NO:254), $^{36}$N-methyl-D-Tyr-PYY(12-36) (SEQ ID NO:255), $^{36}$N-methyl-D-Tyr-PYY(18-36) (SEQ ID NO:256), $^{36}$N-methyl-D-Tyr-PYY(22-36) (SEQ ID NO:257), $^{36}$N-methyl-Tyr-NPY (SEQ ID NO:258), $^{36}$N-methyl-Tyr-NPY(12-36) (SEQ ID NO:259), $^{36}$N-methyl-Tyr-NPY(18-36) (SEQ ID NO:260), $^{36}$N-methyl-Tyr-NPY(22-36) (SEQ ID NO:261), $^{36}$N-methyl-D-Tyr-NPY (SEQ ID NO:262), $^{36}$N-methyl-D-Tyr-NPY(12-36) (SEQ ID NO:263), $^{36}$N-methyl-D-Tyr-NPY(18-36) (SEQ ID NO:264), and $^{36}$N-methyl-D-Tyr-NPY(22-36) (SEQ ID NO:265). Other exemplary carboxypeptidase inhibitors include, but are not limited to, PYY or NPY peptides with a D-Tyr at position 36, a chiral β-Tyr at position 36, a hydroxy-Pro at position 36, Phe at position 36, Phe-CH$_2$SO$_3$H at position 36, or Trp at position 36. Exemplary carboxypeptidase inhibitors include PYY(1-36), PYY(3-36), PYY(12-36), PYY(18-36), PYY(22-36), NPY, NPY(12-36), NPY(18-36), and NPY(22-36) with such modifications at position 36. The carboxy-terminus of these carboxypeptidase inhibitors may be —NH$_2$, —NH—OH, —NH—CH$_3$, or —NH—CH$_2$CH$_3$.

Exemplary carboxypeptidase inhibitors also include PYY or NPY peptides with the position 36 modifications, as described, and with modifications at other sites within the peptide. For example, the PYY or NPY peptides with the position 36 modifications described herein may also have an internal deletion of amino acids, an internal insertion of a linker group, or a combination of an internal amino acid deletion and an internal linker group insertion. Exemplary carboxypeptidase inhibitors of this type include, but are not limited to, $^{36}$N-methyl-Tyr-PYY(3-10, 22-36) IKPEAPGEASLRHYLNLVTRQRY(N-Me) (SEQ ID NO:266), $^{36}$N-methyl-Tyr-PYY(3-10-linker-22-36) IKPEAPGE(linker)ASLRHYLNLV TRQRY (N-Me) (SEQ ID NO:296(linker) SEQ ID NO:252), and $^{36}$N-methyl-Tyr-PYY(3-10-linker-18-36) IKPEAPGE(linker)NRYYASLRHYLNLVTRQRY(N-Me) (SEQ ID NO:296)(linker) (SEQ ID NO:251). The carboxy-terminus of these carboxypeptidase inhibitors may be —NH2, —NH—OH, —NH—CH$_3$, or —NH—CH$_2$CH$_3$. Linker groups for use in these peptides include, for example,

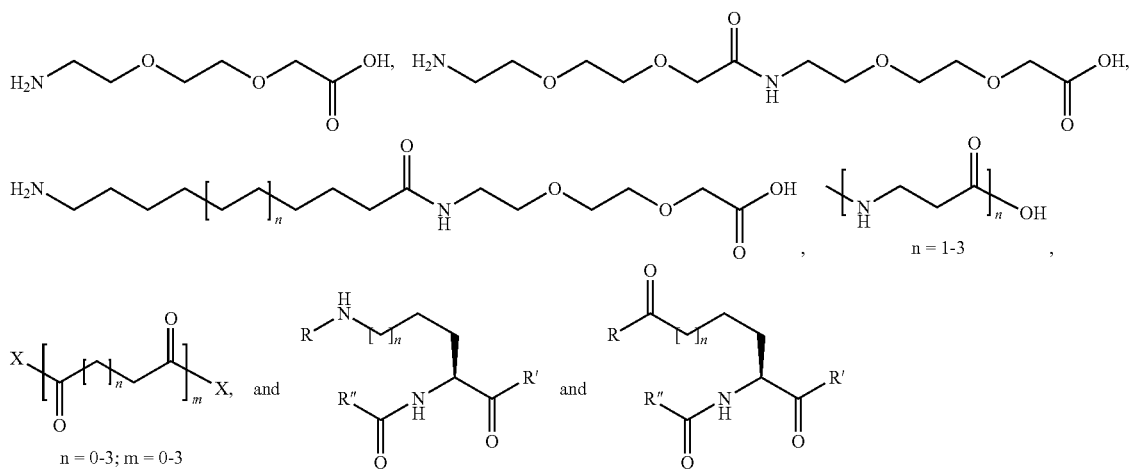

where n=0–3; R=peptide; R'=OH or NH$_2$; R''=peptide.

Exemplary carboxypeptidase inhibitors also include PYY or NPY peptides with modifications at other sites within the peptide with or without the position 36 modifications described herein. For example, the PYY or NPY peptides may have internal D-amino acids, an internal amino acid with a methyl group at the α-amino nitrogen, or a combination of such amino acid residues. Exemplary carboxypeptidase inhibitors of this type include, but are not limited to, $^{35}$N-methyl-Arg-PYY(3-36) (SEQ ID NO:267), $^{35}$D-Arg$^{36}$N-methyl-Tyr-PYY(3-36) (SEQ ID NO:268), $^{35}$ N-methyl-D-Arg-PYY(3-36) (SEQ ID NO:269), $^{34}$N-methyl-Gln-PYY(3-36) (SEQ ID NO:270), $^{34}$D-Gln$^{36}$N-methyl-Tyr-PYY(3-36) (SEQ ID NO:271), $^{34}$N-methyl-D-Gln-PYY(3-36) (SEQ ID NO:272), $^{33}$N-methyl-Arg-PYY(3-36) (SEQ ID NO:273), $^{33}$D-Arg$^{36}$N-methyl-Tyr-PYY(3-36) (SEQ ID NO:274), $^{33}$N-methyl-D-Arg-PYY(3-36) (SEQ ID NO:275), $^{19}$N-methyl-Ala-PYY(3-36) (SEQ ID NO:276), $^{19}$D-Ala$^{36}$N-methyl-Tyr-PYY(3-36) (SEQ ID NO:277), $^{19}$N-methyl-D-Ala-PYY(3-36) (SEQ ID NO:278), $^{35}$N-methyl-Arg-NPY (SEQ ID NO:279), $^{35}$D-Arg$^{36}$N-methyl-Tyr-NPY (SEQ ID NO:280), $^{35}$ N-methyl-D-Arg-NPY (SEQ ID NO:281), $^{34}$N-methyl-Gln-NPY (SEQ ID NO:282), $^{34}$D-Gln$^{36}$N-methyl-Tyr-NPY (SEQ ID NO:283), $^{34}$N-methyl-D-Gln-NPY (SEQ ID NO:284), $^{33}$N-methyl-Arg-NPY (SEQ ID NO:285), $^{33}$D-Arg$^{36}$N-methyl-Tyr-NPY (SEQ ID NO:286), $^{33}$N-methyl-D-Arg-NPY (SEQ ID NO:287), $^{19}$N-methyl-Ala-NPY (SEQ ID NO:288), $^{19}$D-Ala$^{36}$N-methyl-Tyr-NPY (SEQ ID NO:289), and $^{19}$N-methyl-D-Ala-NPY (SEQ ID NO:290). The carboxy-terminus of these carboxypeptidase inhibitors may be —NH2, —NH—OH, —NH—CH$_3$, or —NH—CH$_2$CH$_3$.

The peptide and peptidase inhibitor of the conjugates may be linked in any manner described herein or known in the art. Such conjugate linkages include covalent linkages, non-covalent linkages, or both. A stable linkage may be used or a cleavable linkage may be used. Non-covalent linkages may be mediated by any non-covalent bonding force, including by hydrophobic interaction, ionic (electrostatic) bonding, metal complexation, hydrogen bonds, van der Waals attractions, or a combination of two or more different interactions.

As described herein, the component peptide and component peptidase inhibitor may be covalently linked together through direct amide bonds or chemical linker groups. The conjugate peptide and peptidase inhibitor components may be indirectly linked through chemical or peptide linker groups or turn inducers. Examples of useful linking means and linkages are shown in the P-PI conjugates presented herein.

In one embodiment, the component peptide and peptidase inhibitor may be directly linked to the amino of a second module. In another embodiment, linking groups may be used to attached modules. Exemplary linking groups include, but are not limited to, an alkyl; PEG; amino acid, e.g., Lys, Glu, β-Ala; polyamino acids, e.g., poly-his, poly-arg, poly-lys, poly-ala, Gly-Lys-Arg (GKR); bifunctional linkers, e.g., those sold by Pierce Biotechnology, Inc., Rockford, Ill.; aminocaproyl ("Aca"), β-alanyl, 8-amino-3,6-dioxaoctanoyl, and other cleavable and non-cleavable linker known in the art.

In one aspect, the peptide is linked to the peptidase inhibitor by a linker or turn inducer. The linker or turn inducer may be chemical or peptidic in nature. Linkers may be attached, for example, to the amino-terminus of the peptide, to the carboxy-terminus of the peptide, or to an internal amino acid side chain of the peptide, and are covalently linked to the peptide and the peptidase inhibitor. The linker may be any linker capable of joining the peptidase inhibitor to the peptide, for example, succinic acid, any orthogonally linkable amino acid (e.g., Glu or Lys), and polyamino acids (e.g., polylysine, polyarginine, polyglycine). In some embodiments, a linker is selected from the group consisting of those shown in FIG. 2. In some embodiments, a linker is selected from a group consisting of:

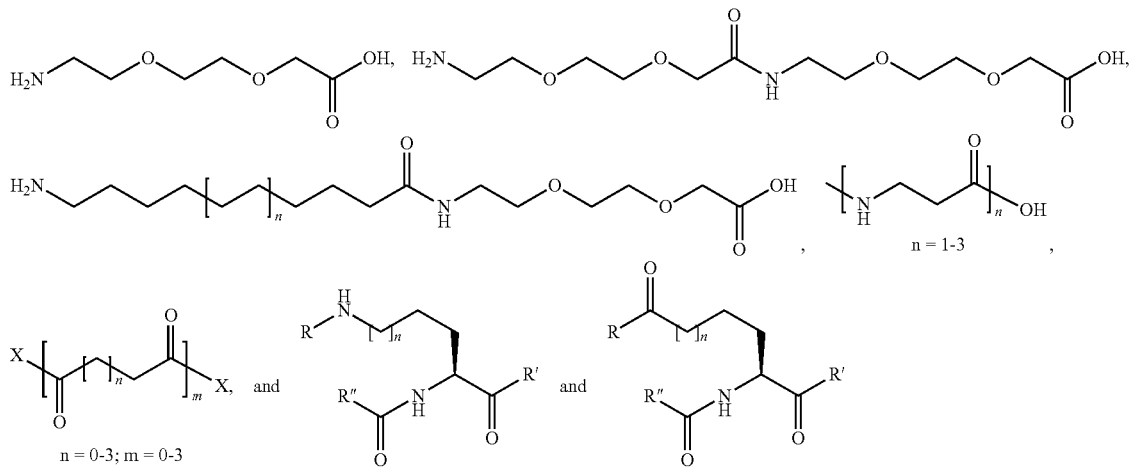

where n=0–3; R=Inhibitors or peptide; R'=OH or NH$_2$; R"=Peptide or Inhibitor.

In one embodiment, linking groups may include peptide mimetics. The use of such mimetics may induce or stabilize the peptide conformation. By way of example, β-turn mimetics include Ala-Aib and Ala-Pro dipeptides, as well as, mimic A and mimic B illustrated as follows:

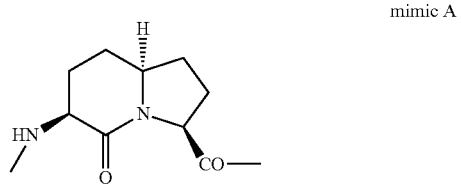

mimic A

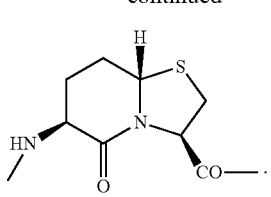

mimic B

Mimic A is N-(3S,6S,9S)-2-oxo-3-amino-1-azabicyclo[4.3.0]-nonane-9-carboxylic acid. Mimic B is N-(3S,6S,9R)-2-oxo-3-amino-7-thia-1-azabicyclo[4.3.0]-nonane-9-carboxylic acid.

In one embodiments, the linker is 1 to 30 amino acid residues in length, in another embodiment, the linker is 2 to 30 amino acid residues in length, and in yet another embodiment, the linker is 3 to 30 amino acid residues in length. In another embodiment, the linker is of any integer length from 2 to 30 amino acid residues inclusive; each integer unit is contemplated, e.g., 2, 3, 4, 5, 6, 7, and so on. In one embodiment, a Gly linker is used. In one embodiment, a three residue Gly linker (Gly-Gly-Gly) is used. In one embodiment, a β-Ala linker, e.g., β-Ala-β-Ala, is used. In one embodiment, a γ-Abu (γ-aminobutyric acid) linker is used.

In some embodiments, the P-PI conjugate exhibits at least biological activity of the component peptide. In some embodiments, the P-PI conjugate exhibits at least inhibitor activity of the component peptidase inhibitor. In other embodiments, the P-PI conjugate exhibits at least biological activity of the peptide and inhibitor activity of the peptidase inhibitor. In some embodiments, the P-PI conjugate has at least increased metabolic stability, chemical stability, receptor interaction, or conformational stability as compared to either the component peptide or the component protease inhibitor not in a conjugate complex.

As described herein, the P-PI conjugates comprise at least one peptide linked (covalently or non-covalently) to at least one peptidase inhibitor. In some embodiments, the P-PI conjugates include two or more peptides linked to a peptidase inhibitor molecule. In some embodiments, the P-PI conjugate includes two peptidase inhibitor molecules linked to a peptide. In some embodiments, the P-PI conjugate includes two different peptidase inhibitors linked to a peptide. In some embodiments, the P-PI conjugate includes three peptidase inhibitor molecules linked to a peptide. In conjugates with three inhibitor molecules, all three inhibitors may be the same, all three inhibitors may be different, or two inhibitors may be the same while the third is different from the other two.

As described herein, a single peptidase inhibitor molecule can inhibit more that one type of peptidase. For example, an NEP/ACE inhibitor has the dual activities of an NEP inhibitor and an ACE inhibitor. Accordingly, a P-PI conjugate molecule comprising one peptidase inhibitor molecule may possess more than one peptidase inhibitor activities. In some embodiments, the P-PI conjugate has two or more peptidase inhibitor activities. In some embodiments, the P-PI conjugate has three or more peptidase inhibitor activities. In some embodiments, linking one or more peptidase inhibitors to a peptide generates a P-PI conjugate with more than one peptidase inhibitor activity. For example, a P-PI comprising a peptide linked with an NEP/ACE inhibitor possesses two inhibitor activities through the linkage of a single peptidase inhibitor molecule. As another example, a P-PI comprising a peptide linked with an NEP/ECE inhibitor and an ACE inhibitor possesses three inhibitor activities through the linkage of a two different peptidase inhibitor molecules.

With regard to any of the P-PI conjugates described herein, the component peptide may be of any length. In some embodiments, the component peptide is less than 200 amino acids in length. In some embodiments, the component peptide is less than 150 amino acids in length, for example, less than 100, less than 50, less than 40, less than 30, or less than 20 amino acids in length. In one embodiment, the component peptide is between about 30 and about 40 amino acid residues in length. In some embodiments, the component peptide is between about 15 and about 25 amino acids in length, between about 20 and about 30 amino acids in length, or between about 25 and about 35 amino acids in length. In some embodiments, the component peptide is about 15, about 17, about 19, about 21, about 23, about 25, about 27, about 29, about 30, about 31, about 32, about 33, about 34, about 35, or about 36 amino acids in length.

Exemplary P-PI conjugates include, but are not limited to, those in which the peptidase inhibitor is covalently linked to a side-chain of the peptide.

An example of a peptide-lisinopril conjugate is:

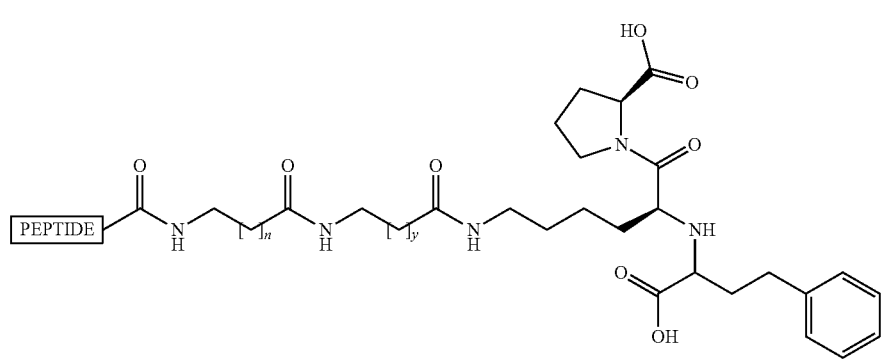

where n=0, 1, or 2; y=0, 1 or 2; and peptide=GLP-1(7-37), exendin-4, other active analogs of GLP-1(7-37) or exendin-4, or other bioactive peptides of interest.

An example of a peptide-peptide/ACE inhibitor conjugate is:

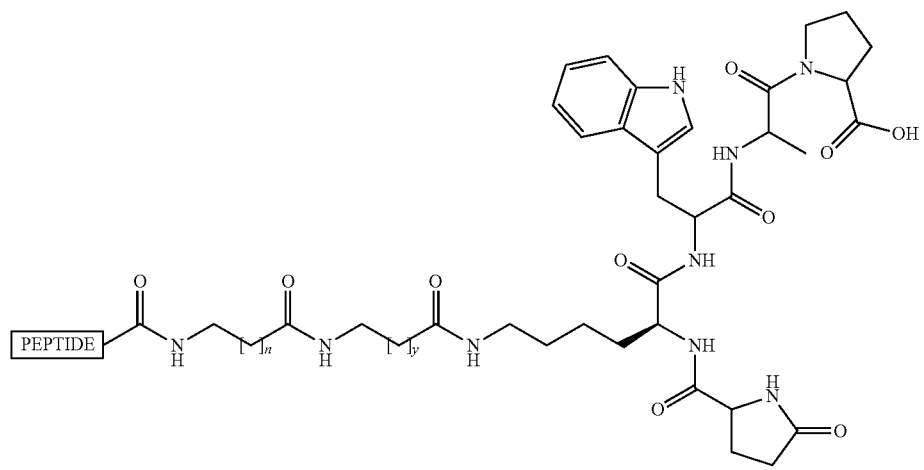

where n=0, 1, or 2; y=0, 1, or 2; peptide=GLP-1(7-37), exendin-4, other active analogs of GLP-1(7-37) or exendin-4, or other bioactive peptides of interest.

In certain embodiments, the P-PI conjugate comprises a peptidase inhibitor, such as lisinopril or pGluKWAP-OH (SEQ ID NO: 325) (ACE inhibitors), conjugated to a GLP-1, such as GLP-1(7-37) (SEQ ID NO:42) or an exendin analog, such as [14]Leu-exendin-4(1-28) (SEQ ID NO:70). In these conjugates, the peptidase inhibitor may be linked, by various linkers, at the carboxy-terminus (SEQ ID NO: 319), at the amino-terminus of the peptide analog, or at an amino acid residue within the peptide analog. Such P-PI conjugates include, but are not limited to, the following:

GLP-1(7-37)-γ-Abu-β-Ala-CONH-Lisinopril monoester:

[14]Leu-exendin-4(1-28)-γ-Abu-β-Ala-CONH-Lisinopril monoester:

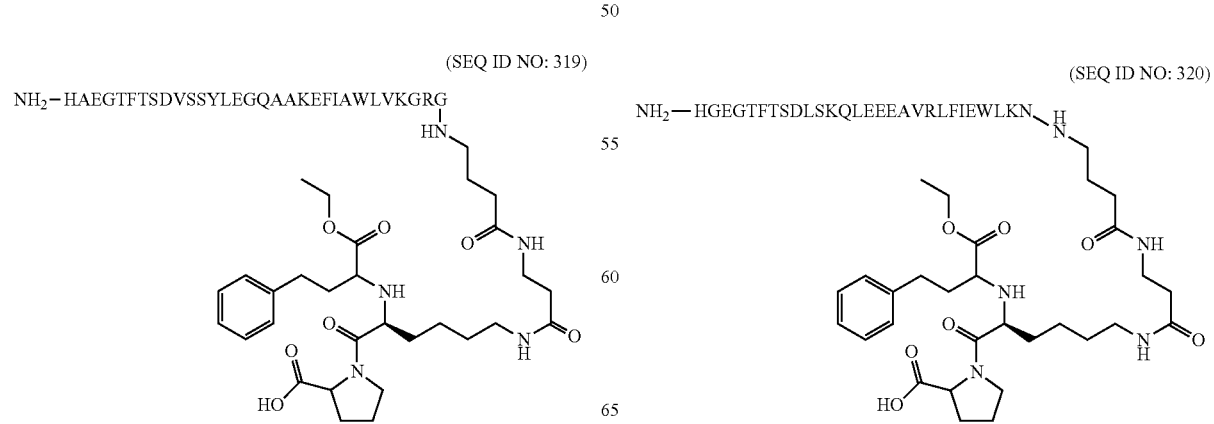

GLP-1(7-37)-γ-Abu-Lys(pGlu)WAP-OH:
(SEQ ID NO: 321)
NH₂—HAEGTFTSDVSSYLEGQAAKEFIAWLVKGRG
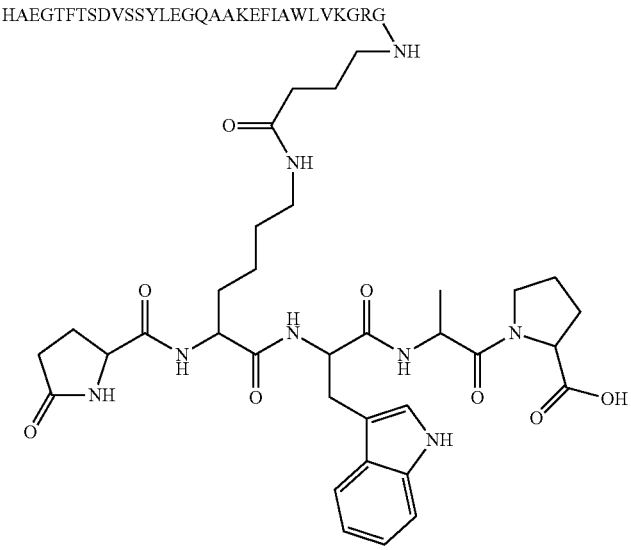
GLP-1(7-37)-γ-Abu-CONH-Lisinopril monoester:
(SEQ ID NO: 322)
NH₂—HAEGTFTSDVSSYLEGQAAKEFIAWLVKGR-N
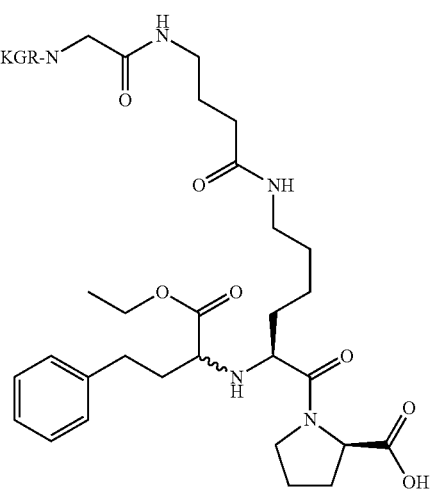
¹⁴Leu-exendin-4(1-28)-γ-Abu-CONH-Lisinopril:
(SEQ ID NO: 323)
NH₂—HGEGTFTSDLSKQLEEEAVRLFIEWLKN
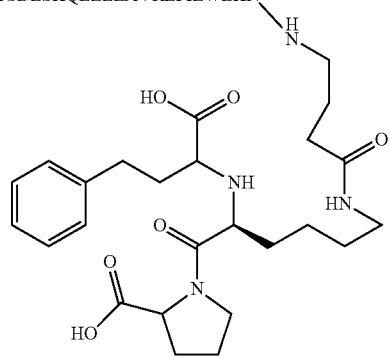
¹⁴Leu-exendin-4(1-28)-Gly-Gly-CONH-Lisinopril:
(SEQ ID NO: 324)
NH₂—HGEGTFTSDLSKQLEEEAVRLFIEWLKN
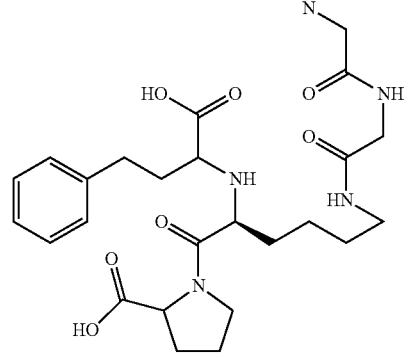

In some embodiments, the P-PI conjugate comprises a peptidase inhibitor and a peptide other than a GLP-1 or an exendin peptide. Accordingly, in some embodiments, the P-PI conjugate comprises at least one peptidase inhibitor linked to a peptide wherein the peptide is not a GLP-1 or a GLP-1 analog. In other embodiments, the P-PI conjugate comprises at least one peptidase inhibitor linked to a peptide wherein the peptide is not an exendin or an exendin analog.

In certain embodiments, the P-PI conjugate comprises a peptidase inhibitor, such as lisinopril or pGluKWAP-OH (SEQ ID NO: 325) (ACE inhibitors) conjugated to a GIP analog or a GIP hybrid molecule, such as GIP(1-30) (SEQ ID NO:79), [Leu$^{14}$]GIP(1-30) (SEQ ID NO:295), [Leu$^{14}$]GIP(1-30)-exendin-4(31-39) (SEQ ID NO:291), [D-Ala$^2$]GIP(1-30)-exendin-4(31-39) (SEQ ID NO:292), [D-Ala$^2$]GIP(1-30) (SEQ ID NO:293) and GIP(1-30)-exendin-4(31-39) (SEQ ID NO:1). In peptide-peptidase inhibitor conjugates with an Ala$^2$ in the peptide, the Ala$^2$ may be either the L or D isomer. In these conjugates, the peptidase inhibitor may be linked, by various linkers, at the carboxy-terminus of the GIP analog, at the amino-terminus of the GIP analog, or at an amino acid residue within the GIP analog, for example, at the e-amino position of $^{30}$Lys. Such P-PI conjugates include, but are not limited to, the following:

[D-Ala$^2$, Leu$^{14}$]GIP-(1-30)-β-Ala-β-Ala-Lys(α-NH-Pyroglutamoyl)-Trp-Ala-Pro-COOH:

(SEQ ID NO: 326)

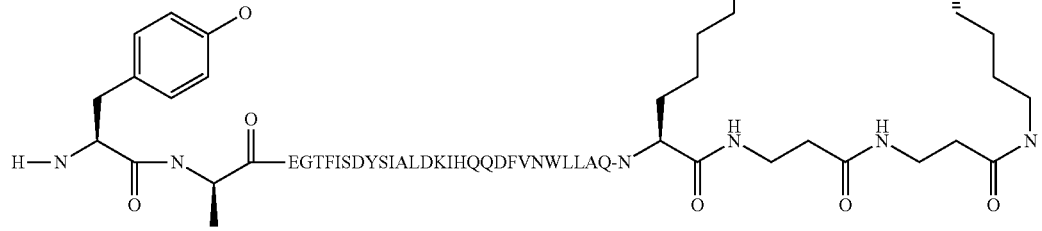

GIP-(1-30)-Ado-Ado-Aun-βAla-βAla-ε-NH-Lys(α-NH-Pyroglutamoyl)-Trp-Ala-Pro:

(SEQ ID NO: 327)

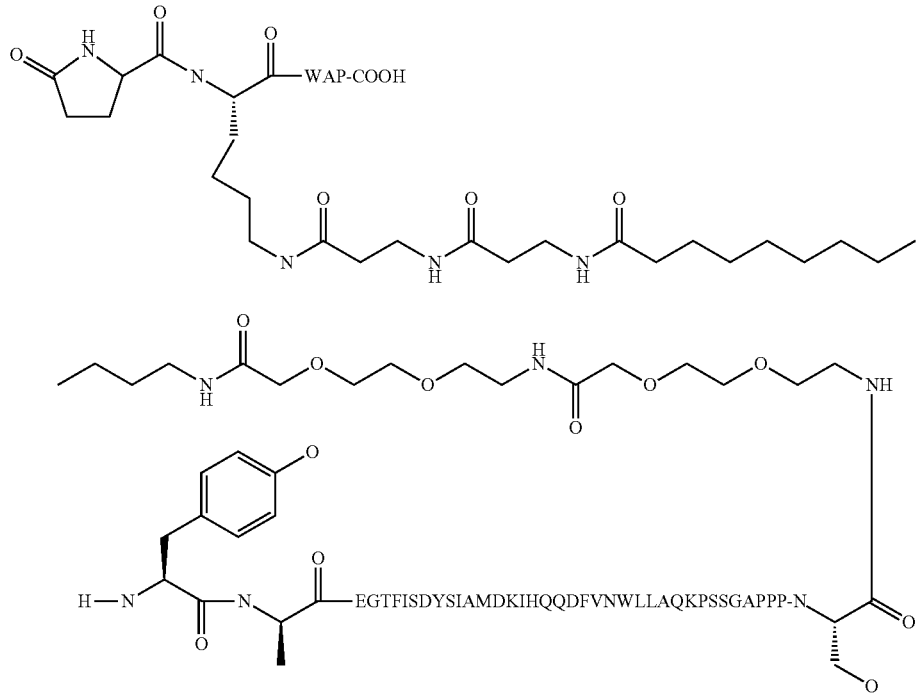

Figure 3:
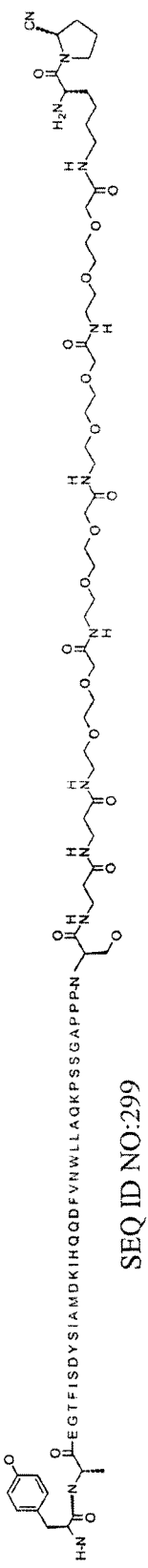
FIG. 3 depicts exemplary peptide-peptidase inhibitor conjugate compounds with GIP analogs. The single letter codes for SEQ ID NOs:299-301 are disclosed in order of appearance.
Figure 3:
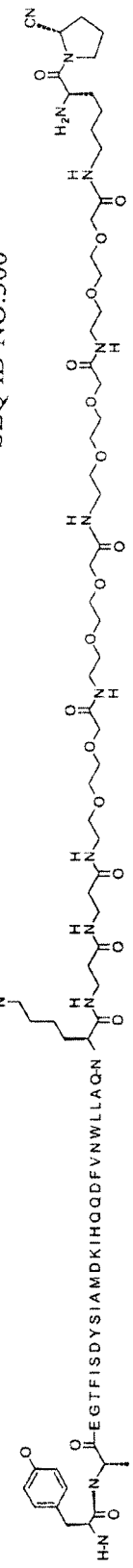
Figure 3:
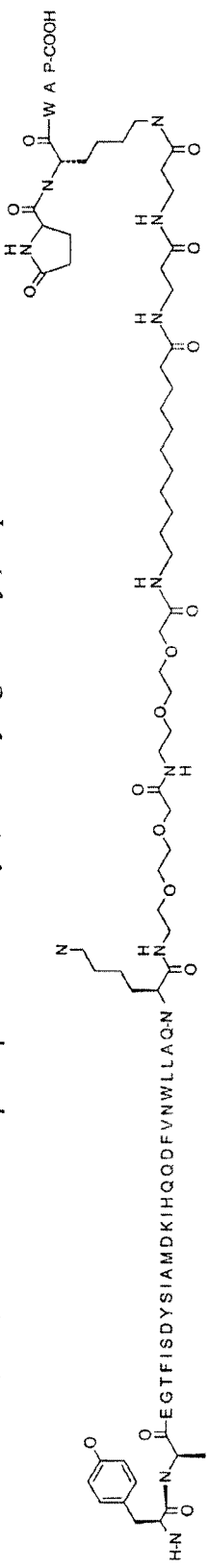

[D-Ala2]GIP-(1-30)-Ado-Ado-Aun-βAla-βAla-c-NH-Lys (α-NH-Pyroglutamoyl)-Trp-Ala-Pro (as shown in FIG. 3).

In certain embodiments, the P-PI conjugate comprises a peptidase inhibitor conjugated to a GIP analog or a GIP hybrid molecule, such as GIP(1-30) (SEQ ID NO:79), [Leu14]GIP(1-30) (SEQ ID NO:295), [Leu14]GIP(1-30)-exendin-4(31-39) (SEQ ID NO:291), [D-Ala2]GIP(1-30)-exendin-4(31-39) (SEQ ID NO:292), [D-Ala2]GIP(1-30) (SEQ ID NO:293) and GIP(1-30)-exendin-4(31-39) (SEQ ID NO:1).

In certain embodiments, the peptidase inhibitor is a DPP-IV inhibitor. In these conjugates, the DPP-IV inhibitor may be linked, by various linkers, at the carboxy-terminus of the GIP analog, at the amino-terminus of the GIP analog, or at an amino acid residue within the GIP analog, for example, at the e-amino position of 30Lys. Such P-PI conjugates include, but are not limited to, the following:

[D-Ala²]GIP(1-30)-exendin-4(31-39)-(Lys(ε-NH-(Aun-Aun-(γ-L-Glu-(2-(S)-cyano pyrrolidyl))))):

(SEQ ID NO: 328)

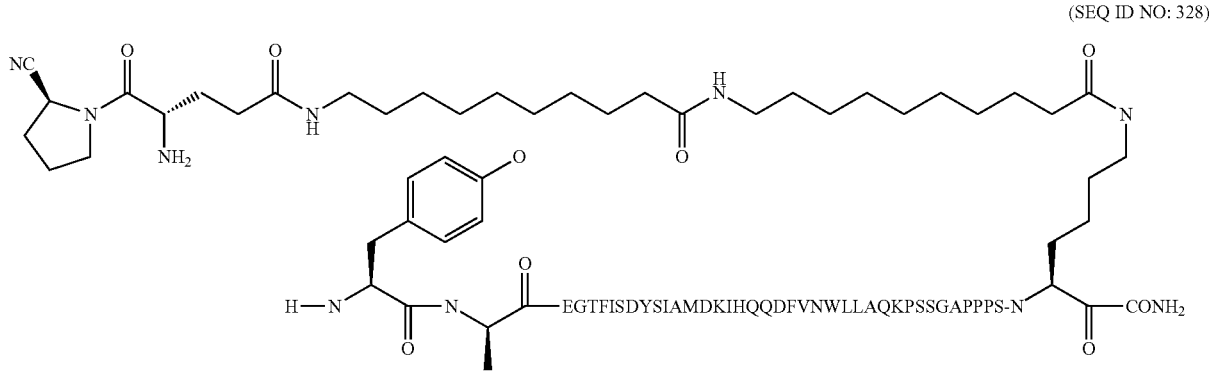

Lys30N-ε-(Ado-(γ-L-Glu-2-(S)-cyano pyrrolidyl)) GIP(1-30):

(SEQ ID NO: 329)

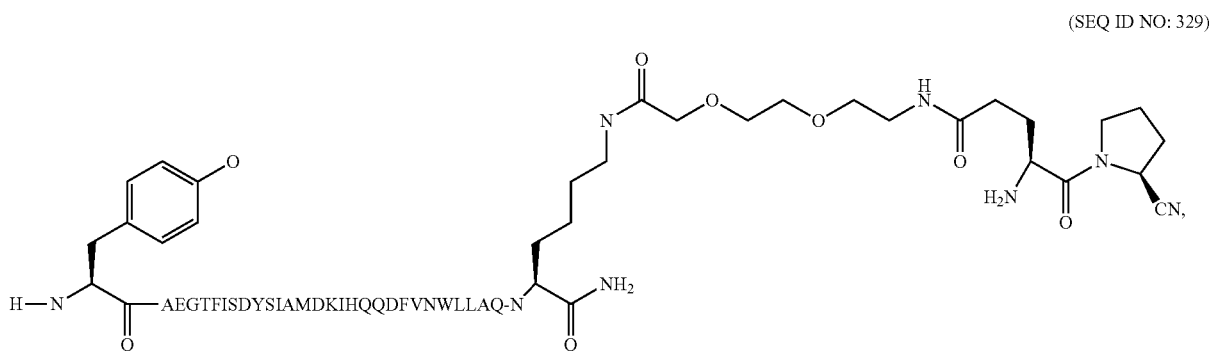

GIP(1-30)-exendin-4(31-39)-Ado-Lys-N-ε-(2-(S)-cyano pyrrolidyl):

(SEQ ID NO: 330)

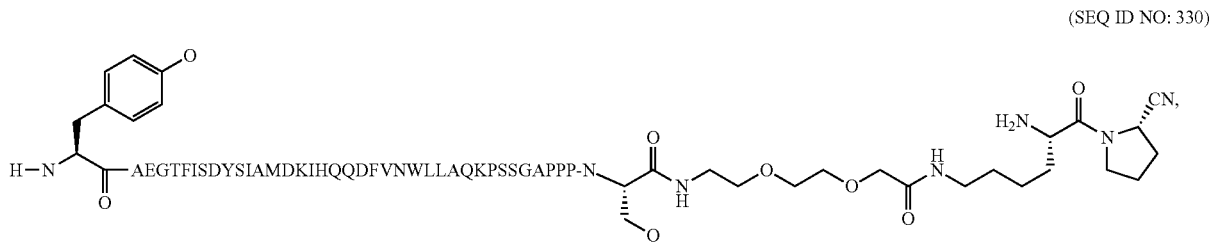

GIP(1-30)-Ado-Lys-N-ε-(2-(S)-cyano pyrrolidyl):
(SEQ ID NO: 331)
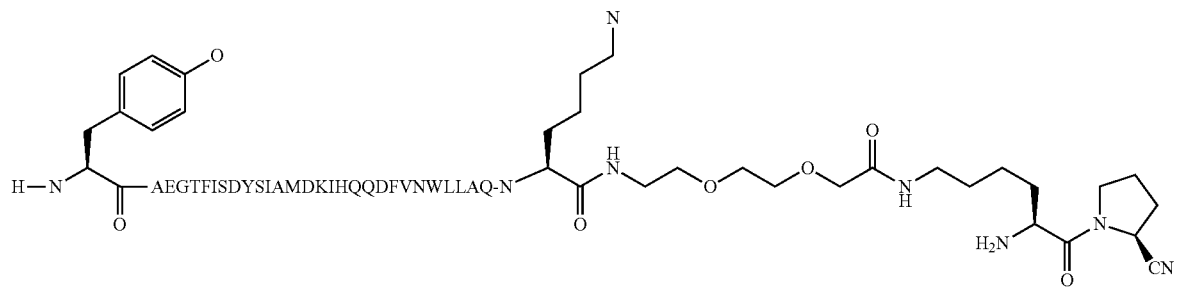
GIP(1-30)-exendin-4(31-39)-Ado-Ado-Lys-N-ε-(2-(S)-cyano pyrrolidyl):
(SEQ ID NO: 332)
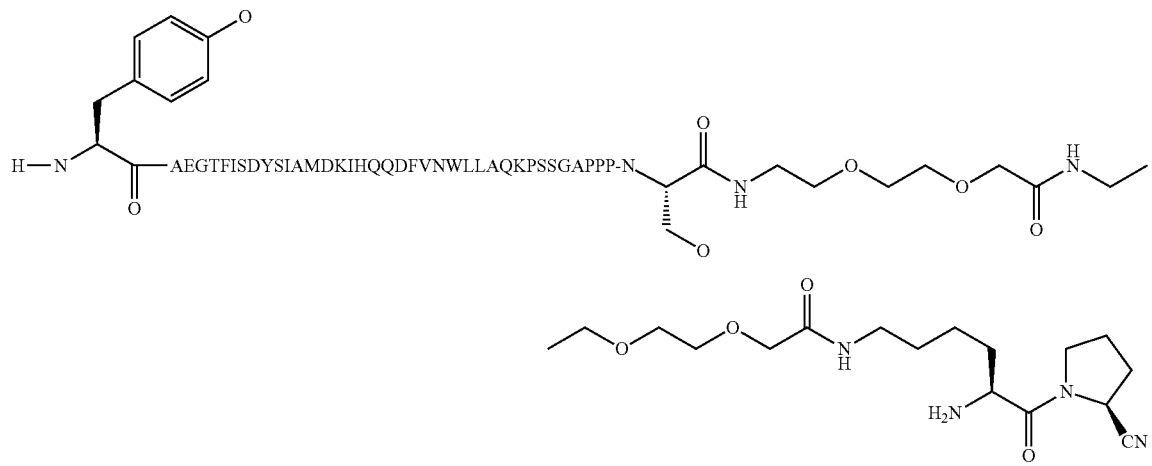
GIP(1-30)-Ado-Ado-Lys-N-ε-(2-(S)-cyano pyrrolidyl):
(SEQ ID NO: 333)
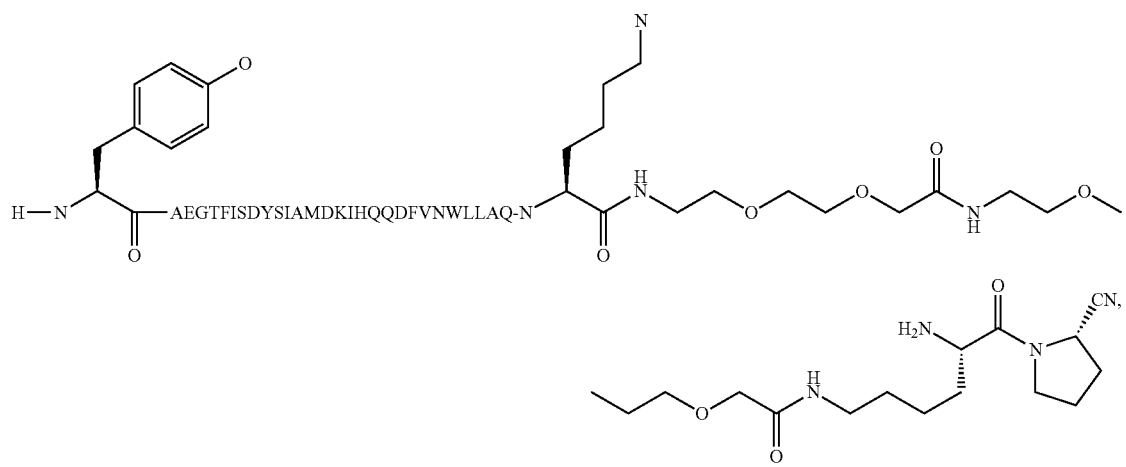

[Leu¹⁴]GIP(1-30)-exendin-4(31-39)-Ado-Lys-N-ε-(2-(S)-cyano pyrrolidyl):
(SEQ ID NO: 334)
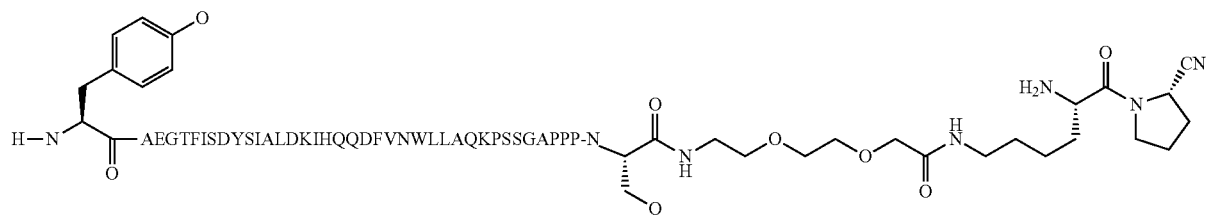
[Leu¹⁴]GIP(1-30)-Ado-Lys-N-ε-(2-(S)-cyano pyrrolidyl):
(SEQ ID NO: 335)
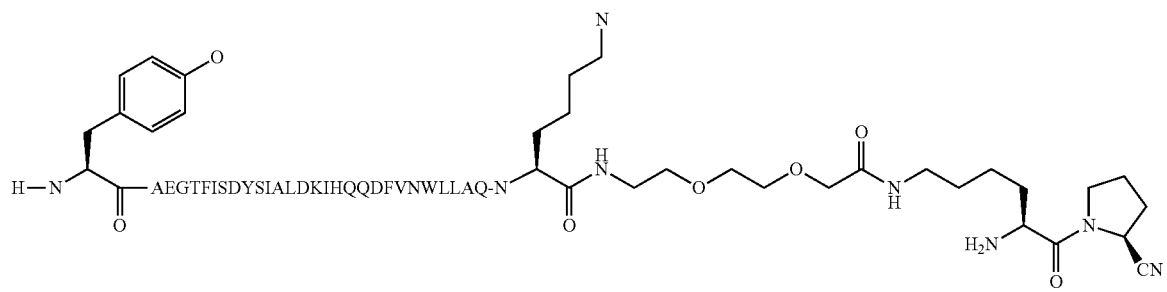
[D-Ala]GIP(1-30)-exendin-4(31-39)-Ado-Lys-N-ε-(2-(S)-cyano pyrrolidyl):
(SEQ ID NO: 336)
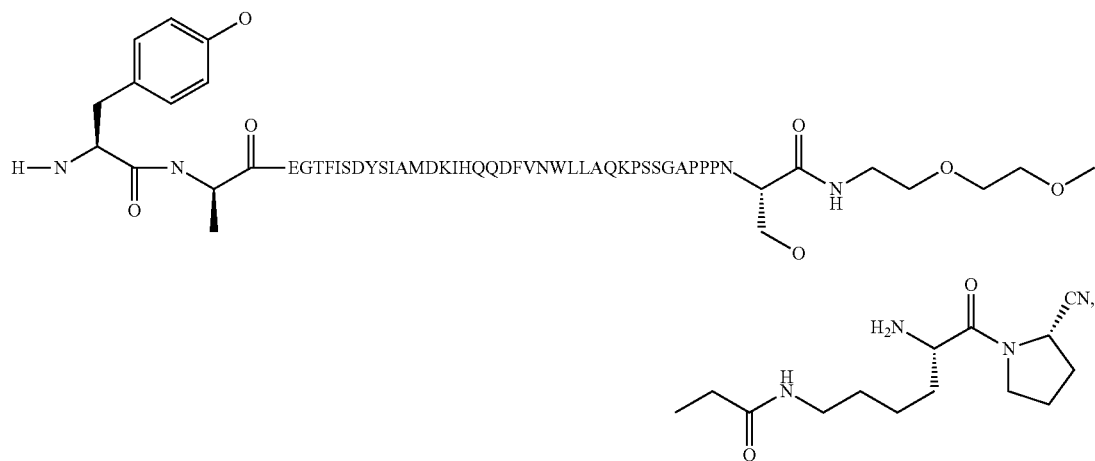

Lys³⁰ N-ε-(Ado-(γ-L-Glu-2-(S)-cyano pyrrolidyl)) GIP(1-30)-exendin-4(31-39):
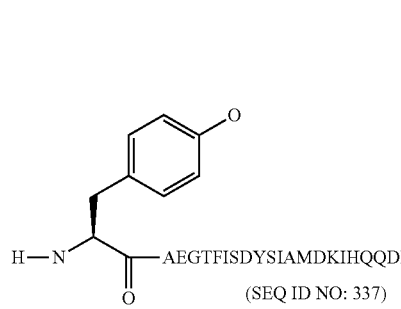
(SEQ ID NO: 337)
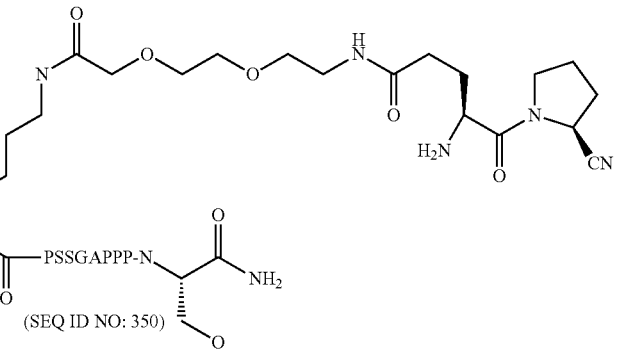
(SEQ ID NO: 350)
[D-Ala²,Lys¹⁶(ε-NH-(Aun-Aun-(γ-L-Glu-(2-(S)-cyano pyrrolidyl))))]GIP(1-30)-exendin-4(31-39):
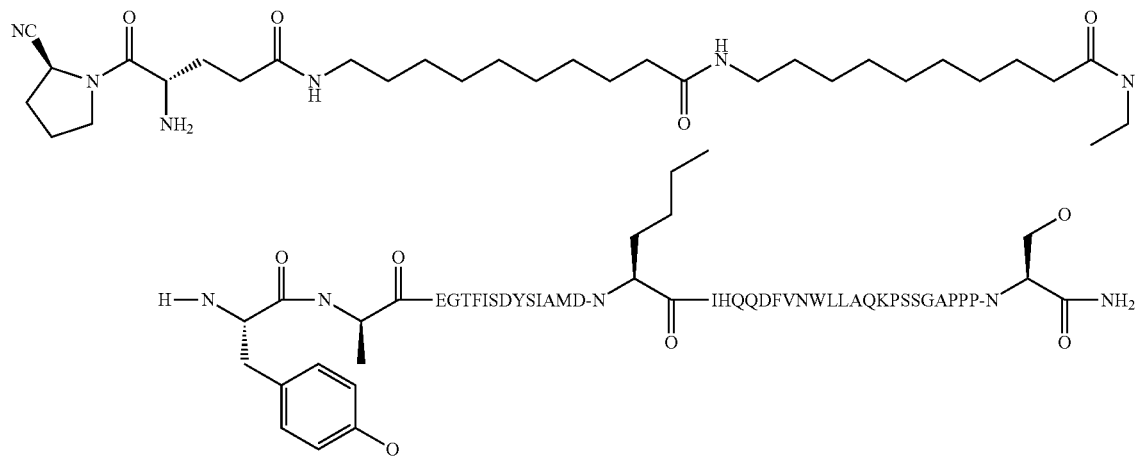
N-(γ-L-Glu-2-(S)-cyano pyrrolidyl)-Ado-Ado) GIP(1-30)-exendin-4(31-39):
(SEQ ID NO: 340)
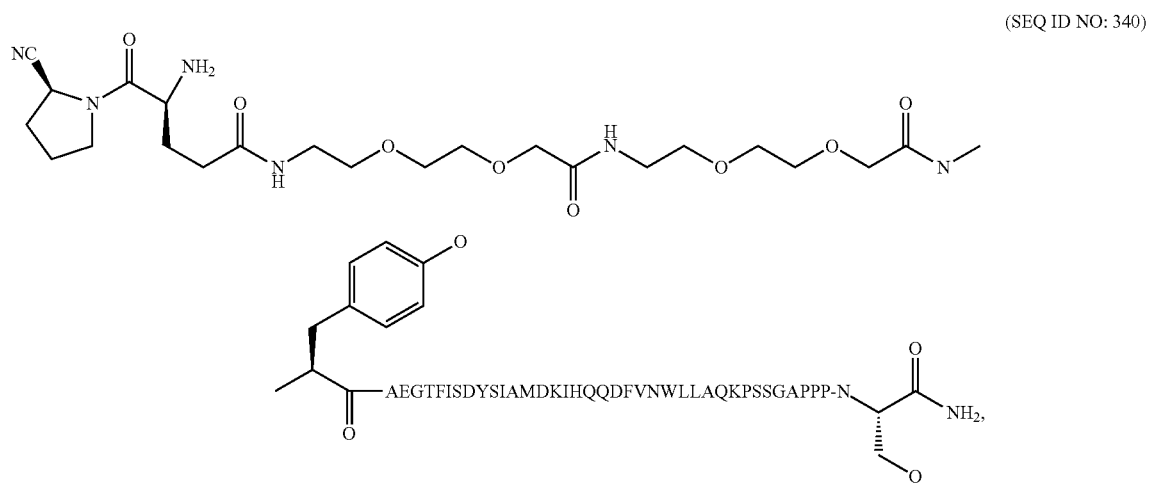

[D-Ala², Lys(ε-NH-(Aun-Aun-(γ-L-Glu-(2-(S)-cyano pyrrolidyl))))]GIP(1-30)-exendin-4(31-39):

(SEQ ID NO: 341)

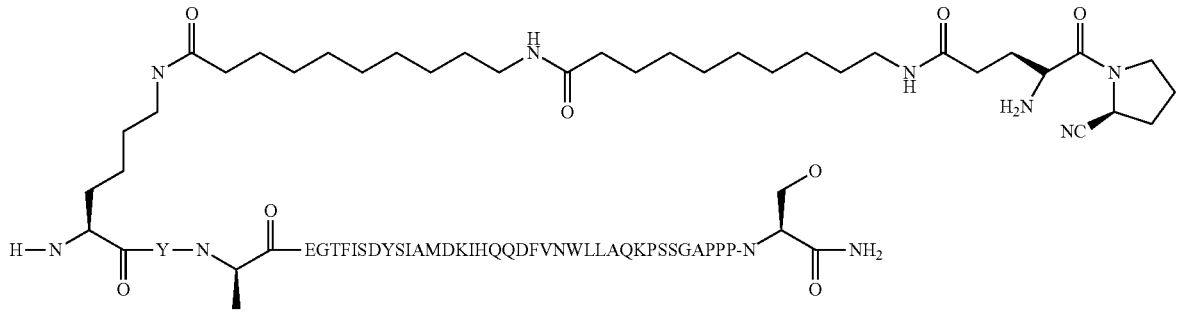

N-(γ-L-Glu-2-(S)-cyano pyrrolidyl)-Ado-Ado) GIP(1-30):

(SEQ ID NO: 342)

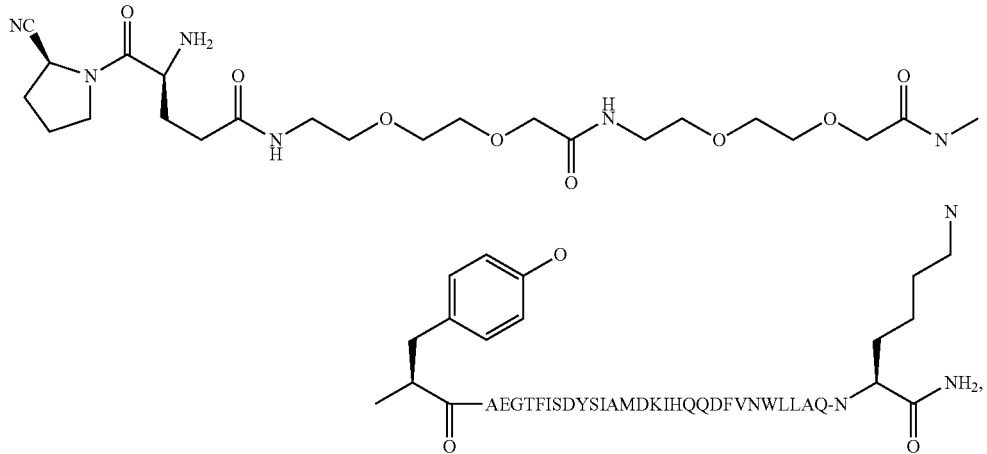

[D-Ala²]GIP(1-30)-exendin-4(31-39)-β-Ala-β-Ala-Ado-Ado-Ado-Ado-Ado-Lys-N-ε-(2-(S)-cyano pyrrolidyl), and [D-Ala²]GIP(1-30)-β-Ala-β-Ala-Ado-Ado-Ado-Ado-Lys-N-ε-(2-(S)-cyano pyrrolidyl), as shown in FIG. 3. As used herein, "Aun" is an abbreviation for 11-amino undecanoic acid and "Ado" is an abbreviation for 8-amino 3,6-dioxaoctanoic acid.

In certain embodiments, the P-PI conjugate comprises a DPP-IV inhibitor conjugated to a GIP analog or a GIP hybrid molecule by various linkers at the carboxy-terminus of the GIP analog, at the amino-terminus of the GIP analog or at an amino acid residue within the GIP analog. Examples of such conjugates include the following:

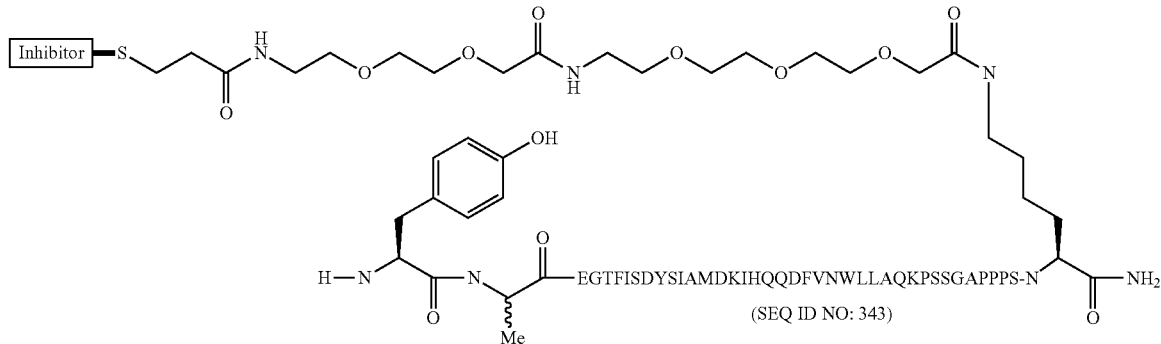

(SEQ ID NO: 343)

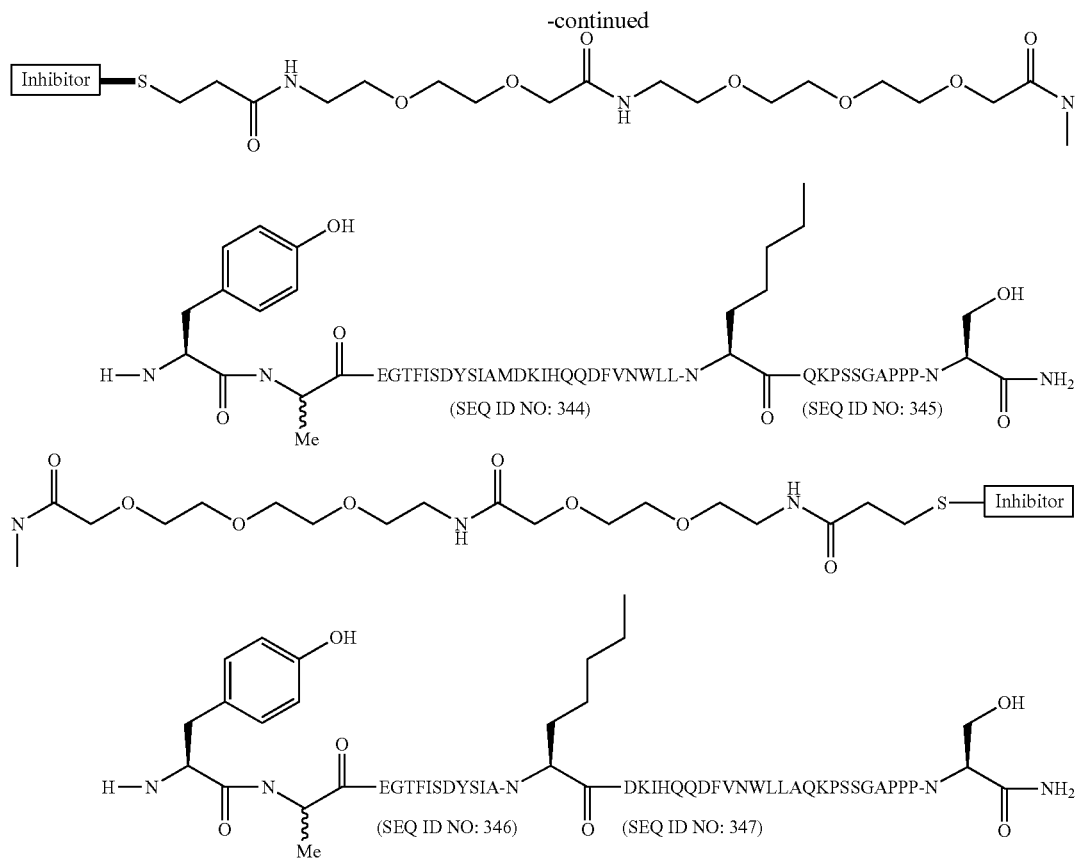

where inhibitors are:

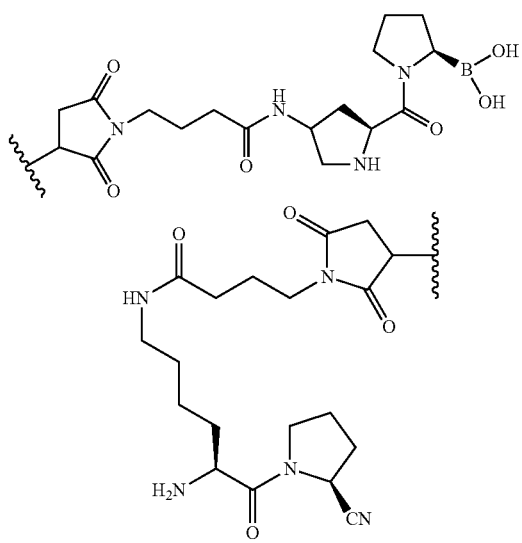

and Me is either R or S isomer.

Figure 4:
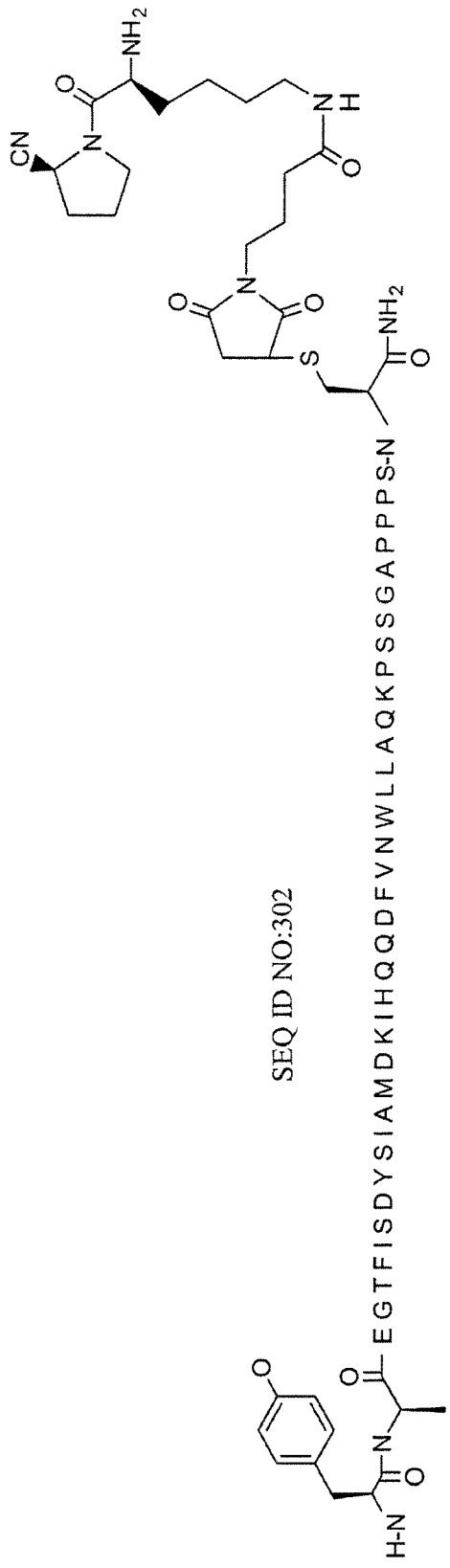
FIG. 4 depicts exemplary peptide-peptidase inhibitor conjugate compounds with GIP-exendin hybrid peptides. The single letter codes for SEQ ID NOs:302-303 are disclosed respectively in order of appearance.
Figure 4:
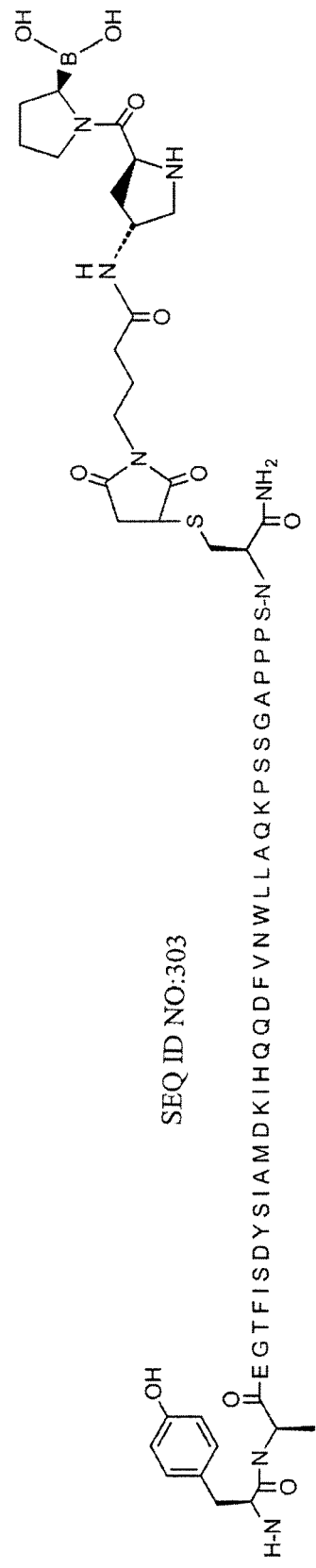

Examples of such P-PI conjugates include, but are not limited to, [D-Ala²]GIP(1-30)-exendin-4(31-39)-Cys-((S-maleimido propanoyl)-Lys-N-ε-(2-(S)-cyano pyrrolidyl)) and [D-Ala]GIP(1-30)-exendin-4(31-39)-Cys-((S-maleimido propanoyl)-(2-(S)-4(s) amino)Pro-(2-(S)-boro pyrrolidyl)), as shown in FIG. 4

In other embodiments, the P-PI conjugate comprises a serine protease inhibitor conjugated to a PYY analog, an NPY analog, or hybrid molecule, such as PYY(3-36). In other embodiments, the P-PI conjugate comprises a carboxypeptidase inhibitor conjugated to a PYY analog, an NPY analog, or hybrid molecule, such as PYY(3-36).

As used herein, the singular form "a", "an", and "the" includes plural references unless otherwise indicated or clear from context. For example, as will be apparent from context, "a" peptide hormone can include one or more peptide hormones.

As used herein, an "analog" refers to a peptide whose sequence was derived from that of a base reference or native peptide, e.g., amylin, PYY, and includes insertions, substitutions, extensions, and/or deletions of the reference amino acid sequence, for example having at least 50 or 55% amino acid sequence identity with the base peptide, in other cases, for example, having at least 70%, 80%, 90%, or 95% amino acid sequence identity with the base peptide. Such analogs may comprise conservative or non-conservative amino acid substitutions (including non-natural amino acids and L and D forms). Analogs include compounds having agonist and compounds having antagonist activity. Analogs may also include compounds having an activity not present in the reference peptide, for example, a peptidase inhibitor activity. Analogs, as herein defined, also include derivatives.

A "derivative" is defined as a reference peptide or analog, described above, having a chemical modification of one or more of its amino acid side groups, α-carbon atoms, terminal amino group, or terminal carboxylic acid group. A chemical modification includes, but is not limited to, adding chemical moieties, creating new bonds, and removing chemical moieties. Modifications at amino acid side groups include, without limitation, acylation of lysine ε-amino groups, N-alkylation of arginine, histidine, or lysine, alkylation of glutamic or aspartic carboxylic acid groups, and deamidation of glutamine or asparagine. Modifications of the terminal amino group include, without limitation, the desamino, N-lower alkyl, N-di-lower alkyl, constrained alkyls (e.g. branched, cyclic, fused, adamantyl) and N-acyl modifications, such as alkyl acyls, branched alkylacyls, alkylaryl-acyls. Modifications of the terminal carboxy group include, without limitation, the amide, lower alkyl amide, constrained alkyls (e.g. branched, cyclic, fused, adamantyl), dialkyl amide, arylamide, alkylarylamide and lower alkyl ester modifications. Lower alkyl is C1-C4 alkyl. Furthermore, one or more side groups, or terminal groups, may be protected by protective groups known to the ordinarily-skilled synthetic chemist. The α-carbon of an amino acid may be mono- or dimethylated.

In general, with respect to an amino acid sequence, the term "modification" includes substitutions, insertions, elongations, deletions, and derivatizations alone or in combination. In some embodiments, the peptides may include one or more modifications of a "non-essential" amino acid residue. In this context, a "non-essential" amino acid residue is a residue that can be altered, e.g., deleted or substituted, in the novel amino acid sequence without abolishing or substantially reducing the activity (e.g., the agonist activity) of the peptide (e.g., the analog peptide). In some embodiments, the peptides may include one or more modifications of an "essential" amino acid residue. In this context, an "essential" amino acid residue is a residue that when altered, e.g., deleted or substituted, in the novel amino acid sequence the activity of the reference peptide is substantially reduced or abolished. In such embodiments where an essential amino acid residue is altered, the modified peptide may possess an activity of use in the P-PI conjugate, for example, a peptidase inhibitor activity. The peptides of use in the P-PI conjugates may include deletions of 1, 2, 3, 4, 5, 6, 7, 8, 9, 10 or more amino acid residues. The peptides of use in the P-PI conjugates may include additions of at least of 1, 2, 3, 4, 5, 6, 7, 8, 9, 10 or more amino acids. The peptides of use in the P-PI conjugates may include substitutions of 1, 2, 3, 4, 5, 6, 7, 8, 9, 10 or more amino acid residues.

Substitutions include conservative amino acid substitutions. A "conservative amino acid substitution" is one in which the amino acid residue is replaced with an amino acid residue having a similar side chain, or physicochemical characteristics (e.g., electrostatic, hydrogen bonding, isosteric, hydrophobic features). The amino acids may be naturally occurring or normatural (unnatural). Families of amino acid residues having similar side chains are known in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, methionine, cysteine), nonpolar side chains (e.g., alanine, valine, leucine, isoleucine, proline, phenylalanine, tryptophan), β-branched side chains (e.g., threonine, valine, isoleucine) and aromatic side chains (e.g., tyrosine, phenylalanine, tryptophan, histidine). Substitutions may also include non-conservative changes.

By "amino acid" or "amino acid residue" is meant natural amino acids, unnatural amino acids, and modified amino acid. Unless stated to the contrary, any reference to an amino acid, generally or specifically by name, includes reference to both the D and the L stereoisomers if their structure allow such stereoisomeric forms. Natural amino acids include alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), Lysine (Lys), methionine (Met), phenylalanine (Phe), proline (Pro), serine (Ser), threonine (Thr), tryptophan (Trp), tyrosine (Tyr) and valine (Val). Unnatural amino acids include, but are not limited to, homolysine, homoarginine, homoserine, azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, tertiary-butylglycine, 2,4-diaminoisobutyric acid, desmosine, 2,2'-diaminopimelic acid, 2,3-diaminopropionic acid, N-ethylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, norleucine, ornithine, pentylglycine, pipecolic acid, pyroglutamate, and thioproline. Additional unnatural amino acids include modified amino acid residues which are chemically blocked, reversibly or irreversibly, or chemically modified on their N-terminal amino group or their side chain groups, as for example, N-methylated D and L amino acids or residues wherein the side chain functional groups are chemically modified to another functional group. For example, modified amino acids include methionine sulfoxide; methionine sulfone; aspartic acid-(beta-methyl ester), a modified amino acid of aspartic acid; N-ethylglycine, a modified amino acid of glycine; or alanine carboxamide, a modified amino acid of alanine. Additional residues that can be incorporated are described in Sandberg et al. (1998) *J. Med. Chem.* 41:2481-2491.

It should be noted that alternatives are written throughout in Markush groups, for example, each amino acid position that contains more than one possible amino acid. It is specifically contemplated that each member of the Markush group should be considered separately, thereby comprising another embodiment, and the Markush group is not to be read as a single unit.

"Sequence identity", as is well understood in the art, is a relationship between two or more polypeptide sequences or two or more polynucleotide sequences, as determined by comparing the sequences. In the art, "identity" can also mean the degree of sequence relatedness between polypeptide or polynucleotide sequences, as determined by the match between strings of such sequences. Identity can be readily calculated by known methods including, but not limited to, those described in *Computational Molecular Biology*, Lesk, A. M., ed., Oxford University Press, New York (1988); *Biocomputing: Informatics and Genome Projects*, Smith, D. W., ed., Academic Press, New York, 1993; *Computer Analysis of Sequence Data, Part I*, Griffin, A. M. and Griffin, H. G., eds., Humana Press, New Jersey (1994); *Sequence Analysis in Molecular Biology*, von Heinje, G., Academic Press (1987); Sequence *Analysis Primer*, Gribskov, M. and Devereux, J., eds., Stockton Press, New York (1991); and Carillo, H., and Lipman, D., SIAM *J Applied Math*, 48:1073 (1988). Methods to determine identity are designed to give the largest match between the sequences tested. Moreover, methods to determine identity are codified in publicly available programs. Computer programs which can be used to determine identity between two sequences include, but are not limited to, GCG (Devereux et al. (1984) *Nucleic Acids Research* 12:387; suite of five BLAST programs, three designed for nucleotide sequences queries (BLASTN, BLASTX, and TBLASTX) and two designed for protein sequence queries (BLASTP and TBLASTN) (Coulson (1994) *Trends in Biotechnology* 12:76-80; Birren et al. (1997) *Genome Analysis* 1:543-559). The BLAST X program is publicly available from NCBI and other sources (*BLAST Manual*, Altschul, S., et al., NCBI NLM NIH, Bethesda, Md. 20894; Altschul et al. (1990) *J. Mol. Biol.* 215:403-410). The well known Smith Waterman algorithm can also be used to determine identity.

Parameters for polypeptide sequence comparison typically include the following: Algorithm: Needleman and Wunsch (1970) *J. Mol. Biol.* 48:443-453; Comparison matrix: BLOSSUM62 from Hentikoff and Hentikoff (1992) *Proc. Natl. Acad. Sci. USA* 89:10915-10919; Gap Penalty: 12; Gap Length Penalty: 4. A program that can be used with these parameters is publicly available as the "gap" program from Genetics Computer Group ("GCG"), Madison, Wis. The above parameters along with no penalty for end gap are the default parameters for peptide comparisons. In one embodiment the BLASTP program of NCBI is used with the default parameters of no compositional adjustment, expect value of 10, word size of 3, BLOSUM62 matrix, gap extension cost of 11, end gap extension cost of 1, dropoff (X) for blast extension (in bits) 7, X dropoff value for gapped alignment (in bits) 15, and final X dropoff value for gapped alignment (in bits) 25.

Parameters for nucleic acid molecule sequence comparison include the following: Algorithm: Needleman and Wunsch (1970) *J. Mol. Bio.* 48:443-453; Comparison matrix: matches—+10; mismatches=0; Gap Penalty: 50; Gap Length Penalty: 3. As used herein, "% identity" is determined using the above parameters as the default parameters for nucleic acid molecule sequence comparisons and the "gap" program from GCG, version 10.2.

In one aspect, use of a P-PI conjugate compound disclosed herein provides a method of increasing the plasma half-life of a peptide hormone in plasma. Administration of a P-PI conjugate increases plasma half-life of the peptide of the conjugate as compared to administration of an unconjugated peptide. The peptidase inhibitor of the P-PI conjugate may also increase plasma half-life of the endogenous component peptide. An increase in plasma half-life of the peptide may lead to a prolonged or an increase in the effective plasma concentration of the peptide.

As used herein, "increasing plasma half-life" means an increase in the half-life of the peptide in plasma compared to a suitable control. For example, the plasma half-life of the peptide in the P-PI conjugate is greater than that of an unconjugated peptide. In one embodiment, the P-PI conjugate increases the plasma half-life of the peptide by at least 5% compared to the plasma half-life of an unconjugated component peptide. In some instances, the P-PI conjugate increases the plasma-life of the peptide by at least 10%, at least 15%, at least 20%, at least 25%, at least 30% compared to the plasma half-life of an unconjugated component peptide. The plasma half-life of a peptide can be measured in vivo or in vitro and may be determined by any method described herein or known in the art.

In another aspect, use of a P-PI conjugate compound disclosed herein provides a method for decreasing or delaying peptide degradation of a peptide hormone in plasma. Administration of a P-PI conjugate decreases or delays degradation of the peptide of the conjugate as compared to administration of an unconjugated peptide. The peptidase inhibitor of the P-PI conjugate may also decrease or delay degradation of the endogenous component peptide in plasma. A decrease or delay in degradation of the peptide in plasma may lead to a prolonged or an increase in the effective plasma concentration of the peptide.

As used herein, "peptide degradation" refers to a process where an endogenous or exogenous peptide is degraded in vivo or in vitro by a biological process, such as by a peptidase. For example, degradation of the peptide in the P-PI conjugate in plasma is less than that of an unconjugated peptide. In one embodiment, the P-PI conjugate decreases or delays peptide degradation in plasma by at least 5% compared to degradation of an unconjugated component peptide in plasma. In some instances, the P-PI conjugate decreases plasma degradation of the peptide by at least 10%, at least 15%, at least 20%, at least 25%, at least 30% compared to plasma degradation of an unconjugated component peptide. Degradation of peptides can be measured in vivo or in vitro and may be determined by any method described herein or known in the art.

In general, the P-PI conjugate compounds disclosed herein are of use in methods where the individual component peptide or peptidase inhibitor would be of use based on their biological activities. In one aspect, certain P-PI conjugates disclosed herein have a prolonged serum half-life relative to the unconjugated peptide. Accordingly, the conjugate is of use in methods in which a skilled artisan would use the component peptide. In another aspect, the peptide in certain P-PI conjugates can serve to specifically and effectively deliver the peptidase inhibitor to a site rich in peptide receptor. Accordingly, this will allow the peptidase inhibitor to reduce peptidase activity on endogenous peptide molecules at their site of action, e.g., the peptide receptor.

In a one general aspect, methods are provided for reducing nutrient availability through administration of a P-PI conjugate compound. Thus, disclosed herein are methods for treating diseases, disorders, and/or conditions that would benefit from a reduction in nutrient availability. Conditions, diseases, and disorders that may benefit from a reduction in nutrient availability include, but are not limited to, obesity, obesity-related conditions, eating disorders, hypertension, pulmonary hypertension, dyslipidemia, hyperlipidemia, cardiovascular disease, insulin-resistance, abnormal postprandial hyperglycemia, and diabetes mellitus of any kind, Dumping Syndrome, and Metabolic Syndrome. Given the increase in serum half-life and thus extended effectiveness of the conjugate as compared to the peptide alone, methods disclosed herein may allow for administration of lower or less frequent dosages of therapeutic agent. Exemplary P-PI conjugate compounds for use in methods for reducing nutrient availability include, but are not limited to, those conjugates in which the component peptide is a PYY, an exendin, a GLP-1, an amylin, sCT, an AFP-6, a leptin, or a hybrid, agonist, analog or derivative of any of these. Accordingly, conjugates in which the component peptide is a PYY, an exendin, a GLP-1, amylin, sCT, an AFP-6, a leptin or a hybrid, agonist, analog or derivative of any of these are nonlimiting examples of P-PI conjugates of use in treating or preventing conditions, diseases, and disorders that may benefit from a reduction in nutrient availability, as described herein.

"Reduced nutrient availability" is meant to include any means by which the body reduces the nutrients available to the body to store as fat. In other words, reducing nutrient availability may be by means that include, but are not limited to, reducing food intake, reducing appetite, increasing satiety, affecting food choice/taste aversion, increasing metabolism, decreasing or inhibiting food absorption, or any combination of the preceding. An exemplary mechanism that may be affected includes delayed gastric emptying.

In one aspect, methods are provided for treating or preventing obesity in a subject, where the method comprises administering a therapeutically or prophylactically effective amount of a P-PI conjugate to the subject. Methods are also provided for treating or ameliorating symptoms or effects of obesity in a subject in need thereof, where the method comprises administering a therapeutically effective amount of a P-PI conjugate to the subject. While "obesity" is generally defined as a body mass index (BMI, kg/m$^2$) over 30, for purposes of this disclosure, any subject, including those with a body mass index of less than 30, who needs or wishes to reduce body weight or prevent body weight gain is included in the scope of "obese." Thus, subjects with a BMI of between 30 and 25 (considered overweight) or below 25 are also included in the subjects of the methods disclosed herein. Morbid obesity refers to a BMI of 40 or greater.

In some embodiments, methods are provided to increase the metabolic rate in a subject, decrease a reduction in the metabolic rate in a subject, or preserve the metabolic rate in a subject. By "metabolic rate" is meant the amount of energy liberated/expended per unit of time. Metabolism per unit time can be estimated by food consumption, energy released as heat, or oxygen used in metabolic processes. It is generally desirable to have a higher metabolic rate when one wants to loose weight. For example, a person with a high metabolic rate may be able to expend more energy (e.g., the body burns more calories) to perform an activity than a person with a low metabolic rate for that activity.

In one embodiment, the metabolic rate may involve the preferential use of the body's fat as an energy source over lean body tissue. In one aspect, lean body mass is not decreased following administration of the P-PI conjugate. In another aspect, a reduction in the lean body mass is lessened or prevented following administration of the P-PI conjugate. In still another aspect, lean body mass is increased following administration of the P-PI conjugate. Such preference for fat as the energy source may be determined by comparing the amount of fatty tissue to lean body tissue, ascertained by measuring total body weight and fat content at the beginning and end of the treatment period. An increase in metabolic rate is a higher level of the use of calories or another energy source by a subject over a period of time compared with the level of use of calories or other energy source by the subject over another period of time under substantially similar or identical conditions without administration of the P-PI conjugate. In one embodiment, the metabolic rate is increased at least about 5% in a subject, in other embodiments, the metabolic rate is increased at least about 10%, 15%, 20% 25%, 30%, or 35% in a subject compared with the level of use of calories or other energy source by the subject over another period of time under substantially similar or identical conditions without administration of the P-PI conjugate. The increase in metabolic rate can be measured using a respiratory calorimeter, for example.

In another embodiment, a method is provided to reduce a decrease in metabolic rate in a subject. Such a decrease in metabolic rate can be the result of any condition or nutritional or physical regimen that leads to a reduction in metabolic rate, e.g., due to a reduced calorie diet, a restricted diet, or weight loss. A restricted diet includes allowances or prohibitions, or both on the types of food or the amounts of food or both permitted in a diet, not necessarily based on calories. For example, as in individual diets, the body compensates with a reduced metabolic rate based on the lower caloric intake. In essence, the body down-regulates the requirement for food, thereby subsisting on less food. As dieting continues, the threshold for caloric intake is reduced. When dieting has ended, the individual typically gains weight while eating a normal diet because of the lowered caloric intake threshold and lower-basal metabolic rate (NIH Technology Assessment Conference Panel (1992) *Ann. Intern. Med.* 116:942-949; Wadden (1993) *Ann. Intern. Med.* 119:688-693). In one aspect, a method is provided to reduce the loss of metabolic rate in a subject, where the loss of metabolic rate is the result of a reduced calorie diet or weight loss. By using such a method, the subject's reduction in metabolic rate is decreased by at least about 10%, 15%, 20% 25%, 30%, 35%, 40%, 50%, 60%, 70%, 80%, 90%, or 95% in a subject. For such methods, it may be desirable to administer the P-PI conjugate at the time the condition or nutritional or physical regimen is initiated which leads to a loss or reduction in metabolic rate. However, it is also contemplated that administration of the P-PI conjugate is commenced before the condition or nutritional or physical regimen is initiated. In one instance, metabolic rate is measured using a respiratory calorimeter.

In another aspect, methods for reducing metabolic plateaus are provided, where a method comprises administering effective amounts of the P-PI conjugate to a subject. In one embodiment, the subject is losing weight, or has lost weight, for example, due to a reduced calorie diet, increased exercise or a combination thereof. By "metabolic plateau" is meant time intervals of steady metabolic rate while the body adjusts to changes in caloric or energy input. Changes in caloric input or expenditure can be the result of, for example, reduced calorie diets or increased physical activity. Such plateaus can be observed, for example, during a weight loss regimen when weight loss slows or stops. In one embodiment, a method provided reduces the duration of a metabolic plateau in a subject compared with the duration of metabolic plateaus in an otherwise identical subject over the same period of time under substantially similar or identical conditions without administration of the P-PI conjugate. In another embodiment, a method provided reduces the frequency of metabolic plateaus compared with the frequency of metabolic plateaus in an otherwise identical subject over the same period of time under substantially similar or identical conditions without administration of the P-PI conjugate. In still another embodiment, a method provided delays the onset of a metabolic plateau compared with the onset of a metabolic plateau in an otherwise identical subject over the same period of time under substantially similar or identical conditions without administration of the P-PI conjugate. In one embodiment, metabolic plateaus are identified by charting periods of reduced or no weight loss. In one embodiment, at least one metabolic plateau is reduced. In other embodiments, at least two, three, four, five, six, seven, eight, nine, or ten metabolic plateaus are reduced. In another aspect, metabolic plateaus are delayed one day as compared to a subject not administered the P-PI conjugate under identical or similar conditions. In other aspects, metabolic plateaus are delayed 2 days, 3 days, 4 days, 5 days, 6 days, 1 week, 10 days, 2 weeks or 3 weeks in a subject.

In yet another embodiment, a method is provided to preserve the metabolic rate in a subject. In one embodiment, the subject may be at risk of losing metabolic rate, for example, due to the initiation of a reduced calorie diet, restricted diet, or anticipated weight loss. A preservation of metabolic rate is a maintenance of the level of the use of calories or another energy source by a subject over a period of time compared with the level of use of calories or other energy source by an otherwise identical subject over the same period of time under substantially similar or identical conditions without administration of the P-PI conjugate. In one aspect, the metabolic rate is maintained within 15% of the subject's metabolic rate prior to the initiation of the event that results in the decrease in metabolic rate. In other aspects, the metabolic rate is maintained within 10%, within 7%, within 5%, within 3% or less of the subject's metabolic rate. In one aspect, the P-PI conjugate is administered at the initiation of a reduced calorie diet, restricted diet, or exercise regimen.

In another embodiment, methods for reducing fat mass by increasing the metabolic rate in a subject are provided, where the methods comprise administering a P-PI in an amount effective to reduce fat mass by increasing the subject's metabolic rate. Fat mass can be expressed as a percentage of the total body mass. In some instances, the fat mass is reduced by at least 1%, at least 5%, at least 10%, at least 15%, at least 20%, or at least 25% over the course of treatment. In one aspect, the subject's lean mass is not decreased over the course of the treatment. In another aspect, the subject's lean mass is maintained or increased over the course of the treatment. In another aspect, the subject is on a reduced calorie diet or restricted diet. By "reduced calorie diet" is meant that the subject is ingesting fewer calories per day than compared to the same subject's normal diet. In one instance, the subject is consuming at least 50 fewer calories per day. In other instances, the subject is consuming at least 100, 150, 200, 250, 300, 400, 500, 600, 700, 800, 900, or 1000 fewer calories per day.

As used herein, "lean mass" or "lean body mass" refers to muscle and bone. Lean body mass does not necessarily indicate fat free mass. Lean body mass contains a small percentage of fat (roughly 3%) within the central nervous system (brain and spinal cord), marrow of bones, and internal organs. Lean body mass is measured in terms of density. In one embodiment, fat mass and lean mass is measured using underwater weighing.

In one embodiment, a method for altering the fat distribution in a subject is provided where the method comprises administering a P-PI conjugate in an amount effective to alter fat distribution in the subject. By "fat distribution" is meant the location of fat deposits in the body. Such locations of fat deposition include, for example, subcutaneous, visceral and ectopic fat depots. In one aspect, the alteration results from an increased metabolism of visceral or ectopic fat, or both in the subject. In some embodiments, the method involves the metabolism of visceral or ectopic fat or both at a rate of at least about 5%, 10%, 15%, 20%, 25%, 30%, 40%, or 50% greater than for subcutaneous fat. In one aspect, the methods result in a favorable fat distribution. In one embodiment, favorable fat distribution is an increased ratio of subcutaneous fat to visceral fat, ectopic fat, or both. In one aspect, the method involves an increase in lean body mass, for example, as a result of an increase in muscle cell mass.

In another embodiment, methods for reducing the amount of subcutaneous fat in a subject are provided, wherein the method comprises administering, to a subject in need thereof, a P-PI conjugate in an amount effective to reduce the amount of subcutaneous fat in the subject. By "subcutaneous fat" is meant the deposit of lipids just below the skin's surface. The amount of subcutaneous fat in a subject can be measured using any method available for the measurement of subcutaneous fat. In one instance, the amount of subcutaneous fat is reduced in a subject by at least about 5%. In other instances, the amount of subcutaneous fat is reduced by at least about 10%, 15%, 20%, 25%, 30% 40%, or 50% compared to the subject prior to administration of the P-PI conjugate.

The methods described herein can be used to reduce the amount of visceral fat in a subject. By "visceral fat" is meant the deposit of fat as intra-abdominal adipose tissue. Visceral fat surrounds vital organs and can be metabolized by the liver to produce blood cholesterol. Visceral fat has been associated with increased risks of conditions such as polycystic ovary syndrome, metabolic syndrome and cardiovascular diseases. Visceral fat can be measured through any means available to determine the amount of visceral fat in a subject. In one instance, the visceral fat is reduced in a subject by at least about 5%. In other instances, the visceral fat is reduced in the subject by at least about 10%, 15%, 20%, 25%, 30% 40%, or 50% compared to the subject prior to administration of the P-PI conjugate.

In one embodiment, a method for preventing the accumulation of ectopic fat or reducing the amount of ectopic fat in a subject is provided, wherein the method comprises administering, to a subject in need thereof, a P-PI conjugate in an amount effective to prevent accumulation of ectopic fat or to reduce the amount of ectopic fat in the subject. By "ectopic fat storage" is meant lipid deposits within and around tissues and organs that constitute the lean body mass (e.g., skeletal muscle, heart, liver, pancreas, kidneys, blood vessels). Generally, ectopic fat storage is an accumulation of lipids outside classical adipose tissue depots in the body. In one instance, the amount of ectopic fat is reduced in a subject by at least about 5% compared to the subject prior to administration of the P-PI conjugate. In other instances, the amount of ectopic fat is reduced in a subject by at least about 10%, or by at least about 15%, 20%, 25%, 30% 40%, or 50%. Alternatively, the amount of ectopic fat is proportionally reduced 5%, 10%, 15%, 20%, 25%, 30%, 40%, 50%, 60%, 70%, 80%, 90%, or 100% in comparison to subcutaneous fat in a subject. Ectopic fat can be measured in a subject using any method available for measuring ectopic fat.

In another embodiment, methods are provided for producing a more favorable fat distribution in a subject, where the method comprises administering to a subject the P-PI conjugate in an amount effective to produce a favorable fat distribution. In one embodiment, administration of the P-PI conjugate reduces the amount of visceral fat or ectopic fat, or both, in a subject. In one embodiment, the methods preferentially reduce the amount of visceral or ectopic fat, or a combination of both, over the reduction in subcutaneous fat. Such methods result in a higher ratio of subcutaneous fat to visceral fat or ectopic fat. Such improved ratios may result in a reduced risk of the development of cardiovascular diseases, polycystic ovary syndrome, metabolic syndrome, or any combinations thereof. In one embodiment, ectopic or visceral fat is metabolized at a rate 5% greater than subcutaneous fat. In other embodiments, ectopic or visceral fat is metabolized at a rate at least 10% 15%, 20%, 25%, 30% 50%, 60%, 70%, 80%, 90%, or 100% greater than subcutaneous fat.

In still another aspect, methods provided include the use of a therapeutically effective amount of the P-PI conjugate administered in combination with glucocortico-steroids. Glucocortico-steroids have the adverse effect of increasing fat mass and decreasing lean mass. Accordingly, it is contemplated that the P-PI conjugate can be used in conjunction with glucocortico-steroids under conditions where glucocortico steroid use is beneficial.

Also provided are methods to reduce weight in a morbidly obese subject by first reducing the subject's weight to a level below that of being morbidly obese, then administering to the subject the P-PI conjugate in an amount effective to further reduce the subject's weight. Methods for reducing a subject's weight to below that of morbid obesity include reducing caloric intake, increasing physical activity, drug therapy, bariatric surgery, such as gastric bypass surgery, or any combinations of the preceding methods. In one aspect, administering the combination of anti-obesity agents further reduces the weight of the subject. In another embodiment, methods are provided for reducing the body mass index in a subject having a body mass index of 40 or less by administering the P-PI conjugate in an effective amount to further reduce the subject's weight.

By reducing weight it is meant that the subject loses a portion of his/her total body weight over the course of treatment, whether the course of treatment be days, weeks, months or years. Alternatively, reducing weight can be defined as a decrease in proportion of fat mass to lean mass (in other words, the subject has lost fat mass, but maintained or gained lean mass, without necessarily a corresponding loss in total body weight). An effective amount of the P-PI conjugate administered in this embodiment is an amount effective to reduce a subject's body weight over the course of the treatment, or alternatively an amount effective to reduce the subject's percentage of fat mass over the course of the treatment. In certain embodiments, the subject's body weight is reduced, over the course of treatment, by at least about 1%, by at least about 5%, by at least about 10%, by at least about 15%, by at least about 20%, by at least about 25%, by at least about 30%, by at least about 40%, or by at least about 50%. In certain embodiments, the subject's BMI is reduced, over the course of treatment, to less than about 35, to about 30, to less than 30, to about 25, to less than 25, or to between 25 and 30. Alternatively, the subject's percentage of fat mass is reduced, over the course of treatment, by at least 1%, at least 5%, at least 10%, at least 15%, at least 20%, or at least 25%.

Also provided are methods of increasing thermogenesis in a subject, the method comprising administering to a subject in need thereof an effective amount of the P-PI conjugate. Thermogenesis is the process of liberating calories as heat by increasing the body's metabolic rate. Thermogenesis is activated by mechanisms, including supplements, nutrition, exercise, and exposure to cold.

Also provided are methods of increasing oxidative metabolism in a subject, the method comprising administering to a subject in need thereof an effective amount of the P-PI conjugate. Oxidative metabolism is the process by which oxygen is used to make energy from carbohydrates (sugars).

In another aspect, a method of inducing a feeling of fullness in a subject is provided, wherein the method comprises administering an effective amount of the P-PI conjugate to the subject. In yet another aspect, a method of controlling hunger in a subject is provided, wherein the method comprises administering an effective amount of the P-PI conjugate to the subject. In yet a further aspect, a method of prolonging a feeling of satiation in a subject is provided, wherein the method comprises administering an effective amount of the P-PI conjugate to the subject.

In yet a further aspect, a method of reducing caloric intake by reducing the size of a meal eaten by a subject is provided, wherein the method comprises administering an effective amount of the P-PI conjugate to the subject. In another aspect, a method of controlling food intake by a subject is provided, wherein the method comprises administering an effective amount of the P-PI conjugate to the subject.

In yet another aspect, a method for ensuring or assisting a subject in compliance with a reduced calorie or restrictive diet is provided, wherein the method comprises administering an effective amount of the P-PI conjugate to the subject. In a further aspect, a method of adjusting a subject's set point so that the body's propensity for homeostasis is adjusted to a healthier set point is provided, wherein the method comprises administering an effective amount of the P-PI conjugate to the subject. In yet a further aspect, a method of maintaining weight loss or maintaining the weight lost by a subject is provided, wherein the method comprises administering an effective amount of the P-PI conjugate to the subject. In one embodiment of this aspect, the weight loss is maintained by re-setting the subject's set point.

In one embodiment, methods are provided that are of use in treating and/or preventing metabolic conditions or disorders that benefit from a reduction in nutrient availability. Accordingly, these methods may be useful in treating and/or preventing of obesity, diabetes (e.g., type 2 or non-insulin dependent diabetes, type 1 diabetes, and gestational diabetes), eating disorders, insulin-resistance syndrome, and cardiovascular disease. In another embodiment, a method for treating or preventing eating disorders (such as Prader-Willi syndrome), hyperphagia, disorders associated with hypernutrition, or any combination thereof is provided, where the method comprises administering an effective amount of the P-PI conjugate to the subject.

As described herein, methods of use in altering fat distribution, reducing fat mass, or both in a subject are provided. Accordingly, subjects for whom altering body composition is of benefit can also benefit from the present methods. Altered body composition, as intended herein, includes loss or maintenance of body fat, with minimization of loss, maintenance, or gain of lean body mass. In such situations, weight may increase as well as decrease. Accordingly, subjects may be lean, overweight, or obese as these terms are generally used in the art. Methods provided may also include reducing fat in non-adipose tissue while sparing lean mass. Uses for this method include treating diseases such as nonalcoholic steatohepatitis or lipodystrophy.

As described herein, conjugates in which the component peptide is a PYY, an exendin, a GLP-1, amylin, sCT, an AFP-6, a leptin, or a hybrid, agonist, analog or derivative of any of these are nonlimiting examples of P-PI conjugates of use in treating or preventing such conditions, diseases, and disorders that may benefit from a reduction in nutrient availability. Accordingly, in another aspect, the P-PI conjugates and compositions described herein are of use in the manufacture of a medicament useful in treating or preventing such conditions, diseases, and disorders that may benefit from a reduction in nutrient availability.

Metabolic rates can be assessed using any method available for determining such rates, for example by using a respiratory calorimeter. Such methods and devices for assaying metabolic rates are known in the art and are described, for example, in U.S. Pat. Nos. 4,572,208, 4,856,531, 6,468,222, 6,616,615, 6,013,009, and 6,475,158. Alternatively, the metabolic rate of an animal can be assessed by measuring the amount of lean tissue versus fatty tissue catabolized by the animal following the diet period. Thus, total body weight and fat content can be measured at the end of the dietary period.

Methods of measuring fat mass and lean mass include, but are not limited to, underwater weighing, air displacement plethysmograph, x-ray, DEXA scans, MRIs and CT scans. Methods of measuring subcutaneous fat are known in the art, for example, those described in U.S. Pat. No. 6,530,886. Visceral fat can be measured through any means available to determine the amount of visceral fat in a subject. Such methods include, for example, abdominal tomography by means of CT scanning and MRI. Other methods for determining visceral fat are described, for example, in U.S. Pat. Nos. 6,864,415, 6,850,797, and 6,487,445. Ectopic fat can be measured in a subject using any method available for measuring ectopic fat. In rats, a frequently used method to determine total body fat is to surgically remove and weigh the retroperitoneal fat pad, a body of fat located in the retroperitoneum, the area between the posterior abdominal wall and the posterior parietal peritoneum. The pad weight is considered to be directly related to percent body fat of the animal. Since the relationship between body weight and body fat in rats is linear, obese animals have a correspondingly higher percent of body fat and retroperitoneal fat pad weight.

In another embodiment, methods are provided for treating, preventing, or ameliorating a symptom or effect of diabetes in a subject, where the method comprises administering a therapeutically or prophylactically effective amount of a P-PI conjugate to the subject. The methods are of use in subjects with any form of diabetes mellitus including type 2 or non-insulin dependent diabetes, type 1 diabetes, and gestational diabetes. As described herein, P-PI conjugates of use in treating diabetes include, but are not limited to, those that stimulate insulin secretion, stimulate insulin sensitivity, enhance glucose-induced insulin release, lower glucagon secretion, inhibit gastric emptying, and enhance glucose utilization. Accordingly, exemplary P-PI conjugate compounds for use in methods for treating, preventing, or ameliorating a symptom or effect of diabetes include, but are not limited to, those conjugates in which the component peptide is an exendin, a GLP-1, a GIP, an amylin, a leptin, or a hybrid, agonist, analog or derivative of any of these.

In another aspect, methods are provided for treating, preventing, or ameliorating a symptom or effect of insulin resistance in a subject, where the method comprises administering a therapeutically or prophylactically effective amount of a P-PI conjugate to the subject. Insulin resistance is the diminished ability of insulin to exert its biologically action across a broad range of concentrations. Exemplary P-PI conjugate compounds for use in methods for treating, preventing, or ameliorating a symptom or effect of insulin resistance include, but are not limited to, those conjugates in which the component peptide is an exendin, a GLP-1, a GIP, a leptin, or a hybrid, agonist, analog or derivative of any of these.

Hypertension, together with insulin resistance and hyperlipidemia, comprise the constellation of symptoms that characterize Metabolic Syndrome, also known as insulin resistance syndrome ("IRS") and syndrome X. In another aspect, methods are provided for treating, preventing, or ameliorating a symptom or effect of Metabolic Syndrome in a subject, where the method comprises administering a therapeutically or prophylactically effective amount of a P-PI conjugate to the subject. Exemplary P-PI conjugate compounds for use in methods for treating, preventing, or ameliorating a symptom or effect of Metabolic Syndrome include, but are not limited to, those conjugates in which the component peptide is an exendin, a GLP-1, a GIP, a CGRP, or a hybrid, agonist, analog or derivative of any of these.

In another general aspect, methods are provided for treating, preventing, or ameliorating a symptom or effect of a cardiovascular disease or condition in a subject, where the method comprises administering a therapeutically or prophylactically effective amount of a P-PI conjugate to the subject. Cardiovascular diseases or conditions include, but are not limited to, hypertension, pulmonary hypertension, myocardial ischemia, myocardial reperfusion, stroke, cardiac arrhythmias, congestive heart failure, hibernating myocardium, myocardium infarction, cardiomyopathies, and coronary artery disease. In one embodiment, methods are provided for treating, preventing, or ameliorating a symptom or effect of a cardiovascular disease or condition associated with obesity in a subject. In another embodiment, methods are provided for treating, preventing, or ameliorating a symptom or effect of a cardiovascular disease or condition not associated with obesity in a subject (i.e., wherein the subject is not obese). Exemplary P-PI conjugate compounds for use in methods for treating, preventing, or ameliorating a symptom or effect of a cardiovascular disease or condition include, but are not limited to, those conjugates in which the component peptide is an exendin, a GLP-1, an amylin, sCT, a CGRP, or a hybrid, agonist, analog or derivative of any of these. Accordingly, in another aspect, the P-PI conjugates and compositions described herein are of use in the manufacture of a medicament useful for treating, preventing, or ameliorating a symptom or effect of a cardiovascular disease or condition in a subject as described herein.

Hypertension (or high blood pressure) is a condition that can occur in many patients in whom the causative agent or disorder is unknown. Such "essential" hypertension is often associated with disorders such as obesity, diabetes and hypertriglyceridemia. Hypertension can result in numerous complications including left ventricular failure, atherosclerotic heart disease, myocardial infarction, retinal hermorrhages, exudates, papilledema, and vascular accidents, cerebrovascular insufficiency with or without stroke, and renal failure. Hypertension can also result in retinal hermorrhages, exudates, papilledema, and vascular accidents. An abnormal blood pressure can also result from specific conditions or diseases, such as heart failure. Heart failure is a chronic or acute state that results when the heart is not capable of providing sufficient cardiac output to satisfy the metabolic needs of the body. Heart failure is commonly referred to as congestive heart failure (CHF), since symptoms of increased venous pressure (e.g., pulmonary congestion with left heart failure and peripheral edema with right heart failure) are often predominant. Symptoms and signs of CHF include fatigue, peripheral and pulmonary edema, and visceral congestion (e.g., dyspnea). These symptoms are produced by diminished blood flow to the various tissues of the body and by accumulation of excess blood in various organs that results from the heart being incapable of pumping out the blood. Heart failure can result from several underlying diseases, most commonly in industrialized nations from atherosclerotic coronary artery disease with myocardial infarction. Metabolic diseases associated with endocrine disorders may cause cardiomyopathies and some cardiomyopathies may result in heart failure. Exemplary P-PI conjugate compounds for use in methods for treating, preventing, or ameliorating a symptom or effect of hypertension, heart failure, and conditions associated therewith include, but are not limited to, those conjugates in which the component peptide is an exendin, a GLP-1, an amylin, sCT, a CGRP, or a hybrid, agonist, analog or derivative of any of these.

As discussed herein, angiotensin converting enzyme (ACE) inhibitors have major roles as vasodialators in hypertension and treating CHF and are known in the art to be among the most efficient drugs in treating these disorders. Also, the survival benefit for the use of ACE inhibitors in patients with acute and chronic myocardial infarction has been established by a series of internationally conducted, randomized, controlled clinical studies and is well known in the art. For example, ACE inhibitors have been shown to be effective in reducing mortality and the incidence of serious nonfatal cardiovascular events in acute myocardial infarction. Clinical trials indicate that ACE inhibitors prolong survival in a broad spectrum of patients with myocardial infarction and heart failure, ranging from those who are asymptomatic with ventricular dysfunction to those who have symptomatic heart failure but are normotensive and hemodynamically stable. Exemplary P-PI conjugate compounds for use in methods for treating, preventing, or ameliorating a symptom or effect of hypertension, heart failure, myocardial infarction, and conditions associated therewith include, but are not limited to, those conjugates in which the component peptidase inhibitor is an ACE inhibitor or a neutral endopeptidase (NEP)/ACE inhibitor.

In one embodiment, methods are provided for treating or preventing cardiac arrhythmias, or for ameliorating a symptom of cardiac arrhythmias, where the method comprises administering to a subject in need thereof an effective amount of the P-PI conjugate. In some embodiments, P-PI conjugate administration provides an anti-arrhythmic effect in patients with myocardial ischemia, myocardial reperfusion, or congestive heart failure. For example, GLP-1 administration has been shown to reduce cardiac injury and enhance recovery in patients with these disorders. GLP-1 and exendin effectively enhance peripheral glucose uptake without inducing dangerous hypoglycemia. GLP-1 and exendin also strongly suppress glucagon secretion and thereby powerfully reduce plasma free fatty acid (FFA) levels substantially more than can be accomplished with insulin. High FFA levels have been implicated as a major toxic mechanism during myocardial ischemia. Accordingly, P-PI conjugates, including those containing a GLP-1 or exendin peptide, are of use in treating or ameliorating a symptom of myocardial ischemia. In another embodiment hybrids are useful for preventing and treating cardiac arrhythmias that reliably reduce injury associated with reperfusion. In yet a further embodiment, P-PI conjugate treatment after acute stroke or hemorrhage provides a means for optimizing insulin secretion, increasing brain anabolism, enhancing insulin effectiveness by suppressing glucagon, and maintaining euglycemia or mild hypoglycemia with no risk of severe hypoglycemia or other adverse side effects.

In other embodiments, methods for improving the lipid profile in a subject are provided, wherein the methods comprise administering to a subject an effective amount of a P-PI conjugate disclosed herein. Improving a lipid profile includes, but is not limited to, reducing LDL cholesterol, reducing triglyceride levels, changing HDL cholesterol levels, or any combination thereof. Exemplary P-PI conjugate compounds for use in methods for a lipid profile include, but are not limited to, those conjugates in which the component peptide is an exendin, a GLP-1, a PYY, an amylin, sCT, or a hybrid, agonist, analog or derivative of any of these.

Hypertension, together with insulin resistance and hyperlipidemia, comprise the constellation of symptoms that characterize Metabolic Syndrome, also known as insulin resistance syndrome ("IRS") and syndrome X. In another aspect, methods are provided for treating, preventing, or ameliorating a symptom or effect of Metabolic Syndrome in a subject, where the method comprises administering a therapeutically or prophylactically effective amount of a P-PI conjugate to the subject. Exemplary P-PI conjugate compounds for use in methods for treating, preventing, or ameliorating a symptom or effect of Metabolic Syndrome include, but are not limited to, those conjugates in which the component peptide is an exendin, a GLP-1, a GIP, or a hybrid, agonist, analog or derivative of any of these.

In another general aspect, methods for treating or preventing diseases or disorders associated with loss or absence of pancreatic beta cells, where the methods comprise administering to a subject an effective amount of a P-PI conjugate. GLP-1 may contribute to beta cell neogenesis and increase beta cell mass and GIP stimulates beta-cell proliferation and cell survival. GLP-2 may promote pancreatic islet growth for example by enlargement and proliferation of the islets. Exemplary P-PI conjugate compounds for use in methods for stimulating pancreatic beta cell proliferation or survival include, but are not limited to, those conjugates in which the component peptide is an exendin, GLP-1, GLP-2, a GIP, or a hybrid, agonist, analog or derivative of any of these.

In another aspect, methods for preventing and treating nephropathy are provided, where the methods comprise administering to a subject an effective amount of a P-PI conjugate. In one embodiment, methods are provided for ameliorating a symptom of nephropathy comprising administration of a P-PI conjugate in an amount effective to ameliorate a nephropathy symptom. Such nephropathy conditions include, but are not limited to, hypertensive nephropathy, diabetic nephropathy, nephropathy associated with insulin resistance, and nephropathy associated with metabolic syndrome. P-PI conjugates are useful in these conditions by, for example, improving or preventing worsening of hypertension, endothelial function, renal function, glomerulosclerosis, or any combination thereof. P-PI conjugates disclosed herein may also find use for improving endothelial function in a subject having reduced vasodilatory capacity, having glomerulosclerosis, or any other reduction in glomerular flow. In another embodiment, P-PI conjugates disclosed herein are useful in preventing or delaying progression of nephropathy to end-stage renal disease and in preventing, treating, or slowing progression of proteinuria or glomerulosclerosis, or both. Exemplary P-PI conjugate compounds for use in methods for preventing and treating nephropathy include, but are not limited to, those conjugates in which the component peptide is an exendin, a GLP-1, or a hybrid, agonist, analog or derivative of any of these.

In another aspect, methods for treating polycystic ovary syndrome (PCOS) are provided, where the methods comprise administering to a subject an effective amount of a P-PI conjugate. As used herein, the terms "polycystic ovary syndrome," "PCOS", or "polycysticovary disease" refer to a clinical symptom complex. Women diagnosed with PCOS may exhibit one or more of the following symptoms: oligomenorrhea, amenorrhea, anovulation, bilateral polycystic ovaries, hyperandrogenism (elevated serum testosterone and/or androstenedione), abnormal uterine bleeding, enlarged multifollicular ovaries, infertility, excess facial hair growth, hair loss, acne, insulin-resistance, obesity, hyperinsulinemia, hypertension, hyperlipidemia, and type-2 diabetes. Accordingly, administration of the P-PI conjugate to a subject with PCOS may restore regular menses, regular ovulation, or fertility in the subject. In general, P-PI conjugates effective in lowering insulin resistance or in increasing insulin sensitivity are useful in treating PCOS. In some embodiments, methods for reducing or preventing insulin resistance in a subject with PCOS are provided, where the methods comprise administering to a subject an effective amount of a P-PI conjugate. In yet another embodiment, administration of the P-PI conjugate to a subject with PCOS is of use in preventing the onset of type-2 diabetes in the subject. Exemplary P-PI conjugate compounds for use in methods for treating PCOS include, but are not limited to, those conjugates in which the component peptide is an exendin, a GLP-1, or a hybrid, agonist, analog or derivative of any of these.

As described herein, the disclosed P-PI conjugate compounds exhibit a broad range of biological activities including some related to the anti-secretory and anti-motility properties of the component peptide. Anti-secretory properties include inhibition of gastric and/or pancreatic secretions. Accordingly, methods are provided for treating or preventing diseases and disorders associated with gastric or pancreatic secretions, where the methods comprise administering to a subject an effective amount of a P-PI conjugate. Diseases and disorders associated with gastric or pancreatic secretions include gastritis, pancreatitis, Barrett's esophagus, and Gastroesophageal Reflux Disease (GERD). Exemplary P-PI conjugate compounds for use in methods for treating or preventing diseases and disorders associated with gastric or pancreatic secretions include, but are not limited to, those conjugates in which the component peptide is a PYY, an exendin, a GLP-1, an amylin, or a hybrid, agonist, analog or derivative of any of these.

In another embodiment, certain P-PI conjugates are of use in inducing, enhancing, potentiating, or restoring glucose responsivity in pancreatic islets or cells. Assays for determining such activity are known in the art and described, for example, in U.S. Pat. Application Publication No. 2004/0228846. Exemplary P-PI conjugate compounds for use in inducing, enhancing, potentiating, or restoring glucose responsivity in pancreatic islets or cells include, but are not limited to, those conjugates in which the component peptide is a PYY, an NPY, or a hybrid, agonist, analog or derivative of any of these.

In another aspect, methods for treating gastrointestinal disorders that are associated with excess intestinal electrolyte and water secretion as well as decreased absorption are provided, where the methods comprise administering to a subject an effective amount of a P-PI conjugate. Such gastrointestinal disorders include infectious diarrhea, inflammatory diarrhea, short bowel syndrome, or the diarrhea which typically occurs following surgical procedures, e.g., ileostomy. (Harrison's Principles of Internal Medicine, McGraw-Hill Inc., New York, 12th Ed.) Examples of infectious diarrhea include, without limitation, acute viral diarrhea, acute bacterial diarrhea (e.g., salmonella, campylobacter, and clostridium or due to protozoal infections), or traveller's diarrhea (e.g., Norwalk virus or rotavirus). Examples of inflammatory diarrhea include, without limitation, malabsorption syndrome, tropical sprue, chronic pancreatitis, Crohn's disease, diarrhea, and irritable bowel syndrome. GLP-2 promotes growth of intestinal tissue and would benefit those subjects suffering from diseases or conditions marked by abnormalities in the small intestinal tract mucosa such as those listed herein. In some embodiments, P-PI conjugates may be used to treat an emergency or life-threatening situation involving a gastrointestinal disorder, e.g., after surgery or due to cholera. Exemplary P-PI conjugate compounds for use in methods for treating gastrointestinal disorders that are associated with excess intestinal electrolyte and water secretion and with decreased absorption include, but are not limited to, those conjugates in which the component peptide is a GLP-2, PYY, or a hybrid, agonist, analog or derivative of any these.

Compounds provided herein may also be useful for treating or preventing intestinal damage as opposed to merely treating the symptoms associated with the intestinal damage (e.g., diarrhea). Such damage to the intestine may be, or a result of, ulcerative colitis, inflammatory bowel disease, bowel atrophy, loss bowel mucosa, loss of bowel mucosal function, or any combination thereof. Assays for such activity are known in the art and described, for example, in PCT Publication No. WO 03/105763 and Morris et al. (1989) Gastroenterology 96:795-803. Exemplary P-PI conjugate compounds for use in methods for treating intestinal damage include, but are not limited to, those conjugates in which the component peptide is a PYY, or a hybrid, agonist, analog or derivative of any PYY.

In another aspect, methods for treating or preventing pancreatic tumors are provided, where the methods comprise administering to a subject an effective amount of a P-PI conjugate. Accordingly, methods for inhibiting or reducing proliferation of pancreatic tumor cells are provided. Methods are also provided for inhibiting growth of a pancreatic tumor. The pancreatic tumor and tumor cells may be benign or malignant. Exemplary types of benign pancreatic tumor cells which may be treated by the methods described herein include serous cyst adenomas, microcystic tumors, and solid-cystic tumors. Exemplary types of malignant pancreatic tumor cells which may be treated by the methods described herein include carcinomas arising from the ducts, acini, or islets of the pancreas. Assays for such activity are known in the art and described, for example, in U.S. Pat. No. 5,574,010. Exemplary P-PI conjugate compounds for use in methods for treating pancreatic tumors include, but are not limited to, those conjugates in which the component peptide is a PYY, or a hybrid, agonist, analog or derivative of any PYY.

In another general aspect, methods for treating bone disorders, such as osteopenia and osteoporosis, are provided, where the methods comprise administering to a subject an effective amount of a P-PI conjugate. Certain P-PI conjugates are useful for promoting bone formation, decreasing bone resorption, decreasing plasma calcium, and inducing an analgesic effect. In yet other embodiments, certain P-PI conjugates are useful to treat pain and painful neuropathy. Exemplary P-PI conjugate compounds for use in methods for treating such pain and or bone disorders include, but are not limited to, those conjugates in which the component peptide is an exendin, GLP-1, GLP-2, an amylin, sCT, or a hybrid, agonist, analog or derivative of any of these.

In another general aspect, methods for treating, preventing or delaying development of neurological and nervous system disorders associated with neuronal loss or dysfunction are provided, where the methods comprise administering to a subject an effective amount of a P-PI conjugate. Such neurological and nervous system disorders include, but are not limited to, Parkinson's disease, Alzheimer's disease, Huntington's disease, amyotropic lateral sclerosis, stroke, attention deficit disorder, neuropsychiatric syndromes, neurodegenerative disorders, memory disorders, and cognitive disorders. Exemplary P-PI conjugate compounds for use in methods for treating, preventing or delaying development of such neurological and nervous system disorders include, but are not limited to, those conjugates in which the component peptide is an exendin, GLP-1, a GIP, a PYY, an NPY, or a hybrid, agonist, analog or derivative of any of these. For example, U.S. Pat. No. 6,734,166 describes the use of PYY receptor agonists for reducing aluminum concentrations in the central nervous system for treating, preventing, or delay the onset of Alzheimer's disease.

Accordingly, in another aspect, the P-PI conjugates and compositions described herein are of use in the manufacture of a medicament useful for treating, preventing, or ameliorating the disease or condition as described herein.

A "subject" is meant to include any animal, including humans, primates, and other mammals including rats, mice, pets such as cats, dogs, livestock such as horses, cattle, sheep and goats, as well as chicken, turkey and any other animal which may benefit from the compositions and methods disclosed herein, for example, those for whom metabolic disease, body weight, or cardiovascular disease may be an issue.

As used herein, and as well-understood in the art, "treatment" is an approach for obtaining beneficial or desired results, including clinical results. "Treating" or "palliating" a disease, disorder, or condition means that the extent and/or undesirable clinical manifestations of a condition, disorder, or a disease state are lessened and/or time course of the progression is slowed or lengthened, as compared to not treating the disorder. For example, in treating obesity, a decrease in body weight, e.g., at least a 5% decrease in body weight, is an example of a desirable treatment result. For purposes of the methods disclosed herein, beneficial or desired clinical results include, but are not limited to, alleviation or amelioration of one or more symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Further, treating does not necessarily occur by administration of one dose, but often occurs upon administration of a series of doses. Thus, a therapeutically effective amount, an amount sufficient to palliate, or an amount sufficient to treat a disease, disorder, or condition may be administered in one or more administrations.

As used herein, the term "therapeutically effective amount" means the amount of the active compounds in the composition that will elicit the biological or medical response in a tissue, system, or subject that is being sought by the researcher, veterinarian, medical doctor or other clinician, which includes alleviation or amelioration of the symptoms of the disorder being treated.

As used herein, the term "prophylactically effective amount" means the amount of the active compounds in the composition that will elicit the biological or medical response in a tissue, system, or subject that is being sought by the researcher, veterinarian, medical doctor or other clinician, to prevent the onset of the disorder, condition, or disease of interest or for which the subject is at risk (e.g., obesity or an obesity-related disorder, condition or disease in subjects as risk for obesity or the obesity-related disorder, condition or disease).

The component peptides and peptide-peptidase inhibitor (P-PI) conjugates described herein may be prepared using chemical peptide synthesis techniques known in the art, e.g., using an automated or semi-automated peptide synthesizer, standard recombinant techniques, or both.

The component peptides and P-PI conjugates may be synthesized in solution or on a solid support in accordance with conventional techniques. Various automated synthesizers are commercially available and may be used in accordance with known protocols. See, e.g., Stewart et al. (1984) *Solid Phase Peptide Synthesis*, 2d. ed., Pierce Chemical Co.; Tam et al. (1983) *J. Am. Chem. Soc.* 105:6442; Merrifield (1986) *Science* 232: 341-347; and Barany et al. (1979) *The Peptides*, Gross et al., eds., Academic Press, NY, 1-284. Solid phase peptide synthesis may be carried out using an automated or semiautomated peptide synthesizer. Typically, using such techniques, an α-N-carbamoyl protected amino acid and an amino acid attached to the growing peptide chain on a resin are coupled at room temperature in an inert solvent such as dimethylformamide, N-methylpyrrolidinone or methylene chloride in the presence of coupling agents such as dicyclohexylcarbodiimide and 1-hydroxybenzotriazole in the presence of a base such as diisopropylethylamine The α-N-carbamoyl protecting group is removed from the resulting peptide-resin using a reagent such as trifluoroacetic acid or piperidine, and the coupling reaction repeated with the next desired N-protected amino acid to be added to the peptide chain. Suitable N-protecting groups are well known in the art, with t-butyloxycarbonyl (tBoc) and fluorenylmethoxycarbonyl (Fmoc) as examples. For example, solid phase peptide synthesis may be carried out with an automated peptide synthesizer (e.g., Model 430A, Applied Biosystems Inc., Foster City, Calif.) using the NMP/HOBt (Option 1) system and tBoc or Fmoc chemistry with capping (see, Applied Biosystems User's Manual for the ABI 430A Peptide Synthesizer, Version 1.3B Jul. 1, 1988, section 6:49-70). Peptides may also be assembled using an Advanced ChemTech Synthesizer (Model MPS 350, Louisville, Ky.). Peptides may be purified by RP-HPLC (preparative and analytical) using, e.g., a Waters® DELTA-PREPT™ 3000 system (Waters Corp., Milford, Mass.) and a C4, C8, or C18 preparative column (10μ, 2.2×25 cm; Grace Vydac, Hesperia, Calif.). The peptide can be readily synthesized and then screened in assays designed to identify peptides with particular activities. Other methods of synthesizing and purifying peptides are known to the skilled artisan.

The component peptides and P-PI inhibitor conjugates disclosed herein may alternatively be produced by recombinant techniques well known in the art. See, e.g., Sambrook et al. (1989) *Molecular Cloning: A Laboratory Manual*, 2d ed., Cold Spring Harbor, N.Y. The peptides produced by recombinant technologies may be expressed from a polynucleotide. One skilled in the art will appreciate that the polynucleotides, including DNA and RNA, that encode such the various fragments of the peptides may be obtained from the wild-type cDNA, taking into consideration the degeneracy of codon usage, or may be engineered as desired. These polynucleotide sequences may incorporate codons facilitating transcription and translation of mRNA in microbial hosts. Such manufacturing sequences may readily be constructed according to the methods well known in the art. The polynucleotides above may also optionally encode an N-terminal methionyl residue. The polynucleotides above may also optionally encode a C-terminal glycyl residue for proper amide formation. Non-peptide compounds useful in composition and methods provided herein may be prepared by art-known methods. For example, phosphate-containing amino acids and peptides containing such amino acids may be prepared using methods known in the art. See, e.g., Bartlett et al. (1986) *Bioorg. Chem.* 14: 356-377.

A variety of cell types may be used to contain and express a peptide coding sequence including, for example, bacteria, yeast, algae, insect cells, plant cells, and animal cells such as mammalian and avian cells. A variety of expression vector/host systems may be used, including, but are not limited to microorganisms such as bacteria transformed with recombinant bacteriophage, plasmid or cosmid DNA expression vectors; yeast transformed with yeast expression vectors; insect cell systems infected with virus expression vectors (e.g., baculovirus); plant cell systems transfected with virus expression vectors (e.g., cauliflower mosaic virus (CaMV); tobacco mosaic virus (TMV) or transformed with bacterial expression vectors (e.g., Ti or pBR322 plasmid); or animal cell systems. Mammalian cells and cell lines that are useful in recombinant protein productions include, but are not limited to, VERO (African green monkey kidney) cells, HeLa cells, Chinese hamster ovary (CHO) cell lines, COS cells (such as COS-7), WI38 (human lung fibroblasts), baby hamster kidney (BHK) cells, HepG2, 3T3, RIN, Madin-Darby canine kidney epithelial (MDCK) cells, A549, PC12, K562 and 293 cells. Exemplary protocols for the recombinant expression of polypeptides are well known in the art.

Host cell strains may be chosen for a particular ability to process the expressed peptide or produce certain post-translation modifications that will be useful in providing peptide activity. Such modifications of the polypeptide include, but are not limited to, acetylation, carboxylation, glycosylation, phosphorylation, lipidation, acylation, and amidation, for example, carboxy-terminal amidation. Post-translational processing, which cleaves a "prepro" form of the polypeptide, may also be important for correct insertion, folding and/or function. Different host cells, such as CHO, HeLa, MDCK, 293, WI38, and the like, have specific cellular machinery and characteristic mechanisms for such post-translational activities, and may be chosen to ensure the correct modification and processing of the introduced foreign protein.

Component peptides and P-PI inhibitor conjugates described herein may be produced using a combination of both automated peptide synthesis and recombinant techniques. For example, a peptide may contain a combination of modifications including deletion, substitution, and insertion by PEGylation. Such a peptide may be produced in stages. For example, in the first stage, an intermediate peptide containing the modifications of deletion, substitution, insertion, and any combination thereof, may be produced by recombinant techniques as described. Then, after an optional purification step, the intermediate peptide is PEGylated through chemical modification with an appropriate PEGylating reagent (e.g., from Nektar Therapeutics, San Carlos, Calif.) to yield the desired peptide. Amidation of a peptide may also be done in stages. One skilled in the art will appreciate that the above-described procedure may be generalized to apply to a peptide containing a combination of modifications selected from deletion, substitution, insertion, derivation, and other means of modification well known in the art and contemplated herein.

Component peptides and P-PI inhibitor conjugates described herein may also be produced using chemical ligation schemes known in the art, including those described, for example, in U.S. Pat. Application Publication Nos. 2003-0191291, 2003-0208046, and 2004-0115774. Chemical ligation refers to a chemoselective reaction involving the covalent joining of two chemical moieties, each of which moieties bears a mutually reactive functional group that is uniquely capable of forming a non-reversible covalent bond with the other. Unique, mutually reactive, functional groups present on the first and second components can be used to render the ligation reaction chemoselective. For example, the chemical ligation of peptides and polypeptides involves the chemoselective reaction of peptide or polypeptide segments bearing compatible unique, mutually reactive, C-terminal and N-terminal amino acid residues. Chemical ligation includes covalent ligation of (1) a first peptide or polypeptide bearing a uniquely reactive C-terminal group with (2) a second peptide or polypeptide bearing a uniquely reactive N-terminal group, where the C-terminal and N-terminal reactive groups form a non-reversible covalent bond therein between. It also includes N-terminal to N-terminal and C-terminal to C-terminal ligation. In particular, chemical ligation includes any chemoselective reaction chemistry that can be applied to ligation of unprotected peptide segments. Several different chemistries have been utilized for this purpose, examples of which include native chemical ligation, oxime forming chemical ligation, thioester forming ligation (Schnolzer et al. (1992) *Science* 256:221-225; Gieselman et al. (2001) *Org. Lett.* 3:1331-1334), thioether forming ligation (Englebretsen et al. (1995) *Tot. Leffs.* 36:8871-8874), hydrazone forming ligation (Gaertner, et al. (1994) *Bioconj. Chem.* 5:333-338), and thiazolidine forming ligation and oxazolidine forming ligation (Zhang et al. (1998) *Proc. Natl. Acad. ScL USA* 95:9184-9189; PCT Publication No. WO 95/00846; U.S. Pat. No. 5,589,356); and Staudinger amide forming chemical ligation (Saxon et al. (2000) *Org. Leff.* 2:2141-2143).

Reaction conditions for a given ligation chemistry are generally selected to maintain the desired interaction of the peptide or polypeptide segments employed for ligation. For example, pH and temperature, water-solubility of the ligation components, ratio of the first segment to the second segment, water content and composition of the reaction mixture can be varied to optimize ligation. Addition or exclusion of reagents that solubilize the ligation segments to different extents may further be used to control the specificity and rate of the desired ligation reaction, i.e., control exposure and presentation of reactive groups by manipulating solubility of the peptide or polypeptide segments. Reaction conditions are readily determined by assaying for the desired chemoselective reaction product compared to one or more internal and/or external controls. These methodologies have proven a robust methodology for generating a native amide bond at the ligation site.

In conjunction with the design of the P-PI conjugates, the peptides or polypeptide segments utilized for synthesizing the polypeptide backbone are constructed. Methods useful in the synthesis of peptides and polypeptides backbones are described in, for example, U.S. Pat. Application Publication Nos. 2004-0138412 (extended native chemical ligation), 2003-0208046 (pseudo-native chemical ligation), 2005-0261473 (carboxy protection strategies for acidic C-terminal amino acids in chemical ligation to eliminate formation of unwanted side products), 2005-0064538 and 2005-0113563 (native chemical ligation with improved efficiency of ligation and chemical ligation with three or more components); in PCT Publication Nos. WO2004/105685 (aqueous-compatible solid phase chemical ligation using a displaceable linker) and WO2004/060925 (multiplex polymer ligation with water-soluble polymeric protecting groups and their replacement with desired adducts); and in U.S. Pat. Nos. 6,307,018 and 6,184,344 (native chemical ligation), U.S. Pat. No. 6,326,468 (solid phase native chemical ligation), 6,217,873 (polyoxime compounds), U.S. Pat. No. 6,174,530 (homogenous polyoxime compositions), U.S. Pat. No. 6,001,364 (heteropolyoxime compounds), and U.S. Pat. No. 6,451,543 (lipid-matrix assisted synthesis). In general, synthesis of a peptide or polypeptide backbone by chemical ligation involves selection of suitable ligation sites that are chosen based on the ligation chemistry selected for assembling the various polypeptide backbone segments, the reversible (or cleavable) polymer attachment chemistry chosen for a given target peptide, and the particular polymer attachment sites. When native chemical ligation is employed, cysteine ligation sites are determined by scanning the target polypeptide backbone amino acid sequence for suitable naturally occurring cysteine residue. When "extended native chemical ligation" is employed, ligation sites can be selected by scanning the target polypeptide backbone amino acid sequence for suitable naturally occurring ligation site junctions that permit robust ligations. Because extended native chemical ligation is not limited to ligation at cysteine residues, any number of residues may serve as the ligation site junction. In some instances, a combination of native and extended native chemical ligation may be part of the design.

In one embodiment, native chemical ligation is used to generate part or all of the full-length polypeptide chain. Cysteines present in the naturally occurring protein or peptide backbone can be used as the chemical ligation sites. Alternatively, where a desired ligation junction is devoid of a suitable cysteine, the non-cysteine amino acid at that position can be replaced with a cysteine or a cysteine can be inserted so as to permit native chemical ligation at that site. If desired, the newly introduced cysteine can be converted to a pseudo amino acid residue corresponding to the original amino acid at that position. Formation of a pseudo amino acid by conversion of a cysteine at native chemical ligation sites is referred to "pseudo native chemical ligation." Alternatively, when the cysteine is introduced at a site for polymer protecting group modification, the side chain thiol can be exploited for the attachment of a thiol reactive water-soluble polymer construct, provided that all other cysteines in the target polypeptide that one does not wish to modify are protected. In another embodiment, extended native chemical ligation can be utilized to generate part or all of the full-length polypeptide. Peptides used for thioester-mediated ligation, such as for native chemical ligation, can be made following standard protocols as well, for example see U.S. Pat. Nos. 6,307,018 and 6,184,344.

As used herein, the term "purified peptide" is intended to refer to a composition, isolated from other components, wherein the peptide is purified to any degree relative to its naturally obtainable state. A purified peptide therefore also refers to a peptide, free from the environment in which it may naturally occur. Generally, "purified" will refer to a component peptide or P-PI conjugate composition that has been subjected to fractionation to remove various other components, and which composition substantially retains a biological activity. Where the term "substantially purified" is used, this designation will refer to a composition in which the component peptide or P-PI conjugate forms the major component of the composition, such as constituting about 50%, about 60%, about 70%, about 80%, about 90%, about 95% or more of the component peptide or P-PI conjugate in the composition.

It may be desirable to purify the component peptides and P-PI conjugates generated by the methods described herein. Peptide purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Purification techniques include, for example, precipitation with ammonium sulfate, PEG, antibodies, and the like; heat denaturation, followed by centrifugation; chromatography steps such as ion exchange, gel filtration, reverse phase, hydroxylapatite and affinity chromatography; isoelectric focusing; gel electrophoresis; and combinations of such and other techniques. Analytical methods particularly suited to the preparation of a pure peptide are ion-exchange chromatography, exclusion chromatography, polyacrylamide gel electrophoresis, and isoelectric focusing. A particularly efficient method of purifying peptides is reverse phase HPLC, followed by characterization of purified product by liquid chromatography/mass spectrometry (LC/MS) and Matrix-Assisted Laser Desorption Ionization (MALDI) mass spectrometry. Additional confirmation of purity is obtained by determining amino acid analysis. As is generally known in the art, it is believed that the order of conducting the various purification steps may be changed, or that certain steps may be omitted, and still result in a suitable method for the preparation of a substantially purified protein or peptide.

There is no general requirement that the peptides or P-PI conjugates always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed, utilizing an HPLC apparatus, will generally result in a greater "-fold" purification than the same technique utilizing a low pressure chromatography system. Methods exhibiting a lower degree of relative purification may have advantages in total recovery of protein product, or in maintaining the activity of the peptide or P-PI conjugates. In some embodiments, a combination of anion exchange and immunoaffinity chromatography may be used to produce purified peptide or P-PI conjugate compositions described herein.

The P-PI conjugate compounds disclosed herein may be administered alone or in combination with pharmaceutically acceptable carriers or excipients, in either single or multiple doses. Accordingly, pharmaceutical compositions are provided comprising a therapeutically or prophylactically effective amount of at least one P-PI conjugate compound, or a pharmaceutically acceptable salt thereof, together with pharmaceutically acceptable diluents, preservatives, solubilizers, emulsifiers, adjuvants and/or carriers useful in the delivery of the P-PI conjugate compounds. Conventional description and preparation techniques for pharmaceutical formulations are disclosed, for example, in Remington's Pharmaceutical Sciences by E. W. Martin and in Wang et al. (1988) *J. of Parenteral Sci. and Tech.*, Technical Report No. 10, Supp. 42:2 S.

The present P-PI conjugate compounds will be, in general, useful in the same way that the individual component peptide or peptidase inhibitor is useful in view of their pharmacological properties. One exemplary use is to peripherally administer such P-PI conjugate compounds for the treatment or prevention of metabolic conditions and disorders. In one embodiment, the P-PI compounds provided possess activity as agents to reduce nutrient availability, reduce of food intake, effect weight loss, or any combination thereof. In another embodiment, the P-PI compounds provided are administered for the treatment of diabetes or diabetes-related conditions and disorders. In another embodiment, the P-PI compounds provided are administered for the treatment of cardiovascular disease or disorders, such as congestive heart failure.

The present P-PI conjugate compounds may be formulated for peripheral administration, including formulation for injection, oral administration, nasal administration, pulmonary administration, topical administration, or other types of administration as one skilled in the art will recognize. Administration of the pharmaceutical compositions described herein may be via any common route so long as the target tissue is available via that route. In one embodiment, the pharmaceutical compositions may be introduced into the subject by any conventional peripheral method, e.g., by intravenous, intradermal, intramuscular, intramammary, intraperitoneal, intrathecal, retrobulbar, intrapulmonary (e.g., term release); by oral, sublingual, nasal, anal, vaginal, or transdermal delivery, or by surgical implantation at a particular site. In some embodiments, the pharmaceutical compositions provided are formulated so as to be suitable for parenteral administration, e.g., via injection or infusion. The treatment may consist of a single dose or a plurality of doses over a period of time. Controlled continual release of the P-PI compositions is also contemplated. Parenteral administration may be carried out with an initial bolus followed by continuous infusion to maintain therapeutic circulating levels of drug product. A form of repository or "depot" slow release preparation may be used so that therapeutically effective amounts of the preparation are delivered into the bloodstream over many hours or days following transdermal injection or delivery. Those of ordinary skill in the art will readily optimize effective dosages and administration regimens as determined by good medical practice and the clinical condition of the individual patient.

The pharmaceutical formulations may be composed in various forms, e.g., solid, liquid, semisolid or liquid. The term "solid", as used herein, is meant to encompass all normal uses of this term including, for example, powders and lyophilized formulations. The presently described formulations may be lyophilized, for example for reconstitution. Aqueous compositions generally comprise an effective amount of the P-PI conjugate, dissolved or dispersed in a pharmaceutically acceptable carrier or aqueous medium. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in therapeutic compositions is contemplated. Supplementary active ingredients also may be incorporated into the compositions. In some cases, it will be convenient to provide a P-PI conjugate compound and another compound, such as a food-intake-reducing, diabetes treating, plasma glucose-lowering, or plasma lipid-altering agent, such as an amylin, an amylin agonist analog, a CCK or CCK agonist, or a leptin or leptin agonist, or an exendin or exendin agonist analog, in a single composition or solution for administration together. In other cases, it may be more advantageous to administer the additional agent separately from the P-PI conjugate. For example, when the two compositions are used, the individual agents can be administered at essentially the same time, i.e., concurrently, or at separately staggered times, i.e., sequentially prior to or subsequent to the administration of the other agent of the method. In some embodiments, administration in combination involves administration of separate compositions during overlapping intervals.

In some embodiments, the P-PI conjugate provided herein may be prepared for administration as solutions of free base, or pharmacologically acceptable salts in water suitably mixed with a surfactant, such as hydroxypropylcellulose. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups also can be derived from inorganic bases such as, for example, sodium, potassium, ammonium, calcium, or ferric hydroxides, and such organic bases as isopropylamine, trimethylamine, histidine, procaine and the like. Such products are readily prepared by procedures well known to those skilled in the art. Dispersions also can be prepared in glycerol, liquid polyethylene glycols, and mixtures thereof and in oils. Typically, these preparations contain a preservative to prevent the growth of microorganisms.

The terms buffer, buffer solution and buffered solution, when used with reference to hydrogen-ion concentration or pH, refer to the ability of a system, particularly an aqueous solution, to resist a change of pH on adding acid or alkali, or on dilution with a solvent. Characteristic of buffered solutions, which undergo small changes of pH on addition of acid or base, is the presence either of a weak acid and a salt of the weak acid, or a weak base and a salt of the weak base. An example of the former system is acetic acid and sodium acetate. The change of pH is slight as long as the amount of hydronium or hydroxyl ion added does not exceed the capacity of the buffer system to neutralize it. In some embodiments, the P-PI conjugate is suspended in an aqueous carrier, for example, in an isotonic buffer solution at a pH of about 3.0 to about 8.0, at a pH of about 3.5 to about 7.4, at a pH of about 3.5 to about 6.0, or at a pH of about 3.5 to about 5.0. In certain embodiments, the pH of the formulation is maintained in the range of about 3.5 to 6.5, in some embodiments from about 3.7 to about 4.3 or about 3.8 to about 4.2. In some embodiments, pH may be about 4.0.

Useful buffers include sodium citrate/citric acid, and sodium phosphate/phosphoric acid, and sodium acetate/acetic acid buffers. In certain embodiments, the buffer with the compound provided herein is an acetate buffer (for example, at a final formulation concentration of from about 1-5 to about 60 mM), a phosphate buffer (for example, at a final formulation concentration of from about 1-5 to about to about 30 mM), a glutamate buffer (for example, at a final formulation concentration of from about 1-5 to about to about 60 mM), or a citrate buffer (for example, at a final formulation concentration of from about 1-5 to about 60 mM). In some embodiments, the buffer is acetate (for example, at a final formulation concentration of from about 5 to about 30 mM).

The pharmaceutical compositions suitable for injectable use include sterile aqueous solutions or dispersions and sterile powders for the extemporaneous preparation of sterile injectable solutions or dispersions. In all cases, the form should be sterile and should be fluid to the extent that easy syringability exists. It is generally desirable for the P-PI conjugates to be stable under the conditions of manufacture and storage and preserved against the contaminating action of microorganisms, such as bacteria and fungi.

The pharmaceutically-acceptable carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants.

A stabilizer may be included in the formulations of P-PI conjugates but, and importantly, is not necessarily needed. If included, however, a stabilizer useful in the provided compositions is a carbohydrate or a polyhydric alcohol. An exemplary suitable stabilizer is approximately 1.0 to 10% (w/v) of a carbohydrate or polyhydric alcohol. The polyhydric alcohols and carbohydrates share the same feature in their backbones, i.e., —CHOH—CHOH—, which is responsible for stabilizing proteins. The polyhydric alcohols include such compounds as sorbitol, mannitol, glycerol, and polyethylene glycols (PEGs). These compounds are straight-chain molecules. The carbohydrates, such as mannose, ribose, sucrose, fructose, trehalose, maltose, inositol, and lactose, on the other hand, are cyclic molecules that may contain a keto or aldehyde group. These two classes of compounds have been demonstrated to be effective in stabilizing protein against denaturation caused by elevated temperature and by freeze-thaw or freeze-drying processes. Suitable carbohydrates include: galactose, arabinose, or lactose. Should the formulation be for administration to an individual with diabetes, the carbohydrate used should be one which does not have an adverse affect on the diabetic patient, i.e., the carbohydrate is not metabolized to form unacceptably large concentrations of glucose in the blood. Such carbohydrates are well known in the art as suitable for diabetics. Sucrose and fructose are suitable for use with the conjugates in non-diabetic applications (e.g., treating obesity).

In certain embodiments, if a stabilizer is included, the P-PI conjugate compound is stabilized with a polyhydric alcohol such as sorbitol, mannitol, inositol, glycerol, xylitol, and polypropylene/ethylene glycol copolymer, as well as various PEGs of molecular weight 200, 400, 1450, 3350, 4000, 6000, and/or 8000. Mannitol is an exemplary polyhydric alcohol in some embodiments.

Another useful feature of the lyophilized formulations provided herein is the maintenance of the tonicity of the lyophilized formulations described herein with the same formulation component that serves to maintain their stability. In some embodiments, mannitol is an exemplary polyhydric alcohol used for this purpose. In many cases, isotonic agents may be included (for example, sugars or sodium chloride). In some cases, excipients are useful in maintenance of the overall tonicity of the compound. An excipient may be included in the presently described formulations at various concentrations. For example, an excipient may be included in the concentration range from about 0.02% to about 20% w/w, for example, between about 0.02% and 0.5% w/w, about 0.02% to about 10% w/w, or about 1% to about 20% w/w. In addition, similar to the present formulations themselves, an excipient may be included in solid (including powdered), liquid, semi-solid or gel form. Exemplary parenteral formulations may be isotonic or substantially isotonic.

A preservative is, in the common pharmaceutical sense, a substance that prevents or inhibits microbial growth and may be added to pharmaceutical formulations for this purpose to avoid consequent spoilage of the formulation by microorganisms. While the amount of the preservative is not great, it may nevertheless affect the overall stability of the peptide. The prevention of the action of microorganisms can be brought about by various antibacterial and antifungal agents, for example, parabens, chlorobutanol, phenol, sorbic acid, thimerosal, and the like. While the preservative for use in the pharmaceutical compositions can range from 0.005 to 1.0% (w/v), in some embodiments range for each preservative, alone or in combination with others, is: benzyl alcohol (0.1-1.0%), or m-cresol (0.1-0.6%), or phenol (0.1-0.8%) or combination of methyl (0.05-0.25%) and ethyl or propyl or butyl (0.005%-0.03%) parabens. The parabens are lower alkyl esters of para-hydroxybenzoic acid.

Surfactants frequently can cause denaturation of protein, both of hydrophobic disruption and by salt bridge separation. Relatively low concentrations of surfactant may exert a potent denaturing activity, because of the strong interactions between surfactant moieties and the reactive sites on proteins. However, judicious use of this interaction can stabilize proteins against interfacial or surface denaturation. Surfactants which could further stabilize the P-PI conjugate may optionally be present in the range of about 0.001 to 0.3% (w/v) of the total formulation and include polysorbate 80 (i.e., polyoxyethylene(20) sorbitan monooleate), CHAPS® (i.e., 3-[(3-cholamidopropyl) dimethylammonio]1-propanesulfonate), Brij® (e.g., Brij 35, which is (polyoxyethylene (23) lauryl ether), poloxamer, or another non-ionic surfactant.

An exemplary vehicle for parenteral products is water. Water of suitable quality for parenteral administration can be prepared either by distillation or by reverse osmosis. Water for injection is typically the aqueous vehicle for use in the pharmaceutical formulations.

It is possible that other ingredients may be present in the pharmaceutical formulations. Such additional ingredients may include, e.g., wetting agents, emulsifiers, oils, antioxidants, bulking agents, tonicity modifiers, chelating agents, metal ions, oleaginous vehicles, proteins (e.g., human serum albumin, gelatin or proteins) and a zwitterion (e.g., an amino acid such as betaine, taurine, arginine, glycine, lysine and histidine). Additionally, polymer solutions, or mixtures with polymers provide the opportunity for controlled release of the peptide. Prolonged absorption of the injectable compositions can be brought about by the use in the compositions of agents delaying absorption (for example, aluminum monostearate and gelatin). Such additional ingredients, of course, should not adversely affect the overall stability of the provided pharmaceutical formulation.

In particular embodiments, a pharmaceutical formulation provided may contain a range of concentrations of the P-PI conjugate compound, e.g., between about 0.01% to about 98% (w/w), or between about 1 to about 98% (w/w), or between 80% and 90% (w/w), or between about 0.01% to about 50% (w/w), or between about 10% to about 25% (w/w). A sufficient amount of water for injection may be used to obtain the desired concentration of solution.

Exemplary pharmaceutical formulations contemplated may comprise approximately 0.01 to 1.0% (w/v), in certain cases 0.05 to 1.0% (w/v), of the P-PI conjugate compound, approximately 0.02 to 0.5% (w/v) of an acetate, phosphate, citrate or glutamate buffer allowing a pH of the final composition of from about 3.0 to about 7.0; approximately 1.0 to 10% (w/v) of a carbohydrate or polyhydric alcohol tonicifier and, optionally, approximately 0.005 to 1.0% (w/v) of a preservative selected from the group consisting of m-cresol, benzyl alcohol, methyl, ethyl, propyl and butyl parabens and phenol. Such a preservative is generally included if the formulated peptide is to be included in a multiple use product.

Sterile injectable solutions may be prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle that contains the basic dispersion medium and the required other ingredients from those enumerated herein. In the case of sterile powders for the preparation of sterile injectable solutions, exemplary methods of preparation are vacuum-drying and freeze-drying techniques that yield a powder of the active ingredient plus any additional desired ingredient from a previously sterile-filtered solution thereof. In certain embodiments, the compounding procedure involves dissolution of ingredients in a specific order (for example, preservative followed by stabilizer/tonicity agents, buffers and peptide) or dissolving at the same time. In some cases, the P-PI conjugates can be lyophilized in to vials, syringes or cartridges for subsequent reconstitution. Liquid formulations provided can be filled into one or two chambered cartridges, or one or two chamber syringes.

Alternative formulations, e.g., non-parenteral, may not require sterilization. However, if sterilization is desired or necessary, any suitable sterilization process can be used in developing the peptide pharmaceutical formulation provided herein. Typical sterilization processes include filtration, steam (moist heat), dry heat, gases (e.g., ethylene oxide, formaldehyde, chlorine dioxide, propylene oxide, beta-propiolacctone, ozone, chloropicrin, peracetic acid methyl bromide and the like), exposure to a radiation source, and aseptic handling. Filtration is an exemplary method of sterilization for provided liquid formulations. The sterile filtration involves filtration through 0.45 μm and 0.22 μm (1 or 2) which may be connected in series. After filtration, the solution is filled into appropriate vials or containers.

Generally, a therapeutically or prophylactically effective amount of the present P-PI conjugate will be determined by the age, weight, and condition or severity of the diseases, conditions or disorders of the recipient. Appropriate dosages may be ascertained through the use of established assays for determining level of metabolic conditions or disorders in conjunction with relevant dose-response data. The final dosage regimen will be determined by the attending physician, considering factors that modify the action of drugs, e.g., the drug's specific activity, severity of the damage and the responsiveness of the patient, the age, condition, body weight, sex and diet of the patient, the severity of any infection, time of administration and other clinical factors. As studies are conducted, further information will emerge regarding appropriate dosage levels and duration of treatment for specific diseases and conditions.

Typically, a dosage of between about 0.001 µg/kg body weight/day to about 1000 µg/kg body weight/day may be used, but more or less, as a skilled practitioner will recognize, may be used. Typical doses may contain from a lower limit of about 1 µg, 5 µg, 10 µg, 50 µg to 100 µg to an upper limit of about 100 µg, 500 µg, 1 mg, 5 mg, 10 mg, 50 mg or 100 mg of the pharmaceutical compound per day. The doses per day may be delivered in discrete unit doses, provided continuously in a 24 hour period or any portion of that the 24 hours. The number of doses per day may be from 1 to about 4 per day, although it could be more. Dosing may be one or more times daily, or less frequently, such as one or more times weekly or one or more times monthly, and may be in conjunction with other compositions as described herein. It should be noted that the present methods and compositions are not limited to the dosages recited herein.

Typical doses may contain from a lower limit of about 0.5 µg, 1 µg, 5 µg, 10 µg, 50 µg to 100 µg to an upper limit of about 100 µg, 500 µg, 1 mg, 5 mg, 10 mg, 50 mg or 100 mg of the pharmaceutical compound per day. The doses per day may be delivered in discrete unit doses, provided continuously in a 24 hour period or any portion of that the 24 hours. The number of doses per day may be from 1 to about 4 per day, although it could be more.

In some embodiments, an effective dose will typically be in the range of about 1 to 30 µg to about 5 mg/day, about 10 to 30 µg to about 2 mg/day, about 5 to 100 µg to about 1 mg/day, or about 5 µg to about 500 µg/day, for a 50 kg patient, administered in a single or divided doses. In some embodiments, dosages are between about 0.01 to about 100 µg/kg/dose. In other embodiments, the composition is formulation so as to deliver a dose of P-PI conjugate ranging from 1 µg/kg to 100 mg/kg body weight/day or at doses ranging from 0.1 mg/kg to about 50 mg/kg body weight/day. Dosages for certain routes, for example oral administration, may be increased to account for decreased bioavailability, for example, by about 5-100 fold.

The frequency of dosing will depend in part on the pharmacokinetic parameters of the agents and the routes of administration. Pharmaceutical formulations may influence the physical state, stability, rate of in vivo release and rate of in vivo clearance of the administered agents. Depending on the route of administration, a suitable dose may be calculated according to body weight, body surface areas or organ size. Further refinement of the calculations necessary to determine the appropriate treatment dose is routinely made by those of ordinary skill in the art without undue experimentation, especially in light of the dosage information and assays disclosed herein, as well as pharmacokinetic data observed in animals or human clinical trials.

Administration should begin whenever the desired effect, e.g., suppression of nutrient availability, food intake, weight, blood glucose or plasma lipid modulation, is of benefit to the recipient, for example, at the first sign of symptoms or shortly after diagnosis of obesity, diabetes mellitus, or insulin-resistance syndrome. It will be appreciated that the pharmaceutical compositions and treatment methods provided herein may be useful in fields of human medicine and veterinary medicine.

In addition, a kit is provided comprising a P-PI conjugate compound, components suitable for preparing said P-PI conjugate compound for pharmaceutical application, and instructions for using said P-PI conjugate and components for pharmaceutical application.

As described herein, a variety of liquid vehicles are suitable for use in the formulations of peptidic anti-obesity agents, for example, water or an aqueous/organic solvent mixture or suspension.

Administration of the pharmaceutical compositions described herein may be via any common route so long as the target tissue is available via that route. In one embodiment, the P-PI conjugates are administered peripherally to the subjects. In one embodiment, the P-PI conjugates are administered locally to the subjects. In some embodiments, the liquid pharmaceutical formulations of the P-PI conjugate are intended for parenteral administration. Suitable routes of administration include intramuscular, intravenous, subcutaneous, intradermal, intraarticular, intrathecal, intramammary, intraperitoneal, retrobulbar, intrapulmonary (e.g., term release), and the like. In some embodiments, the subcutaneous route of administration is of use. In certain embodiments, mucosal delivery is also exemplary. These routes include, but are not limited to, oral, nasal, sublingual, pulmonary, buccal, anal, vaginal, and transdermal routes which may include administration of the conjugate in liquid, semi-solid or solid form. Administration via these routes may require substantially more conjugate to obtain the desired biological effects due to decreased bioavailability compared to parenteral delivery. Parenteral administration may be carried out with an initial bolus followed by continuous infusion to maintain therapeutic circulating levels of drug product.

Controlled continual release of the P-PI conjugate compositions is also contemplated. Continuous delivery can be in the form of continuous infusions. Exemplary doses and infusion rates include from 0.005 nmol/kg to about 20 nmol/kg per discrete dose or from about 0.01/pmol/kg/min to about 10 pmol/kg/min in a continuous infusion. These doses and infusions can be delivered by intravenous administration (i.v.) or subcutaneous administration (s.c.). Exemplary total dose/delivery of the pharmaceutical composition given i.v. may be about 2 mg to about 8 mg per day, whereas total dose/delivery of the pharmaceutical composition given s.c may be about 6 mg to about 6 mg per day.

A form of repository or "depot" slow release preparation may be used so that therapeutically effective amounts of the preparation are delivered into the bloodstream over many hours or days following transdermal injection or delivery. Those of ordinary skill in the art will readily optimize effective dosages and administration regimens as determined by good medical practice and the clinical condition of the individual patient. Parenteral controlled release delivery can be achieved by forming polymeric microcapsules, matrices, solutions, implants and devices and administering the same parenterally or by surgical means. Examples of controlled release formulations are described in U.S. Pat. Nos. 6,368, 630, 6,379,704, and 5,766,627. These dosage forms may have a lower bioavailability due to entrapment of some of the conjugates in the polymer matrix or device. See e.g., U.S. Pat. Nos. 6,379,704, 6,379,703, and 6,296,842.

The following Examples are provided to illustrate, but not limit, the invention.

EXAMPLES

Example 1

Synthesis of Peptide-Peptidase Inhibitor Conjugates

Conjugate molecules were prepared by linking the peptide GLP-1(7-37) (SEQ ID NO:42) or [Leu$^{14}$]-exendin(1-28)

(SEQ ID N:70) to an angiotensin converting enzyme (ACE) inhibitor. The ACE inhibitors used included the small molecule lisinopril and the peptide pGluKWAP-OH (SEQ ID NO: 325). The following depicts the synthesis scheme for conjugate molecules 3633/21, 3633/24, 3633/42/1, 3633/42/2, 3633/42/3, and 3633/38 where the inhibitor motif is placed on the C-terminus of the GLP-1(7-37) and [Leu$^{14}$]-exendin-(1-28). $AA_1$ and $AA_2$ are 2 or 3 carbons chain.
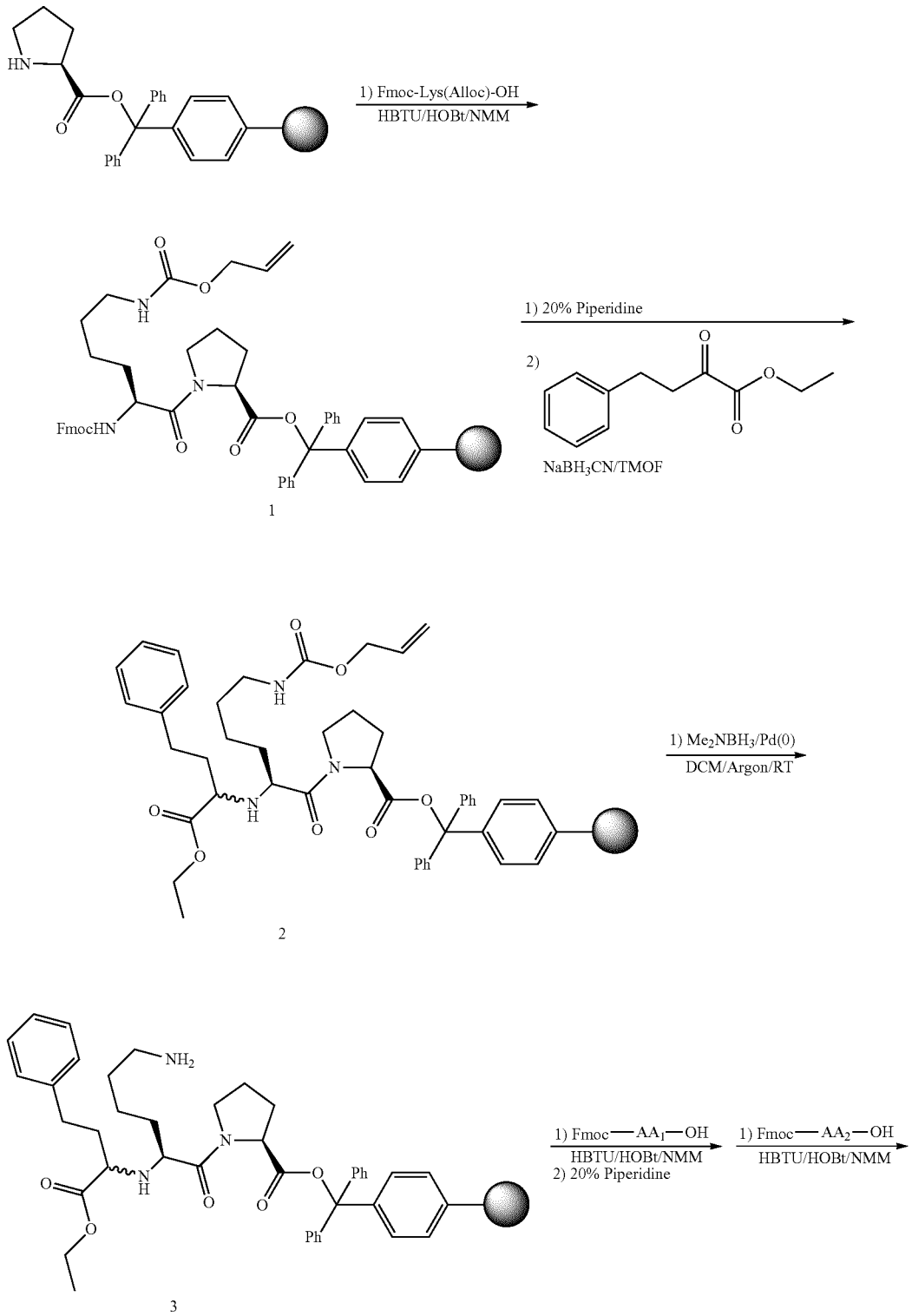

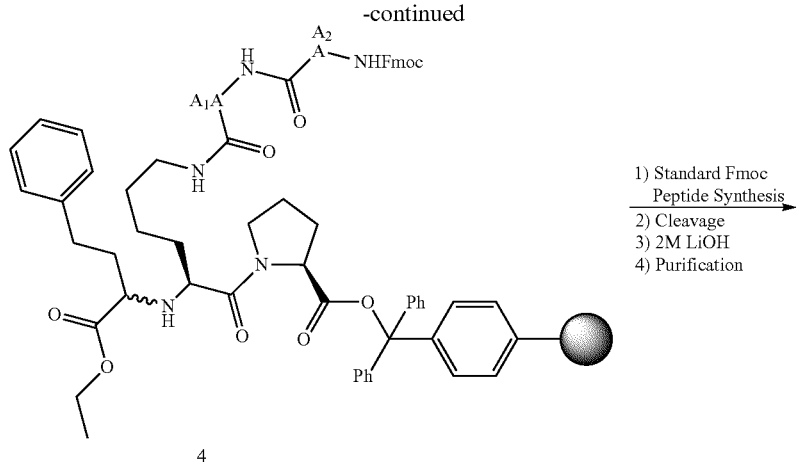

4

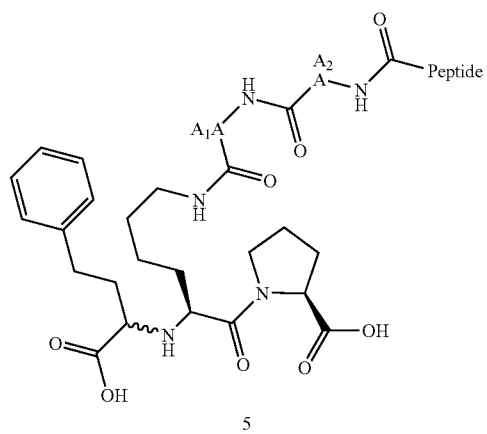

5

Preparation of resin-bound intermediate 1: 0.75 g of H-Proline-Trityl-Resin (0.68 mmol/g) was swollen in dimethylformamide (DMF) for 20 min. in a 20 mL polypropylene syringe with a frit. To the resin slurry was added a mixture of Fmoc-Lys(alloc)-OH (0.6 g, 2.6 eq), HBTU (0.51 g, 2.6 eq), HOBt (0.174 g) and N-Methylmorpholine (0.22 mL, 4 eq). The resin was shaken at room temperature for 2.5 h. Chloranil test showed negative. The resin was washed with DMF (4×), DCM (2×), MeOH (2×), DCM and MeOH and dried under high vacuum. Resin loading was calculated by weight gain (0.54 mmol/g, 100% yield).

Preparation of resin-bound intermediate 2: Resin 1 was swollen in DMF for 10 min., drained and then treated with 20% piperidine in DMF for 15 min., washed with DMF (6×) and the procedure repeated. Chloranil test showed positive. The resin was then swollen in 10 mL of trimethylorthoformate (TMOF). To this mixture was added ethyl-2-oxo-4-phenylbutyrate (2.2 g, 20 eq) dissolved in 1 mL of TMOF. The resin was shaken for 1 h followed by addition of NaBH$_3$CN (0.673 g, 20 eq) dissolved in 5.1 mL of TMOF and 0.7 mL of MeOH. The resin slurry was shaken at room temperature for 5 h then washed with TMOF and the process repeated. A sample of resin was cleaved with 1% TFA in DCM and the crude product analyzed by LCMS. Calculated mass for $C_{27}H_{39}N_3O_7$ (M+H)$^+$ 518.28, found 518.3.

Preparation of resin-bound intermediate 3: Resin 2 (0.78 g) was swollen in dry DCM under argon for 10 min. To the mixture was added Me$_2$NH—BH$_3$ (0.141 g, 6 eq) under agitation, followed after 5 min. by addition of Pd(PPh$_3$)$_4$ (0.047 g, 10 mol %). After 10 min. the solution is drained and the resin washed with DCM (4×). This procedure was repeated and then the resin washed with DCM (8×30 s), DIEA 5% in DCM (3×60 s) and DCM (5×30 s). The resin showed a positive chloranil test. A sample of resin was cleaved with 1% TFA in DCM and the crude product analyzed by LCMS. Calculated mass for $C_{23}H_{35}N_3O_5$ (M+H)$^+$ 434.26, found 434.3.

Preparation of resin-bound intermediate 4: AA$_1$=CH$_2$—CH$_2$, AA$_2$=CH$_2$—CH$_2$—CH$_2$ Resin 3 (0.51 g, 0.4 mmol/g) was swollen in DMF for 10 min, drained and treated with a mixture of β-Ala-OH (0.094 g, 1.5 eq), HBTU (0.115 g, 1.5 eq), HOBT (0.041 g, 1.5 eq) and N-methylmorpholine (0.066 mL, 3 eq) in 3 mL of DMF. After 3 h chloranil test showed a negative test. The resin was washed with DMF (6×30 s) followed by treatment with 20% piperidine (2×15 min), washed with DMF (6×30 s) and coupled with a mixture of γ-Abu-OH (0.1 g, 1.5 eq), HOBT, HBTU and N-methylmorpholine. After 3 h, the coupling was complete as indicated by chloranil test. The resin was washed with DMF (6×), DCM and MeOH, dried. A sample of resin was cleaved with 1% TFA in DCM and the crude product analyzed by LCMS. Calculated mass for $C_{30}H_{47}N_5O_7$ (M+H)$^+$589.35, found 589.3. (>90% pure).

Synthesis of GLP-1-(7-37)-γ-Abu-β-Ala-CONH-Lisinopril (3633/42/1)

A calculated 110 μmol of the modified trityl resin 4 was weighed into a reaction vessel in a Symphony® peptide synthesizer (Protein Technologies, Inc.) and the peptide elongation was carried out following standard Fmoc peptide synthesis protocol. The peptide was cleaved from the resin with 20 mL TFA/phenol/H$_2$O/TIPS (95:2:2:1). The crude peptide was precipitated using tert-butyl methyl ether. Calculated mass for C$_{174}$H$_{265}$N$_{43}$O$_{53}$ (M+H)$^+$ 3807.31, found by LC-MS 1269.1 (M+3H)$^3$. The crude peptide was dissolved in 1 mL of a 60:40 mixture of H$_2$O/ACN and to this mixture was added 0.2 mL of a 2M solution of LiOH. The mixture was stirred at room temperature for three hours. The crude peptide was purified by LCMS-PrepExpress (mass triggered collection) (C$_{18}$, 25-60% CH$_3$CN in 0.1% TFA/H$_2$O over 30 min gradient) to afford the titled compound as a white powder (23.3 mg, 5.7%): Retension time in RP-HPLC(C$_{18}$, 5-75% CH$_3$CN in 0.1% TFA/H$_2$O over 15 min) is 9.64. LCMS Calculated mass for C$_{172}$H$_{261}$N$_{43}$O$_{53}$ (M+H)$^+$ 3779.25, found by LC-MS 1259.7 (M+3H)$^3$.

Synthesis of GLP-1-(7-37)-γ-Abu-β-Ala-CONH-Lisinopril (3633/42/2)

A calculated 110 μmol of the modified trityl resin 4 was weighed into a reaction vessel in a Symphony® peptide synthesizer and the peptide elongation was carried out following standard Fmoc peptide synthesis protocol. The peptide was cleaved from the resin with 20 mL TFA/phenol/H$_2$O/TIPS (95:2:2:1). The crude peptide was precipitated using tert-butyl methyl ether. Calculated mass for C$_{174}$H$_{266}$N$_{42}$O$_{52}$ (M+H)$^+$ 3778.31, found by LC-MS 1259.4 (M+3H)$^3$. The crude peptide was dissolved in 1 mL of a 60:40 mixture of H$_2$O/ACN and to this mixture was added 0.2 mL of a 2M solution of LiOH. The mixture was stirred at room temperature for 3 hours. The crude peptide purified by LCMS-PrepExpress (mass triggered collection) (C$_{18}$, 25-60% CH$_3$CN in 0.1% TFA/H$_2$O over 30 min gradient) to afford the titled compound as a white powder (21 mg, 5.5%): Retension time in RP-HPLC(C$_{18}$, 5-75% CH$_3$CN in 0.1% TFA/H$_2$O over 15 min) is 9.80. LCMS Calculated mass for C$_{172}$H$_{262}$N$_{42}$O$_{52}$ (M+H)$^+$ 3750.26, found by LC-MS 1250.1 (M+3H)$^3$.

Synthesis of GLP-1-(7-37)-γ-Abu-β-Ala-CONH-Lisinopril (3633/42/3)

A calculated 110 μmol of the modified trityl resin 4 was weighed into a reaction vessel in a Symphony® peptide synthesizer and the peptide elongation was carried out following standard Fmoc peptide synthesis protocol. The peptide was cleaved from the resin with 20 mL TFA/phenol/H$_2$O/TIPS (95:2:2:1). The crude peptide was precipitated using tert-butyl methyl ether and purified by LCMS-PrepExpress (mass triggered collection) (C$_{18}$, 25-60% CH$_3$CN in 0.1% TFA/H$_2$O over 30 min gradient) to afford the ester compound as a white powder (5.8 mg, 1.2%): Retension time in RP-HPLC (C$_{18}$, 5-50% CH$_3$CN in 0.1% TFA/H$_2$O over 15 min) is 8.13; Calculated mass for C$_{181}$H$_{273}$N$_{45}$O$_{53}$ (M+H)$^+$ 3927.36, found by LC-MS 1310.7 (M+3H)$^3$. The crude peptide was dissolved in 1 mL of a 60:40 mixture of H$_2$O/ACN to this mixture it was added 0.160 mL of a 2M solution of LiOH. The mixture was stirred at room temperature for two hours. The crude peptide purified by LCMS-PrepExpress (mass triggered collection) (C$_{18}$, 25-60% CH$_3$CN in 0.1% TFA/H$_2$O over 30 min gradient) to afford the titled compound as a white powder (11 mg, 2.4%): Retension time in RP-HPLC(C$_{18}$, 5-75% CH$_3$CN in 0.1% TFA/H$_2$O over 15 min) is 9.51. LCMS Calculated mass for C$_{179}$H$_{269}$N$_{45}$O$_{53}$ (M+H)$^+$ 3899.41, found by LC-MS 1300.8 (M+3H)$^3$.

Synthesis of [Leu$^{14}$]-Exendin-4-(1-28)-γ-Abu-β-Ala-CONH-Lisinopril (3633/21)

The procedure described above was followed up to the preparation of intermediate 4. A calculated 120 μmol of the modified trityl resin 4 was weighed into a reaction vessel in a Symphony® peptide synthesizer, and the peptide elongation was carried out following standard Fmoc peptide synthesis protocol. The peptide was cleaved from the resin with 20 mL TFA/phenol/H$_2$O/TIPS (95:2:2:1). The crude peptide was precipitated using tert-butyl methyl ether and purified by LCMS-PrepExpress (mass triggered collection) (C$_{18}$, 25-60% CH$_3$CN in 0.1% TFA/H$_2$O over 30 min gradient) to afford the precursor ester compound as a white powder (11 mg, 2.2%): Retention time in RP-HPLC(C$_{18}$, 5-75% CH$_3$CN in 0.1% TFA/H$_2$O over 15 min) is 9.17; Calculated mass for C$_{177}$H$_{271}$N$_{45}$O$_{53}$ (M+H)$^+$ 3849.39, found by LC-MS 1284.7 (M+3H)$^3$, 963.5 (M+4H)$^4$. A solution of 0.8 mg of the purified ester precursor in 100 μL of H$_2$O was treated with 12 μL of a 2M LiOH solution. After two hours LCMS showed quantitative transformation to the desired compound 3633/21. LCMS Calculated mass for C$_{175}$H$_{267}$N$_{45}$O$_{53}$ (M+H)$^+$ 3821.34, found by LC-MS 1274.7 (M+3H)$^3$.

Synthesis of GLP-1-(7-37)-γ-Abu-CONH-Lisinopril (3633/24)

The procedure described above was followed up to the preparation of intermediate 4. A calculated 120 μmol of the modified trityl resin 4 was weighed into a reaction vessel in a Symphony® peptide synthesizer, and the peptide elongation was carried out following standard Fmoc peptide synthesis protocol. The peptide was cleaved from the resin with 15 mL TFA/phenol/H$_2$O/TIPS (95:2:2:1). The crude peptide was precipitated using tert-butyl methyl ether and purified by LCMS-PrepExpress (mass triggered collection) (C$_{18}$, 25-60% CH$_3$CN in 0.1% TFA/H$_2$O over 30 min gradient) to afford the precursor ester compound as a white powder (6.2 mg, 2.2%): Retention time in RP-HPLC(C$_{18}$, 5-75% CH$_3$CN in 0.1% TFA/H$_2$O over 15 min) is 8.86; Calculated mass for C$_{179}$H$_{272}$N$_{44}$O$_{51}$ (M+H)$^+$ 3856.43, found by LC-MS 1286.7 (M+3H)$^3$, 965.5 (M+4H)$^4$. A solution of 0.8 mg of the purified ester precursor in 100 μL of H$_2$O was treated with 12 μL of a 2M LiOH solution. After two hours LCMS showed quantitative transformation to the desired compound 3633/24. LCMS Calculated mass for C$_{176}$H$_{264}$N$_{44}$O$_{52}$ (M+H)$^+$ 3828.33, found by LC-MS 1277.1 (M+3H)$^3$.

Synthesis of GLP-1-(7-37)-γ-Abu-N$^{\epsilon 2}$Lys-(Pyr)-WAP-OH (3633/38)

A calculated 340 μmol of H-Pro-Trytil-resin (0.68 mmol/g) was weighed into a reaction vessel manual peptide synthesizer, and the peptide elongation was carried out following standard Fmoc peptide synthesis protocol using the following amino acids: FmocAla-OH, FmocTrp(Boc)-OH, FmocLys (Alloc)-OH and pyroglutamic acid-OH. The pentapeptide was then treated swollen in dry DCM under argon for 10 min. To the mixture was added Me$_2$NH—BH$_3$ (0.073 g, 6 eq) under agitation, followed after 5 min. by addition of Pd(PPh$_3$)$_4$ (0.024 g, 10 mol %). After 10 min. the solution was drained and the resin washed with DCM (4×). This procedure was repeated and then the resin washed with DCM (8×30 s), DIEA 5% in DCM (3×60 s) and DCM (5×30 s). The resin shows a positive chloranil test. The modified trityl resin was weighed into a reaction vessel in a Symphony® peptide synthesizer, and the peptide elongation was carried out following standard Fmoc peptide synthesis protocol. The peptide was cleaved from the resin with 20 mL TFA/phenol/H$_2$O/TIPS (95:2:2:1). The crude peptide was precipitated using tert-butyl methyl ether and purified by LCMS-PrepExpress (mass triggered collection) (C$_{18}$, 25-60% CH$_3$CN in 0.1% TFA/H$_2$O over 30 min gradient) to afford the titled compound as a white powder (8.5 mg, 2.1% yield). Retention time in RP-HPLC(C$_{18}$, 5-75% CH$_3$CN in 0.1% TFA/H$_2$O over 15 min) is 9.86; Calculated mass for C$_{185}$H$_{274}$N$_{48}$O$_{54}$ (M+H)$^+$ 4034.54, found by LC-MS 1344.8 (M+3H)$^3$.

Synthesis of Glu(γ-methylamido)-(2)-S-cyanopyrrolidinamide

The following depicts the synthesis scheme for the DPP-IV inhibitor based molecule Glu(γ-methylamido)-(2)-S-cyanopyrrolidinamide.

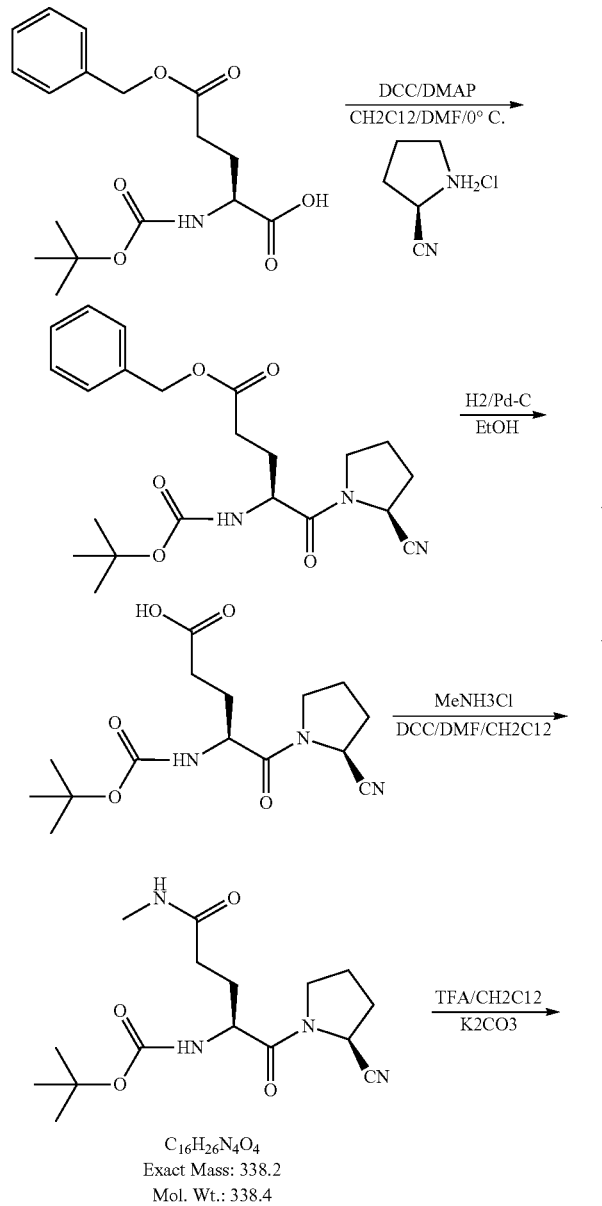

Synthesis of Lys(ε-NH-acetoyl)-(2)-S-cyanopyrrolidinamide

The following depicts the synthesis scheme for the DPP-IV inhibitor based molecule Lys(ε-NH-acetoyl)-(2)-S-cyanopyrrolidinamide.

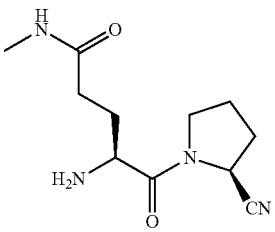 [SMILES: CNC(=O)CC[C@H](N)C(=O)N1CCC[C@H]1C#N]

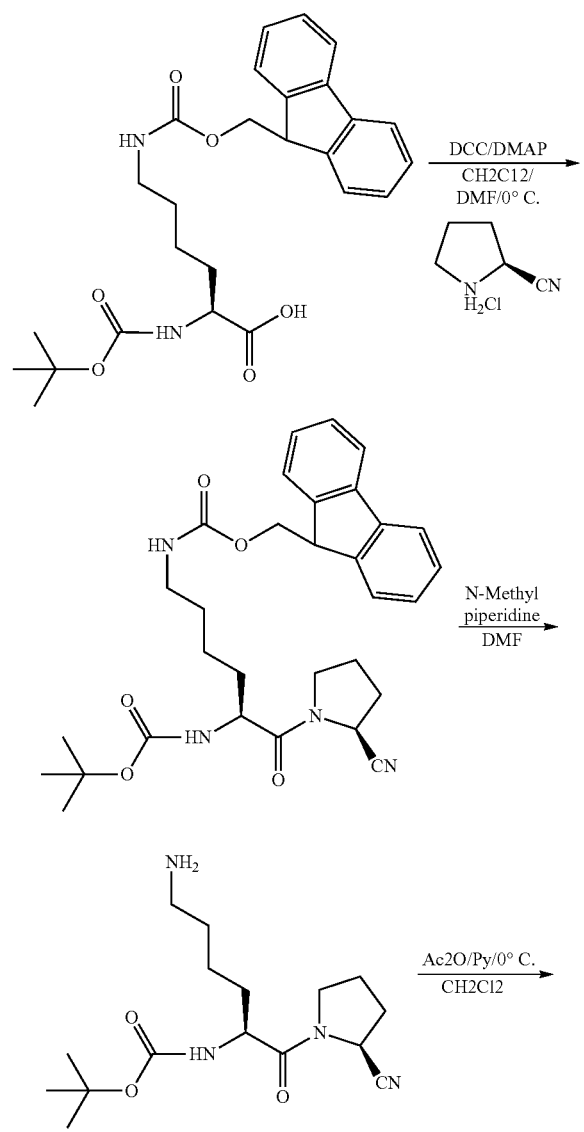

99
-continued
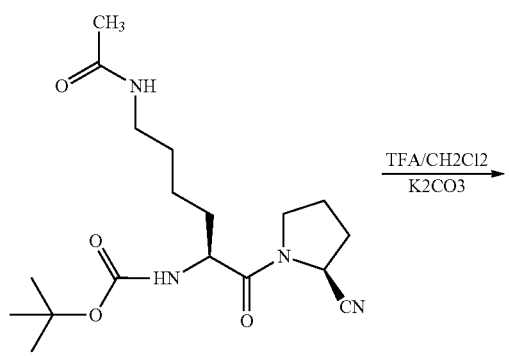
→ TFA/CH2Cl2 / K2CO3 →
100
-continued
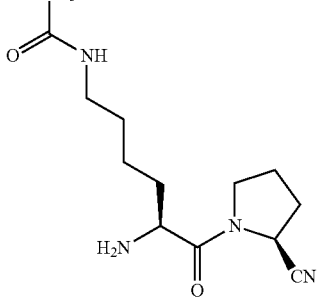
Synthesis of Maleimido DPP-IV Inhibitor-GIP Analogs
The following is a typical procedure for coupling of maleimido DPP-IV inhibitor analogs to GIP peptides (such as those depicted in FIG. 4).
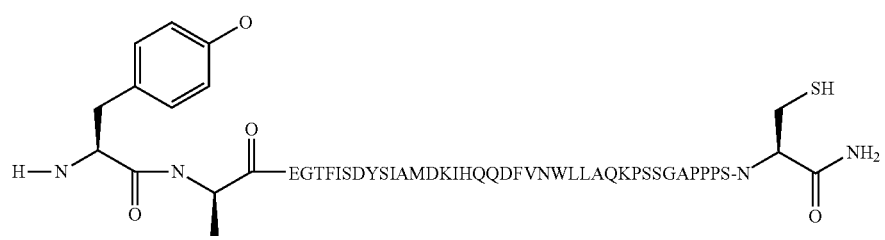
(SEQ ID NO: 302)
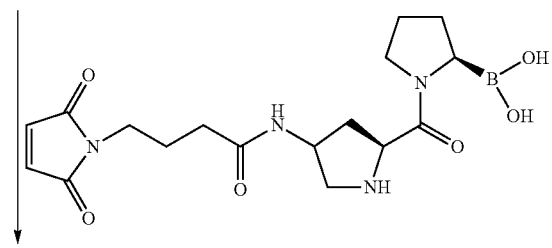
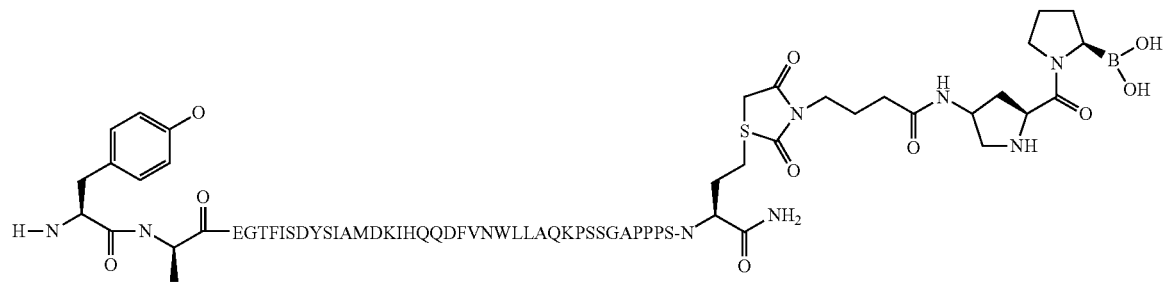
(SEQ ID NO: 303)

A 25 mM HEPES buffer (5 mL) was degassed under argon for about 10 min. and added to the desired peptide (10 mg 1:1 v/v $CH_3CN:H_2O$) with a free cysteine. A solution of the maleimido-DPPIV analog (ca. 2-3 equivalent) in 1:1 v/v $CH_3CN:H_2O$ (5 mL) was added to the peptide and stirred the solution under argon atmosphere. After an hour, when the LCMS showed the complete conversion to the desired product, the reaction was frozen and lyophilized. The crude peptide was purified using reverse phase HPLC with a gradient of $CH_3CN$ and $H_2O$ as eluents.

Example 2

Synthesis of GLP-1-Peptidase Inhibitor Conjugates

Conjugate molecules were prepared by linking the peptide GLP-1 to a peptidase inhibitor. The peptidase inhibitors used included DPP-IV inhibitors and vasopeptidase (neutral endopeptidase, ACE, and endothelin converting enzyme-1) inhibitors. The following depicts the synthesis scheme for GLP-1/DPP-IV inhibitor conjugate molecules 4844 and 4845 where the inhibitor motif is placed on the C-terminus of the GLP-1 and GLP-1/vasopeptidase inhibitor conjugate molecules 4983 and 4984 where the inhibitor motif is placed on the N-terminus of the GLP-1.

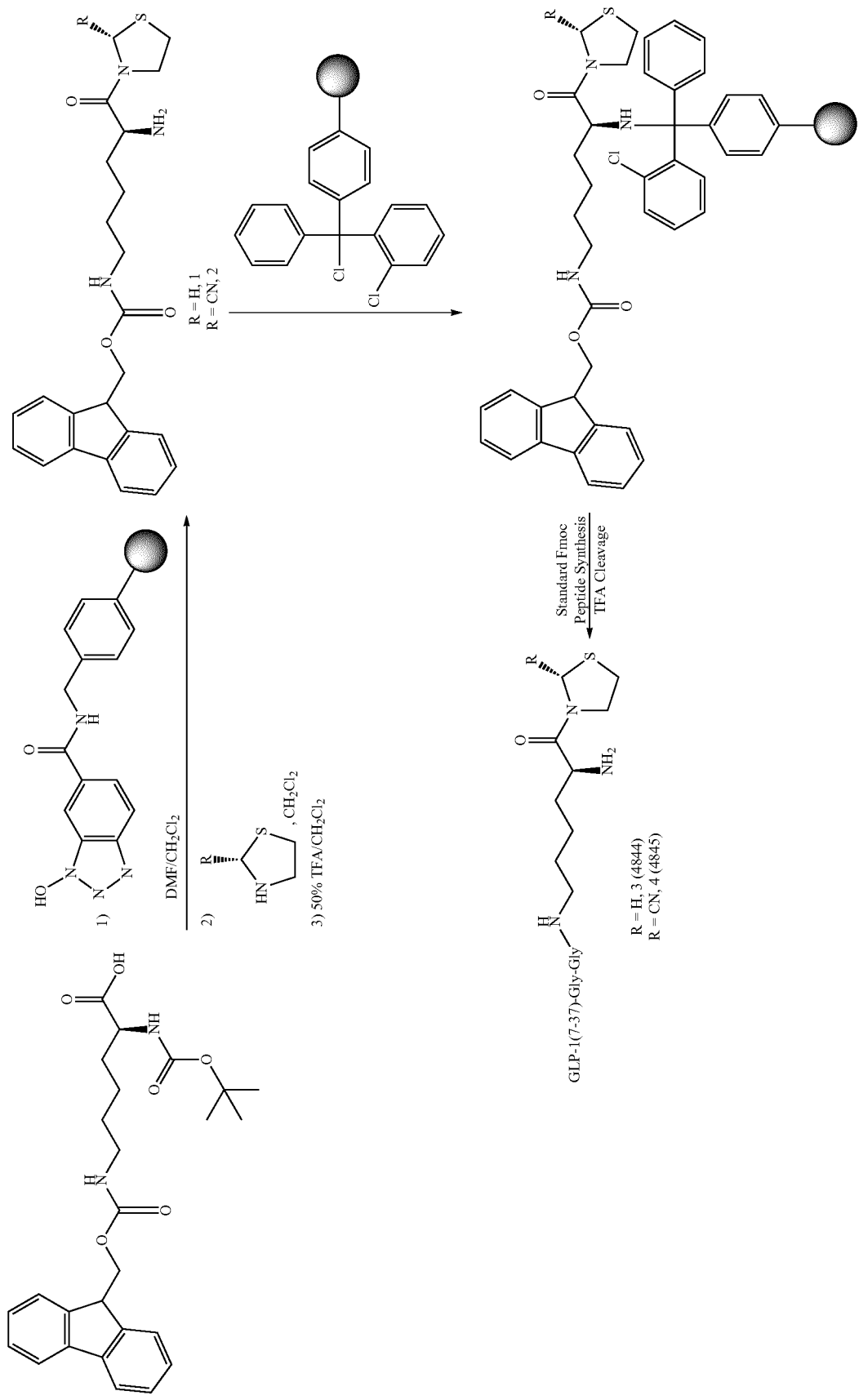

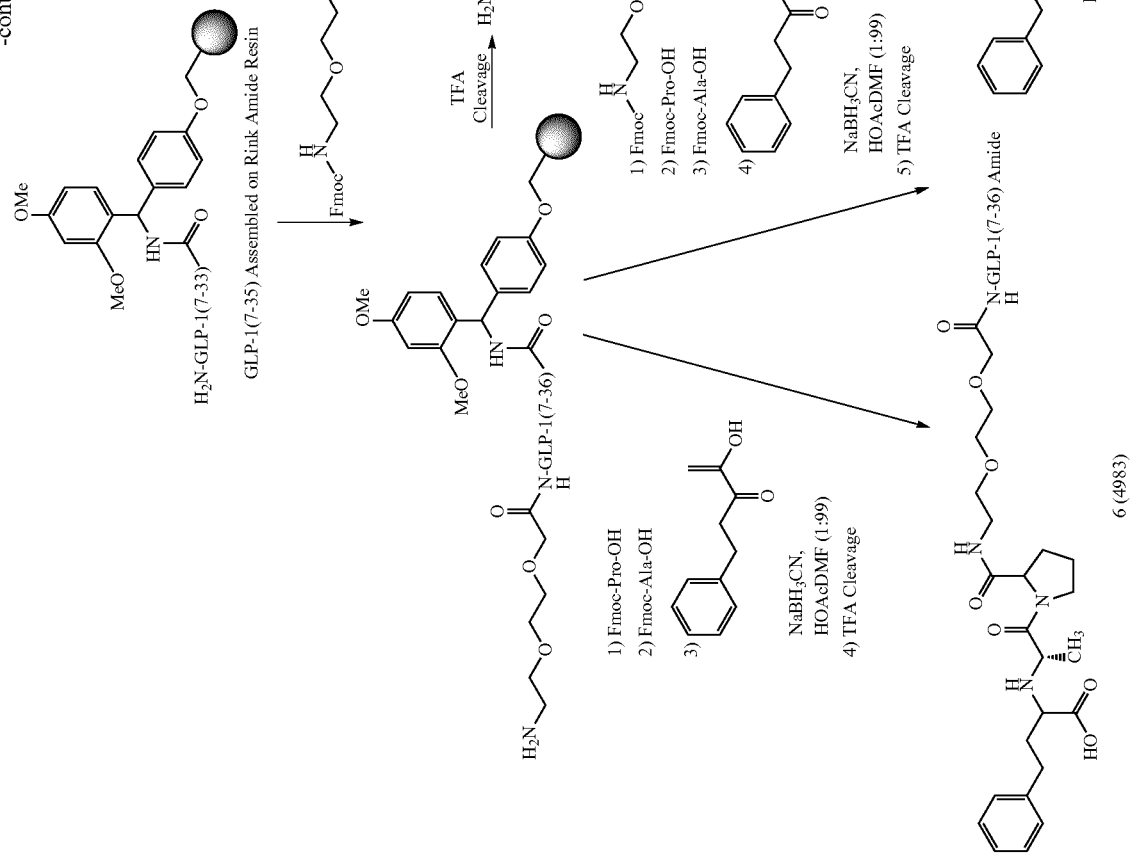

Preparation of thiazolidinyl (S)-2-amino-6-(fluorenylmethoxycarbonyl) aminohexylcarbamate (1): Boc-Lys (Fmoc)-OH (0.703 g, 1.5 mmol), polystyrene-HOBt (1 mmol/g, 1 g, 1 mmol), 8 ml $CH_2Cl_2$, and 2 ml DMF were added to a 20-ml reaction vessel, and the mixture was gently agitated on a horizontal shaker at room temperature for 2 hours. The suspension was filtered and the resin was washed extensively with DMF followed by dry $CH_2Cl_2$. The resin was re-suspended in 10 ml dry $CH_2Cl_2$, and thiazolidine (83 μl, 1.0 mmol) was added to the suspension. The mixture was then gently agitated on a horizontal shaker at room temperature overnight. The resin was filtered off and the filtrate was collected and evaporated to dryness under reduced pressure. The residue was then treated with 10 ml 50% TFA in $CH_2Cl_2$ at room temperature for 2 hours. The desired product was obtained as TFA salt after drying in vacuum overnight (0.41 g, 73% yield): $^1$H-NMR (CDCl$_3$, 300 MHz) δ 7.74 (d, J=4.5 Hz, 2H), 7.57 (d, J=4.1 Hz, 2H), 7.38 (t, J=4.5 Hz, 2H), 7.29 (t, J=4.4 Hz, 2H), 5.21 (s, b, 1H), 4.53 (t, J=6.2 Hz, 1H), 4.41 (m, 1H), 4.34 (d, J=4.3 Hz, 2H), 4.26 (m, 1H), 4.17 (m, 1H), 3.84 (m, 1H), 3.64 (m, 1H), 3.14 (m, 2H), 3.03 (t, J=3.3 Hz, 1H), 2.94 (t, J=3.8 Hz, 1H), 1.86 (m, 2H), 1.48 (m, 4H); Retention time in RP-HPLC($C_{18}$, 30-95% $CH_3CN$ in 0.1% $TFA/H_2O$ over 5 min) is 2.91; Calculated mass for $C_{24}H_{30}N_3O_3S$ $(M+H)^+$ 440.2, found by LC-MS 440.2.

Preparation of 2-cyanothiazolidinyl (S)-2-amino-6-(fluorenylmethoxycarbonyl) aminohexylcarbamate (2): Boc-Lys (Fmoc)-OH (0.487 g, 1.0 mmol), polystyrene-HOBt (1 mmol/g, 1 g, 1.0 mmol), 8 ml $CH_2Cl_2$, and 2 ml DMF were added to a 25-ml reaction vessel, and the mixture was gently agitated in a horizontal shaker at room temperature for 2 hours. The suspension was filtered and the resin was washed extensively with DMF followed by dry $CH_2Cl_2$. The resin was re-suspended in 10 ml dry $CH_2Cl_2$, and 2-cyanothiazolidine HCl salt (0.172 g, 1.1 mmol) was added to the suspension. The mixture was then gently agitated on a horizontal shaker at room temperature overnight. The suspension was filtered and the resin was washed with 10 ml $CH_2Cl_2$. The filtrate was pooled and evaporated to dryness under reduced pressure. The residue was applied to a silica gel chromatography eluted with 60% $CH_2Cl_2$/EtOAc to give the fully protected product as crystalline solid (0.186 g, 33%). The solids were treated with 10 ml 50% TFA/$CH_2Cl_2$ at room temperature for 2 hours, and the solvents were removed under reduced pressure. The residue was applied to a reverse-phase HPLC column ($C_{18}$, 20-50% $CH_3CN$ in 0.1% $TFA/H_2O$ over 30 min gradient) to afford the titled compound as a white powder (0.142 g, 94%): $^1$H-NMR (CDCl$_3$, 300 MHz) δ 7.74 (d, J=4.5 Hz, 2H), 7.56 (m, 2H), 7.38 (t, J=4.5 Hz, 2H), 7.29 (t, J=4.5 Hz, 2H), 5.27 (s, b, 1H), 5.10 (m, 1H), 4.66 (d, J=5.1 Hz, 1H), 4.50 (d, J=4.8 Hz, 1H), 4.33 (d, J=4.1 Hz, 2H), 4.18 (m, 1H), 3.22 (m, 2H), 3.13 (m, 2H), 1.91 (m, 2H), 1.47 (m, 4H); Retention time in RP-HPLC ($C_{18}$, 30-95% $CH_3CN$ in 0.1% $TFA/H_2O$ over 5 min) is 2.96; Calculated mass for $C_{25}H_{29}N_4O_3S$ $(M+H)^+$ 465.2, found by LC-MS 465.3.

Preparation of GLP-1-(7-37)-GG-(S)-2,6-diamino-1-(thiazolidin-3-yl)hexan-1-one amide (3, 4844): Thiazolidinyl (S)-2-amino-6-(fluorenylmethoxycarbonyl) aminohexylcarbamate (1) (0.41 g, 0.93 mmol), trityl chloride resin (1.0 mmol/g, 0.25 g, 0.25 mmol), 15 ml anhydrous DMF were added to a 25-ml reaction vessel, and the mixture was gently swirled at room temperature overnight. The suspension was filtered and the resin was washed sequentially with 30 ml DMF, 30 ml $CH_2Cl_2$, and 30 ml $CH_2Cl_2$/MeOH/DIPEA (17:2:1), and 30 ml $CH_2Cl_2$. The resin was dried in vacuo over KOH overnight. The LC-MS of the test cleavage products showed the presence of the first attached fragment. A calculated 50 μmol of the modified trityl-resin was weighed into a reaction vessel in a Symphony peptide synthesizer, and the peptide elongation was carried out following standard Fmoc peptide synthesis protocol. The peptide was cleaved from the resin with 10 ml TFA/$H_2O$/TIPS (95:2.5:2.5) and applied to a reverse-phase HPLC column ($C_{18}$, 20-50% $CH_3CN$ in 0.1% $TFA/H_2O$ over 30 min gradient) to afford the titled compound as a white powder (5.5 mg, 3%): Retention time in RP-HPLC ($C_{18}$, 15-45% $CH_3CN$ in 0.1% $TFA/H_2O$ over 15 min) is 10.52; Calculated mass for $C_{164}H_{252}N_{45}O_{49}S$ $(M+H)^+$ 3670.2, found by LC-MS 1836.0 $(M+2H)^{2+}$, 1224.7 $(M+3H)^{3+}$, 918.5 $(M+4H)^{4+}$.

Preparation of GLP-1-(7-37)-GG-(S)-2,6-diamino-1-(thiazolidin-2-cyano-3-yl)hexan-1-one amide (4, 4845): 2-Cyanothiazolidinyl (S)-2-amino-6-(fluorenylmethoxycarbonyl)aminohexylcarbamate TFA salt (2) (0.045 g, 0.078 mmol), trityl chloride resin (1.0 mmol/g, 0.10 g, 0.10 mmol), DIEA (14 μl, 0.078 mmol), 5 ml anhydrous $CH_2Cl_2$ were added to a 25-ml reaction vessel, and the mixture was gently swirled at room temperature overnight. The suspension was filtered and the resin was washed sequentially with 30 ml DMF, 30 ml $CH_2Cl_2$, and 30 ml $CH_2Cl_2$/MeOH/DIPEA (17:2:1), and 30 ml $CH_2Cl_2$. The resin was dried in vacuo over KOH overnight. The LC-MS of the test cleavage products showed the presence of the first attached fragment. A calculated 50 μmol of the modified trityl resin was weighed into a reaction vessel in a Symphony peptide synthesizer, and the peptide elongation was carried out following standard Fmoc peptide synthesis protocol. The peptide was cleaved from the resin with 10 ml TFA/$H_2O$/TIPS (95:2.5:2.5) and applied to a reverse-phase HPLC column ($C_{18}$, 20-50% $CH_3CN$ in 0.1% $TFA/H_2O$ over 30 min gradient) to afford the titled compound as a white powder (1.7 mg, 0.9%): Retention time in RP-HPLC($C_{18}$, 15-45% $CH_3CN$ in 0.1% $TFA/H_2O$ over 15 min) is 10.60; Calculated mass for $C_{165}H_{251}N_{46}O_{49}S$ $(M+H)^+$ 3695.2, found by LC-MS 1848.0 $(M+2H)^{2+}$, 1232.7 $(M+3H)^{3+}$, 924.5 $(M+4H)^{4+}$.

Preparation of 8-Amino-3,6-dioxaoctanoyl-GLP-1-(7-36) amide (5, 4992): The titled peptide was assembled on 0.20 mmol Rink amide resin (0.610 mmol/g, 0.328 g) with an ABI-433A peptide synthesizer following the standard FastMoc protocol. The final Fmoc group was removed and the resin was dried in vacuum to give a dry weight of 0.90 g. One third of the resin, 0.30 g, was treated with 10 ml TFA/$H_2O$/TIPS (95:2.5:2.5) in a reaction vessel fitted with a filtration frit for 2 hours, and the cleavage solution was filtered into 35 ml TMBE. The precipitates were collected through centrifugation and applied to a reverse-phase HPLC column ($C_{18}$, 20-50% $CH_3CN$ in 0.1% $TFA/H_2O$ over 30 min gradient, 20 ml/min flow rate) to afford the titled compound as a white powder (3.0 mg, 1.3%): Retention time in RP-HPLC($C_{18}$, 15-45% $CH_3CN$ in 0.1% $TFA/H_2O$ over 15 min) is 10.99; Calculated mass for $C_{155}H_{238}N_{41}O_{48}$ $(M+H)^+$ 3443.9, found by LC-MS 1722.9 $(M+2H)^{2+}$, 1148.6 $(M+3H)^{3+}$, 861.5 $(M+4H)^{4+}$.

Preparation of (R,S)-1-[$N^2$-(1-carboxy-3-phenylpropyl)-L-ala]-L-pro-8-amino-3,6-dioxaoctanoyl-GLP-1-(7-36) amide (6, 4983): The 8-Amino-3,6-dioxaoctanoyl-GLP-1-(7-36) fragment was assembled as described previously, and one third of the resin, 0.30 g, was allowed to couple with Fmoc-Pro-OH and Fmoc-Ala-OH, sequentially, following the standard FastMoc protocol. The Fmoc group was removed and the resin was mixed with 2-keto-4-phenylbutyric acid (0.117 g, 0.66 mmol), NaBH$_3$CN (0.045 g, 0.72 mmol) in 4 mL DMF/HOAc (99:1). The resin was washed extensively with DMF, $CH_2Cl_2$, and MeOH, and dried in vacuum. The resin was then treated with 10 ml TFA/$H_2O$/

TIPS (95:2.5:2.5) in a reaction vessel fitted with a filtration frit for 2 hours, and the cleavage solution was filtered into 35 ml TMBE. The precipitates were collected through centrifugation and applied to a reverse-phase HPLC column ($C_{18}$, 20-50% $CH_3CN$ in 0.1% $TFA/H_2O$ over 30 min gradient, 20 ml/min flow rate) to afford the titled compound as a white powder (1.8 mg, 0.7%): Retention time in RP-HPLC($C_{18}$, 15-45% $CH_3CN$ in 0.1% $TFA/H_2O$ over 15 min) is 11.58; Calculated mass for $C_{173}H_{260}N_{43}O_{52}$ $(M+H)^+$ 3774.3, found by LC-MS 1888.0 $(M+2H)^{2+}$, 1258.7 $(M+3H)^{3+}$, 944.5 $(M+4H)^{4+}$.

Preparation of (R,S)-1-[$N^2$-(1-carboxy-3-phenylpropyl)-L-ala]-L-pro-8-amino-3,6-dioxaoctanoyl-8-amino-3,6-dioxaoctanoyl-GLP-1-(7-36) amide (7, 4984): The 8-Amino-3,6-dioxaoctanoyl-GLP-1-(7-36) fragment was assembled as described previously, and one third of the resin, 0.30 g, was allowed to couple with Fmoc-8-amino-3,6-dioxaoctanoyl acid, Fmoc-Pro-OH and Fmoc-Ala-OH, sequentially, following the standard FastMoc protocol. The Fmoc group was removed and the resin was incubated with 2-keto-4-phenylbutyric acid (0.117 g, 0.66 mmol), $NaBH_3CN$ (0.045 g, 0.72 mmol) in 4 ml DMF/HOAc (99:1) overnight. The resin was washed extensively with DMF, $CH_2Cl_2$, and MeOH, and dried in vacuum. The resin was then treated with 10 ml $TFA/H_2O$/TIPS (95:2.5:2.5) in a reaction vessel fitted with a filtration frit for 2 hours, and the cleavage solution was filtered into 35 ml TMBE. The precipitates were collected through centrifugation and applied to a reverse-phase HPLC column ($C_{18}$, 20-50% $CH_3CN$ in 0.1% $TFA/H_2O$ over 30 min gradient, 20 ml/min flow rate) to afford the titled compound as a white powder (6.4 mg, 2.4%): Retention time in RP-HPLC($C_{18}$, 15-45% $CH_3CN$ in 0.1% $TFA/H_2O$ over 15 min) is 11.49; Calculated mass for $C_{179}H_{271}N_{44}O_{55}$ $(M+H)^+$ 3919.4, found by LC-MS 1961.1 $(M+2H)^{2+}$, 1307.7 $(M+3H)^{3+}$, 980.5 $(M+4H)^{4+}$.

Example 3

Characterization of GLP-1-Peptidase Inhibitor Conjugates

The GLP-1 receptor binding activity (RBA) of the GLP-1-peptidase inhibitor conjugates were assessed using a binding displacement assay in which the receptor source was the endogenous GLP-1 receptors expressed by RINm5f cells. Membrane fractions were prepared from confluent cultures of RIN m5f cells. Homogenized RINm5F cell membranes were incubated in 20 mM HEPES buffer with 40,000 cpm [$^{125}I$] GLP-1 tracer and varying concentrations of test compounds. The reaction mixtures were constantly mixed at 23° C. for 2 hours. The reaction mixtures were filtered through glass filter pads presoaked with 0.3% PEI solution and rinsed with ice-cold phosphate buffered saline. Counts bound to the filer pads were determined using a scintillation counter and binding affinities were calculated using GraphPad PRISM® software (GraphPad Software, Inc., San Diego, Calif.).

The GLP-1-peptidase inhibitor conjugates were assessed in a GLP-1 cyclase assay as follows. Membrane fractions were prepared from confluent cultures of RIN m5f cells. The test compounds were serially diluted with an assay buffer, and then added to a 96-well assay plate containing RIN m5f cell membranes in an ATP/GTP mixture. Cyclase activities were determined by measuring the production of cAMP induced through GLP-1 receptor activation. Quantification of cAMP production was achieved through a competitive chemiluminescence assay with a biotinylated-cAMP probe using Perkin Elmer Fusion™-Alpha Microplate Analyzer (AlphaScreen™ technology). The compound EC50 values were obtained through fitting the concentration-response curves to a four-parameter logistic equation within GraphPad PRISM® software. Results from the receptor binding and cyclase assays are presented in Table 1.

GLP-1-peptidase inhibitor conjugate compounds 4844 and 4845 were assessed in a DPP-IV inhibition assay using purified DPP-IV enzyme and chromogenic substrates. Recombinant DPP-IV (Chemicon International, Inc., Temecula, Calif.; purity>95%, specific activity 5.66±0.49 mU) was dissolved in 100 µl buffer (20 mM Tris-HCl, pH 8.0, 5 mM $CaCl_2$, 1 mM $ZnCl_2$, 0.05% $NaN_3$, pH 8.0), the solution divided into 10 microcentrifuge tubes, and stored at −20° C. For the inhibition assay, 2 µl H-Gly-Pro-pNA (5 mM, dissolved in PBS buffer, pH 7.4) was incubated in 146 µl assay buffer (25 mM Tris-HCl, 140 mM NaCl, 10 mM KCl, pH 7.4) with 1 µl compound 4844 or 4845 at varying concentrations in a 96-well flat bottom microtiter plate at 37° C. The reactions were initiated by adding 1 µl DPP-IV enzyme (0.05 mU) into each well and the absorbance at 410 nm was measured with 20-sec intervals over a 30-min period using a SpectraMax plate reader (Molecular Devices, Corp., Sunnyvale, Calif.). The velocities of each reaction at different inhibitor concentrations were calculated and the reciprocal velocities were plotted against inhibitor concentrations in Dixon graphs. The $IC_{50}$ values of reaction velocities were calculated through fitting the plots with linear equation. The DPP-IV enzyme inhibitor Diprotin A (Ile-Pro-Ile, Calbiochem, EMD Biosciences, San Diego, Calif.) was used as a positive control for the reactions. The $IC_{50}$ value for Diprotin A was determined to be 5.1 µM, corresponding closely with the published value of 3.5 µM (Leiting et al. (2003) *Biochem. J.* 371:525). Results from the DPP-IV inhibitor assay are presented in Table 1.

A peptide stability assay was performed with the GLP-1-peptidase inhibitor conjugates in human kidney brush border membranes (hKBBM), a preparation rich in various peptidases. Solutions of peptides (compounds 4992, 4983, 4984, and control peptides) in 50% ACN (300 µM, 70 µl) were transferred into LoBind microcentrifuge tubes (Eppendorf North America, Westbury, N.Y.) each containing 0.78 µl hKBBM in 100 µl HEPES buffer (25 mM, pH 7.4). The tubes were incubated in VorTemp 56™ (Eurotech Labs, UK) at 37° C. vortexed at 500 RPM. At time points of 0, 1, 2, 3, 4, and 5 hours, 200 µl STOP solution (50% ACN, 1% formic acid) was added to a given tube, and the samples were allowed to incubate until the end of the experiment. The samples were collected after 5 hours, centrifuged, and 200 µl of the supernatants were transferred into mass spectrometry vials. The intensities of the mother ions in each vial were analyzed with API 150EX™ mass spectrometer (Applied Biosystems, Foster City, Calif.) and quantified using the ANALYST™ program. Results from the hKBBM stability assay are presented in Table 1.

Peptide-ACE peptidase inhibitor conjugate compounds were assessed in an ACE inhibition assay using purified ACE enzyme and chromogenic substrates. An ACE stock solution was prepared by dissolving 0.1 unit of enzyme (ACE from rabbit lung, Sigma Chemical Co., St. Louis, Mo.) in 0.640 mL of HEPES buffer (0.1 M, pH=8). A 2 mM stock solution of substrate (N-benzyloxycarbonyl-Phe-His-Leu-OH) dissolved in methanol. The ACE inhibitor compounds were dissolved in phosphate buffer (0.1 M, pH=8) at concentrations of 0.0, 1, 10, 20, 60 and 100 µM. For the inhibition assay, six 2 mL microcentrifuge tubes were prepared containing 1.45 mL of phosphate buffer pH=8, 0.05 mL of 10% NaCl and 0.015 mL of substrate solution. To each microcentrifuge tube was added 0.015 mL of one of the ACE inhibitor compound's stock solutions. The solutions were heated at 37° C. for about 5 minutes. The reaction was started by the addition of 5 µl of the ACE stock solution to each tube mixture (30 seconds in between). The reaction mixtures were incubated at 37° C. After 5 min, 10 min, 30 min and 60 min., aliquots of 100 µL were taken from each tube (each sample was taken in intervals of 30 seconds). Tubes containing the 100 µL sample were floated in a boiling water bath for 5 min. and then cooled. The reaction samples were then treated with 20 µL of 2M NaOH and 20 µL of 0.1% phthaldialdehyde solution. The tubes were shaken for 4 minutes and 10 µl of 6 M HCl were added. After 60-90 min., 120 µL of this solution were transferred to a 96 well flat bottom-nonbinding-surface plate (top read), and the fluorescence read at $\lambda_{ex}$=365 nm, $\lambda_{em}$=500 using a FlexStation® spectrofluorimeter (Molecular Devices Corp., Sunnyvale, Calif.). Initial rates were determined from linear portions of product release curves. Starting substrate concentration in all assays was 20 µM. Apparent binding constants ($K_d^{app}$ or $K_i^{app}$) of inhibitors to ACE were determined by fitting inhibition curves (initial rate vs. inhibitor concentration) to equation:

$$v = v_0 \frac{K_i^{app}}{[I] + K_i^{app}},$$

where $v_0$ is reaction rate in the absence of inhibitor and [I]—inhibitor concentration. Fits were done by least-squares method using KaleidaGraph 3.6 (Synergy Software, Reading Pa.). Results from the ACE inhibition assay are presented in Table 2.

TABLE 1

GLP-1/peptidase inhibitor conjugate activity assays.

| Compound | GLP RBA IC$_{50}$ (nM) | GLP Cyclase EC$_{50}$ (nM) | DPP-IV IC$_{50}$ (nM) | Stability in hKBBM |
|---|---|---|---|---|
| GLP-1 | 0.15 | 0.28 | >3300 | – |
| 4844 | 0.087 | 0.13 | 91 | ND |
| 4845 | 0.10 | 0.40 | 76 | ND |
| 4992 | 13.0 | 15 | ND | + |
| 4983 | 13.0 | 239 | ND | +++ |
| 4984 | 8.1 | 135 | ND | +++ |

(ND = not done)

TABLE 2

GLP-1 analog/ACE inhibitor conjugate activity assays.

| Compound | GLP RBA IC$_{50}$ (nM) | GLP Cyclase EC$_{50}$ (nM) | ACE inhibition IC$_{50}$ (nM) |
|---|---|---|---|
| GLP-1 | 0.15 | 0.28 | ND |
| 3633/21 | ND | ND | 1200 |
| 3633/21 ester | 2 | 0.49 | >10000 |
| 3633/24 | ND | ND | 250 |
| 3633/24 ester | 0.49 | 1.2 | >100,000 |
| 3633/42/1 | ND | ND | 1500 |
| 3633/42/2 | ND | ND | 1500 |
| 3633/42/3 | ND | ND | 180 |
| 3633/38 | ND | ND | >10000 |

(ND = not done)

As described in Example 2, compounds 4844 and 4845 are GLP-1/DPP-IV inhibitor conjugates where the inhibitor motif is at the C-terminus of the GLP-1(7-37). Compounds 4983 and 4984 are GLP-1/vasopeptidase inhibitor conjugates where the inhibitor motif is at the N-terminus of the GLP-1 (7-37). Compound 4992 is GLP-1(7-37) with a linker at the N-terminus and the linker is the same as that in compounds 4983 and 4984. Compounds 3633/21, 3633/24, 3633/42/1, 3633/42/2, 3633/42/3, and 3633/38 are conjugate compounds where an ACE inhibitor motif is at the C-terminus of GLP-1 (7-37) or [Leu$^{14}$]-exendin(1-28) as described in Example 1.

As shown in Tables 1 and 2, conjugation of the peptidase inhibitor motif to the C-terminus of GLP-1 or exendin-1 analog preserves the ability of the conjugate to interact with the GLP-1 receptor, as demonstrated in both the receptor binding assay and the cyclase assay. Compare, for example, the results for compounds 4844 and 4845 with the results with GLP-1. The conjugate compounds tested also retained DPP-IV or ACE inhibitor activity.

Conjugation of the peptidase inhibitor motif to the N-terminus of GLP-1 reduces the GLP-1 activities by approximately 55-80-fold in receptor binding assay and approximately 500-800-fold in cyclase assay. Compare, for example, the results for compounds 4983 and 4984 with the results with GLP-1. Compound 4992 carries a linker at the same position as compounds 4983 and 4984 and undergoes similar reductions in activities. Accordingly, the decreases in activities seen in compounds 4983 and 4984 essentially can be attributed to the positional effect of the linker and inhibitor motif.

Figure 5A:
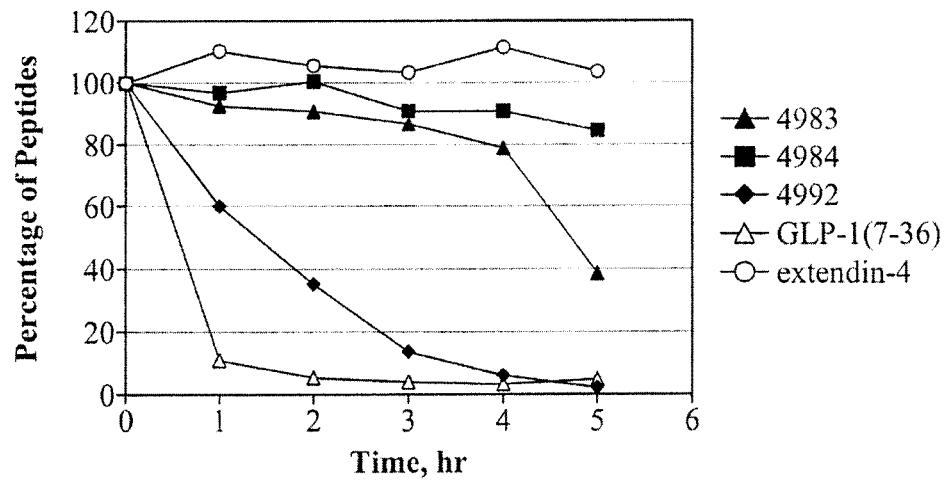
FIG. 5(a-b) are graphs depicting peptide stability in hKBBM assays in the absence (5a) and presence (5b) valinepyrrolidide.
Figure 5B:
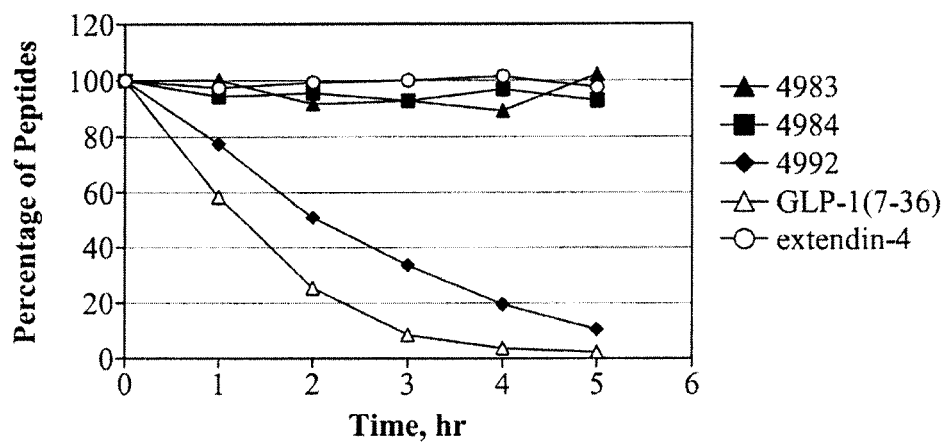
Figure 6A:
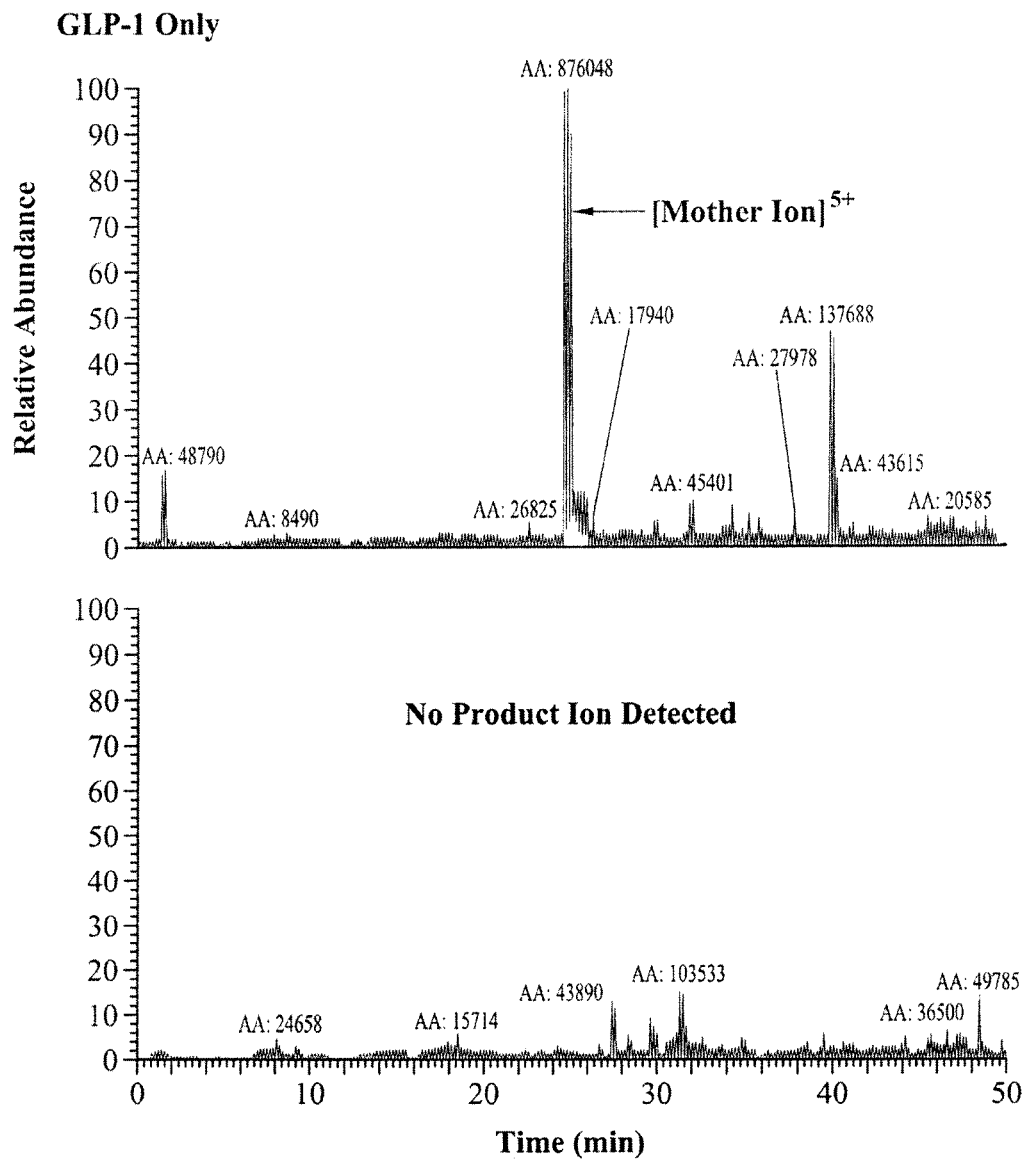
FIG. 6 are graphs depicting mass spectrometer results of DPP-IV resistance assays of GLP-1 (3a), GLP-1+DPP-IV (3b), GLP-1 conjugate compound 4844+DPP-IV (3c), and GLP-1 conjugate compound 4845+DPP-IV (3d).
Figure 6B:
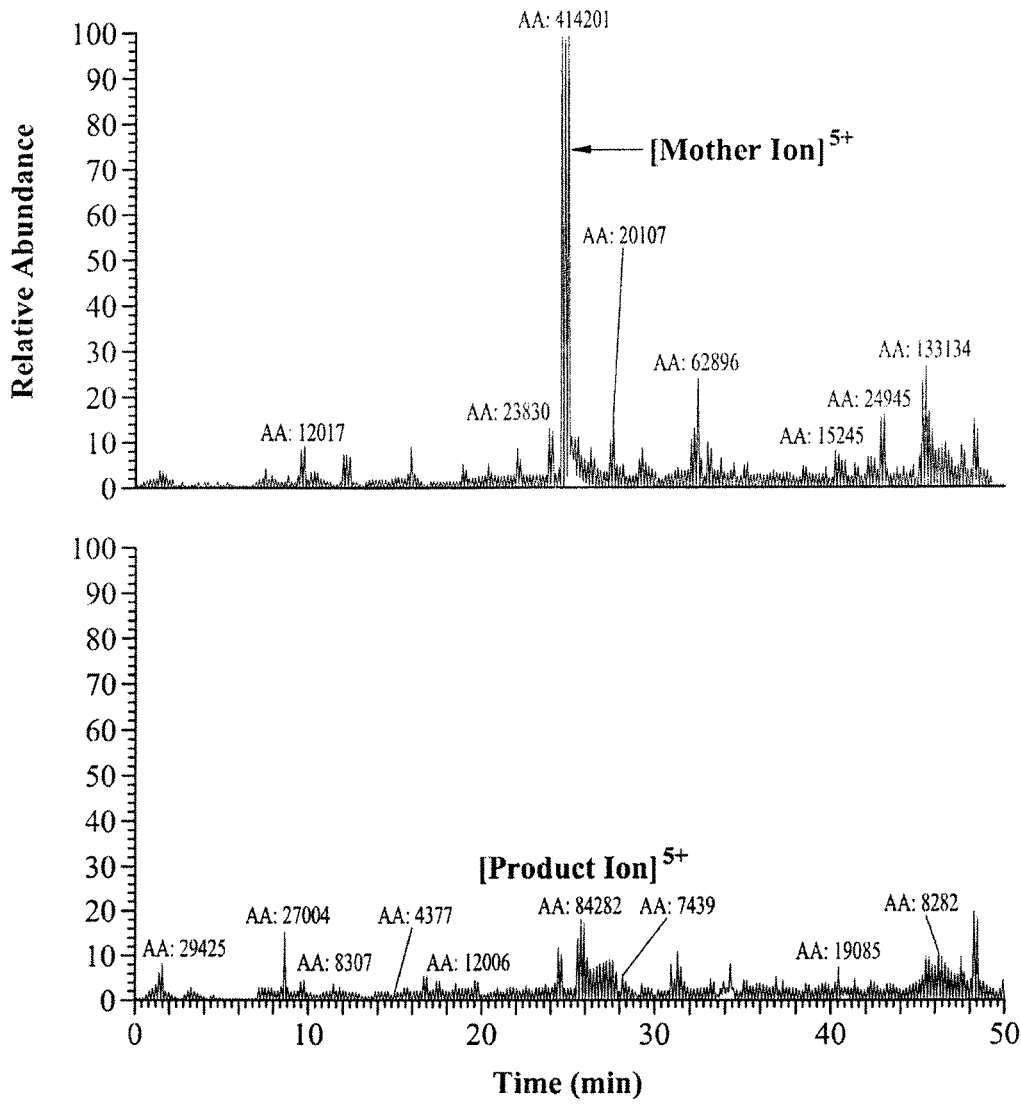
Figure 6C:
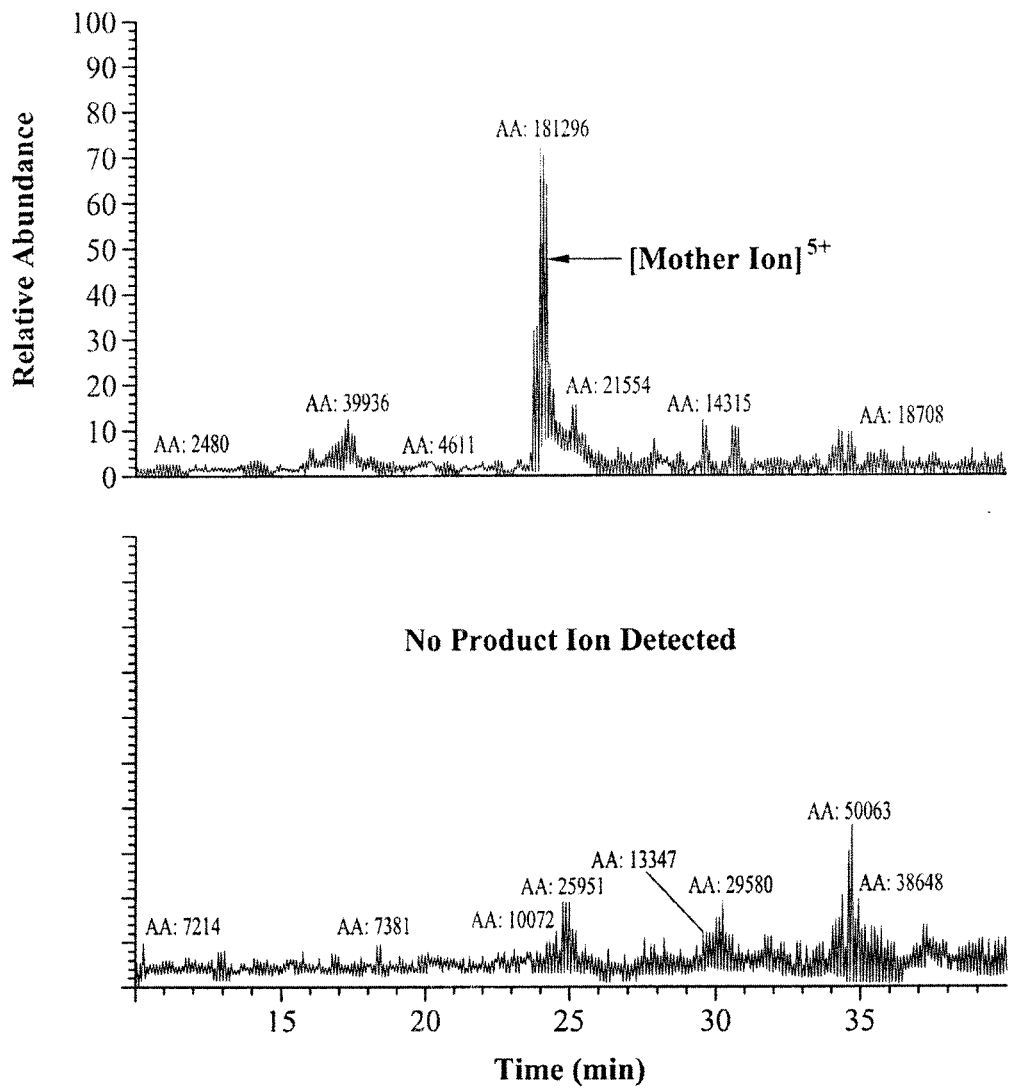
Figure 6D:
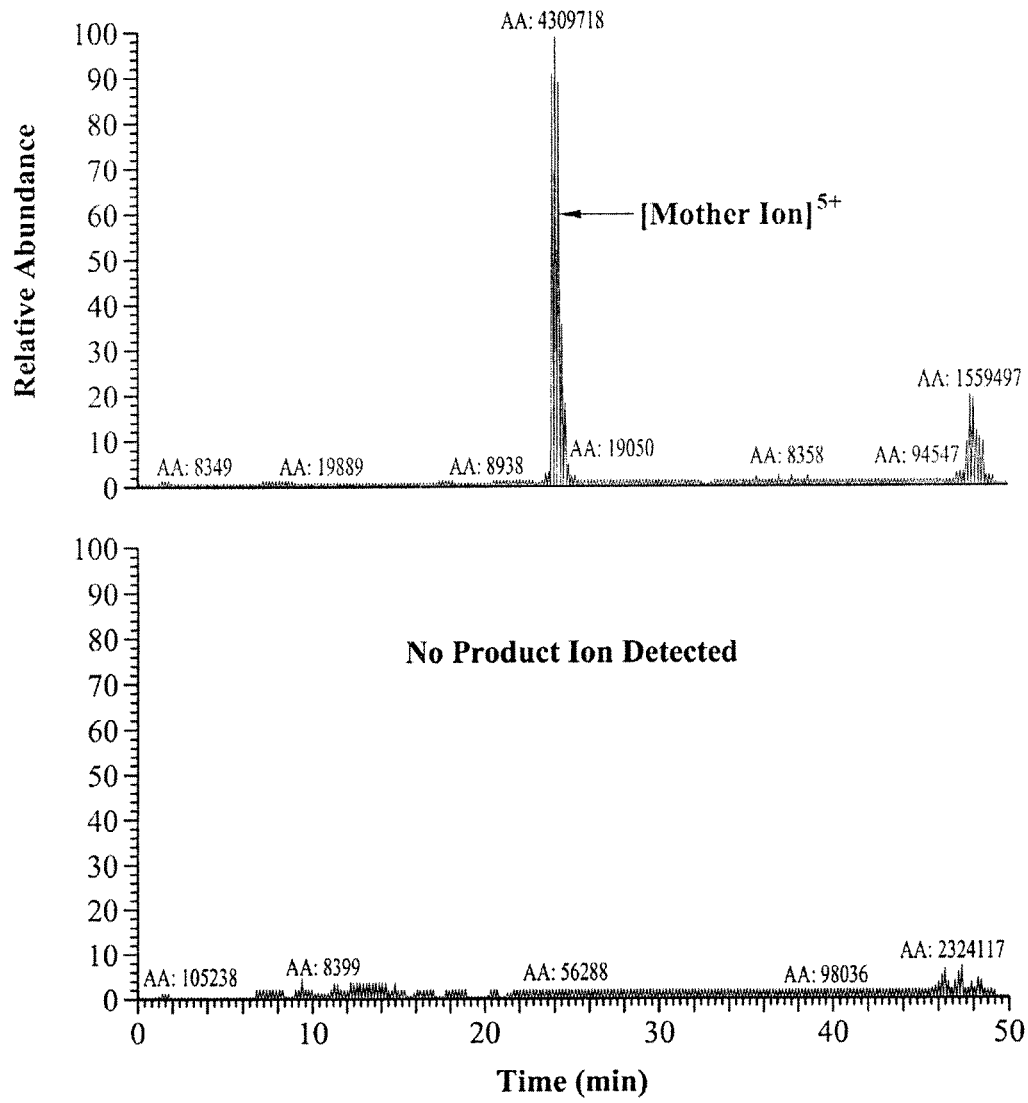

FIG. 5 depicts analysis of the peptide stabilities in hKBBM analyzed by an LC-MS system in which the parent ions were followed over the course of the incubation and quantified through ion intensities. As shown in FIG. 5a, GLP-1(7-36) peptide (HAEGTFTSDVSSYLEGQAAKEFIAWLVKGR-NH$_2$) (SEQ ID NO: 348) degraded rapidly in 1 hour while the N-terminus acylated GLP-1 analog 4992 degraded at a slower rate. The incretin mimetic exendin-4 (HGEGTFTSDL-SKQMEEEAVRLFIEWLKNGGPSSGAPPPS-NH$_2$) (SEQ ID NO: 349) showed essentially complete stability over the course of the incubation. The GLP-1 conjugate compounds 4983 and 4984 were remarkably stable compared to GLP-1 (7-36) and the N-terminus acylated GLP-1, with greater than 80% of the intact conjugate compound being present after 4 hours. The hKBBM assay was also performed in the presence of valinepyrrolidide, a DPP-IV inhibitor. As shown in FIG. 5b, in the presence of valinepyrrolidide, the stabilities of all peptides tested improved to some degree. Since the stabilities did not improve to the full extent, the hKBBM assay appears to involve other peptidases.

Figure 2:
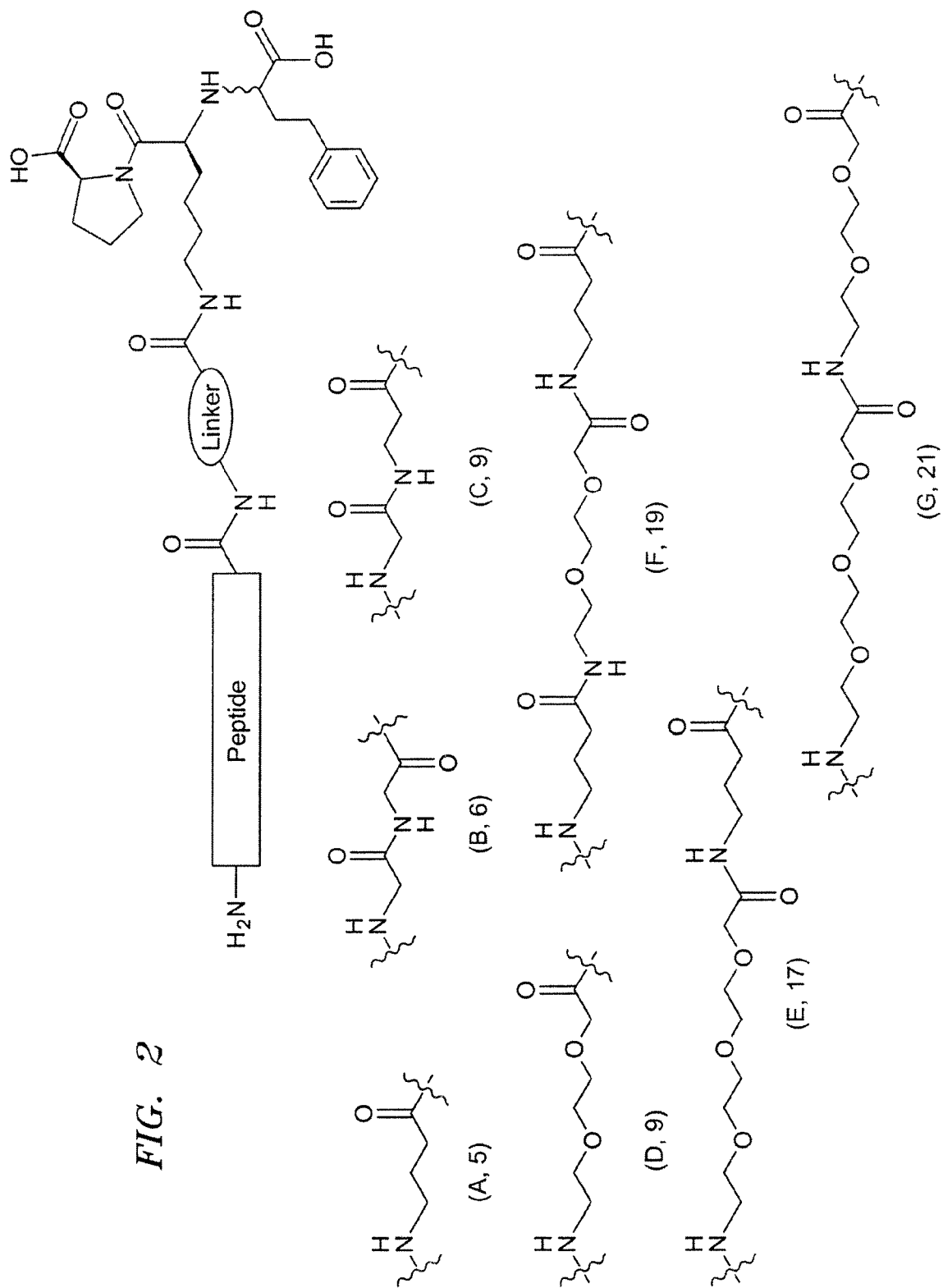
FIG. 2 depicts exemplary designs of a peptide-peptidase inhibitor conjugate compound with the ACE inhibitor lisinopril joined at the C-terminus of the peptide through a variety of depicted linkers.

Additional conjugates with the ACE inhibitor lisinopril were made as assessed for biological activity. These conjugate compounds have lisinopril joined at the C-terminus of the peptide through a variety of linkers as depicted in FIG. 2. The peptide components include exendin-4 and GLP-1 analogs as indicated in Table 3. The compounds were tested in ACE inhibition assays as described herein. Results from these assays are presented in Table 3.

The conjugates described in Table 3 were tested for GLP-1 cyclase activity using a whole cell assay which measure increases in cAMP in a cell line via the peptide-induced activation of the endogenously expressed GLP-1 receptor. Cells from the thyroid c-cell carcinoma line 6-23 were grown to confluence and harvested by treatment with Versene (0.5M EDTA). Upon harvest, cells were washed free of EDTA and resuspended in stimulation buffer (1×HBSS, 0.1% BSA, 5 mM HEPES, 500 uM IBMX, pH 7.4) at a concentration of 2.5×10$^{-6}$ cell/ml. Accumulation of cAMP was measured following 30' conjugate or control agent treatment using an HTRF® cell-based cAMP assay kit (Cisbio-US, Inc., Bedford, Mass.) in 384-well format. The compounds were tested at final concentrations from 1 µM to 10 pM. The cell-conjugate mixture was incubated for 30' at room temperature, at which time the reaction was terminated by the addition of kit-provided α-cAMP Cryptate solution. Plates were then sealed and stored at room temperature overnight to allow components to come to full equilibrium. cAMP content was then measured by time resolved fluorescence. Efficacy of the tested agents was determined relative to cell treatment with 10 µM forskolin (a constitutive activator of adenylate cyclase), and potency ($EC_{50}$) of test agents was determined by the analysis of a concentration-response curve using non-linear regression analysis fitted to a 4-parameter model. Results from the GLP-1 cyclase assays are presented in Table 3. Unlike the other results in Table 3, the GLP-1 cyclase assay result for compound 5711 was from a cell membrane assay as described above.

TABLE 3

| Compound | Peptide | Linker type (see FIG. 2) | GLP Cyclase $EC_{50}$ (nM) | ACE inhibition $IC_{50}$ (nM) |
|---|---|---|---|---|
| 5545 | [Leu$^{14}$]-exendin(1-28) | B6 | 0.15 | 1500 |
| 5546 | [Leu$^{14}$]-exendin(1-28) | A5 | 0.06 | 1500 |
| 5609 | [Leu$^{14}$]-exendin(1-28) | E17 | 0.65 | 1000 |
| 5605 | [Leu$^{14}$]-exendin(1-28) | F19 | 1.24 | 300 |
| 5606 | [Leu$^{14}$]-exendin(1-28) | G21 | 0.23 | 700 |
| 4828 | [Leu$^{14}$]-exendin(1-28); not conjugated | none | 0.025 | 25 |
| 5547 | GLP-1(7-37) | C9 | 0.40 | 180 |
| 5608 | GLP-1(7-37) | D9 | 2.20 | 190 |
| 5607 | GLP-1(7-37) | G21 | 0.55 | 100 |
| 5610 | [Gly$^{8}$]-GLP-1(7-37) | C9 | 2.0 | 50 |
| 5711 | [Gly$^{8}$]-GLP-1(7-37) | G21 | 11.0 (membr. assay) | 460 |
| 5712 | [Aib$^{8}$]-GLP-1(7-37) | C9 | 0.35 | 100 |
| 3521 | GLP-1(7-37); not conjugated | none | 0.02 | ND |
| 5713 | fGLP-1 | G21 | 2.89 | 700 |
| 5714 | fGLP-1 | C9 | 2.93 | 350 |
| 5715 | [Leu$^{14}$, Gln$^{28}$]-exendin-4(1-31)-fGLP-1(33-37) | G21 | 0.06 | 260 |
| 5716 | [Leu$^{14}$, Gln$^{28}$]-exendin-4(1-31)-fGLP-1(33-37) | C9 | 0.14 | 140 |
| 4202 | fGLP-1 | none | 0.03 | ND |
| 5131 | [Leu$^{14}$, Gln$^{28}$]-exendin-4(1-31)-fGLP-1(33-37) | none | 0.02 | ND |
| Lisinopril (commercial; synthesized) | — | — | ND | 1.3; 2.8 |

(ND = not done)

Additional conjugates with the ACE inhibitor lisinopril were made as assessed for biological activity. These conjugate compounds have lisinopril joined at the C-terminus of the peptide through a variety of linkers as depicted in FIG. 2. The peptide components include exendin-4 and GLP-1 analogs as indicated in Table 3. The compounds were tested in GLP-1 cyclase assays and ACE inhibition assays as described herein. Results from these assays are presented in Table 3.

Example 4

Characterization of GLP-1-Peptidase Inhibitor Conjugate Stability

DPP-IV resistance of the GLP-1-peptidase inhibitor conjugate compounds was also assessed using mass spectrometry. Mass spectrometry provides an excellent tool for analyzing the degradation products of peptides in vitro. For the stability assay, 2 µl of GLP-1, compound 4844, or compound 4845 (1 mM, dissolved in PBS buffer, pH 7.4, 2 nmol) was incubated in 146 µl assay buffer (25 mM Tris-HCl, 140 mM NaCl, 10 mM KCl, pH 7.4) with 2 µl recombinant DPP-IV (0.05 mU/µl) at room temperature for 15 hours in microcentrifuge tubes. The peptides were then desalted and concentrated on a C18 peptide micro trap (Michrom Bioresources, Inc., Auburn, Calif.) prior to introduction to a LTQ FT™ mass spectrometer (Thermo-Electron Corp., Waltham, Mass.) via an autosampler (Michrom Bioresources, Inc.). Peptides were eluted from a C5 packed 75 µm fused silica pico-frit column (New Objective, Inc., Woburn, Mass.) using a 5-60% acetonitrile/water gradient over 50 minutes at a flow rate of 500 nl/min. Extracted ion mass windows for the calculated m/z values of the most dominant charge states were used to search for both the parent compound and the theoretical hydrolyzed products within a given chromatogram. Exact mass was confirmed for each charge state by FT. The percentage of hydrolysis catalyzed by DPP-IV was estimated by dividing the area of product ions by the area of the total (parent+product) ions.

As demonstrated in FIG. 6, the DPP-IV mediated cleavage of GLP-1 (7-36) to produce GLP-1 (9-36) can be monitored with ESI-MS with high sensitivity, and both the presence of mother ions and product ions can be quantified using the ion-extraction protocol. FIG. 6a depicts results of 50 fmol of GLP-1 in the assay buffer and FIG. 6b depicts results of 50 fmol of GLP-1 treated with 0.1 mU DPP-IV enzyme in the assay buffer for 12 hours. FIG. 6c depicts results of 200 fmol of conjugate compound 4844 treated with 0.1 mU DPP-IV enzyme in the assay buffer for 12 hours and FIG. 6d depicts results of 200 fmol of conjugate compound 4845 treated with 0.1 mU DPP-IV enzyme in the assay buffer for 12 hours. The N-terminal two-residue cleaved product was only observed in GLP-1 (FIG. 6b) and not in compound 4844, compound 4845, or GLP-1 alone (FIG. 6c, FIG. 6d, FIG. 6a, respectively). The estimated cleavage product conversion is based on the ratio of the ion extract area (indicated on top of the peaks) for [product ion]$^{5+}$ over that for total ions ([Mother Ion]$^{5+}$+[product ion]$^{5+}$). The m/z ratios used to search for the expected ions are listed on the right side of the plots.

For GLP-1, it was found that the DPP-IV catalyzed cleavage afforded the GLP-1 (9-36) product in 17% yield. For the compounds 4844 and 4845 (DPP-IV inhibitory motif conjugated to the C-terminus of GLP-1), the expected product ions were not observed, indicating that these two compounds are DPP-IV resistant under the test conditions. Accordingly, the conjugate compounds have improved peptide stability against peptidase-mediated cleavage.

Example 5

Characterization of GLP-1-Peptidase Inhibitor Conjugate Activity

Glucose lowering effects of GLP-1 analog-peptidase inhibitor conjugates were determined in oral glucose tolerance tests (OGTT). Test compounds were injected IP (t=0 min) immediately following baseline measurements of 2 hour fasted NIH/Swiss mice. Blood samples were taken at 60, 120, and 180 minutes after injection. In some assays, samples were also taken at 240 minutes after the injection. Blood glucose was measured with a One-Touch® Ultra® glucose meter (LifeScan, Inc., Milipitas, Calif.). Analysis of variance (ANOVA) was performed and, in FIGS. 4 and 5, the data are represented as mean±SEM and significant differences versus the vehicle control are indicated by *(P-value<0.05).

Figure 7:
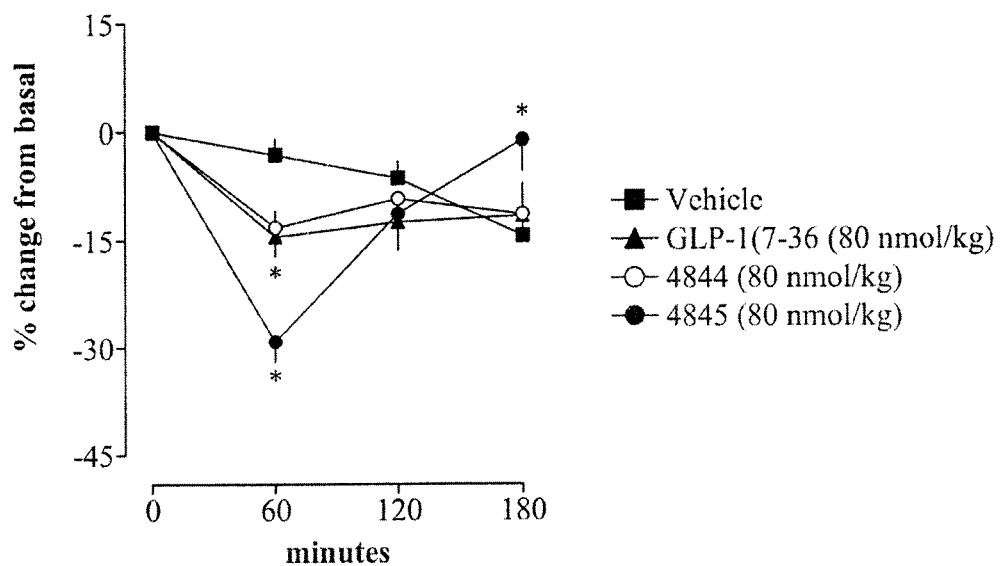
FIG. 7 is a graph depicting changes in blood glucose levels after administration of control compounds and conjugate compounds 4844 and 4845.
Figure 8:
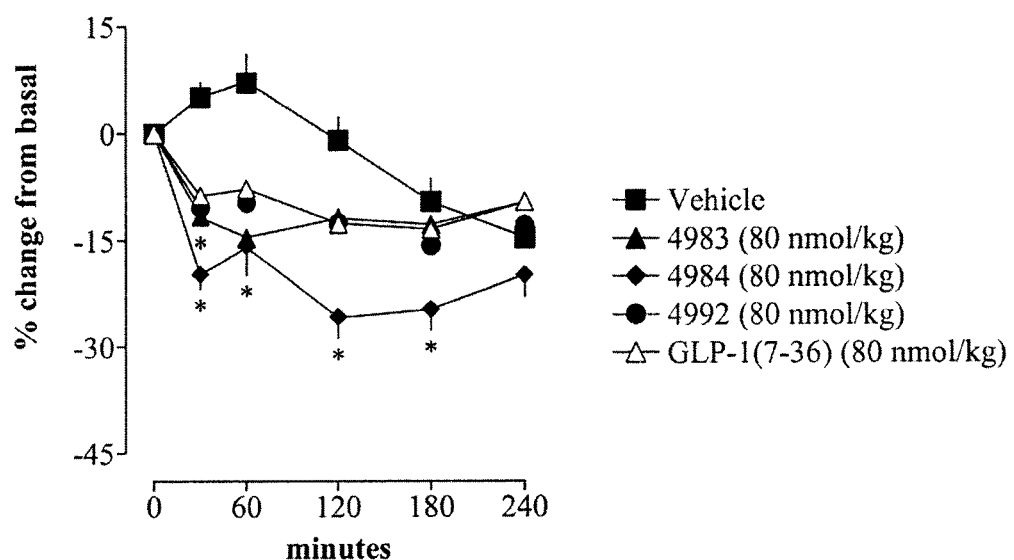
FIG. 8 is a graph depicting changes in blood glucose levels after administration of control compounds and conjugate compounds 4983 and 4984.

Results from glucose lowering assays with conjugate compounds 4844 and 4845 are presented in FIG. 7. Results from glucose lowering assays with conjugate compounds 4983 and 4984 are presented in FIG. 8. These data demonstrate that these conjugate compounds not only retain the glucose-lowering activity of GLP-1 but generally offer enhance glucose-lowering action compared to GLP-1. Conjugate compound 4984, for example, demonstrated a prolonged effect 4 hours after dosing. Although compounds 4983 and 4984 were significantly less active in vitro in the GLP-1 cylclase assay (see Table 1), the prolonged duration of action by these conjugates support the importance of peptide half-life for activity in vivo.

Example 6

GIP-Peptidase Inhibitor Conjugates

Peptide-peptidase inhibitor conjugate molecules with a GIP analog as the peptide component were prepared using peptidase inhibitor and linker components described herein. In some conjugates, an N-(substituted glycyl)-2-cyanopyrrolidine was used as a DPP-IV inhibitor.

The GIP receptor binding activity (RBA) of the GIP analog-peptidase inhibitor conjugates was assessed using a binding displacement assay in which the receptor source was an HEK293 cell line stably expressing the human GIP receptor (HEK-GIPR). Membrane fractions were prepared from confluent cell cultures of HEK-GIPR, snap frozen, and stored at −80° C. until use. At the time of assay, membranes were thawed on ice and diluted to 0.02 mg/mL in ice cold binding buffer (20 mM HEPES pH 7.4, 0.5% BSA, 5 mM MgCl$_2$, 1 mM CaCl$_2$, 170 μM Phosphoramidon, 1.5 mM Bestatin-HCl, and 70 mM Bacitracin). Heterologous binding assays were initiated by combining membranes with 30 pM $^{125}$I-GIP and 10 nM unlabeled GIP-peptidase inhibitor conjugates diluted in assay buffer. Reactions were allowed to proceed to equilibrium for 90 minutes at room temperature with constant shaking. The reaction mixtures were then filtered through 96-well glass fiber filter plates separating bound and unbound fractions of radioligand. Displacement of radioligand for each conjugate was calculated relative to maximal displacement by human GIP(100%) and to non-specific binding (0%) in the absence of any competing ligand. Results for the GIP RBA (% inhibition at 10 nM) are shown in Table 4.

Glucose lowering effects of GIP analog-peptidase inhibitor conjugates were determined in oral glucose tolerance tests (OGTT). The tests were performed as described in Example 5. Results from the glucose lowering assays (% maximal decrease) using the conjugate at 30 nM/kg are shown in Table 4.

TABLE 4

| GIP analog-peptidase inhibitor conjugate | GIP RBA % inhibition at 10 nM | OGTT (30 nM/kg) % maximal decrease |
|---|---|---|
| Lys$^{30}$ N-ε-(Ado-(γ-L-Glu-2-(S)-cyano pyrrolidyl)) GIP(1-30)-exendin-4(31-39) | 90% | −11% |
| Lys$^{30}$ N-ε-(Ado-(γ-L-Glu-2-(S)-cyano pyrrolidyl)) GIP(1-30) | 33% | −10% |
| N-(γ-L-Glu-(2-(S)-cyano pyrrolidyl)-Ado-Ado) GIP(1-30)-exendin-4(31-39) | 25% | 3% |
| N-(γ-L-Glu-2-(S)-cyano pyrrolidyl)-Ado-Ado) GIP(1-30) | 32% | −8% |
| GIP(1-30)-exendin-4(31-39)-Ado-Lys-N-ε-(2-(S)-cyano pyrrolidyl) | 98% | −18% |
| GIP(1-30)-Ado-Lys-N-ε-(2-(S)-cyano pyrrolidyl) | 99% | −18% |
| GIP(1-30)-exendin-4(31-39)-Ado-Ado-Lys-N-ε-(2-(S)-cyano pyrrolidyl) | 100% | −22% |
| GIP(1-30)-Ado-Ado-Lys-N-ε-(2-(S)-cyano pyrrolidyl) | 97% | −17% |
| [Leu$^{14}$] GIP(1-30)-exendin-4(31-39)-Ado-Lys-N-ε-(2-(S)-cyano pyrrolidyl) | 99% | −24% |
| [Leu$^{14}$] GIP(1-30)-Ado-Lys-N-ε-(2-(S)-cyano pyrrolidyl) | 100% | −9% |
| [D-Ala$^2$] GIP(1-30)-exendin-4(31-39)-Ado-Lys-N-ε-(2-(S)-cyano pyrrolidyl) | 93% | −20% |
| Lys$^{16}$ (N-ε-(Aun-Aun-(γ-L-Glu-2-(S)-cyano pyrrolidyl))) GIP(1-30)-exendin(31-39) | ND | −3% |
| [D-Ala$^2$, Leu$^{14}$] GIP(1-30)-βAla-βAla-ε-NH-Lys(α-NH-Pyroglutamoyl)-Trp-Ala-Pro | 66% | −12 |
| [D-Ala$^2$] GIP(1-30)-Ado-Ado-Aun-βAla-βAla-ε-NH-Lys(α-NH-Pyroglutamoyl)-Trp-Ala-Pro | 70% | −6% |
| [D-Ala$^2$, Leu$^{14}$] GIP(1-30)-exendin-4(31-39)-Ado-Ado-Aun-βAla-βAla-ε-NH-Lys(α-NH-Pyroglutamoyl)-Trp-Ala-Pro | 86% | −21% |

(ND = not done)

DPP-IV inhibition assays with GIP analog-DPPIV inhibitor conjugates and control compounds were were performed as described in Example 3. Results from the DPP-IV inhibition assays (IC$_{50}$) are shown in Table 5. The IC$_{50}$ (nM) values in Table 5 are expressed as the mean SEM of at least three independent determinations.

TABLE 5

| GIP-1 analog-peptidase inhibitor conjugate or control compound | DPP-IV IC50 (nM) |
|---|---|
| Lys$^{30}$ N-ε-(Ado-(γ-L-Glu-2-(S)-cyano pyrrolidyl)) GIP(1-30)-exendin-4(31-39) | 164 ± 14 |
| Lys$^{30}$ N-ε-(Ado-(γ-L-Glu-2-(S)-cyano pyrrolidyl)) GIP(1-30) | 49 ± 6 |
| N-(γ-L-Glu-(2-(S)-cyano pyrrolidyl)-Ado-Ado) GIP(1-30)-exendin-4(31-39) | 110 ± 2 |
| N-(γ-L-Glu-2-(S)-cyano pyrrolidyl)-Ado-Ado) GIP(1-30) | 64 ± 8 |
| GIP(1-30)-exendin-4(31-39)-Ado-Lys-N-ε-(2-(S)-cyano pyrrolidyl) | 103 ± 2 |
| GIP(1-30)-Ado-Lys-N-ε-(2-(S)-cyano pyrrolidyl) | 98 ± 5 |
| GIP(1-30)-exendin-4(31-39)-Ado-Ado-Lys-N-ε-(2-(S)-cyano pyrrolidyl) | 133 ± 9 |
| GIP(1-30)-Ado-Ado-Lys-N-ε-(2-(S)-cyano pyrrolidyl) | 114 ± 17 |
| [Leu$^{14}$] GIP(1-30)-exendin-4(31-39)-Ado-Lys-N-ε-(2-(S)-cyano pyrrolidyl) | 82 ± 2 |
| [Leu$^{14}$] GIP(1-30)-Ado-Lys-N-ε-(2-(S)-cyano pyrrolidyl) | 109 ± 1 |

TABLE 5-continued

| GIP-1 analog-peptidase inhibitor conjugate or control compound | DPP-IV IC50 (nM) |
| --- | --- |
| [D-Ala²] GIP(1-30)-exendin-4(31-39)-Ado-Lys-N-ε-(2-(S)-cyano pyrrolidyl) VILDAGLIPTIN (LAF237) | 85 ± 4<br>3.4 ± 0.2 |
| Lys(ε-NH-acetoyl)-(2)-S-cyanopyrrolidinamide | 1400 ± 140 |
| Glu(γ-methylamido)-(2)-S-cyanopyrrolidinamide | 4840 ± 280 |

A peptide stability assay was performed with GIP analog-DPPIV inhibitor conjugates in human kidney membrane proteins, a preparation rich in various peptidases. A solution of Kidney Membrane Protein (KMP) for use in the assay was prepared by diluting a KMP preparation (approximately 7.7 ug protein/ul solution in 5 mM Tris-HCl) 1:125 in phosphate-buffered saline (PBS). The diluted KMP solution (630 ul) was dispensed in a deep well plate and a conjugate compound or control peptide (70 ul of 200 ug/ml) was mixed with the KMP solution. The deep well plate was incubated in a VorTemp 56™ incubator/shaker (Labnet International, Inc., Woodbridge, N.J.) at 37° C. while mixing at 500 PRM over a period of 5 hours. At time points of 0, 1, 2, 3, 4, 4, and 5 hours, aliquots of 25 ul were removed from each well and mixed with 100 ul of 5% phosphoric acid to a final conjugate or peptide concentration of 4 ug/ml. All samples were analyzed in triplicates over the time course. The plates were covered with plate mats and analyzed by on-line solid phase extraction LC/MS methods of the API 4000 Q TRAP or the API 3000 LC/MS/MS system.

Figure 9:
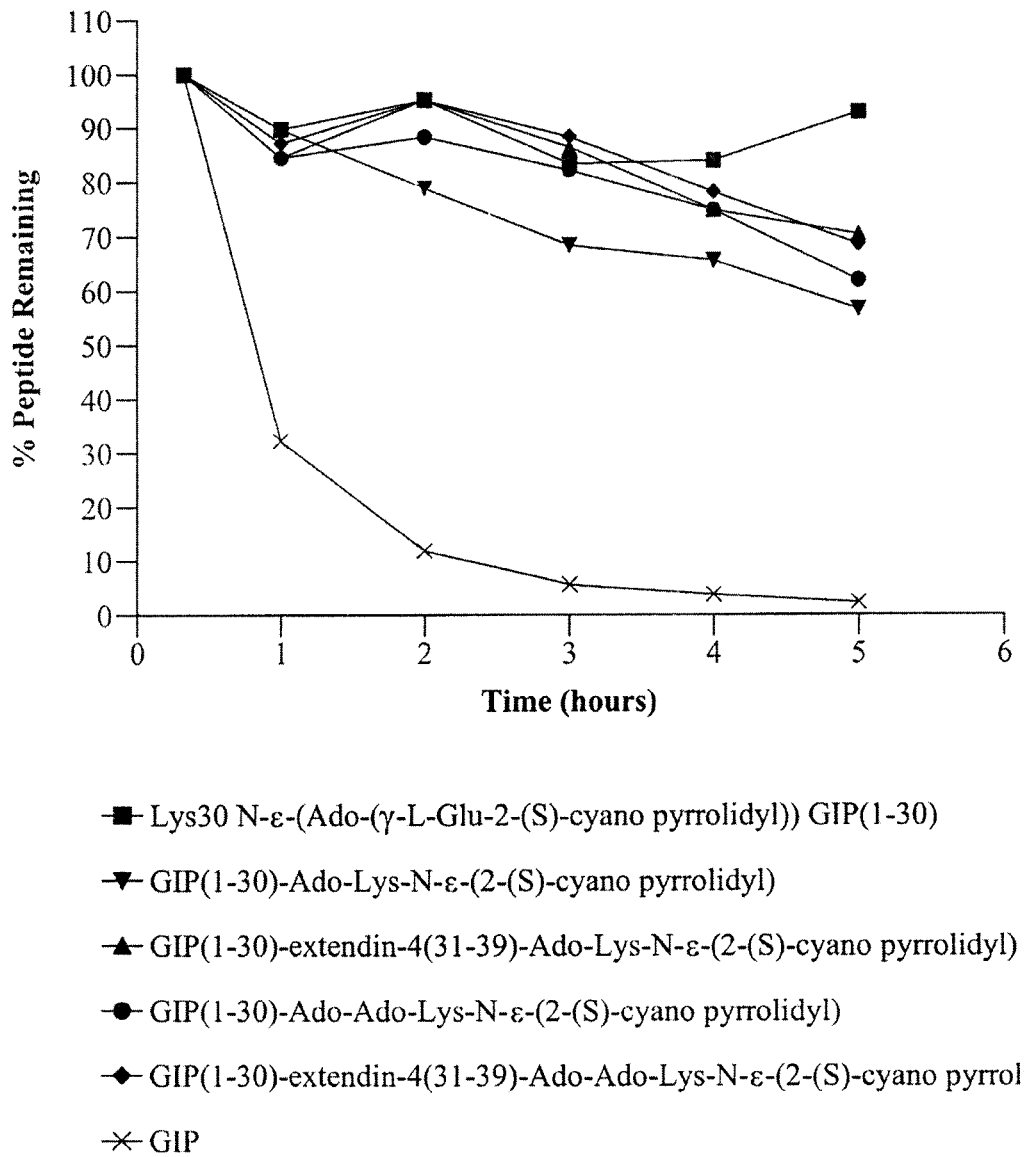
FIG. 9 is a graph depicting peptide stability of conjugate compounds in a KMP assay.

The LC/MS results were quantified with ANALYST™ software by generating quantitation tables where a select compound ion is integrated and listed as peak area in triplicates and at 6 time points. Positive control and negative control compounds were included in the analysis and the final results are presented as % area under the curve and normalized to 100% positive control. Results from this assay for several of the conjugate compounds are shown in FIG. 9 and plotted as % parent peptide remaining based on peak area ratios versus time in KMP.

As shown in Table 4, conjugation of the peptidase inhibitor motif to the N-terminus or C-terminus of a GIP analog preserves the ability of the conjugate to interact with the GIP receptor. Three of the four conjugates shown in Table 4 with the peptidase inhibitor motif conjugated to the N-terminus of GIP had a reduced GIP receptor biding capacity compared to the conjugates with the peptidase inhibitor motif conjugated to the C-terminus of GIP. The GIP analog-peptidase inhibitor conjugate compounds have glucosed lowering activity (Table 4). The GIP analog-DPPIV inhibitor conjugate compounds retained DPP-IV inhibitor activity (Table 5). FIG. 9 depicts analysis of the peptide stabilities in kidney membrane extract analyzed by an LC-MS system in which parent ions were followed over the course of the incubation and quantified through ion intensities. As shown in FIG. 9, the GIP analog-peptidase inhibitor conjugates were remarkably stable compared to GIP in the kidney membrane assay.

Example 7

Characterization of Carboxypeptidase Inhibitor Activity

Cleavage of the C-terminal tyrosylamide from PYY(3-36) forming PYY(3-35) has been demonstrated in rat, mouse and human plasma. This plasma carboxypeptidase appears to be a serine protease since its activity was inhibited by 4-(2-aminoethyl)-benzenesulfonylfluoride (AEBSF) but not by the metalloprotease inhibitors EDTA or phosphoramidon (each protease inhibitor at a final concentration of 1 mM). Carboxypeptidase activity assays were performed in the presence of various agents to test for carboxypeptidase inhibitor activity of the agents.

Carboxypeptidase activity assays were performed by preparing 10 µg/ml of amidated PYY(3-36) as substrate in human plasma in a sufficient volume to remove 100 µL it samples every 10 minutes for sixty minutes, starting at the zero time point. Following the addition of substrate PYY(3-36) to the human plasma, the sample is mixed gently and a 100 µl sample of the mixture was transferred to a microcentrifuge tube to represent the zero time point. The remainder of the sample was placed in an incubator at 37° C., mixing at 600 RPM for sixty minutes. At 10 minute intervals, a 100 µL sample of the mixture was removed and transferred to a separate microcentrifuge tubes. Following the transfer of the 100 µL sample at the zero time point and each 10 minute interval, each collected sample was extracted by slow addition of 100 µl cold 0.2% formic acid:acetonitrile, while mixing. After addition of the acetonitrile solution, the sample was vortex mixed at high speed for 15 seconds. The extracted samples were stored at −20° C. for at least 20 minutes and then centrifuged at 11,000×g for 10 minutes at 5° C. The supernatant of each sample was transferred to a new microcentrifuge tube, centrifuged again, and finally transferred for LC/MS analysis. The MS analysis was a Q1 single ion monitoring method that detects the most intense ion of the parent molecule and the peptide fragment of interest. The carboxypeptidase activity was measured by the appearance of PYY(3-35).

Figure 10:
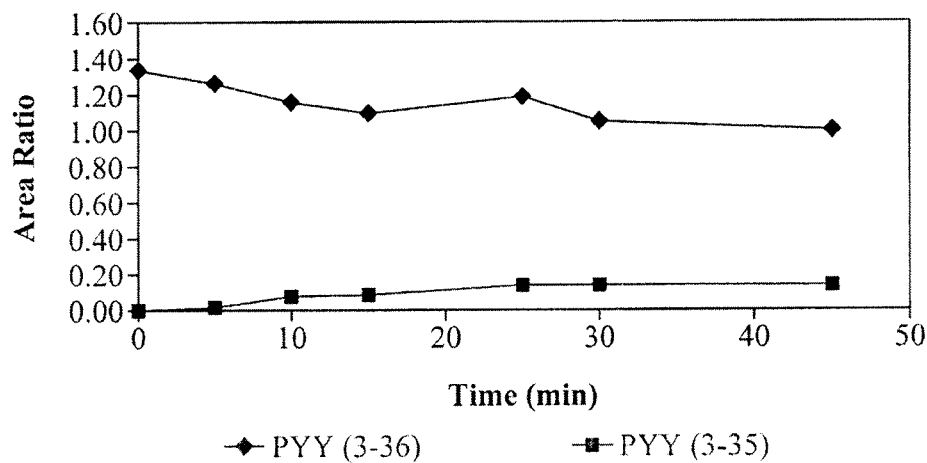
FIG. 10 is a graph depicting changes in the amount of PYY (3-36) and its metabolite PYY (3-35) over time when PYY (3-36) is incubated in human plasma.

As shown in FIG. 10, incubation of PYY(3-36) in human plasma results in a disappearance of PYY(3-36) and an accompanying appearance of PYY(3-35), the metabolite of PYY(3-36).

Figure 11:
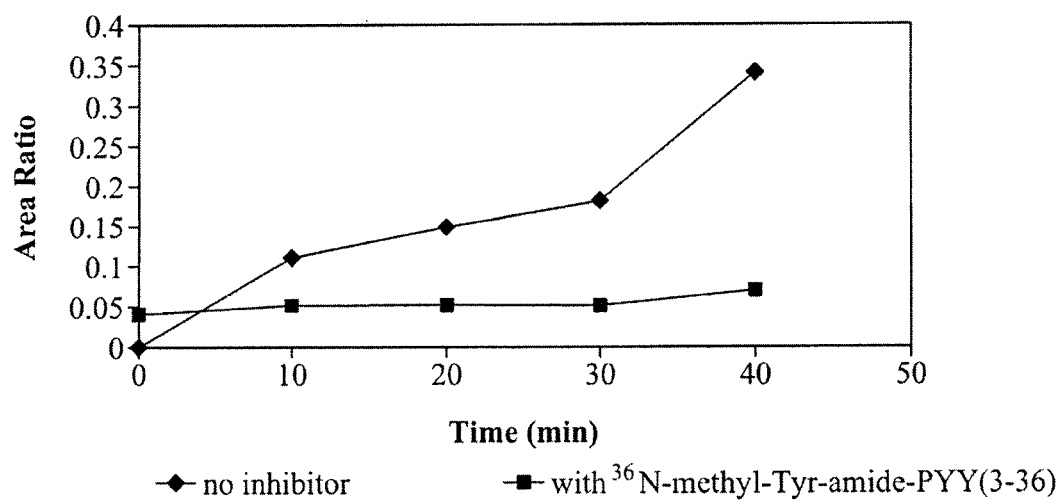
FIG. 11 is a graph depicting the formation of PYY (3-35) during incubation of PYY (3-36) in plasma in the absence or presence of $^{36}$N-methyl-Tyr-amide-PYY (3-36).
Figure 12:
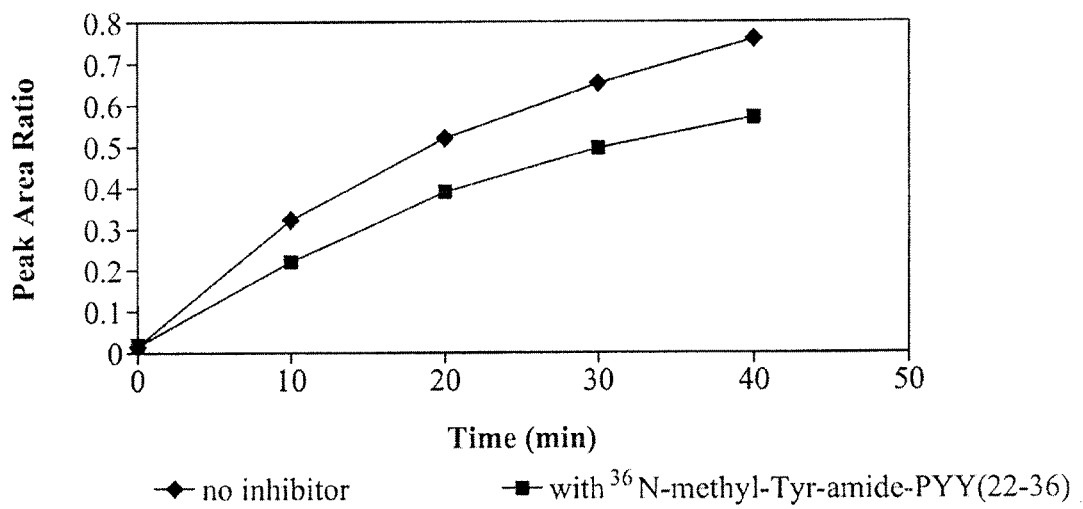
FIG. 12 is a graph depicting the formation of PYY (3-35) during incubation of PYY (3-36) in plasma in the absence or presence of $^{36}$N-methyl-Tyr-amide-PYY (22-36).
Figure 13:
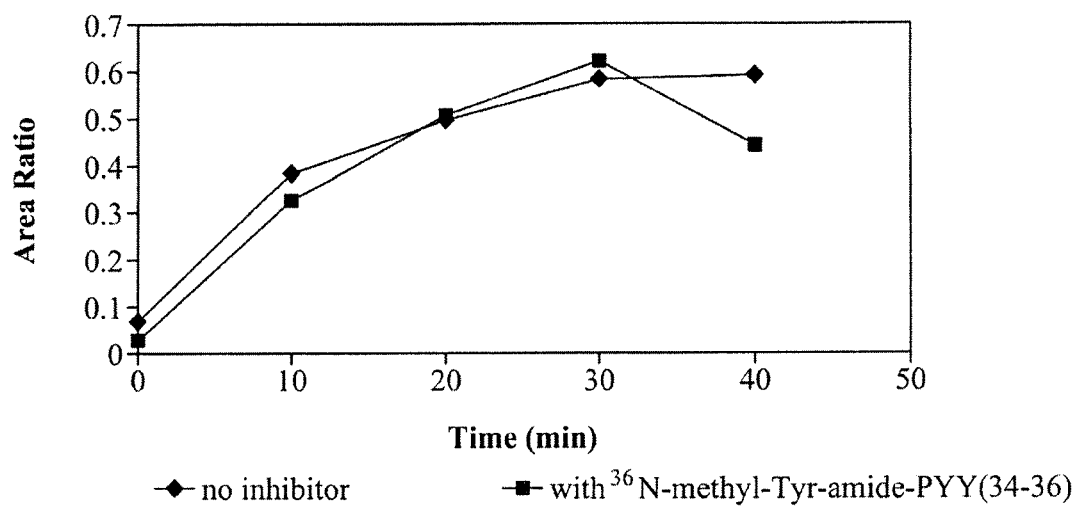
FIG. 13 is a graph depicting the formation of PYY (3-35) during incubation of PYY (3-36) in plasma in the absence or presence of $^{36}$N-methyl-Tyr-amide-PYY (34-36).
Figure 14:
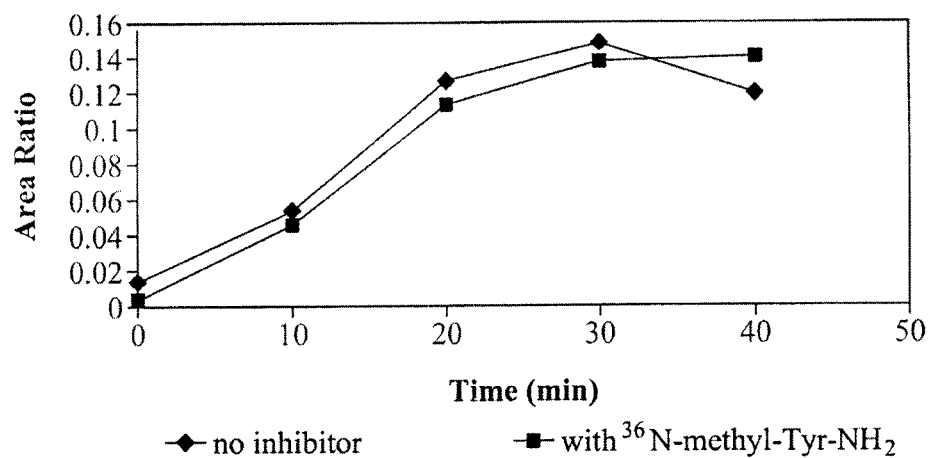
FIG. 14 is a graph depicting the formation of PYY (3-35) during incubation of PYY (3-36) in plasma in the absence or presence of N-methyl-Tyr-NH$_2$.

A series of peptide-based inhibitors were created by adding a methyl group to the α-amino nitrogen on Tyr$^{36}$ of PYY ($^{36}$N-methyl-Tyr-amide-PYY(3-36)) and N-terminal truncations of this peptide. The peptide-based inhibitors were tested for inhibitor activity in the carboxypeptidase activity assay. $^{36}$N-methyl-Tyr-amide-PYY(3-36) demonstrated inhibitory activity in the presence of PYY(3-36) inhibiting the formation of PYY(3-35) by ~100% at 0.5 mM in human plasma. See, for example, FIG. 11. As shown in FIG. 12, $^{36}$N-methyl-Tyr-amide-PYY(22-36) (0.5 mM) had measurable but lower activity to inhibit the formation of PYY(3-35). Shorter fragments of this peptide, $^{36}$N-methyl-Tyr-amide-PYY(34-36) and N-methyl-Tyr-NH$_2$ did not inhibit the formation of PYY(3-35) at 0.5 mM (FIGS. 13 and 14, respectively).

Example 8

Peptide-Peptidase Inhibitor Conjugates in Congestive Heart Failure Assay

P-PI conjugates comprising an exendin analog and the ACE inhibitor lisinopril were tested in a congestive heart failure (CHF) in vivo assay. The conjugates tested were compounds 5715 and 5131 as described in Table 3. In this assay, Dahl salt-sensitive (DSS) male rats were weaned at 21 days of age, maintained on a low-salt (LS) diet (0.2% NaCl) for 2 weeks. Rats were anesthetized with ketamine/xylazine (50 mg/kg/10 mg/kg, IP) and telemetry transmitters (Data Sciences, Inc.) were inserted to the aortic artery when rats were at 5 weeks of age. After surgery, the rats were allowed 10 days to recuperate before their BP (systolic and diastolic pressures) was recorded.

Starting from 5 weeks of age, DSS rats were fed a high-salt (HS) diet (8% NaCl$_3$) and were infused subcutaneously with conjugate compound 5715 (10 µg/kg/day) (n=3 rats) or conjugate compound 5131 (10 µg/kg/day) (n=7 rats) via osmotic alzet pumps (Durect Corp., Cupertino, Calif.) for 5 weeks. HS control animals (n=10 rats) were administered vehicle (50% DMSO) and fed HS in the same manner. LS control animals (n=5 rats) were maintained on the LS diet.

Figure 15A:
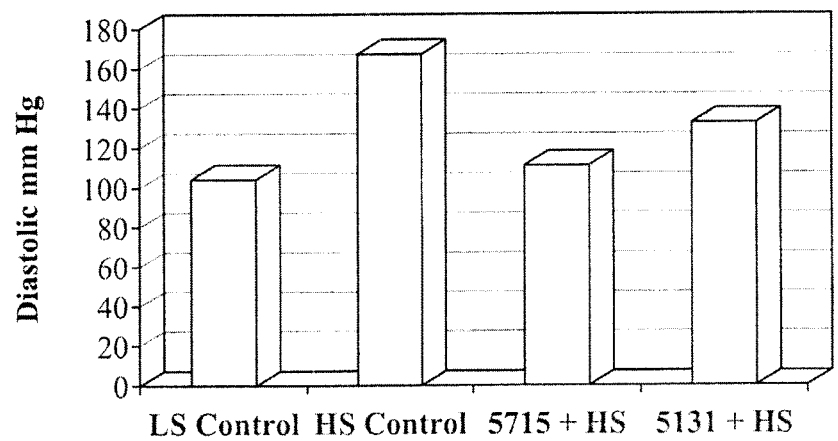
FIG. 15(a-b) are a graphs depicting mean diastolic (a) and systolic (b) blood pressure determined at week 5 of an in vivo CHF assay.
Figure 15B:
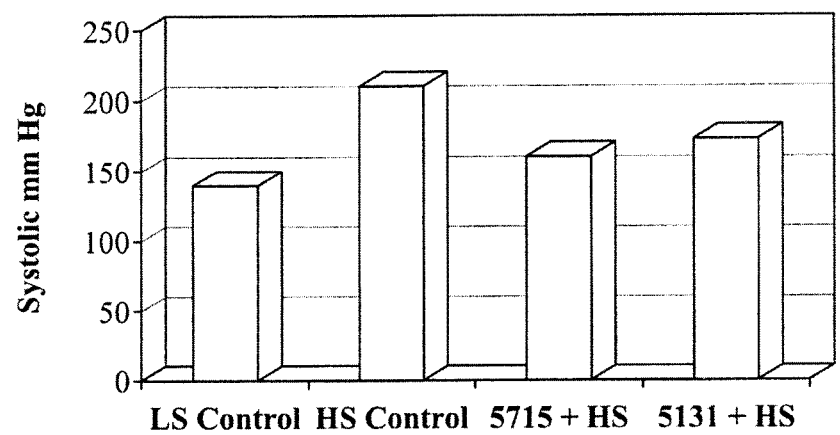

FIG. 15 depicts the mean diastolic (FIG. 15a) and systolic (FIG. 15b) blood pressure determined at week 5 (mean of all the animals in each group). As measured at week 5, administration of the P-PI conjugates to the animals on a HS diet resulted in a mean lower diastolic blood pressure (134 mmHg for compound 5131 and 112 mmHg for compound 5715) and systolic blood pressure (175 mmHg for compound 5131 and 161 mmHg for compound 5715) compared to that of the animals in the HS control (167 mmHg diastolic and 213 mmHg systolic). Also at week 5, the mean heart rate of the animals was 363 for those receiving compound 5131, 381 for those receiving compound 5715, 401 for the HS control animals and 386 for the LS control animals.

While the foregoing description discloses the present invention, with examples provided for the purpose of illustration, it will be understood that the practice of the present invention encompasses all of the usual variations, adaptations, or modifications as being within the scope of the claimed invention. Therefore, descriptions and examples should not be construed as limiting the scope of the invention, which is delineated by the appended claims.

What is claimed is:

1. A peptide-peptidase inhibitor conjugate comprising a peptide covalently linked to a peptidase inhibitor, wherein the peptide comprises exendin-3, exendin-4, or an exendin analog comprising the sequence set forth in any one of SEQ ID NOs:65-71 and 73, wherein the peptidase inhibitor comprises an angiotensin-converting enzyme inhibitor, and wherein the peptide-peptidase inhibitor conjugate is synthesized chemically or recombinantly.

2. The conjugate of claim 1 wherein the plasma half-life of the conjugate is greater than the plasma half-life of the peptide not conjugated to the peptidase inhibitor.

3. A pharmaceutical composition comprising the conjugate of claim 1.

4. A method for treating a metabolic disease or a cardiovascular disease in a subject in need thereof comprising administering a therapeutically effective amount of the conjugate of claim 1.

5. A method of decreasing degradation of a peptidase-sensitive peptide in a subject comprising administering a composition comprising the peptide-peptidase inhibitor conjugate compound according to claim 1 to a subject in an amount effective to decrease degradation of a peptidase-sensitive peptide.

6. A method of increasing plasma concentration of a biologically active, peptidase-sensitive peptide in a subject comprising administering a composition comprising the peptide-peptidase inhibitor according to claim 1 to a subject in an amount effective to increase plasma half-life of a biologically active, peptidase-sensitive peptide.

* * * * *